United States Patent
Kuhn et al.

(10) Patent No.: US 10,629,815 B2
(45) Date of Patent: Apr. 21, 2020

(54) CONJUGATED POLYMERS

(71) Applicants: INNOVATIONLAB GMBH, Heidelberg (DE); KARLSRUHER INSTITUT FUER TECHNOLOGIE, Karlsruhe (DE); TECHNISCHE UNIVERSITAET BRAUNSCHWEIG, Braunschweig (DE); MAX-PLANCK-GESELLSCHAFT ZUR FOERDERUNG DER WISSENSCHAFTEN E.V., Munich (DE)

(72) Inventors: Marius Kuhn, Heidelberg (DE); Torben Adermann, Heidelberg (DE); Manuel Hamburger, Heidelberg (DE); Klaus Muellen, Cologne (DE); Janusz Schinke, Braunschweig (DE); Alexander Colsmann, Karlsruhe (DE); Stefan Hoefle, Karlsruhe (DE); Ulrich Lemmer, Karlsruhe (DE)

(73) Assignees: INNOVATIONLAB GMBH (DE); KARLSRUHER INSTITUT FUER TECHNOLOGIE (DE); TECHNISCHE UNIVERSITAET BRAUNSCHWEIG (DE); MAX-PLANCK-GESELLSCHAFT ZUR FOERDERUNG DER WISSENSCHAFTEN E.V. (DE)

( * ) Notice: Subject to any disclaimer, the term of this patent is extended or adjusted under 35 U.S.C. 154(b) by 0 days.

(21) Appl. No.: 15/120,581

(22) PCT Filed: Feb. 10, 2015

(86) PCT No.: PCT/EP2015/000276
§ 371 (c)(1),
(2) Date: Aug. 22, 2016

(87) PCT Pub. No.: WO2015/124272
PCT Pub. Date: Aug. 27, 2015

(65) Prior Publication Data
US 2017/0331043 A1     Nov. 16, 2017

(30) Foreign Application Priority Data

Feb. 20, 2014   (EP) .................................. 14000593

(51) Int. Cl.
*C08K 3/04*   (2006.01)
*H01M 4/60*   (2006.01)
(Continued)

(52) U.S. Cl.
CPC ........ *H01L 51/0036* (2013.01); *C07D 209/86* (2013.01); *C07D 285/10* (2013.01);
(Continued)

(58) Field of Classification Search
CPC .... C08G 63/00; H01L 21/335; H01L 21/0271
(Continued)

(56) References Cited

U.S. PATENT DOCUMENTS

| 5,484,943 A | 1/1996 | Zambounis et al. |
| 2004/0038459 A1 | 2/2004 | Brown et al. |

(Continued)

FOREIGN PATENT DOCUMENTS

| CN | 1478309 A | 2/2004 |
| CN | 1957484 A | 5/2007 |

(Continued)

OTHER PUBLICATIONS

Bundgaard et al., Removal of Solubilizing Side Chains at Low Temperature: A New Route to native Poly(thiophene), Macromolecules, 2012, DOI:10.1021.

(Continued)

*Primary Examiner* — Khanh T Nguyen
(74) *Attorney, Agent, or Firm* — Kim IP Law Group PLLC

(57) ABSTRACT

The invention relates to new conjugated semiconducting polymers containing thermally cleavable side groups. The (Continued)

thermally cleavable side groups are selected from among carbonate groups and carbamate groups. By thermally cleaving side groups, the solubility or the polymers can be reduced in a targeted manner. The polymers are used as semiconductors in organic electronic (OE) devices, especially in organic photovoltaic (OPV) devices, organic photodetectors (OPDs), organic light emitting diodes (OLEDs), and organic field effect transistors (OFETs).

17 Claims, 12 Drawing Sheets

(51) Int. Cl.
| | |
|---|---|
| H01L 51/00 | (2006.01) |
| C08G 61/12 | (2006.01) |
| C07D 333/16 | (2006.01) |
| C08L 65/00 | (2006.01) |
| C07D 285/10 | (2006.01) |
| C07D 471/06 | (2006.01) |
| C07D 209/86 | (2006.01) |
| C08G 61/10 | (2006.01) |
| C12Q 1/6869 | (2018.01) |
| H01L 51/05 | (2006.01) |
| H01L 51/42 | (2006.01) |
| H01L 51/50 | (2006.01) |
| H01L 51/52 | (2006.01) |

(52) U.S. Cl.
CPC ......... *C07D 333/16* (2013.01); *C07D 471/06* (2013.01); *C08G 61/10* (2013.01); *C08G 61/124* (2013.01); *C08G 61/126* (2013.01); *C08K 3/045* (2017.05); *C08L 65/00* (2013.01); *C12Q 1/6869* (2013.01); *H01L 51/0026* (2013.01); *H01L 51/0034* (2013.01); *H01L 51/0035* (2013.01); *H01L 51/0039* (2013.01); *H01L 51/0046* (2013.01); *H01M 4/602* (2013.01); *C08G 61/12* (2013.01); *C08G 61/123* (2013.01); *C08G 2261/11* (2013.01); *C08G 2261/124* (2013.01); *C08G 2261/142* (2013.01); *C08G 2261/149* (2013.01); *C08G 2261/1426* (2013.01); *C08G 2261/1646* (2013.01); *C08G 2261/18* (2013.01); *C08G 2261/3142* (2013.01); *C08G 2261/3162* (2013.01); *C08G 2261/3223* (2013.01); *C08G 2261/3241* (2013.01); *C08G 2261/3246* (2013.01); *C08G 2261/41* (2013.01); *C08G 2261/411* (2013.01); *C08G 2261/412* (2013.01); *C08G 2261/417* (2013.01); *C08G 2261/51* (2013.01); *C08G 2261/526* (2013.01); *C08G 2261/91* (2013.01); *C08G 2261/92* (2013.01); *C08G 2261/94* (2013.01); *C08G 2261/95* (2013.01); *H01L 51/0541* (2013.01); *H01L 51/4253* (2013.01); *H01L 51/5012* (2013.01); *H01L 51/5296* (2013.01); *Y02E 10/549* (2013.01)

(58) Field of Classification Search
USPC .................. 528/310; 438/142; 156/345.3
See application file for complete search history.

(56) References Cited

U.S. PATENT DOCUMENTS

| | | |
|---|---|---|
| 2004/0119049 A1 | 6/2004 | Heeney et al. |
| 2004/0176560 A1 | 9/2004 | Heeney et al. |
| 2005/0184274 A1 | 8/2005 | Heeney et al. |
| 2008/0067475 A1 | 3/2008 | McCulloch et al. |
| 2008/0197319 A1 | 8/2008 | Klasen-Memmer et al. |
| 2011/0045628 A1 | 2/2011 | Krebs |
| 2011/0269917 A1 | 11/2011 | Fujiwara et al. |
| 2013/0276887 A1 | 10/2013 | Worfolk et al. |
| 2014/0202632 A1* | 7/2014 | Wang ............... H01L 21/0271 |
| | | 156/345.3 |
| 2014/0338750 A1 | 11/2014 | Iijima et al. |

FOREIGN PATENT DOCUMENTS

| | | |
|---|---|---|
| CN | 101570533 A | 11/2009 |
| CN | 102858761 A | 1/2013 |
| CN | 103154808 A | 6/2013 |
| JP | 2003231702 A | 8/2003 |
| WO | 2013094456 A1 | 4/2015 |

OTHER PUBLICATIONS

Durban et al., "Synthesis and Characterization of Solution-Processable Ladderized n-Type Naphthalene Bismide Copolymers for OFET Applications", Macromolecules, 2011, vol. 44, pp. 4721-4728.

Helgesen et al., "Advanced Materials and Processes for Polymer Solar Cell Devices", Journal of Materials Chemistry, 2010, vol. 20, pp. 36-60.

Kazarinoff et al., "OTEF Performace of Air-Stable Ester-Functionalized Polythiophenes", Journals of Materials Chemistry, 2010, vol. 20, pp. 3040-3045.

Krebs et al., "Significant Improvement of Polymer Solar Cell Stability", Chem. Mater., 2005, vol. 17, pp. 5235-5237.

Lee at al., "Inversion of Dominant Polarity in Ambipolar Polydiketopyrrolopyrrole with Thermally Removable Groups", Advanced Functional Materials, 2012, vol. 22, pp. 4128-4138.

Sun et al., "Diketopyrrolopyrrole-based Semiconducting Polymer Bearing Thermocleavable Side Chains", Journal of Materials Chemistry, 2012, DOI: 10.1039.

Suna et al., "Ambipolar Behavior of Hydrogen-Bonded Diketopyrrolopyrrole-Thiophene Co-oligomers Formed from Their Soluble Precursors", Organic Letters, 2012, vol. 14, No. 13, pp. 3356-3559.

Yu et al., "Solid-State Thermoltic and Catalytic Reactions in Functionalized Regioregular Polythiophenes", Macromolecules, 2000, vol. 33, pp. 5073-5079.

Zambounis et al., "Latent Pigments Activated by Heat", Nature, 1997, vol. 388, pp. 131.

Liu et al., "Polythiophene Containing Thermally Removable Solubilizing Groups Enhances the Interface and the Performance of Polymer-Titania Hybrid Solar Cells," J. Am. Chem. Soc., vol. 126, No. 31, pp. 9486-9487 (2004).

Edder et al., "Benzothiadiazole- and pyrrole-based polymers bearing thermally cleavable solubilizirig groups as precursors for low bandgap polymers," Chem. Commun., pp. 1965-1967 (2006).

Office Action dated May 21, 2018 in Chinese Patent Application Serial No. 201580015244.X.

Office Action dated Nov. 13, 2018 in Japanese Patent Application No. 2016-570169.

* cited by examiner

CONJUGATED POLYMERS

RELATED APPLICATIONS

This application is a national stage entry, filed pursuant to 35 U.S.C. § 371, of PCT/EP2015/000276, filed Feb. 10, 2015, which claims the benefit of European Patent Application No. 14000593.5, filed Feb. 20, 2014, which is incorporated herein by reference in its entirety.

The invention relates to novel conjugated polymers containing thermally detachable side groups, to monomers and processes for preparation thereof, to the use thereof as semiconductors in organic electronic (OE) devices, especially in organic photovoltaic (OPV) devices, organic photodetectors (OPDs), organic light-emitting diodes (OLEDs), organic field-effect transistors (OFETs), and to OE, OPV, OPD, OLED and OFET devices comprising these polymers.

In the last few years, organic semiconductor materials have been developed, in order to produce more versatile and less costly OE devices. Materials of this kind find use in a multitude of devices or appliances, for example in OFETs, OLEDs, OPD or OPV devices, sensors, memory elements and logic circuits. The organic semiconductor materials in the OE device are typically in the form of a thin layer of thickness, for example, less than 1 micrometer.

A particularly important field is that of OPV devices such as organic solar cells. Conjugated polymers find use as organic semiconductors in organic solar cells, since they enable simple production of the photoactive layer by processing techniques from solution, such as spin coating, dip coating or inkjet printing. Compared to evaporation techniques as used for production of inorganic semiconductor layers, processing from solution can be conducted at lower cost and on a larger scale. For organic solar cells having polymeric semiconductors, efficiencies of more than 7% have been reported.

A further important field is that of OFETs. The performance thereof is based mainly on the charge carrier mobility of the semiconductor material and the on/off ratio of the current; therefore, the ideal semiconductor should have a low conductivity in the off state in conjunction with a high charge carrier mobility ($>1\times10^{-3}$ $cm^2$ $V^{-1}$ $s^{-1}$). It is also important that the semiconductor material is relatively oxidation-resistant, i.e. has a high ionization potential, since oxidation leads to a reduction in performance of the device. Further demands on the semiconductor material are good processability, especially for the industrial scale production of thin layers and desired patterns, as are high stability, homogeneity of the film and integrity of the organic semiconductor layer.

However, there is still a need for organic semiconductor materials which can be easily synthesized and are especially suitable for mass production, have good structural organization and film-forming properties, and exhibit good electronic properties, especially high charge carrier mobility, good processability, especially high solubility in organic solvents, and high stability in air. For use in OPV elements, there is especially a need for organic semiconductor materials having a small energy gap, which can enable improved exploitation of light by the photoactive layer and lead to higher efficiency of the elements. For the use in OFETs, there is especially a need for organic semiconductor materials having high charge carrier mobility and high oxidation resistance.

In order to achieve improved solubility of the organic semiconductors in organic solvents, semiconductors used in the prior art are typically conjugated polymers having solubility-promoting side chains that are generally unconjugated, for example alkyl groups. However, these side chains can disrupt the organization of the conjugated polymer backbones in the functional layer and especially the crystallization of the polymers, and hence impair charge transport between the polymer molecules. Moreover, the solubility-promoting side groups used to date often do not exhibit the desired increase in solubility. Moreover, such solubility-promoting side chains can have the effect that the polymers are likewise soluble in solvents which are used for application of further layers to the functional layer. As a consequence of this, the application of a further layer can damage the previously applied functional polymer layer. What would be desirable, by contrast, would be an organic semiconductor material which has a high solubility in the solvent used for application of the semiconductor layer but has zero or only sparing solubility, i.e. high orthogonality, in a solvent used for application of further layers.

It was an aim of the present invention to provide compounds for use as organic semiconductor materials which do not have the abovementioned disadvantages of the prior art materials, can be easily synthesized, especially by processes suitable for mass production, and especially have good processibility, high stability, good solubility in organic solvents, high orthogonality with respect to adjacent layers in the device, high charge carrier mobility and a low energy gap. A further aim was the extension of the spectrum of organic semiconductor materials available to the person skilled in the art. Further aims of the present invention will be apparent to the person skilled in the art from the disclosure which follows.

It has been found that these aims can be achieved by the provision of conjugated semiconductor polymers according to the present invention as described below. These polymers have solubility-improving carbonate side chains or carbamate side chains which are thermally detachable.

Conjugated polymers having solubility-improving groups are known from the prior art. These typically consist, however, either of groups such as very long alkyl or fluoroalkyl radicals, for example, that are not detachable and hence remain in the film after processing, or of groups that can be detached only at very high temperatures (>300° C.).

For example, US 2011/0045628 A1, J. Yu, S. Holdcroft, *Macromolecules* 2000, 33, 5073-5079, M. Helgesen, R. Søndergaard, F. C. Krebs, *J. Mater Chem,* 2010, 20, 36-60, P. D. Kazarinoff, P. J. Shamburger, F. S. Ohuchi, C. K. Luscombe, *J. Mater. Chem.* 2010, 20, 3040-3045, E. Bundgaard, O. Hagemann, M. Bjerring, N. C. Nielsen, J. W. Andreasen, B. Andreasen, F. C. Krebs, *Macromolecules* 2012, 45, 3644-3646, F. C. Krebs, H. Spanggaard, *Chem. Mater.* 2005, 17, 5235-5237, J. Lee, A.—R. Han, J. Hong, J. H. Seo, J. H. Oh, C. Yang, *Adv. Funct, Mater.* 2012, 22, 4128-4138, or B. Sun, W. Hong, H. Aziz, Y. Li, *J. Mater, Chem,* 2012, 22, 18950-18955 disclose polymers having thermally detachable carbonyl, carbonyloxy or THP ether groups in the side chain.

However, the operation for detachment of such groups entails very high temperatures exceeding 200° C. and up to 310° C., as shown by way of example in the scheme which follows. Such high operating temperatures, however, are disadvantageous since they can damage the semiconductor layer applied or other components of the device.

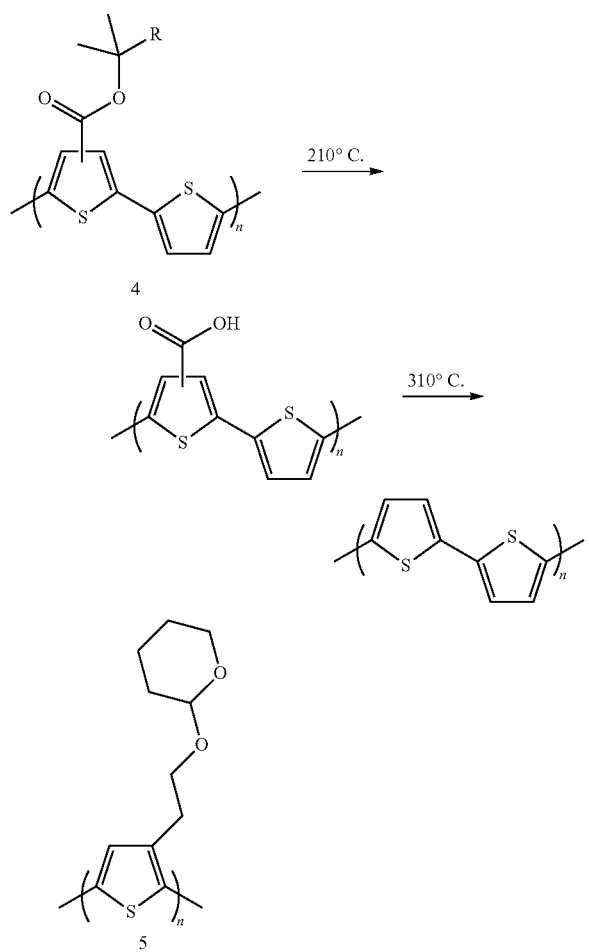

M. M. Durban, P. D. Kazarinoff, Y. Segawa, C. K. Luscombe, *J. Macromolecules* 2011, 44, 4721-4728 disclose precursor polymers of the following formulae (PNDI-1Boc, PNDI-2Boc) containing a phenylene-2,5-diyl unit having one or two carbamate side groups and an adjacent benzo[lmn][3,8]phenanthroline-1,3,6,8-tetraone-4,9-diyl unit (also referred to in the literature as "naphthalenebis(dicarboximide)" or "NDI") in which R is a 2-octyldodecyl radical:

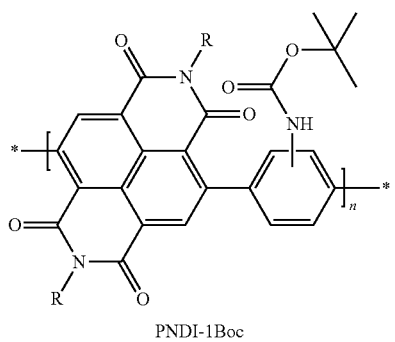

PNDI-1Boc

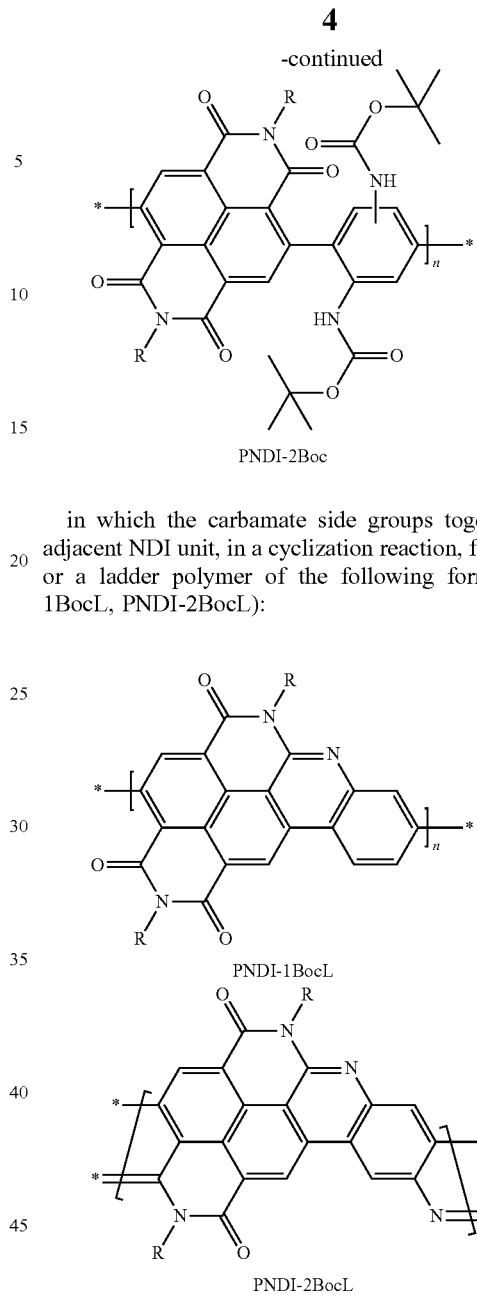

PNDI-2Boc in which the carbamate side groups together with the adjacent NDI unit, in a cyclization reaction, form a polymer or a ladder polymer of the following formulae (PNDI-1BocL, PNDI-2BocL):

PNDI-1BocL

PNDI-2BocL

However, the thermal detachment of the carbamate side group, or the use of the carbamate-substituted precursor polymers without any need for further cyclization reaction in a semiconductor layer, is not disclosed therein.

For the method disclosed therein, it is necessary to position the thermally labile carbamate in the immediate proximity of a carbonyl group (here the imide group of the NDI comonomer). This very greatly restricts the range of variation of this approach.

U.S. Pat. No. 5,484,943 discloses low molecular weight pyrrolo[3,4-c]pyrroles in which the nitrogen atoms in the pyrrole ring may also be substituted by a carbonyl group (forming a carbamate group), and the use thereof as fluorescent pigments for coloring plastics. It is also stated therein that the substituted pyrrolo[3,4-c]pyrroles can be converted by thermal, photolytic or chemical treatment with detachment of the carbonyl group to the corresponding compounds having unsubstituted ring nitrogen atoms, which gives rise to a new crystal form of the pigment having better color properties. However, conjugated polymers or the use thereof according to the present invention are neither disclosed nor suggested therein.

J. Lee et al., *Adv. Funct. Mater.* 2012, 22, 4128-4138 discloses ambipolar polymers of the following formula:

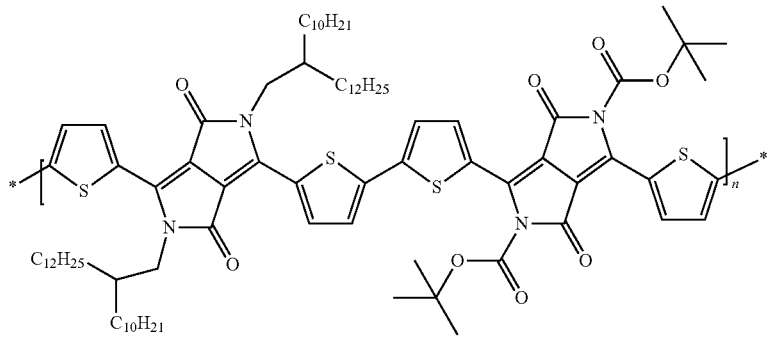

which contain 3,6-dithienyldipyrrolopyrrole units having thermally detachable carbonyl groups, and the use thereof in ambipolar OFETs, in which the free NH groups in the polymer form hydrogen bonds after detachment of the carbonyl groups. However, the use of DPP in the conjugated polymers leads to ambipolar charge transport at most. Conjugated polymers according to the present invention which can be used as pure n-channel material are not disclosed.

It has now been found that, surprisingly, polymers of the invention having solubility-improving carbonate side chains or carbamate side chains enable partial or complete detachment of the side chains even at temperatures below 200° C. The polymers of the invention additionally have improved solubility compared to the materials known from the prior art. It has additionally been found that these polymers, after detachment of the side chains and optional thermal treatment, enable better crystallization and higher order of the polymer chains, which leads to improved charge transport in the semiconductor layer and to higher efficiency in the case of use in organic solar cells.

The detachability of the side groups in a polymer according to the invention also enables the variation of the solubility thereof. Thus, after the application of the polymeric semiconductor layer from solution, the solubility of the polymer can be distinctly reduced by the detachment of the side chains. This can distinctly increase the stability of the semiconductor layer with respect to solvents which are used for application of further organic layers. Furthermore, for the application of further organic layers, it is possible to use the same solvent or a similar solvent to that used for the application of the semiconductor layer. The use of orthogonal solvents or corresponding materials for the subsequent layer is thus no longer absolutely necessary. This enables greater variability in the selection of the materials and operations used.

The monomers and polymers of the present invention are especially suitable for industrial production on a large scale. At the same time, they have good processibility, high solubility in organic solvents, high charge carrier mobility, high long-term stability, high stability with respect to solvents and high oxidation stability, and constitute promising materials for organic electronic OE devices, especially for OPV devices.

The invention thus relates to a conjugated polymer containing one or more identical or different repeat units, in which at least one of the repeat units is substituted by a carbonate group or a carbamate group, preferably by a carbonate group, with the provisos that the polymer does not contain any phenylene units substituted by one or more carbamate groups that are directly adjacent to an optionally substituted benzo[lmn][3,8]phenanthroline-1,3,6,8-tetraone-4,9-diyl unit, and that the polymer does not contain any pyrrolo[3,4-c]pyrrole-1,4-dione-3,6-diyl units in which both nitrogen atoms are substituted by a carbonyl group.

The invention further relates to a conjugated polymer containing one or more identical or different repeat units of the formula I:

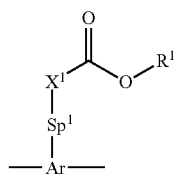

I in which the individual radicals are defined as follows:

Ar is mono- or polycyclic aryl or heteroaryl which may additionally be substituted in one or more positions, $Sp^1$ is a single bond or straight-chain, branched and/or cyclic alkylene which has 1 to 20 carbon atoms and is unsubstituted or mono- or polysubstituted by F, Cl, Br, I or CN, and in which one or more nonadjacent $CH_2$ groups may each independently also be replaced by —O—, —S—, —C(O)—, —C(S)—, —C(O)—O—, —O—C(O)—, —$NR^0$—, —$SiR^0R^{00}$—, —$CF_2$—, —$CHR^0$=$CR^{00}$—, —$CY^1$=$CY^2$—, or —C≡C— in such a way that no oxygen and/or sulfur atoms are joined directly to one another, $X^1$ is $NR^0$ or O, preferably O, where, if the $Sp^1$-$X^1$—C(O)—$OR^1$ radical is bonded to a nitrogen atom in the Ar radical, the $Sp^1$-$X^1$ radical may also be a single bond, $R^1$ is hydrocarbyl having 1 to 40 carbon atoms, $Y^1$ and $Y^2$ are each independently H, F, Cl or CN, $R^0$ and $R^{00}$ are each independently H or alkyl having 1 to 12 carbon atoms, excluding repeat units of the formula I in which Ar is phenylene which is mono- or polysubstituted by —NH—C(O)—$OR^1$, and which, in the polymer backbone, is directly adjacent to an optionally substituted benzo[lmn][3,8]phenanthroline-1,3,6,8-tetraone-4,9-diyl unit, and repeat units of the formula I in which Ar is pyrrolo[3,4-c]pyrrole-1,4-dione-3,6-diyl in which both nitrogen atoms are substituted by —C(O)—OR$^1$.

The invention further relates to a conjugated polymer containing one or more repeat units substituted by a carbonate group or a carbamate group, preferably by a carbonate group, and preferably selected from the repeat units of the formula I, and additionally containing one or more optionally substituted mono- or polycyclic aryl or heteroaryl units.

The invention further relates to a process for partial or complete detachment of the carbonate or carbamate groups of a polymer as described above and below, by heating the polymer, or a layer comprising the polymer, to a temperature of ≤200° C., and to a polymer obtainable by this process.

The invention further relates to a polymer obtainable by detaching the carbamate and carbonate groups of a polymer as described above and below, preferably by thermal or chemical detachment.

The invention further relates to monomers containing a unit of the formula I and one or more reactive groups that are suitable for the preparation of polymers as described above and below.

The invention further relates to the use of polymers according to the present invention as semiconductors, for example as electron donors or p-type semiconductors, or as electron acceptors or n-type semiconductors.

The invention further relates to the use of polymers according to the present invention as semiconductive material, preferably as electron donor, in an organic electronic device or a component of an organic electronic device.

The invention further relates to the use of polymers according to the present invention as light-emitting material in an organic electronic device or a component of an organic electronic device.

The invention further relates to a semiconductive and/or light-emitting material, to an organic electronic device or to a component of an organic electronic device comprising a polymer according to the present invention having electron donor properties and one or more additional compounds or polymers having electron acceptor properties.

The invention further relates to a semiconductive and/or light-emitting material, to an organic electronic device or to a component of an organic electronic device comprising a polymer according to the present invention having electron acceptor properties and one or more additional compounds or polymers having electron donor properties.

The invention further relates to a semiconductive and/or light-emitting material, to an organic electronic device or to a component of an organic electronic device comprising one or more polymers according to the present invention having electron donor properties and one or more polymers according to the present invention having electron acceptor properties.

The invention further relates to a mixture or polymer blend comprising one or more polymers according to the present invention and one or more additional compounds or polymers that are preferably selected from compounds and polymers having semiconductor, charge transport, hole/electron transport, hole/electron-blocking, electrically conducting, photoconductive or light-emitting properties.

The invention further relates to a mixture or polymer blend comprising one or more polymers according to the present invention having electron donor properties and one or more additional compounds selected from electron acceptors and organic n-type semiconductors, preferably selected from the group consisting of fullerenes and substituted fullerenes.

The invention further relates to a formulation comprising one or more polymers, mixtures or polymer blends according to the present invention and one or more solvents, preferably selected from organic solvents.

The invention further relates to the use of polymers, formulation, mixtures and polymer blends according to the present invention as charge transport material, semiconductor material, electrically conductive material, photoconductive material or light-emitting material, preferably in a device having optical, electrooptical, electronic, electroluminescent or photoluminescent properties, in a component of such a device, or in a product comprising such a device.

The invention further relates to a charge transport material, semiconductor material, electrically conductive material, photoconductive material or light-emitting material, comprising a polymer, formulation, mixture or polymer blend according to the present invention.

The invention further relates to an optical, electrooptical, electronic, electroluminescent or photoluminescent device, to a component of such a device, or to a product comprising such a device, comprising a polymer, formulation, mixture or polymer blend according to the present invention.

The optical, electrooptical, electronic, electroluminescent and photoluminescent devices include, but are not limited to, organic field-effect transistors (OFETs), organic thin-film transistors (OTFTs), organic light-emitting diodes (OLEDs), organic light-emitting transistors (OLETs), organic photovoltaic devices (OPVs), organic photodetectors (OPDs), organic solar cells, Schottky diodes, laser diodes and organic photoconductors.

Particular preference is given to OFETs, OPV devices, organic solar cells and OPDs, especially OPV devices and organic solar cells in which the organic semiconductors in the photoactive layer form a bulk heterojunction or "BHJ" (BHJ-OPV).

The components of the devices of the invention include, but are not limited to, charge injection layers, charge transport layers, interlayers, planarization layers, antistatic films, polymer electrolyte membranes (PEMs), conductive substrates, conductive patterns.

The products comprising the devices of the invention include, but are not limited to, integrated circuits (ICs), capacitors, RFID tags (RFID=radiofrequency identification) or security labels or security devices comprising these, flat display screens, backlighting for display screens, electrophotographic devices, organic memory devices, sensor devices, biosensors and biochips.

The invention further relates to the use of polymers, formulation, mixtures and polymer blends according to the present invention as electrode materials in batteries and in components or devices for the detection and distinction of DNA sequences.

FIGS. 1a-c show the topography of a layer of a polymer from example 3.2 before (1a) and after thermal treatment (1b) and after rinsing with toluene (1c).

FIG. 2 shows the emission spectrum (2a) and the color locus (2b) of an OLED comprising a polymer according to example 3.2 before and after thermal aftertreatment.

FIGS. 3a-d show the optoelectronic characteristics of an OLED comprising a polymer according to example 3.2 as emitter.

Figure 1A:
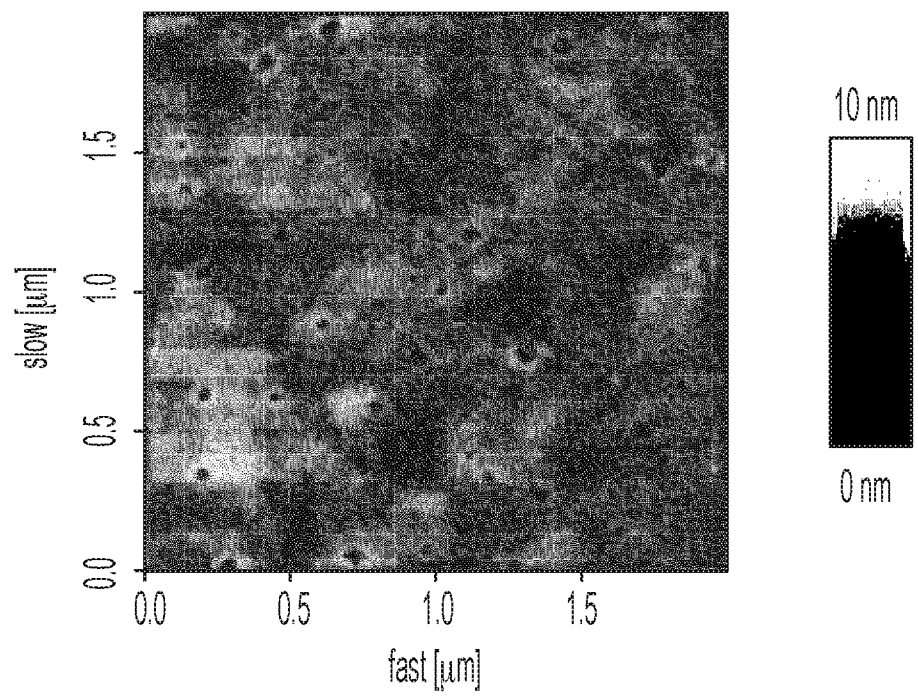

The monomers and polymers of the present invention can be easily synthesized and have several advantageous properties, such as a low energy gap, high charge carrier mobility, high solubility in organic solvents, good processibility in the production of the device, high oxidation stability and long lifetime in electronic devices.

The carbonate or carbamate side chains increase the solubility of the polymer in customary organic solvents, which permits simpler processing of the material from solution.

The carbonate or carbamate side chains can be thermally detached after processing of the polymer from the solution, for example in the form of a thin layer. This increases the stability of the polymer layer to solvents which are used, for example, for subsequent application of additional layers. In addition, the crystallization of the polymer is improved and improved pi-pi stacking of the polymer chains in the solid state is enabled, which leads to improved charge transport properties in the form of higher charge carrier mobility.

The solubility-improving groups in the polymers of the invention show better solubility compared to standard groups, such as alkyl radicals, in conventional solvents. This was demonstrated by gel permeation chromatography (GPC) on the basis of the M$_n$ values of the polymers. This was done by analyzing standard polymers such as poly-3-hexylthiophene (P3HT) with the polymers of the invention in various solvents (comparison between acetone and chloroform).

The term "polymer" generally refers to a molecule of high relative molecular mass, the structure of which essentially comprises the multiple repetition of units derived, actually or conceptually, from molecules of low relative molecular mass (PAC, 1996, 68, 2291). The term "oligomer" generally refers to a molecule of intermediate relative molecular mass, the structure of which essentially comprises a small plurality of units derived, actually or conceptually, from molecules of lower relative molecular mass (PAC, 1996, 68, 2291). In a preferred definition according to the present invention, a polymer refers to a compound having >1, preferably ≥5, repeat units, and an oligomer refers to a compound having >1 and <10, preferably <5, repeat units.

Unless stated otherwise, the molecular weight reported is the number-average molecular weight M$_n$ or weight-average molecular weight M$_w$, which is determined by gel permeation chromatography (GPC) against polystyrene standards in eluting solvents such as tetrahydrofuran, trichloromethane (TCM, chloroform), chlorobenzene or 1,2,4-trichlorobenzene. Unless stated otherwise, trichloromethane is used as solvent. The polymerization level (n) refers to the number-average polymerization level, given by n=M$_n$/Mu, in which Mu is the molecular weight of the individual repeat unit, as described in J. M. G. Cowie, *Polymers: Chemistry & Physics of Modern Materials*, Blackie, Glasgow, 1991.

Above and below, in any formula that shows a polymer or a repeat unit, such as the formula I and the subformulae thereof, an asterisk (*) indicates a linkage to the adjacent repeat unit in the polymer chain.

The terms "repeat unit" and "monomer unit" refer to the constitutional repeat unit (CRU), which is the smallest constitutional unit the repetition of which constitutes a regular macromolecule, a regular oligomer molecule, a regular block or a regular chain (PAC, 1996, 68, 2291). The term "unit" refers to a structural unit which may itself be a repeat unit or, together with other units, may form a repeat unit.

The term "leaving group" refers to an atom or a group (charged or uncharged) which is separated by involvement in a specific reaction from an atom in the portion which is referred to as the residual or main part of the molecule (see also PAC, 1994, 66, 1134).

The term "conjugated" refers to a compound containing predominantly carbon atoms having sp$^2$ hybridization (or as the case may be also sp hybridization), which may also be replaced by heteroatoms. In the simplest case, this is, for example, a compound having alternating C—C single and double (or triple) bonds, but also includes compounds having units such as 1,3-phenylene. "Mainly" in this context means that a compound having naturally (spontaneously) occurring defects which can lead to interruption of the conjugation is likewise regarded as a conjugated compound.

The terms "donor" and "acceptor" refer respectively to an electron donor and acceptor. The term "electron donor" refers to a chemical compound or group that releases electrons to another chemical compound or group. The term "electron acceptor" refers to a chemical compound or group that accept electrons from another chemical compound or group (see U.S. Environmental Protection Agency, 2009, Glossary of technical terms) http://www.epa.gov/oust/cat/TUMGLOSS.HTM The term "n-type" or "n-type semiconductor" refers to an extrinsic semiconductor in which the density of the conducting electrons is higher than the density of the mobile holes. The term "p-type" or "p-type semiconductor" refers to an extrinsic semiconductor in which the density of the conducting electrons is lower than the density of the mobile holes (see J. Thewlis, *Concise Dictionary of Physics*, Pergamon Press, Oxford, 1973).

The term "benzo[lmn][3,8]phenanthroline-1,3,6,8-tetraone-4,9-diyl" refers to a group of the following formula ("NDI"):

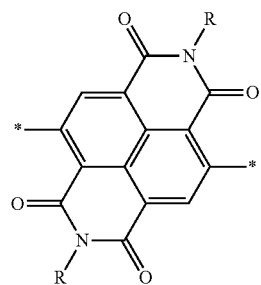

in which R is a substituent, for example a carbyl or hydrocarbyl group as defined above and below, or a hydrogen atom.

The term "pyrrolo[3,4-c]pyrrole-1,4-dione-3,6-diyl" refers to a group of the following formula:

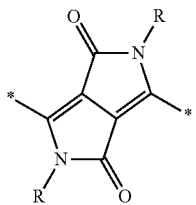

in which R is a substituent, for example a carbyl or hydrocarbyl group as defined above and below, or a hydrogen atom.

The term "carbyl group" as used above and below represents any monovalent or polyvalent organic molecular radical which contains at least one carbon atom either without any non-carbon atoms (for example —C≡C—) or optionally in conjunction with at least one non-carbon atom such as N, O, S, P, Si, Se, As, Te or Ge (e.g. carbonyl etc.). The term "hydrocarbyl group" refers to a carbyl group which additionally contains one or more hydrogen atoms and optionally one or more heteroatoms, for example N, O, S, P, Si, Se, As, Te or Ge.

A carbyl or hydrocarbyl group having a chain of 3 or more carbon atoms may also be linear, branched and/or cyclic, including spiro and/or fused rings.

The preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25 and very preferably 1 to 18 carbon atoms, and additionally optionally substituted aryl or aryloxy having 6 to 40 and preferably 6 to 25 carbon atoms, and additionally alkylaryloxy, arylcarbonyl, aryloxycarbonyl, arylcarbonyloxy and aryloxycarbonyloxy, each of which is optionally substituted and has 6 to 40 and preferably 7 to 40 carbon atoms, where all these groups optionally contain one or more heteroatoms, preferably selected from N, O, S, P, Si, Se, As, To and Ge.

The carbyl or hydrocarbyl group may be a saturated or unsaturated acyclic group or a saturated or unsaturated cyclic group. Unsaturated acyclic or cyclic groups are preferred, especially aryl, alkenyl and alkynyl groups (especially ethynyl). An acyclic $C_1$-$C_{40}$ carbyl or hydrocarbyl group may be straight-chain or branched. The $C_1$-$C_{40}$ carbyl or hydrocarbyl group includes, for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group and the like. Among the above groups, preference is given to a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_6$-$C_{12}$ aryl group or a $C_4$-$C_{20}$ polyenyl group. Likewise included are combinations of groups having carbon atoms and groups having heteroatoms, for example an alkynyl group, preferably ethynyl, substituted by a silyl group, preferably a trialkylsilyl group.

Aryl and heteroaryl are preferably a monovalent, bi- or tricyclic aromatic or heteroaromatic group having 4 to 30 ring carbon atoms, which may also contain fused rings and is optionally substituted by one or more L groups as defined above.

Particularly preferred substituents L are selected from halogen, especially preferably F, or alkyl, alkoxy, oxaalkyl, thioalkyl, fluoroalkyl and fluoroalkoxy having 1 to 12 carbon atoms, or alkenyl or alkynyl having 2 to 12 carbon atoms.

Particularly preferred aryl and heteroaryl groups are phenyl in which one or more CH groups may additionally be replaced by N, naphthalene, thiophene, selenophene, thienothiophene, dithienothiophene, fluorene and oxazole, each of which may be unsubstituted or mono- or polysubstituted by L as defined above. Very preferred rings are selected from pyrrole, preferably N-pyrrole, pyridine, preferably 2- or 3-pyridine, pyrimidine, thiophene, preferably 2-thiophene, selenophene, preferably 2-selenophene, thieno[3,2-b]thiophene, thiazole, thiadiazole, oxazole and oxadiazole, more preferably thiophen-2-yl, 5-substituted thiophen-2-yl or pyridin-3-yl, each of which may be unsubstituted or mono- or polysubstituted by L as defined above.

An alkyl or alkoxy radical, i.e. where the $CH_2$ end group is replaced by —O—, may be straight-chain or branched. It is preferably straight-chain, has 2, 3, 4, 5, 6, 7 or 8 carbon atoms and is thus preferably, for example, ethyl, propyl, butyl, pentyl, hexyl, heptyl, octyl, ethoxy, propoxy, butoxy, pentoxy, hexoxy, heptoxy or octoxy, and additionally methyl, nonyl, decyl, undecyl, dodecyl, tridecyl, tetradecyl, pentadecyl, nonoxy, decoxy, undecoxy, dodecoxy, tridecoxy or tetradecoxy.

An alkenyl group in which one or more $CH_2$ groups are replaced by —CH=CH— may be straight-chain or branched. It is preferably straight-chain, has 2 to 10 carbon atoms and is thus preferably vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Particularly preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, especially $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

An oxaalkyl group, i.e. where a $CH_2$ group is replaced by —O—, is preferably, for example, straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, oxaalkyl, i.e. where a $CH_2$ group is replaced by —O—, is preferably, for example, straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

In an alkyl group in which one $CH_2$ group is replaced by —O— and one by —CO—, these radicals are preferably adjacent. Thus, these radicals together form a carbonyloxy group —CO—O— or an oxycarbonyl group —O—CO—. Preferably, this group is straight-chain and has 2 to 6 carbon atoms. Thus, it is preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)butyl.

An alky group in which two or more $CH_2$ groups are replaced by —O— and/or —COO— may be straight-chain or branched. It is preferably straight-chain and has 3 to 12 carbon atoms. It is thus preferably biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl, 5,5-bis(ethoxycarbonyl)hexyl.

A thioalkyl group, i.e. where a $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), in which it is preferably the $CH_2$ group adjacent to the $sp^2$-hybridized vinyl carbon atom which is replaced.

A fluoroalkyl group is preferably straight-chain perfluoroalkyl $C_iF_{2i+1}$ in which i is an integer from 1 to 15, especially $CF_3$, $C_2F_5$, $C_3F_7$, $C_4F_9$, $C_6F_{13}$, $C_7F_{15}$ or $C_8F_{17}$, very preferably $C_6F_{13}$.

The abovementioned alkyl, alkoxy, alkenyl, oxaalkyl, thioalkyl, carbonyl and carbonyloxy groups may be achiral or chiral groups. Particularly preferred chiral groups are, for example, 2-butyl (=1-methylpropyl), 2-methylbutyl, 2-methylpentyl, 3-methylpentyl, 2-ethylhexyl, 2-propylpentyl, especially 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6 methyloctanoyloxy, 5-methylheptyloxycarbonyl, 2-methylbutyryloxy, 3-methylvaleroyloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1 butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy. The following are very preferred: 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl methylpropyl), isopentyl (=3-methylbutyl), tert-butyl, isopropoxy, 2-methylpropoxy and 3-methylbutoxy.

In a further preferred embodiment of the present invention, the alkyl and alkoxy groups are selected from primary, secondary and tertiary alkyl and alkoxy having 1 to 30 carbon atoms, in which one or more hydrogen atoms are optionally replaced by F, and aryl, aryloxy, heteroaryl and heteroaryloxy, which is optionally alkylated or alkoxylated and has 4 to 30 ring atoms. Very preferred groups of this kind are selected from the group consisting of the following formulae:

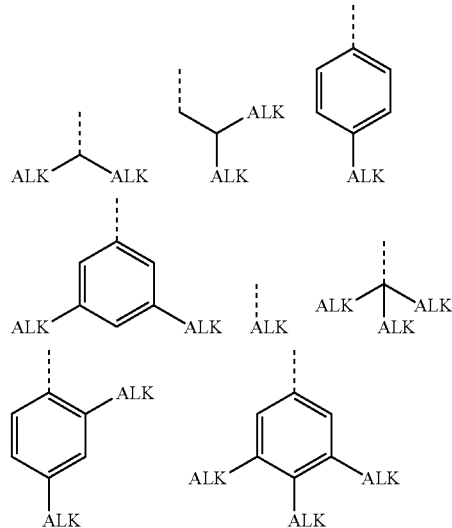

in which "ALK" is optionally fluorinated, preferably linear, alkyl or alkoxy having 1 to 20 and preferably 1 to 12 carbon atoms, and in the case of tertiary groups very preferably 1 to 9 carbon atoms, and the dotted line indicates the bond to the ring by which these groups are joined. Particularly preferred among these groups are those in which all ALK component groups are the same.

—$CY^1$=$CY^2$— is preferably —CH=CH—, —CF=CF— or —CH=C(CN)—.

Halogen is F, Cl, Br or I, preferably F, Cl or Br.

The conjugated polymers of the invention preferably do not contain any repeat units selected from optionally substituted pyrrolo[3,4-c]pyrrole-1,4-dione-3,6-diyl.

The conjugated polymers of the invention preferably do not contain any repeat units selected from phenylene substituted by one or more carbamate groups, and more preferably any optionally substituted phenylene units.

A preferred embodiment is directed to conjugated polymers of the invention, in which the repeat units substituted by a carbonate group or a carbamate group, or the units of the formula I, are selected from the group consisting of the following formulae which preferably have electron donor properties:

(D1)

(D2)

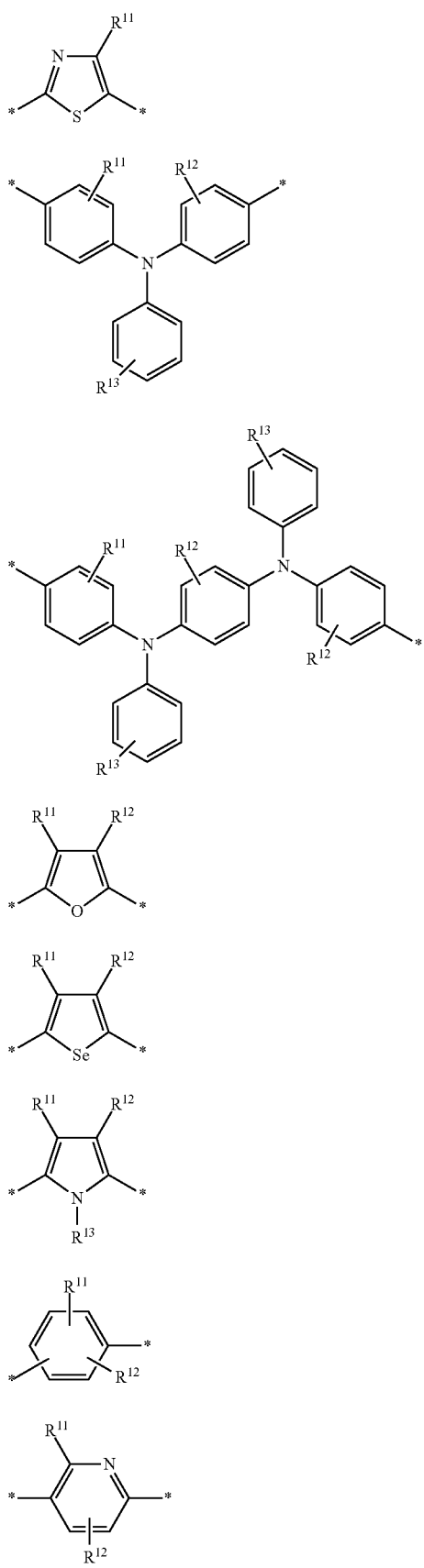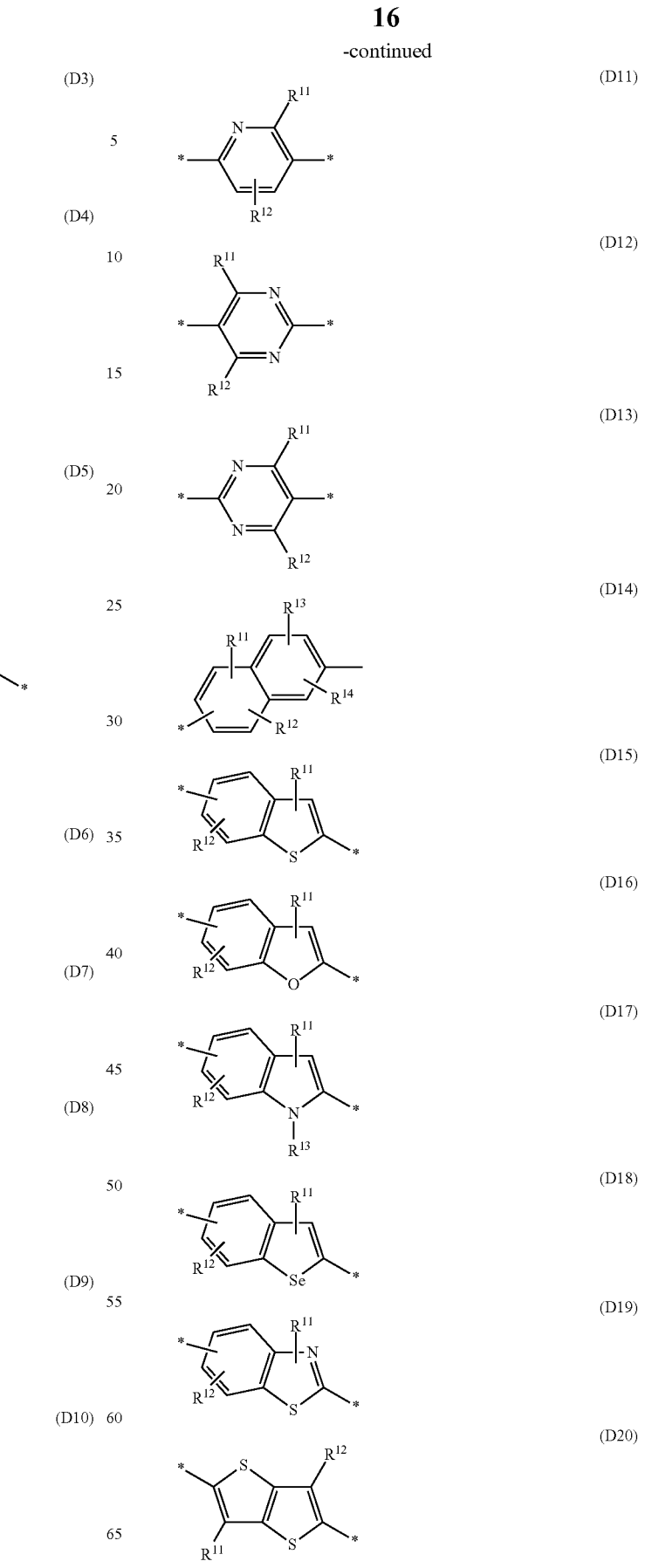

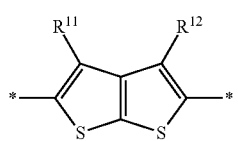
(D21)
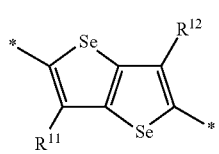
(D22)
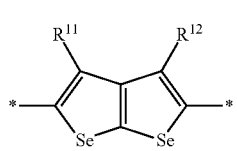
(D23)
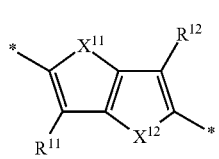
(D24)
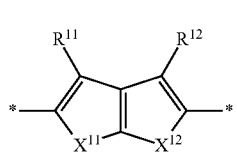
(D25)
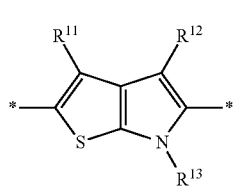
(d26)
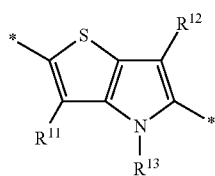
(D27)
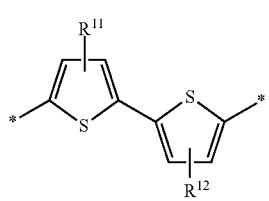
(D28)
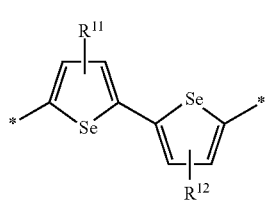
(D29)
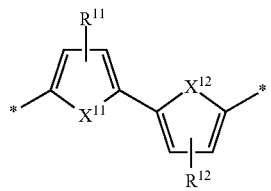
(D30)
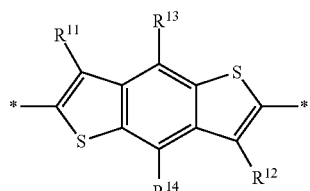
(D31)
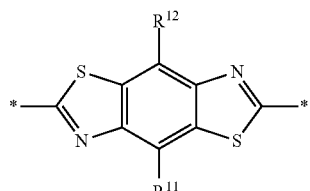
(D32)
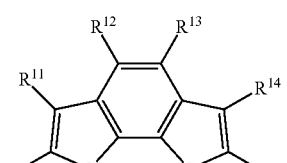
(D33)
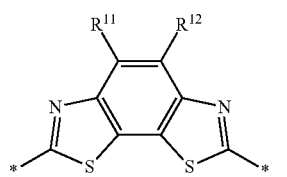
(D34)
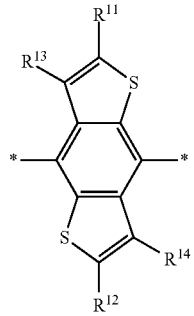
(D35)
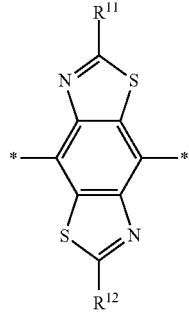
(D36)

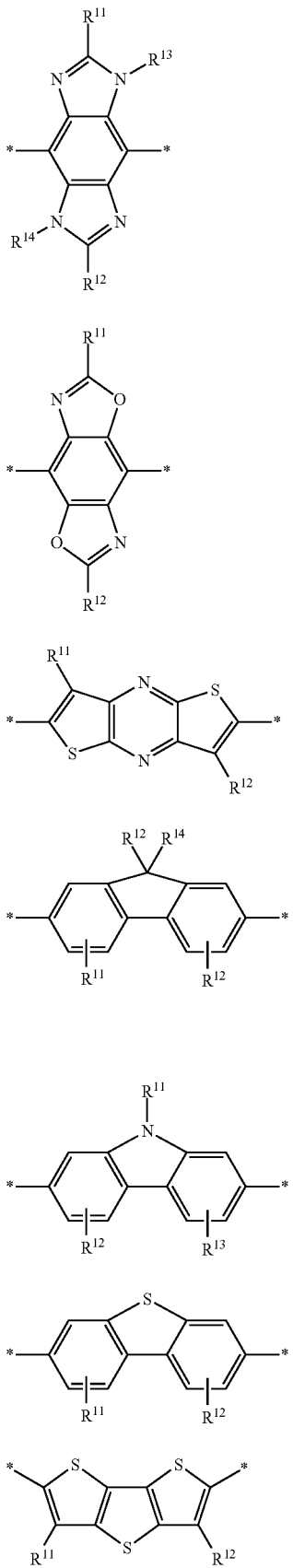
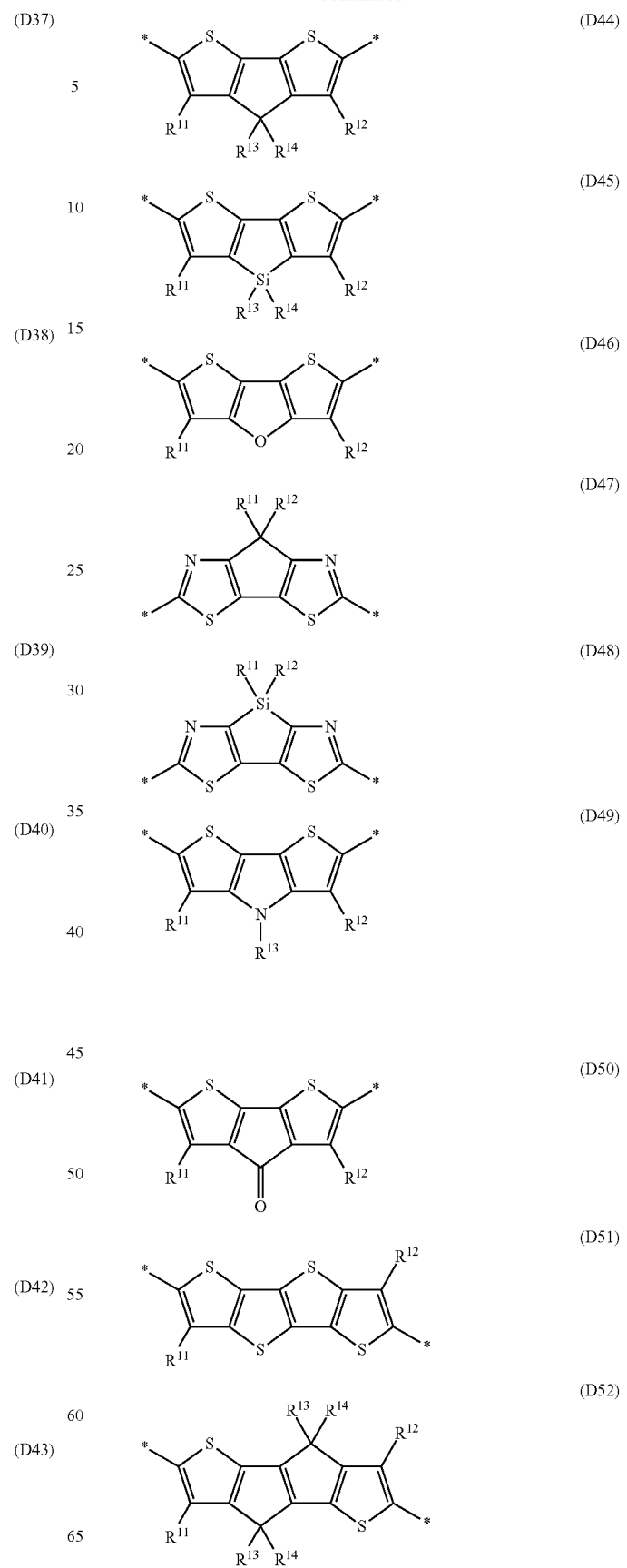

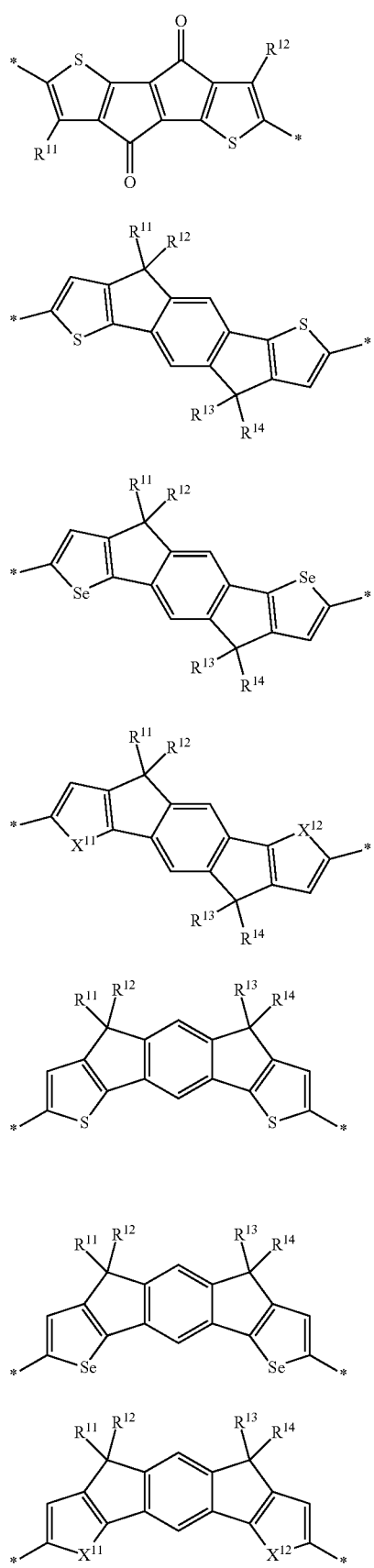
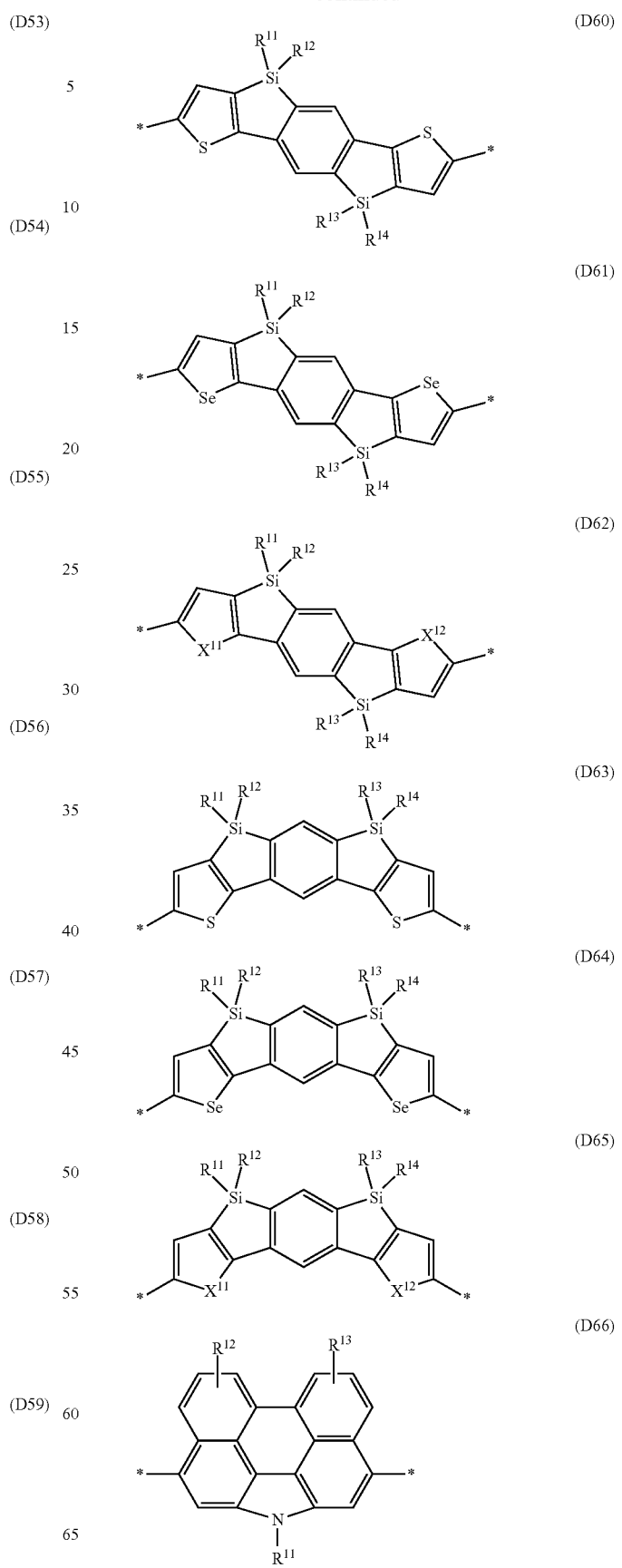

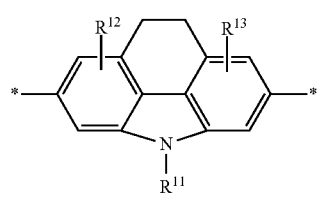 (D67)
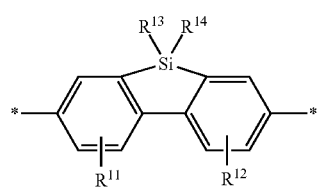 (D68)
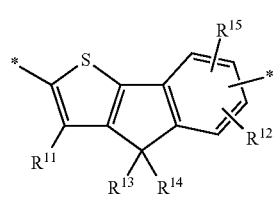 (D69)
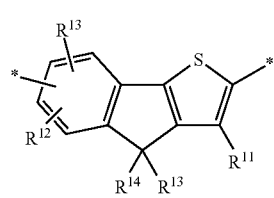 (D70)
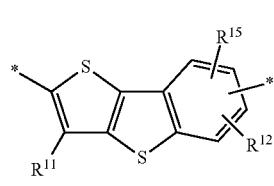 (D71)
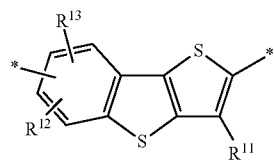 (D72)
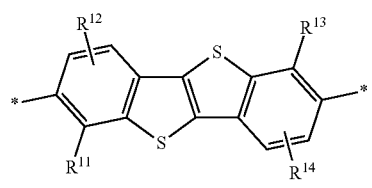 (D73)
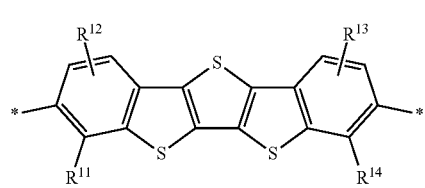 (D74)
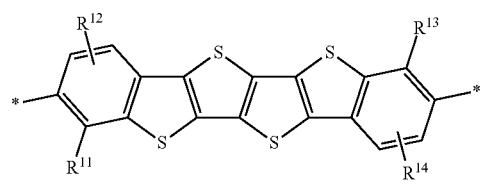 (D75)
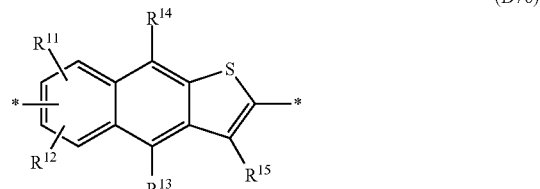 (D76)
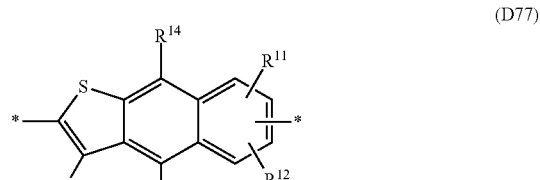 (D77)
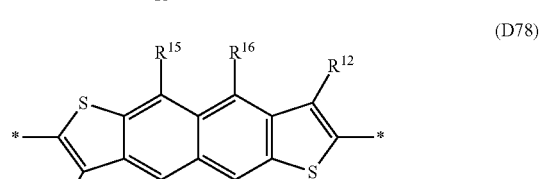 (D78)
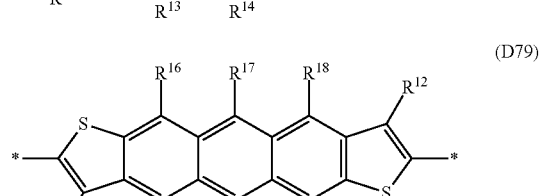 (D79)
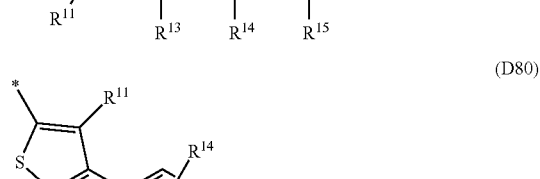 (D80)
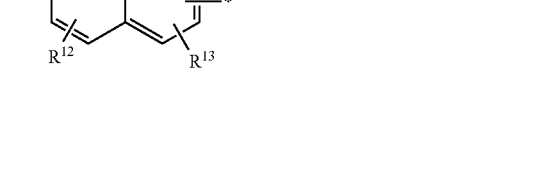 (D81)

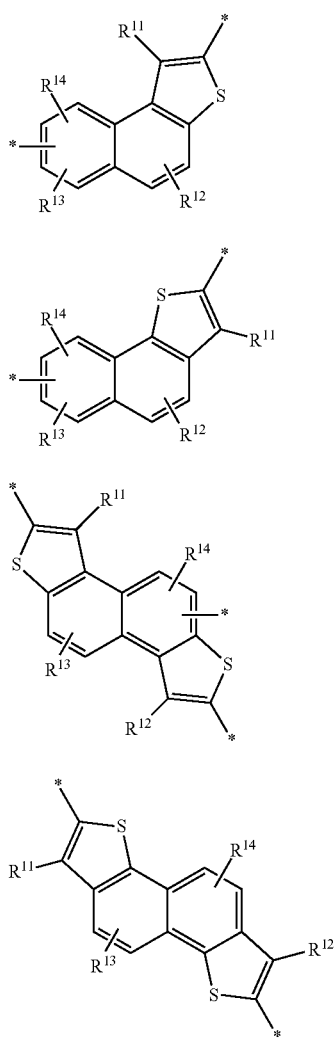
(D82)
(D83)
(D84)
(D85)
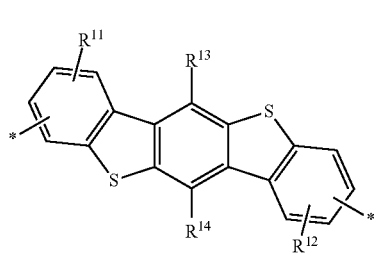
(D86)
(D87)
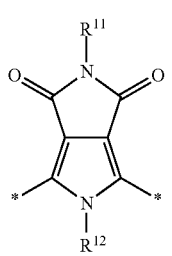
(D88)
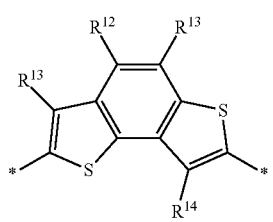
(D89)
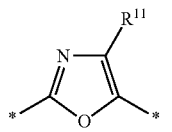
(D90)
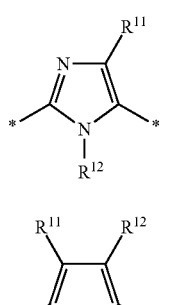
(D91)
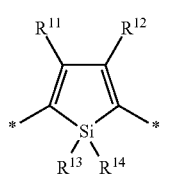
(D92)
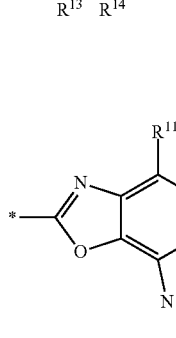
(D93)
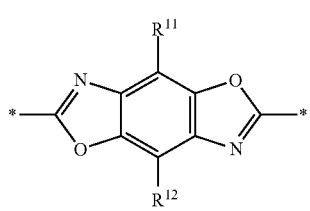
(D94)

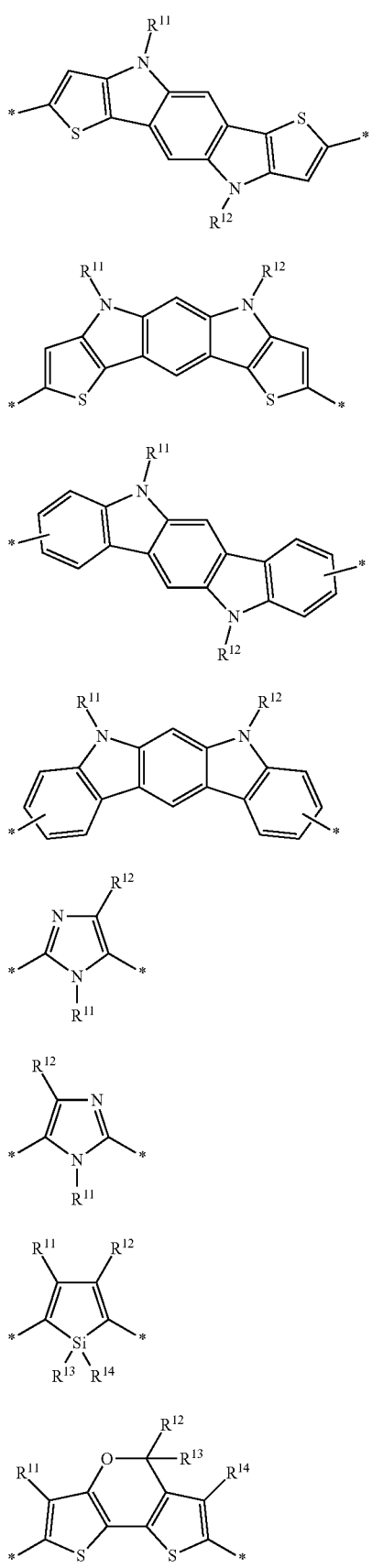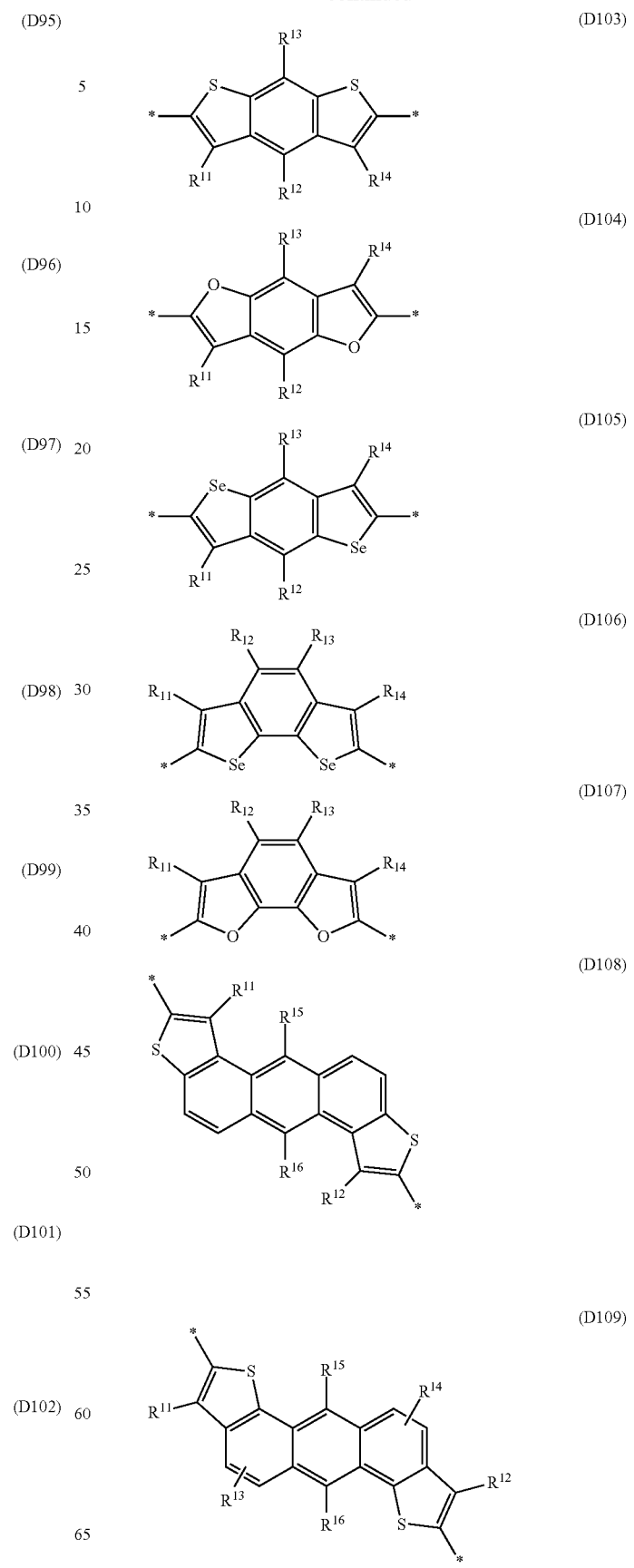

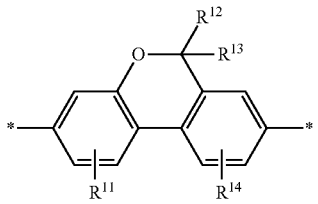
(D110)

in which one of the X$^{11}$ and X$^{12}$ radicals is S and the other is Se, and R$^{11}$, R$^{12}$, R$^{13}$, R$^{14}$, R$^{15}$, R$^{16}$, R$^{17}$ and R$^{18}$ are each independently H or R$^1$ as defined in formula I, and in which one or more of the R$^{11}$, R$^{12}$, R$^{13}$, R$^{14}$, R$^{15}$, R$^{16}$, R$^{17}$ and R$^{18}$ radicals is a -Sp$^1$-X$^1$—C(O)—O—R$^1$ group as defined in formula I.

A preferred embodiment is directed to conjugated polymers of the invention, in which the repeat units substituted by a carbonate group or a carbamate group, or the units of the formula I, are selected from the group consisting of the following formulae which preferably have electron acceptor properties:

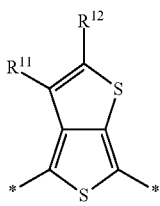
(A1)

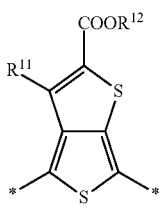
(A2)

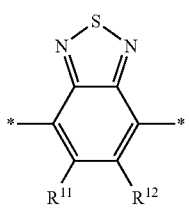
(A3)

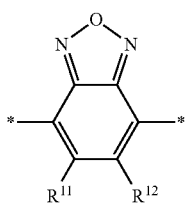
(A4)

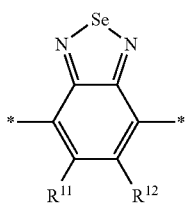
(A5)

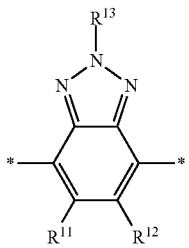
(A6)

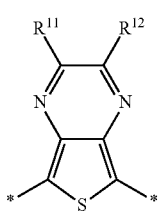
(A7)

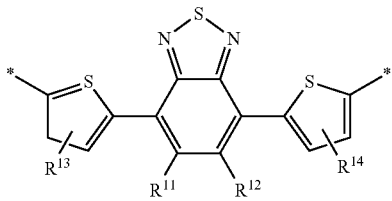
(A8)

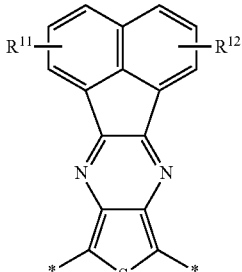
(A9)

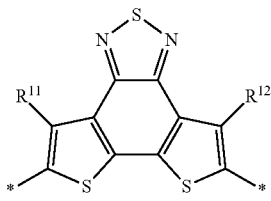
(A10)

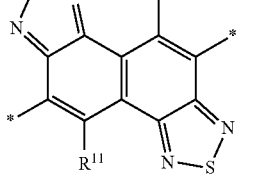
(A11)

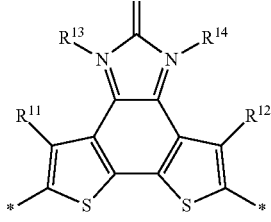
(A12)

-continued
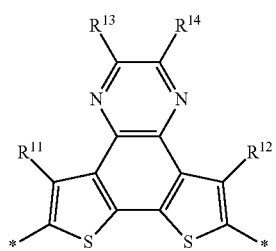 (A13)
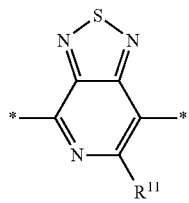 (A14)
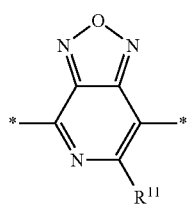 (A15)
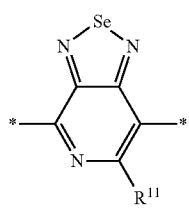 (A16)
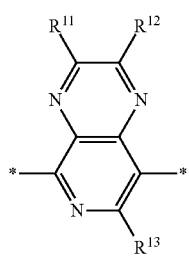 (A17)
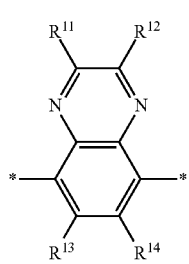 (A18)
-continued
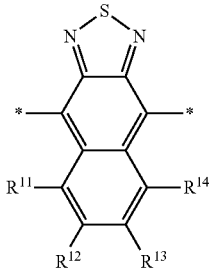 (A19)
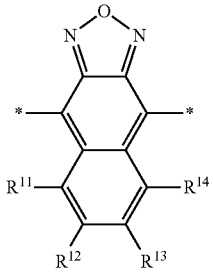 (A20)
 (A21)
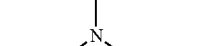 (A22)
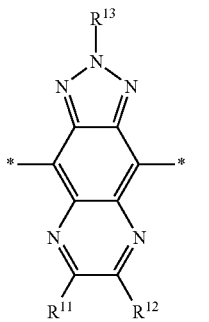 (A23)

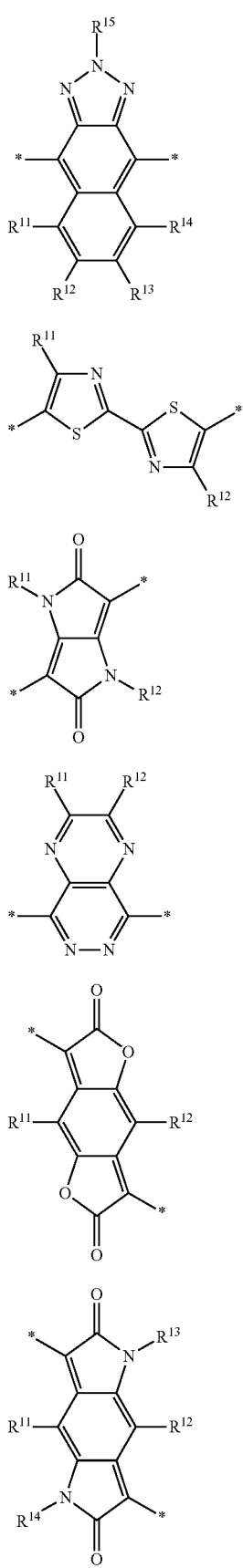

-continued
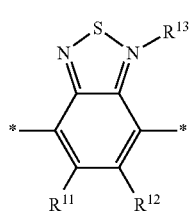
(A36)
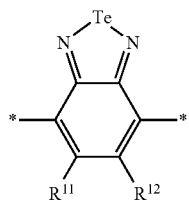
(A36)
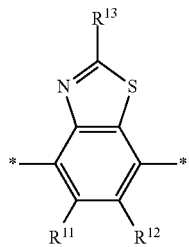
(A37)
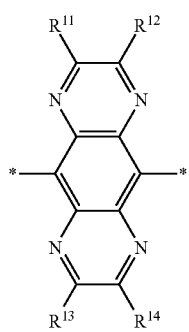
(A37)
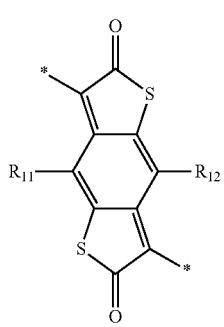
(A38)
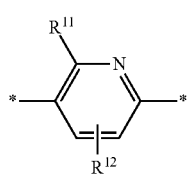
(A39)
-continued
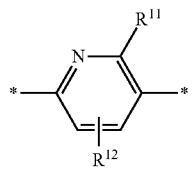
(A40)
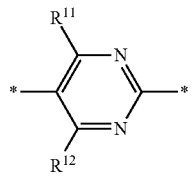
(A41)
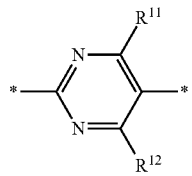
(A42)
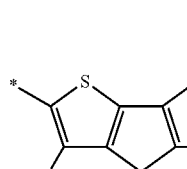
(A43)
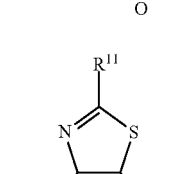
(A44)
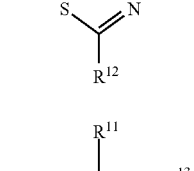
(A45)
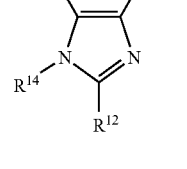
(A46)

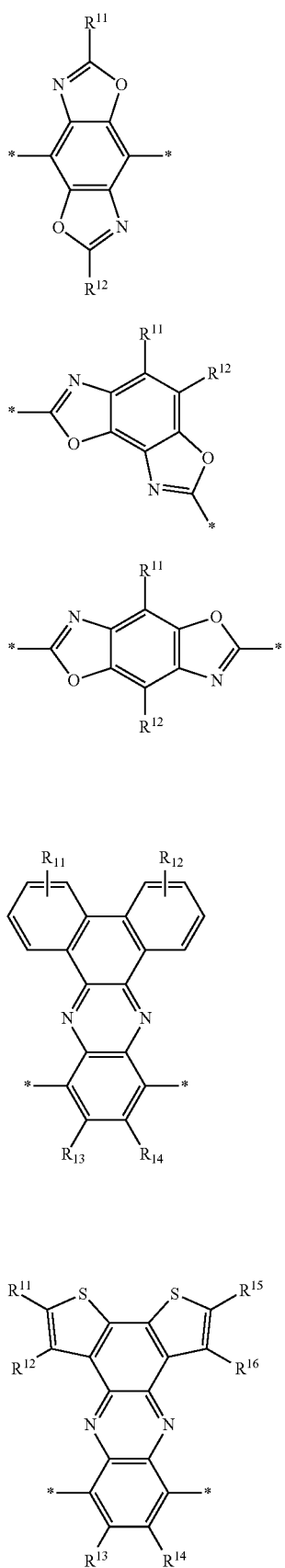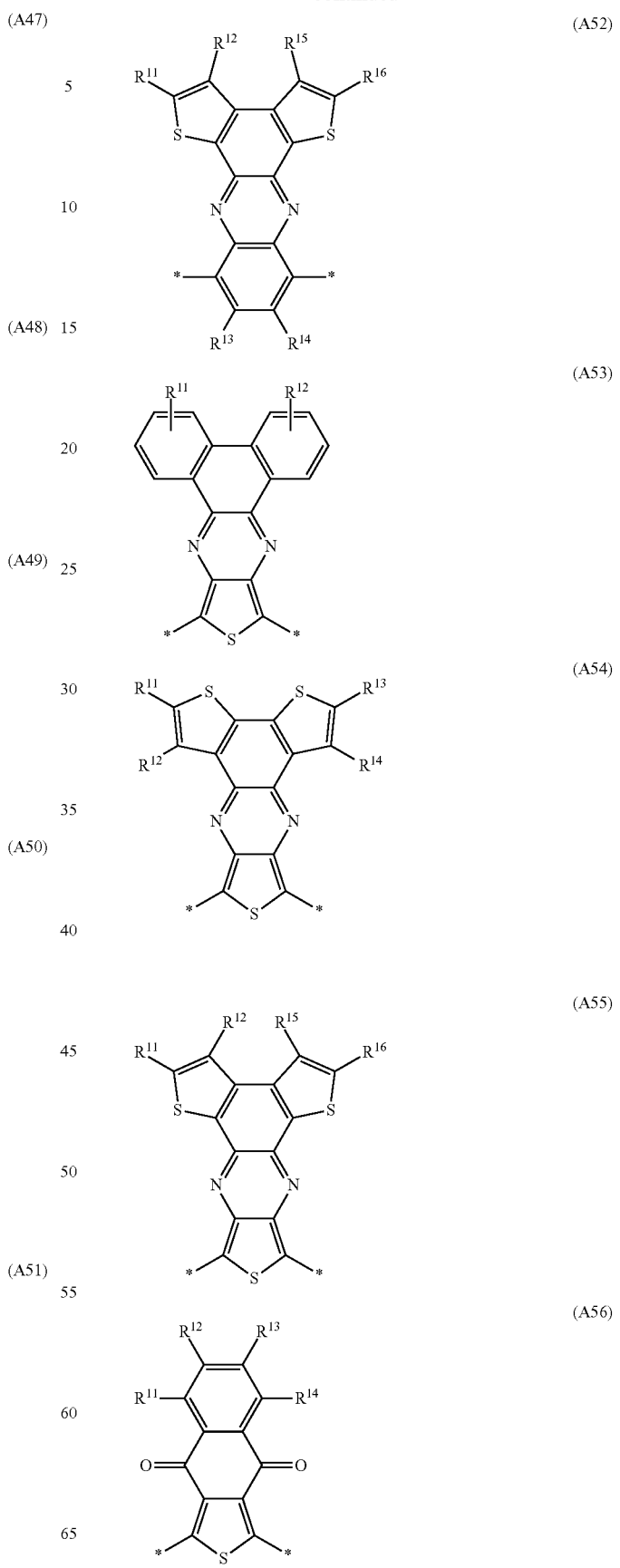

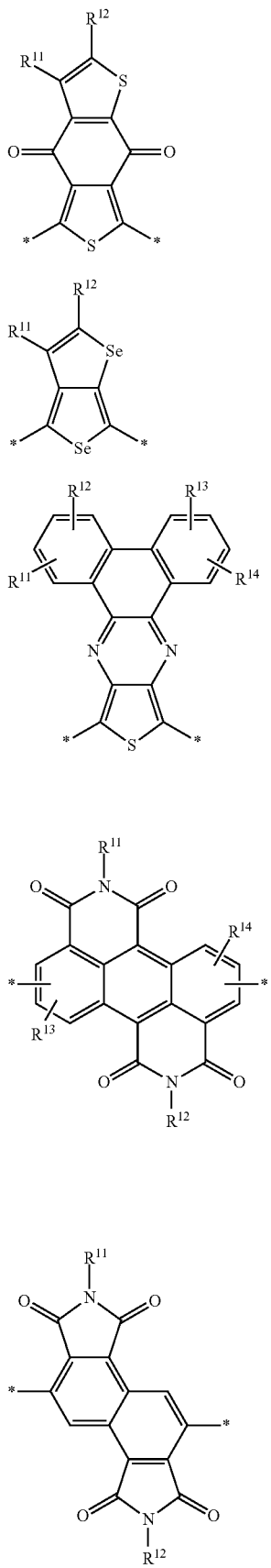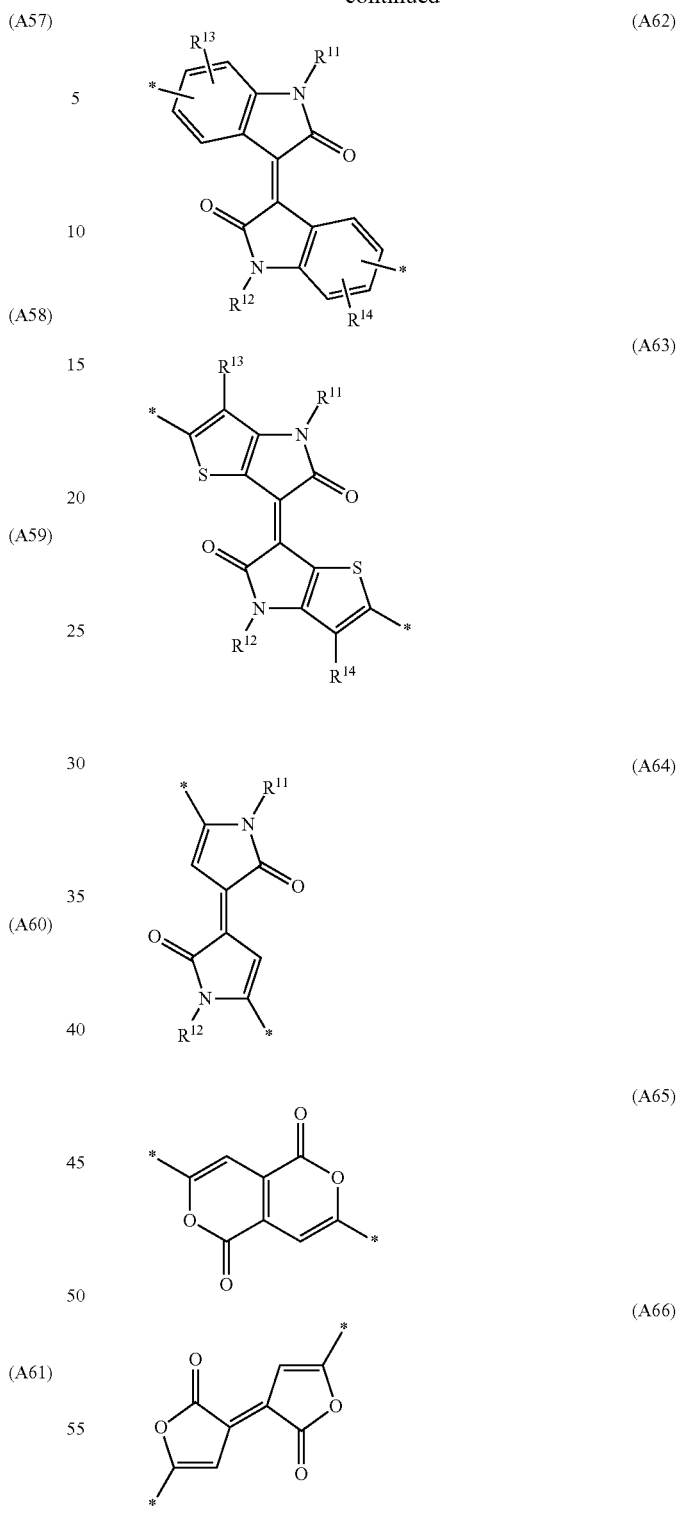

in which one of the $X^{11}$ and $X^{12}$ radicals is S and the other is Se, and $R^{11}$, $R^{12}$, $R^{13}$, $R^{14}$ and $R^{15}$ are each independently H or $R^1$ as defined in formula I, and in which one or more of the $R^{11}$, $R^{12}$, $R^{13}$, $R^{14}$ and $R^{15}$ radicals is a -$Sp^1$-$X^1$—C(O)—O—$R^1$ group as defined in formula I.

Particularly preferred repeat units of the formula I are selected from the following subformulae:

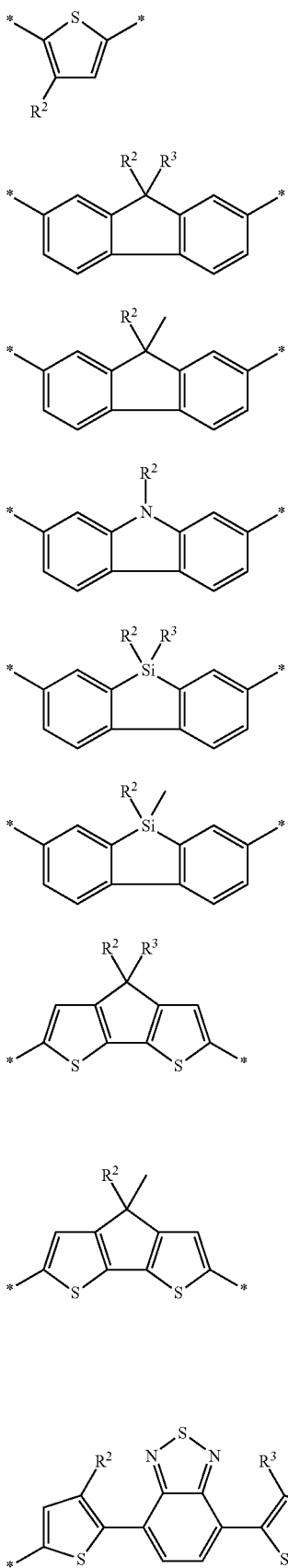

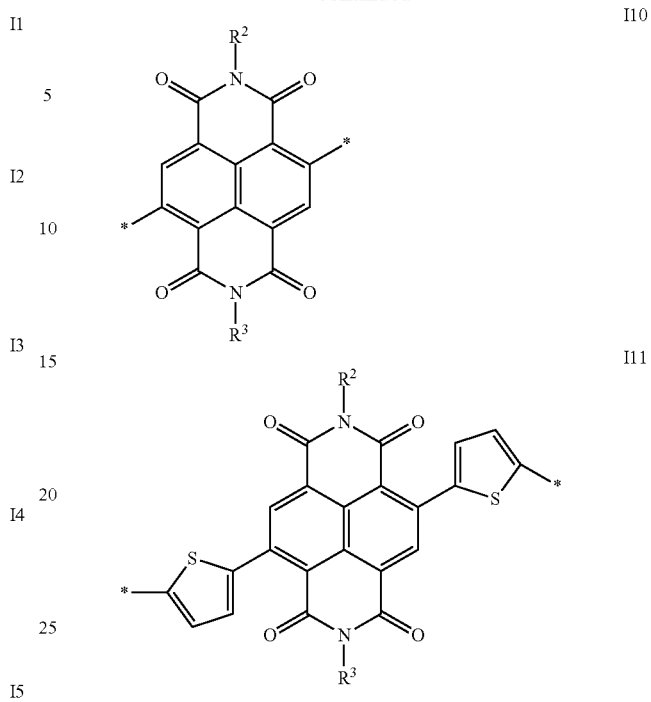

in which $R^2$ and $R^3$ are the same or different at each instance and are each independently a -$Sp^1$-$X^1$—C(O)—O—$R^1$ radical, and $Sp^1$, $X^1$ and $R^1$ have the definitions given above or below.

The $X^1$ radical in formula I and the subformulae thereof is preferably O or NH, more preferably O.

The $Sp^1$ radical in formula I and the subformulae thereof is preferably alkylene having 1 to 20 and more preferably having 1 to 8 carbon atoms, most preferably methylene, ethylene or propylene.

The $R^1$ radical in formula I and the subformulae thereof is preferably straight-chain, branched or cyclic alkyl which has 1 to 25 carbon atoms and is unsubstituted or mono- or polysubstituted by F, Cl, Br, I or CN, and in which one or more nonadjacent $CH_2$ groups may each independently also be replaced by —O—, —S—, —C(S)—, —C(O)—O—, —O—C(O)—, —$NR^0$—, —$SiR^0R^{00}$—, —$CF_2$—, —$CHR^0$=$CR^{00}$—, —$CY^1$=$CY^2$— or —C≡C— in such a way that no oxygen and/or sulfur atoms are joined directly to one another, where $R^0$ and $R^{00}$ have the definition given in formula I.

More preferably, $R^1$ is alkyl or alkenyl having 1 to 25 and preferably 1 to 20 carbon atoms, which may be straight-chain, branched and/or cyclic.

Preferred -$Sp^1$-$X^1$—C(O)—O—$R^1$ radicals are selected from the formula S:

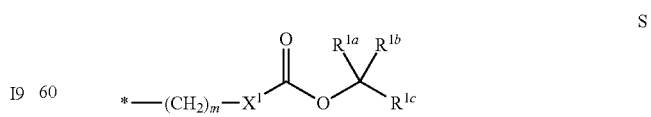

in which $X^1$ has the definition given above and below, $R^{1a}$, $R^{1b}$ and $R^{1c}$ are each independently H or a straight-chain, branched or cyclic alkyl radical having 1 to 25 carbon atoms or a straight-chain, branched or cyclic alkenyl radical or alkynyl radical each having 2 to 25 carbon atoms, where two of the $R^{1a}$, $R^{1b}$ and $R^{1c}$ radicals together may also form a cyclic alkyl radical, alkenyl radical or alkynyl radical each having 5 to 12 carbon atoms, m is 0 or an integer from 1 to 12, preferably 2, 3, 4, 5 or 6, and the symbol * denotes the linkage to the Ar radical. Preferably, at least two and more preferably three $R^{1a}$, $R^{1b}$ and $R^{1c}$ radicals are different than H.

Particularly preferred -$Sp^1$-$X^1$—C(O)—O—$R^1$ radicals are selected from the following subformulae:

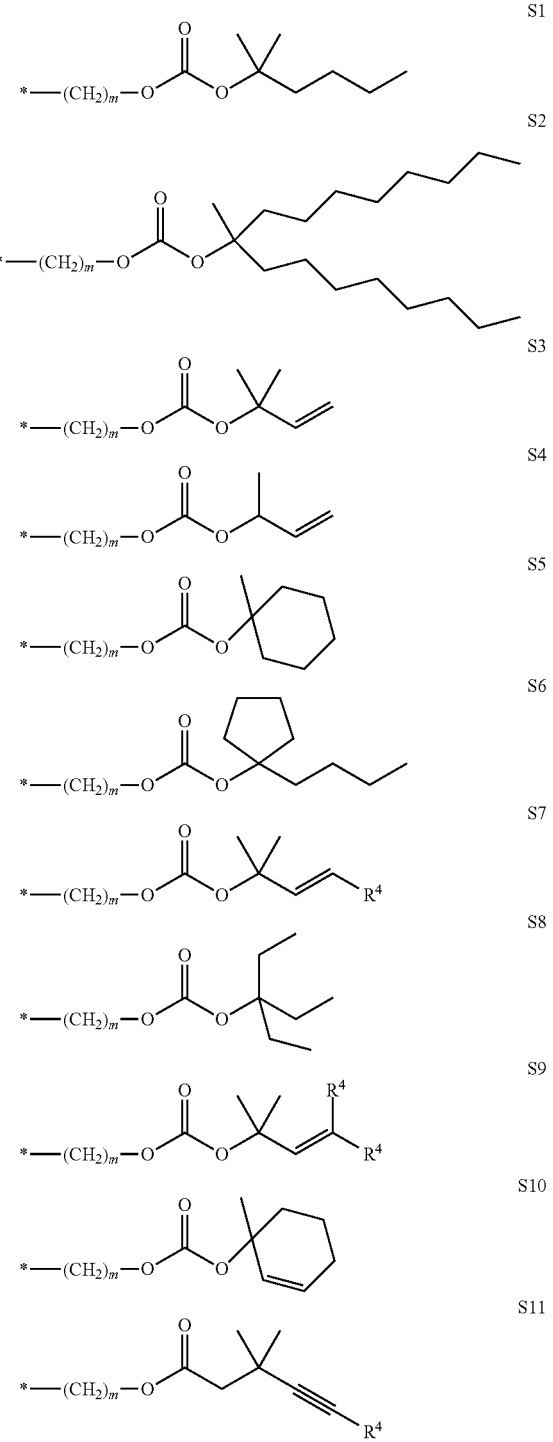

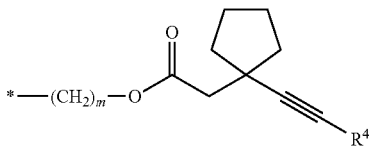

in which $R^4$ is the same or different at each instance and is H or a straight-chain or branched alkyl radical having 1 to 25 carbon atoms, m is an integer from 1 to 12, preferably 2, 3, 4, 5 or 6, and the symbol * denotes the linkage to the Ar radical. Preferably, $R^4$ is different than H.

A further preferred embodiment of the present invention is directed to repeat units of the formula I in which the Ar radical contains one or more nitrogen atoms, and the side chain $Sp^1$-$X^1$—C(O)—O—$R^1$ is bonded to one of these nitrogen atoms in the Ar radical, for example repeat units of the formula I4, I10 or I11. In a particularly preferred embodiment, in these repeat units, the $Sp^1$-$X^1$ radical is a single bond, such that the nitrogen atom which is present in the Ar radical and serves as bonding site for the side chain, together with the —C(O)—O—$R^1$ radical, forms a carbamate group.

Particularly preferred repeat units of this preferred embodiment are those selected from the following formulae:

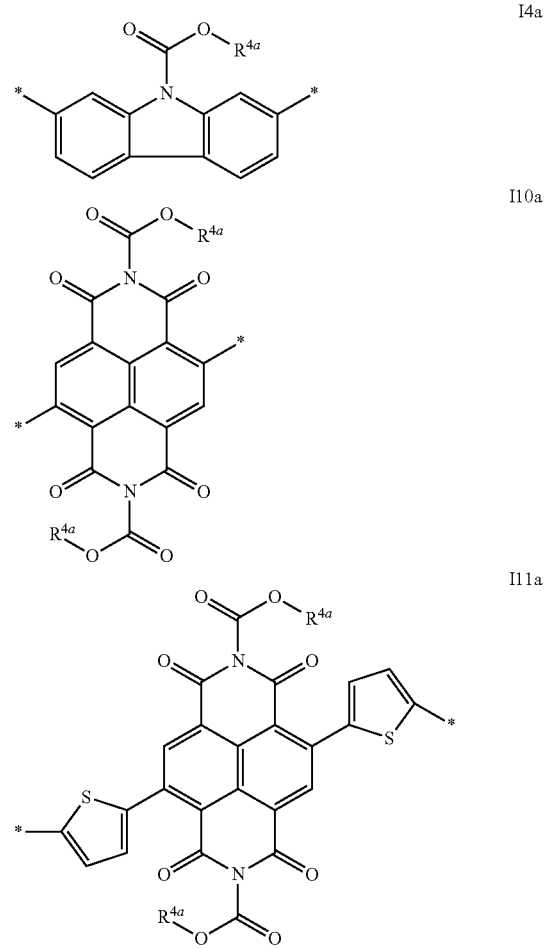

in which $R^{4a}$ is a straight-chain or branched alkyl radical having 1 to 25 carbon atoms. Preferred $R^{4a}$ radicals are 2-methylhexyl and 9-methylheptadecyl.

Preferred polymers according to the present invention contain one or more repeat units of the formula IIa or IIb:

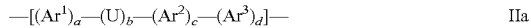   IIa

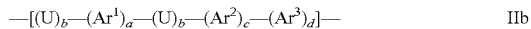   IIb in which the individual radicals are defined as follows:
U is the same or different at each instance and is a unit of the formula I or the subformulae I1 to I14 thereof,
$Ar^1$, $Ar^2$, $Ar^3$ are each independently the same or different at each instance and are aryl or heteroaryl which is different than U, preferably has 5 to 30 ring atoms and is optionally substituted, preferably by one or more $R^S$ groups,
$R^S$ is the same or different at each instance and is F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl or hydrocarbyl which has 1 to 40 carbon atoms and is optionally substituted and optionally contains one or more heteroatoms,
$R^0$ and $R^{00}$ are as defined in formula I,
$X^0$ is halogen, preferably F, Cl or Br,
a, b and c are the same or different at each instance and are each independently 0, 1 or 2,
d is the same or different at each instance and is 0 or an integer from 1 to 10,
where the polymer of the invention contains at least one repeat unit of the formula IIa or IIb in which b is at least 1.

$R^S$ is the same or different at each instance and is preferably H, straight-chain, branched or cyclic alkyl having 1 to 30 carbon atoms, in which one or more nonadjacent CH$_2$ groups may each independently also be replaced by —O—, —C(O)—, —C(S)—, —C(O)—O—, —O—C(O)—, —SiR$^0$R$^{00}$—, —CF$_2$—, —CHR$^0$=CR$^{00}$—, —CY$^1$=CY$^2$— or —C≡C— in such a way that oxygen and/or sulfur atoms are not joined directly to one another, and in which one or more hydrogen atoms may also be replaced by F, Cl, Br, I or CN, or is aryl, heteroaryl, aryloxy or heteroaryloxy which has 4 to 20 ring atoms and is optionally substituted, preferably by halogen or alkyl or cycloalkyl as defined above.

Further preferred polymers according to the present invention contain, in addition to the units of the formula I IIa or IIb, one or more repeat units selected from the group consisting of mono- and polycyclic aryl and heteroaryl groups which are optionally substituted.

These additional repeat units are preferably selected from formula IIIa and IIIb

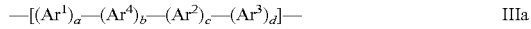   IIIa

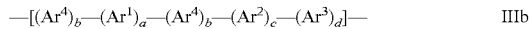   IIIb in which $Ar^1$, $Ar^2$, $Ar^3$, a, b, c and d are as defined in formula II, and $Ar^4$ is an aryl or heteroaryl group which is different than U and $Ar^{1-3}$, preferably has 5 to 30 ring atoms and is optionally substituted, preferably by one or more $R^S$ groups, where the polymer of the invention contains at least one repeat unit of the formula IIIa or IIIb in which b is at least 1.

Particularly preferred $Ar^1$, $Ar^2$, $Ar^3$ and $Ar^4$ groups are selected from the group consisting of the abovementioned formulae D1 to D110, in which one of the $X^{11}$ and $X^{12}$ radicals is S and the other is Se, and $R^{11}$, $R^{12}$, $R^{13}$, $R^{14}$, $R^{15}$, $R^{16}$, $R^{17}$ and $R^{18}$ are each independently H or $R^1$ as defined in formula I.

Further preferred $Ar^1$, $Ar^2$, $Ar^3$ and $Ar^4$ groups are selected from the group consisting of the abovementioned formulae A1 to A66, in which one of the $X^{11}$ and $X^{12}$ radicals is S and the other is Se, and $R^{11}$, $R^{12}$, $R^{13}$, $R^{14}$ and $R^{15}$ are each independently H or $R^1$ as defined in formula I.

If Ar in formula I, or U in formulae IIa and IIb, is selected from the group consisting of the formulae D1 to D110, $Ar^4$ in formulae IIIa and IIIb is preferably an aryl or heteroaryl group having electron acceptor properties. More preferably, $Ar^4$ in this case is selected from the group consisting of the formulae A1 to A66, in which one of the $X^{11}$ and $X^{12}$ radicals is S and the other is Se, and $R^{11}$, $R^{12}$, $R^{13}$, $R^{14}$ and $R^{15}$ are each independently H or $R^1$ as defined in formula I.

If Ar in formula I, or U in formulae IIa and IIb, is selected from the group consisting of the formulae A1 to A66, $Ar^4$ in formulae IIIa and IIIb is preferably an aryl or heteroaryl group having electron donor properties. More preferably, $Ar^4$ in this case is selected from the group consisting of the formulae D1 to D110, in which one of the $X^{11}$ and $X^{12}$ radicals is S and the other is Se, and $R^{11}$, $R^{12}$, $R^{13}$, $R^{14}$, $R^{15}$, $R^{16}$, $R^{17}$ and $R^{18}$ are each independently H or $R^1$ as defined in formula I.

The conjugated polymers of the present invention are preferably selected from formula IV:

   IV in which the individual radicals are defined as follows:
A, B, C are each independently a different unit of the formula I, I1 to I9, IIa, IIb, IIIa or IIIb,
x is >0 and ≤1,
y is ≥0 and <1,
z is ≥0 and <1,
x+y+z is 1, and
n is an integer >1.

Preferred polymers of the formula IV are selected from the following subformulae

   IVa

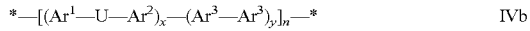   IVb

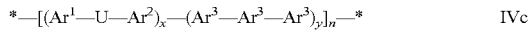   IVc

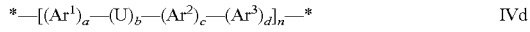   IVd

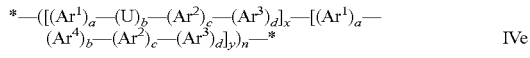   IVe

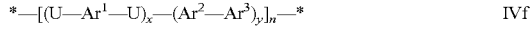   IVf

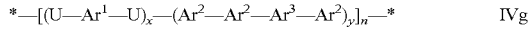   IVg

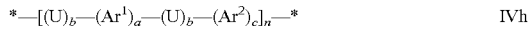   IVh

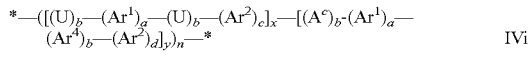   IVi

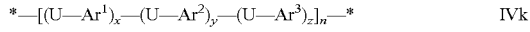   IVk in which U, $Ar^1$, $Ar^2$, $Ar^3$, a, b, c and d are the same or different at each instance and have one of the definitions given in formula IIa, $Ar^4$ is the same or different at each instance and has one of the definitions given in formula IIIa, and x, y, z and n are as defined in formula IV, where these polymers may be alternating or random copolymers, and where, in formula IVd and IVe, in at least one repeat unit [(Ar¹)$_a$—(U)$_b$—(Ar²)$_c$—(Ar³)$_d$] and in at least one repeat unit [(Ar¹)$_a$—(Ar⁴)$_b$—(Ar²)$_c$—(Ar³)$_d$], b is at least 1, and, in formula IVh and IVi, in at least one repeat unit [(U)$_b$—(Ar¹)$_a$—(U)$_b$—(Ar²)$_d$] and in at least one repeat unit [(U)$_b$—(Ar¹)$_a$—(U)$_b$—(Ar²)$_d$], b is 1.

In the polymers of the formulae IV and IVa to IVk, b in all repeat units is preferably at least 1.

In the polymers of the formulae IV and IVa to IVk, x is preferably 0.1 to 0.9, more preferably 0.3 to 0.7.

In a preferred embodiment of the invention, y and z are 0. In a preferred embodiment of the invention, y and z are >0. In a further preferred embodiment of the invention, one of the indices y and z is 0 and the other is >0. In the polymers of the formulae IV and IVa to IVk in which y or z is >0, it is preferably 0.1 to 0.9, more preferably 0.3 to 0.7.

In the polymers according to the present invention, the total number of repeat units n is preferably ≥5, very preferably ≥10, especially preferably ≥50, and preferably up to 500, very preferably up to 1000, especially preferably up to 2000, including any combinations of the aforementioned upper and lower limits for n.

The polymers of the present invention include homopolymers and copolymers, such as random copolymers, alternating copolymers and block copolymers, and combinations thereof.

Particular preference is given to polymers selected from the following groups:
- group A consisting of homopolymers of the repeat unit U or (Ar¹—U) or (Ar¹—U—Ar²) or (Ar¹—U—Ar³) or (U—Ar²—Ar³) or (Ar¹—U—Ar²—Ar³), i.e. in which all the repeat units are identical,
- group B consisting of random or alternating copolymers formed from identical repeat units (Ar¹—U—Ar²) and identical repeat units (Ar³),
- group C consisting of random or alternating copolymers formed from identical repeat units (Ar¹—U—Ar²) and identical repeat units (Ar¹),
- group D consisting of random or alternating copolymers formed from identical repeat units (Ar¹—U—Ar²) and identical repeat units (Ar¹—Ar⁴—Ar²), in which D¹, Ar¹, Ar² and Ar³ in all these U groups are as defined above and hereinafter, Ar¹, Ar² and Ar³ in the A, B and C groups are different than a single bond, and one of the Ar¹ and Ar² radicals in the D group may also be a single bond.

Particularly preferred polymers of the formula IV are selected from the following subformulae:

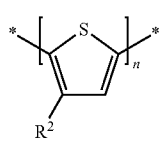
IV1

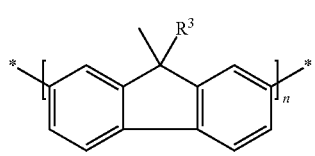
IV2

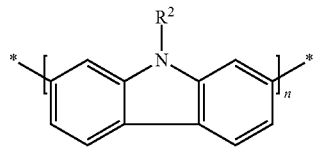
IV3

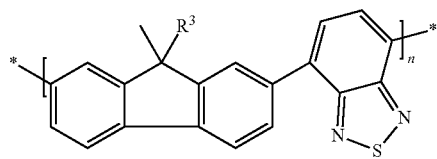
IV4

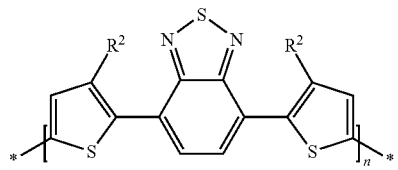
IV5

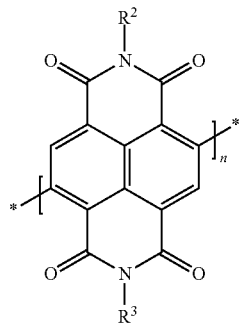
IV6

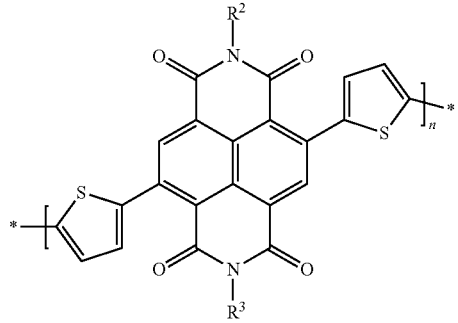
IV7

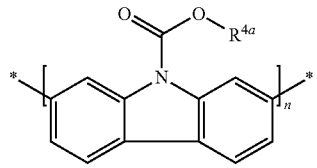
IV8

-continued

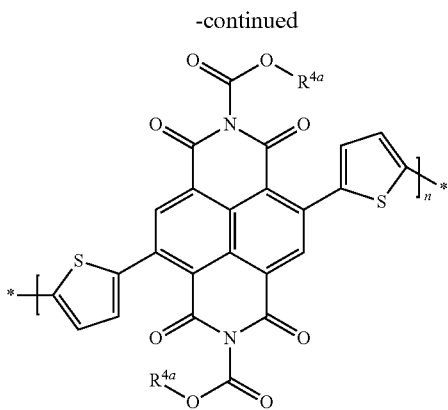
IV9 in which $R^2$, $R^3$ and $R^4$ have the definition given in formula I1-I14, and n has the definition given in formula IV.

Preferred polymers of the formulae IV, IVa to IVk and VI1 to IV9 are selected from the following formula:

$$R^5\text{-chain-}R^6 \qquad V$$

in which "chain" denotes a polymer chain selected from the above formulae IV, IVa to IVk and IV1 to IV9, and $R^5$ and $R^6$ each independently have one of the definitions given for $R^S$ in formula IIa, or H, F, Br, Cl, I, —CH$_2$Cl, —CHO, —CR'=CR"$_2$, —SiR'R"R"', —SiR'X'X", —SiR'R"X', —SnR'R"R"', —BR'R", —B(OR')(OR"), —B(OH)$_2$, —O—SO$_2$—R', —C≡CH, —C≡C—SiR'$_3$ or —ZnX', in which X' and X" are halogen, R', R" and R"' each independently have one of the definitions given for $R^0$ in formula I, and two of the R', R" and R"' radicals together with the respective heteroatom to which they are bonded may also form a cyclosilyl, cyclostannyl, cycloborane or cycloboronate group having 2 to 20 carbon atoms.

$R^5$ and $R^6$ are preferably H, $C_1$-$C_{20}$-alkoxy, $C_2$-$C_{20}$-alkenyl, $C_1$-$C_{20}$-fluoroalkyl, or optionally substituted $C_{6-12}$ aryl or $C_{2-10}$ heteroaryl, more preferably H, phenyl, or triphenylamine which may also be mono- or polysubstituted by C1-C4-alkyl groups, for example methyl.

In the polymers of the formulae IV, IVa to IVk, IV1 to IV9 and V, x, y and z each mean the molar proportion of the units A, B and C, and n is the degree of polymerization or the total number of all units A, B and C. These formulae include block copolymers, random copolymers and alternating copolymers of A, B and C, and also homopolymers of A in the case that x>0 and y=z=0.

The invention further provides monomers of the formulae VIa and VIb:

$$R^7\text{—}(Ar^1)_a\text{—}U\text{—}(Ar^2)_c\text{—}R^8 \qquad VIa$$

$$R^7\text{—}U\text{—}(Ar^1)_a\text{—}U\text{—}R^8 \qquad VIb$$

in which U, $Ar^1$, $Ar^2$, a and b have the definition given in formula IIa and $R^7$ and $R^8$ are each independently selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, in which X$^0$ is halogen, preferably Cl, Br or I, $Z^{1-4}$ is selected from the group consisting of alkyl and aryl which may optionally be substituted, and two $Z^2$ radicals together with the boron and oxygen atoms may also form a cycloboronate group having 2 to 20 carbon atoms, excluding monomers of the formula VIa in which a and c are 0 and U is a phenylene-2,5-diyl group substituted by a carbamate group.

Particular preference is given to monomers selected from the following formulae:

$$R^7\text{—}Ar^1\text{—}U\text{—}Ar^2\text{—}R^8 \qquad VI1$$

$$R^7\text{—}U\text{—}R^8 \qquad VI2$$

$$R^7\text{—}Ar^1\text{—}U\text{—}R^8 \qquad VI3$$

$$R^7\text{—}U\text{—}Ar^2\text{—}R^8 \qquad VI4$$

$$R^7\text{—}U\text{—}Ar^1\text{—}U\text{—}R^8 \qquad VI5$$

in which U, $Ar^1$, $Ar^2$, $R^7$ and $R^8$ are as defined in formula VIa.

Particular preference is given to repeat units, polymers and monomers of the formulae I, IIe, IIb, IIIa, IIIb, IVa, IVb, V, VIa and VIb and the subformulae thereof according to the following preferred embodiments and combinations thereof:

y is >0 and <1 and z is 0,
y is >0 and <1 and z is >0 and <1,
n is at least 5, preferably at least 10, more preferably at east 50, and up to 2000, preferably up to 500.
$M_w$ is at least 5000, preferably at least 8000, more preferably at least 10 000, and preferably up to 300 000, more preferably up to 100 000,
$M_w$ is at least 5000, preferably at least 8000, more preferably at least 10 000, and up to 300 000, preferably up to 100 000,
$X^1$ is O or NH, more preferably O,
$Sp^1$ is alkylene having 1 to 20 and more preferably having 1 to 8 carbon atoms, most preferably methylene, ethylene, propylene or hexylene,
$Ar^1$ and $Ar^2$ are the same or different at each instance and are each independently selected from 1,4-phenylene, thiophene-2,5-diyl, thiazole-2,5-diyl, selenophene-2,5-diyl, furan-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl or selenopheno[2,3-b]thiophene-2,5-diyl, where all these radicals may be unsubstituted or mono- or polysubstituted, preferably by $R^S$ as defined above and below,
$Ar^3$ and $Ar^4$ are the same or different at each instance and are each independently selected from 1,4-phenylene, thiophene-2,5-diyl, selenophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, 2,2-dithiophene, 2,2-diselenophene, dithieno[3,2-b:2',3'-d]silole-5,5-diyl, 4H-cyclopenta[2,1-b:3,4-b']dithiophene-2,6-diyl, carbazole-2,7-diyl, fluorene-2,7-diyl, indaceno[1,2-b:5,6-b']dithiophene-2,7-diyl, benzo[1",2":4,5;4",5":4',5']bis(silolo[3,2-b:3',2'-b']thiophene)-2,7-diyl, phenanthro[1,10,9,8-c,d,e,f,g]carbazole-2,7-diyl, benzo[2,1,3]thiadiazole-4,7-diyl, benzo[2,1,3]selenadiazole-4,7-diyl, benzo[2,1,3]oxadiazole-4,7-diyl, 2H-benzotriazole-4,7-diyl, 3,4-difluorothiophene-2,5-diyl, thieno[3,4-b]pyrazine-2,5-diyl, quinoxaline-5,8-diyl, thieno[3,4-b]thiophene-4,6-diyl, thieno[3,4-b]thiophene-6,4-diyl, 3,6-dithien-2-ylpyrrolo[3,4-c]pyrrole-1,4-dione or [1,3]thiazolo[5,4-d][1,3]thiazole-2,5-diyl, where all these radicals may be unsubstituted or mono- or polysubstituted, preferably by $R^S$ as defined above and below.
Ar is the same or different at each instance and is selected from 1,4-phenylene, thiophene-2,5-diyl, selenophene- 2,5-diyl, thieno[3,2-b]thiophene-2,5-diyl, thieno[2,3-b]
thiophene-2,5-diyl, selenopheno[3,2-b]selenophene-2,
5-diyl, selenopheno[2,3-b]selenophene-2,5-diyl,
selenopheno[3,2-b]thiophene-2,5-diyl, selenopheno[2,
3-b]thiophene-2,5-diyl, benzo[1,2-b:4,5-b]dithio-
phene-2,6-diyl, 2,2-dithiophene, 2,2-diselenophene,
dithieno[3,2-b:2′,3′-d]silole-5,5-diyl, 4H-cyclopenta[2,
1-b:3,4-b′]dithiophene-2,6-diyl, carbazole-2,7-diyl,
fluorene-2,7-diyl, indaceno[1,2-b:5,6-b′]dithiophene-2,
7-diyl, benzo[1″,2″:4,5;4″,5″:4′,5′]bis(silolo[3,2-b:3′,
2′-b′]thiophene)-2,7-diyl, phenanthro[1,10,9,8-c,d,e,f,
g]carbazole-2,7-diyl, benzo[2,1,3]thiadiazole-4,7-diyl,
benzo[2,1,3]selenadiazole-4,7-diyl, benzo[2,1,3]oxadi-
azole-4,7-diyl, 2H-benzotriazole-4,7-diyl, 3,4-difluo-
rothiophene-2,5-diyl, thieno[3,4-b]pyrazine-2,5-diyl,
quinoxaline-5,8-diyl, thieno[3,4-b]thiophene-4,6-diyl,
thieno[3,4-b]thiophene-6,4-diyl, [1,3]thiazolo[5,4-d]
[1,3]thiazole-2,5-diyl or benzo[lmn][3,8]phenanthro-
line-1,3,6,8-tetraone-4,9-diyl, where all these radicals
may be unsubstituted or mono- or polysubstituted,
preferably by $R^S$ as defined above and below, and all
radicals are at least monosubstituted by $Sp^1$-$X^1$—C
(O)—O—$R^1$ as defined above and below, the polymer does not contain any optionally substituted
benzo[lmn][3,8]phenanthroline-1,3,6,8-tetraone-4,9-
diyl units directly adjacent to a phenylene-1,4-diyl unit
substituted by a carbamate or carbonate group, Ar and $Ar^{1-4}$ are different than optionally substituted
pyrrolo[3,4-c]pyrrole-1,4-dione-3,6-diyl, Ar and $Ar^{1-4}$ are different than optionally substituted
phenylene-1,4-diyl, $R^1$ is different than H, $R^1$ is primary alkyl having 1 to 20 carbon atoms, second-
ary alkyl having 3 to 30 carbon atoms or tertiary
alcohol having 4 to 30 carbon atoms, where one or
more hydrogen atoms in all these groups are optionally
replaced by F, $R^1$ is straight-chain or branched alkenyl having 2 to 20
carbon atoms, in which one or more hydrogen atoms
are optionally replaced by F, $R^1$ is cyclic alkyl having 3 to 20 carbon atoms, in which
one or more hydrogen atoms are optionally replaced by
F, $R^1$ is a radical containing straight-chain and cyclic alkyl
groups and having a total of 5 to 20 carbon atoms, in
which one or more hydrogen atoms are optionally
replaced by F, $R^0$ and $R^{00}$ are selected from H and $C_1$-$C_{10}$-alkyl, $R^S$ is the same or different at each instance and is selected
from straight-chain, branched and/or cyclic alkyl,
alkoxy or sulfanylalkyl having 1 to 30 carbon atoms, in
which one or more hydrogen atoms are optionally
replaced by F, $R^S$ is the same or different at each instance and is selected
from aryl, aryloxy, heteroaryl and heteroaryloxy, which
is optionally substituted by F, alkyl or alkoxy and has
4 to 30 ring atoms, $R^S$ is the same or different at each instance and is selected
from straight-chain, branched and/or cyclic alkylcar-
bonyl, alkoxycarbonyl and alkylcarbonyloxy, in which
one or more hydrogen atoms are optionally replaced by
F, $R^S$ is the same or different at each instance and is F, Cl, Br,
I, CN, $R^9$, —C(O)—$R^9$, —C(O)—O—$R^9$, —O—C
(O)—$R^9$, —SO$_3$—$R^9$, in which $R^9$ is straight-chain,
branched and/or cyclic alkyl having 1 to 20 carbon
atoms, in which one or more nonadjacent CH$_2$ groups may each independently also be replaced by —O—,
—S—, —C(O)—, —C(S)—, —C(O)—O—, —O—C
(O)—, —NR$^0$—, —SiR$^0$R$^{00}$—, —CF$_2$—,
—CHR$^0$=CR$^{00}$—, —CY$^1$=CY$^2$— or —C≡C— in
such a way that oxygen and/or sulfur atoms are not
joined directly to one another, and in which one or more
hydrogen atoms may also be replaced by F, Cl, Br, I or
CN, or is aryl, heteroaryl, aryloxy or heteroaryloxy
which has 4 to 20 ring atoms and is optionally substi-
tuted, preferably by halogen or alkyl or cycloalkyl as
defined above, $R^0$ and $R^{00}$ are each independently H or $C_1$-$C_{10}$-alkyl, $R^5$ and $R^6$ are the same or different at each instance and
are each independently selected from H, halogen,
—CH$_2$Cl, —CHO, —CH=CH$_2$—SiR'R″R‴, —Sn-
R'R″R‴, —BR'R″, —B(OR')(OR″), —B(OH)$_2$,
$C_1$-$C_{20}$-alkyl, $C_1$-$C_{20}$-alkoxy, $C_2$-$C_{20}$-alkenyl, $C_1$-$C_{20}$-
fluoroalkyl and optionally substituted aryl or heteroaryl
having 4 to 10 ring atoms, preferably phenyl, $R^7$ and $R^8$ are the same or different at each instance and
are each independently selected from Cl, Br, I, O-to-
sylate, O-triflate, O-mesylate, O-nonaflate, —SiMe$_2$F,
—SiMeF$_2$, —SO$_2$Z$^1$, —B(OZ$^2$)$_2$, —CZ$^3$=C(Z$^4$)$_2$,
—C≡CH, C≡CSi(Z$^1$)$_3$, —ZnX$^0$ and —Sn(Z$^4$)$_3$, in
which $X^0$ is halogen, preferably Cl, Br or I, $Z^{1-4}$ is
selected from the group consisting of alkyl and aryl
which may optionally be substituted, and two $Z^2$ radi-
cals together with the boron and oxygen atoms may
also form a cycloboronate group having 2 to 20 carbon
atoms.

The polymers and monomers according to the present
invention can be synthesized according to or in analogy to
methods that are known to those skilled in the art and are
described in the literature. Other preparation methods can be
inferred from the examples.

For example, it is possible to prepare polymers of the
invention in a suitable manner by aryl-aryl coupling reac-
tions, such as Yamamoto coupling, Suzuki coupling, Stifle
coupling, Kumada coupling, Negishi coupling, Sonogashira
coupling, Heck coupling, Buchwald coupling or synthesis
according to Yokozawa. Suzuki coupling, Yamamoto cou-
pling and Stille coupling are particularly preferred.

The monomers which are polymerized to form the repeat
units of the polymers can be prepared by methods known to
those skilled in the art.

The polymers are preferably prepared from monomers of
the formula VIa or VIb or the preferred subformulae thereof
as described above and below.

A further aspect of the invention is a process for preparing
a polymer of the invention by coupling one or more identical
or different monomer units of the formula I or one or more
identical or different monomers of the formula VIa or VIb to
one another and/or to one or more comonomers in a polym-
erization reaction, preferably in an aryl-aryl coupling reac-
tion.

Suitable and preferred comonomers are selected from the
following formulae:

  VIII

  IX

  X in which $Ar^1$, $Ar^2$, $Ar^3$, $Ar^4$, a and c have the definition
given in formula IIa and IIIa, and $R^7$ and $R^8$ have the
definition given in formula VIa.

Particular preference is given to a process for preparing a polymer by reaction of one or more identical or different monomers of the formula VIa or VIb with one or more monomers of the formula VIII, and optionally with one or more monomers selected from the formulae IX and X, in an aryl-aryl coupling reaction, preferably in which $R^7$ and $R^8$ are selected from Cl, Br, I, —B(OZ$^2$)$_2$ and —Sn(Z$^4$)$_3$.

Particularly preferred processes are selected from the following embodiments:

a) a process for preparing a polymer by aryl-aryl coupling reaction of a monomer of the formula VI1

$$R^7—Ar^1—U—Ar^2—R^8 \qquad \text{VI1}$$

with a monomer of the formula IX $$R^7—Ar^1—R^8 \qquad \text{IX}$$

b) a process for preparing a polymer by aryl-aryl coupling reaction of a monomer of the formula VI2

$$R^7—U—R^8 \qquad \text{VI2}$$

with a monomer of the formula VIII1

$$R^7—Ar^1—Ar^4—Ar^2—R^8 \qquad \text{VIII1}$$

c) a process for preparing a polymer by aryl-aryl coupling reaction of a monomer of the formula VI2

$$R^7—U—R^8 \qquad \text{VI2}$$

with a monomer of the formula VIII2

$$R^7—Ar^4—R^8 \qquad \text{VIII2}$$

d) a process for preparing a polymer by aryl-aryl coupling reaction of a monomer of the formula VI2

$$R^7—U—R^8 \qquad \text{VI2}$$

with a monomer of the formula VIII2

$$R^7—Ar^4—R^8 \qquad \text{VIII2}$$

and a monomer of the formula IX $$R^7—Ar^1—R^8 \qquad \text{IX}$$

e) a process for preparing a polymer by aryl-aryl coupling reaction of a monomer of the formula VI1

$$R^7—U—Ar^1—U—R^8 \qquad \text{VI5}$$

with a monomer of the formula IX $$R^7—Ar^1—R^8 \qquad \text{IX}$$

f) a process for preparing a polymer by aryl-aryl coupling reaction of a monomer of the formula VI2

$$R^7—U—R^8 \qquad \text{VI2}$$

with a monomer of the formula IX $$R^7—Ar^1—R^8 \qquad \text{IX}$$

and a monomer of the formula X $$R^7—Ar^3—R^8 \qquad \text{X}$$

in which $R^7$, $R^8$, U, Ar$^{1,2,3,4}$ are as defined in formula IIa, IIIa and VIa, and $R^7$ and $R^8$ are preferably selected from Cl, Br, I, —B(OZ$^2$)$_2$ and —Sn(Z$^4$)$_3$ as defined in formula VIa.

Preferred aryl-aryl coupling methods and polymerization methods are Yamamoto coupling, Kumada coupling, Negishi coupling, Suzuki coupling, Stille coupling, Sonogashira coupling, Heck coupling, C—H activation coupling, Ullmann coupling and Buchwald coupling, and synthesis according to Yokozawa. Particular preference is given to Suzuki, Negishi, Stille and Yamamoto coupling, and synthesis according to Yokozawa. The latter is described, for example, in Yokozawa (R. Miyakoshi, A. Yokoyama, T. Yokozawa, J. Am. Chem. Soc. 2005, 127, 17542-17547). Suzuki coupling is described, for example, in WO 00/53656 A1 or M. Ranger, D. Rondeau, M. Leclerc, Macromolecules 1997, 30, 7686-7691. Negishi coupling is described, for example, in J. Chem. Soc., Chem. Common., 1977, 683-684. Yamamoto coupling is described, for example, in T. Yamamoto et al., Prog. Polym Sci., 1993, 17, 1153-1205, WO 2004/022626 A1 or N. Kobayashi, R. Koguchi, M. Kijima, Macromolecules 2006, 39, 9102-9111, and Stille coupling is described, for example, in Z. Bao et al., J. Am. Chem. Soc., 1995, 117, 12426-12435.

For example, for Yamamoto coupling, preference is given to using monomers as described above having two reactive halide groups. For Suzuki coupling, preference is given to using monomers as described above having two reactive boronic acid or boronic ester groups and monomers having two reactive halide groups, or monomers having one reactive boronic acid or boronic ester group and one reactive halide group. For Stille coupling, preference is given to using monomers as described above having two reactive stannyl groups and monomers having two reactive halide groups, or monomers having one reactive stannyl group and one reactive halide group. For Negishi coupling, preference is given to using monomers as described above having two reactive organozinc groups and monomers having two reactive halide groups, or monomers having one reactive organozinc group and one reactive halide group.

Preferred catalysts, especially for Suzuki, Negishi or Stifle coupling, are selected from Pd(0) complexes and Pd(II) salts. Preferred Pd(0) complexes are those which bear at least one phosphine ligand such as Pd(PPh$_3$)$_4$. A further preferred phosphine ligand is tris(ortho-tolyl)phosphine, i.e. Pd(o-Tol)$_4$. The preferred Pd(II) salts include palladium acetate, i.e. Pd(OAc)$_2$. The Pd(0) complex can also be prepared, for example, by mixing a Pd(0)-dibenzylideneacetone complex, for example tris(dibenzylideneacetone)dipalladium(0), bis(dibenzylideneacetone)palladium(0), or a Pd(II) salt, for example palladium acetate, with a phosphine ligand, for example triphenylphosphine, tris(ortho-tolyl) phosphine or tri(tert-butyl)phosphine. Suzuki polymerization is conducted in the presence of a base, for example sodium carbonate, potassium phosphate, lithium hydroxide or potassium phosphate, or of an organic base, such as tetraethylammonium carbonate or tetraethylammonium hydroxide. In Yamamoto polymerization, an Ni(0) complex, e.g. bis(1,5-cyclooctadienyl)nickel(0), is used.

Suzuki polymerization can be used in order to prepare both homopolymers and random and alternating copolymers, and randomly distributed block copolymers. Random or block copolymers can be prepared, for example, from the above monomers in which one of the reactive groups is halogen and the other reactive group is a boronic acid or boronic acid derivative group. The synthesis of the random, alternating and block copolymers is described in more detail, for example, in WO 03/048225 A2 or WO 2005/014688 A2.

As alternatives to halogens, as described above, it is possible to use leaving groups of the formula —O—SO$_2$Z$^1$ in which Z$^1$ is as described above. Specific examples of such leaving groups are tosylate, mesylate and triflate.

Monomers of the formula VIa and VIb can be prepared, for example, according to scheme 1 or in analogy thereto.

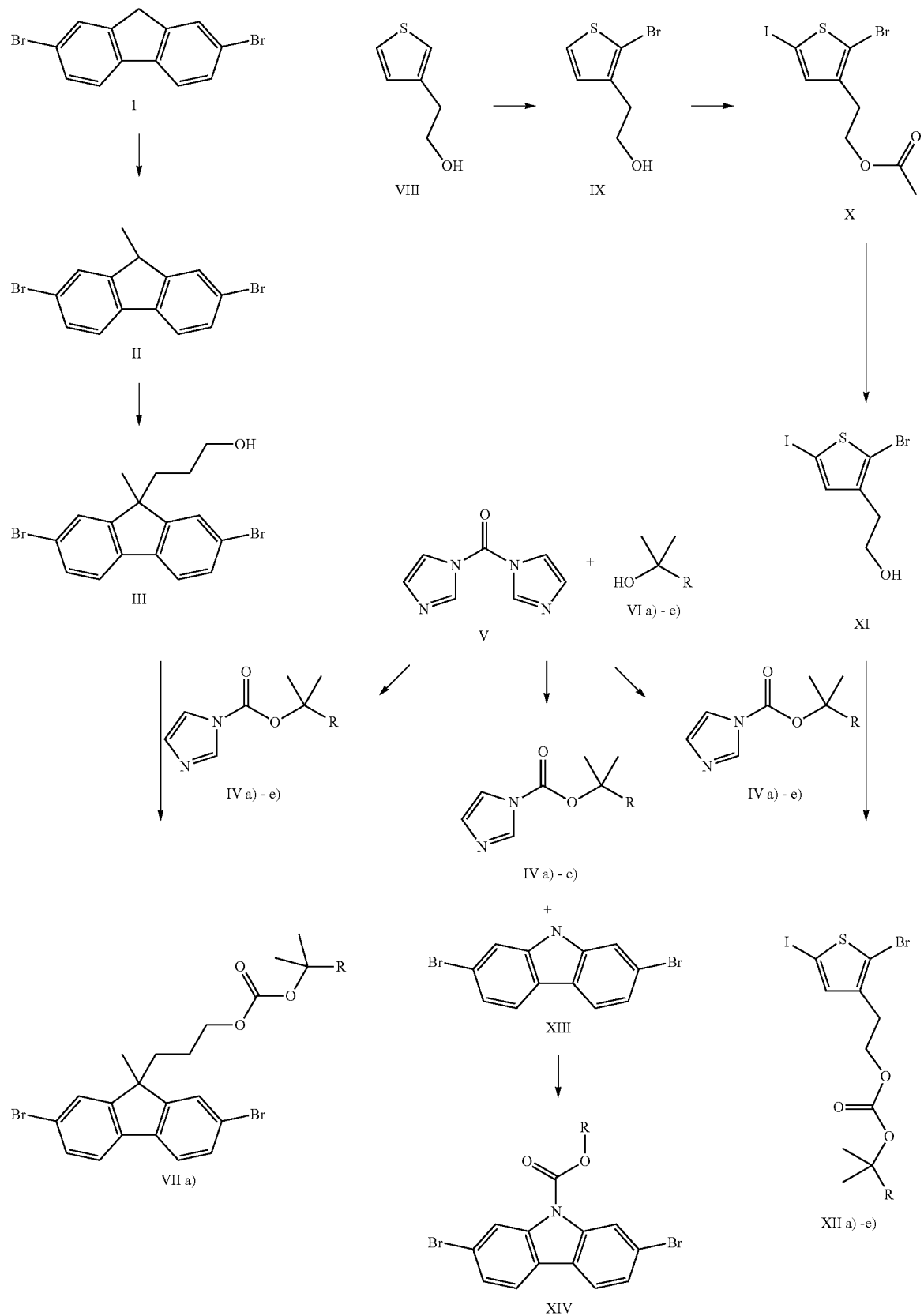
Scheme 1

The monomers of the formula VIa and VIb based on the benzo[lmn][3,8]phenanthroline-1,3,6,8-tetraone-4,9-diyl units IV6 and IV7 can be prepared, for example, according to scheme 2 or in analogy thereto.
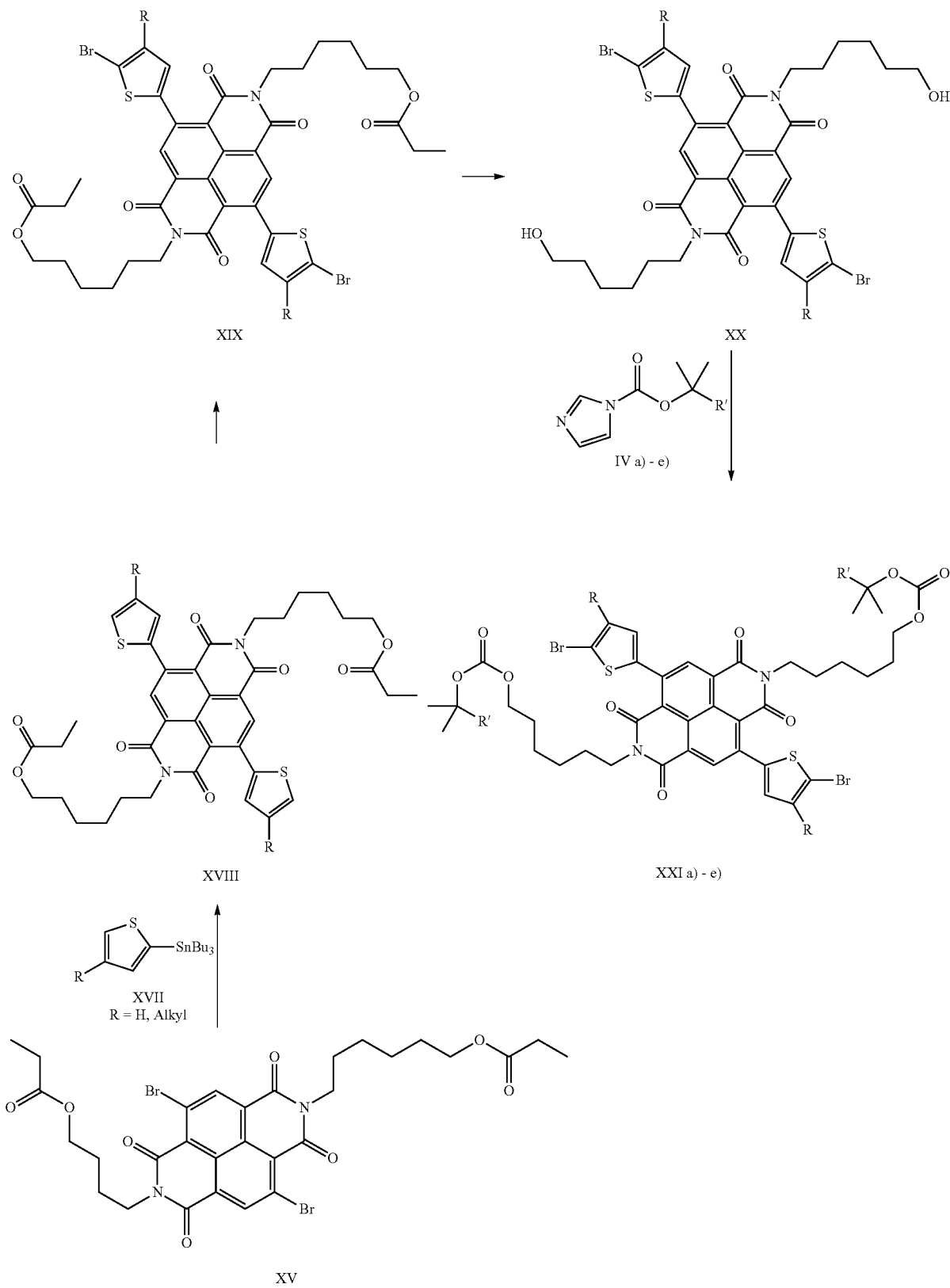
Scheme 2

-continued
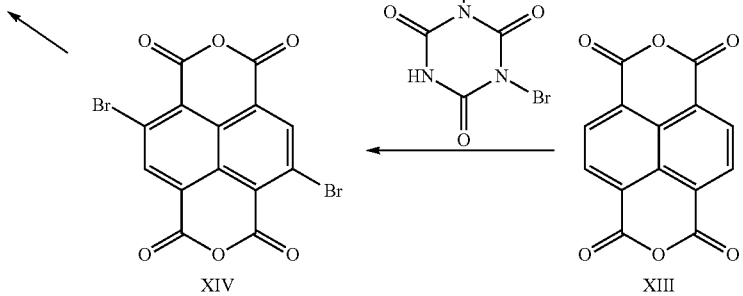
The monomers of the formula IV9 and IV10 based on the benzo[lmn][3,8]phenanthroline-1,3,6,8-tetraone-4,9-diyl units I10a and I11a can be prepared, for example, according to scheme 3 or in analogy thereto.
Scheme 3:
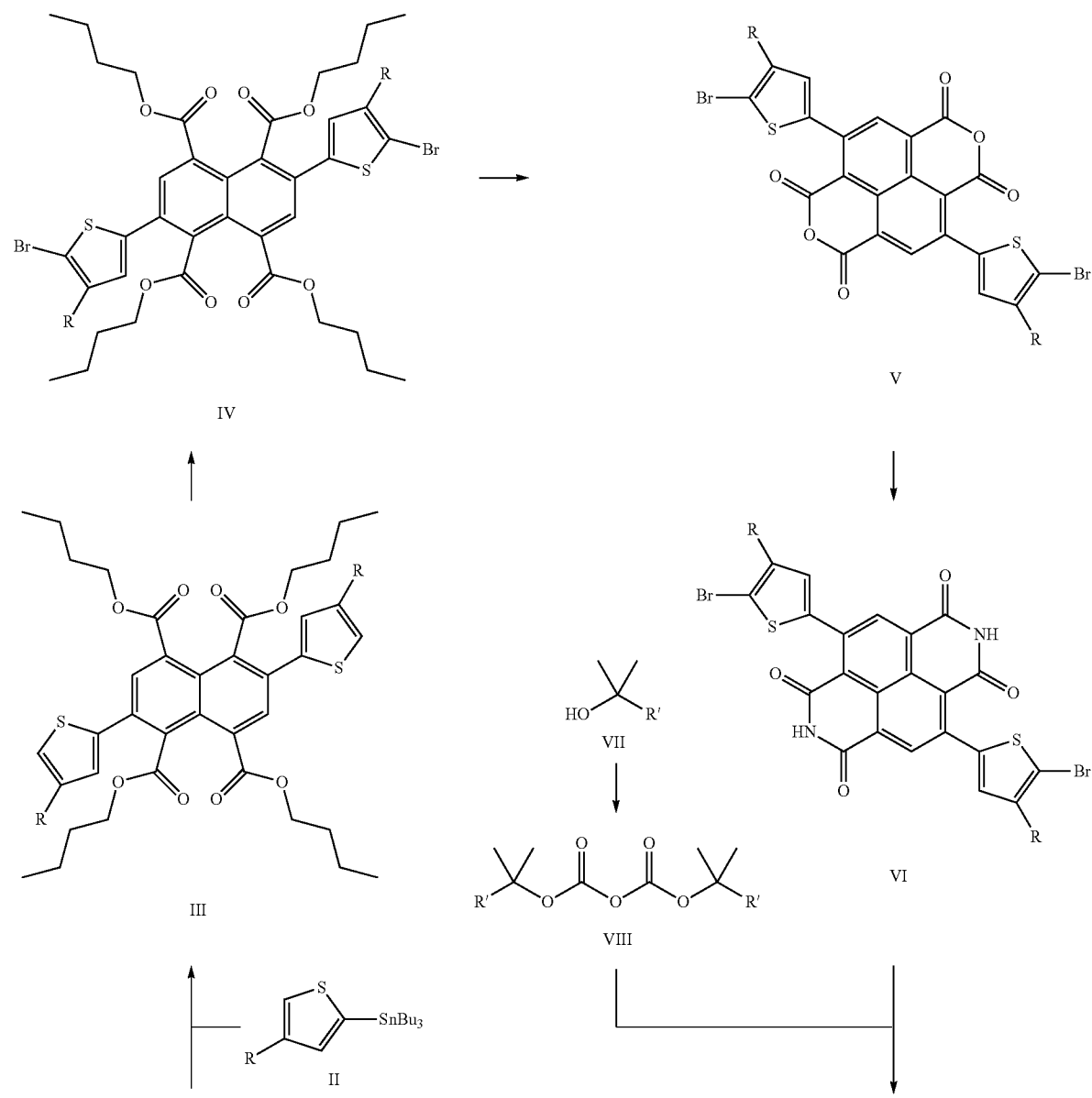

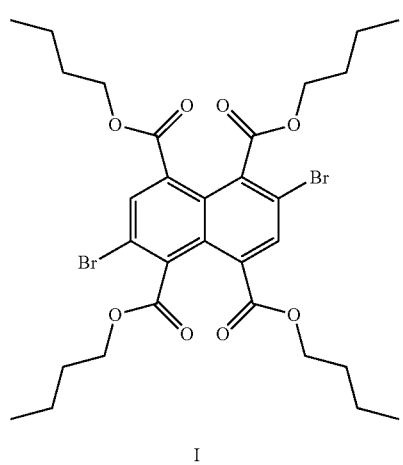

I

R, R' = H Alkyl

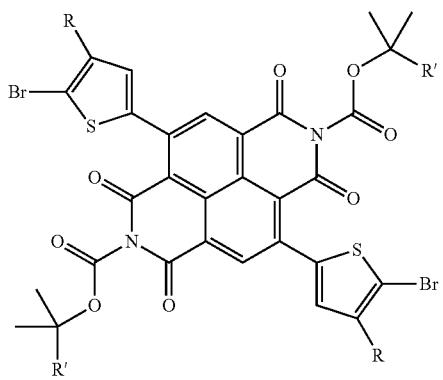

IX

The invention further provides the novel processes for preparing monomers and polymers as described above and below.

The detachment of the carbonate or carbamate side chains from a polymer of the invention can be effected simply by heating, for example after the polymer, or a material containing the polymer, has been applied as a semiconductor layer to a substrate or electronic component.

The temperature for the detachment can be determined by means of thermogravimetric analysis (TGA) and differential scanning calorimetry (DSC). In the case of the side chains known from the literature, the temperature is typically 210° C. or 310° C. in order to arrive at the completely defunctionalized polymer backbone. In the case of the thermally detachable groups of the invention, by contrast, this temperature is <200° C. and can be lowered even further, for example by replacing the alkyl radicals with, for example, alkenyl radicals. The semiconductive polymers described in this invention, after detachment, typically have an alcohol group, an amine function or an imide function. These may form hydrogen bonds which lower the solubility further.

An example shown in scheme 4 is the thermal detachment reaction for an inventive polymer of the formula IV2.

Scheme 4

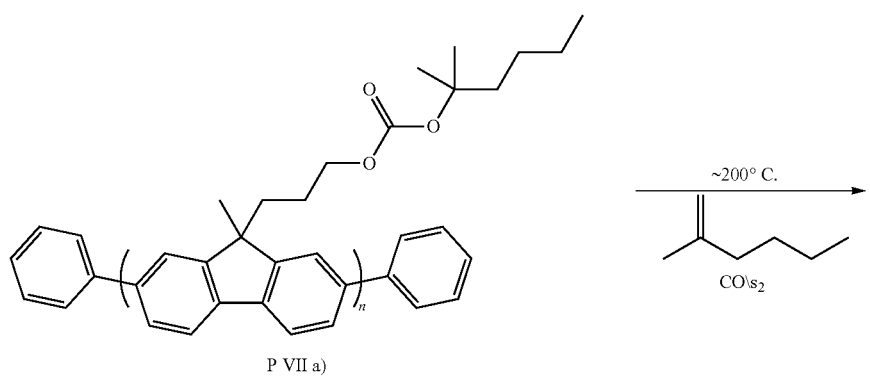

P VII a)

very good solubility and hence processible

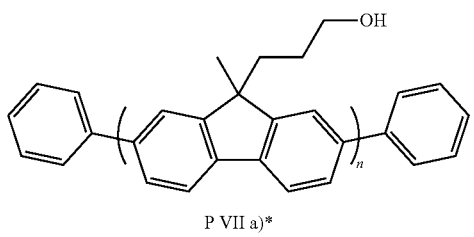

P VII a)* completely insoluable

Preferably, the detachment reaction is conducted by heating the polymer of the invention to a temperature of <200° C.

The invention further provides a process for partly or fully detaching the carbonate or carbamate groups of a polymer of the invention by heating the polymer or a layer, for example a semiconductor layer, comprising the polymer of the invention to a temperature of ≤200° C., preferably of 150° C. to 200° C. The invention further provides a polymer or a semiconductor layer obtainable by this process.

The polymers according to the present invention can also be used in mixtures or polymer blends, for example together with monomeric compounds or together with other polymers having charge transport properties, semiconductor properties, electrically conductive properties, photoconductive properties and/or light-emitting semiconductor properties or, for example, with polymers having hole-blocking or electron-blocking properties for use as interlayers or charge blocking layers in OLED devices. A further aspect of the invention therefore relates to a polymer blend comprising one or more polymers according to the present invention and one or more further polymers having one or more of the abovementioned properties. These blends can be produced by conventional methods that are described in the prior art and are known to those skilled in the art. Typically, the polymers are mixed with one another or dissolved in suitable solvents and the solutions are combined.

A further aspect of the invention relates to a formulation comprising one or more polymers, mixtures or polymer blends as described above and below and one or more organic solvents.

Preferred solvents are aliphatic hydrocarbons, chlorinated hydrocarbons, aromatic hydrocarbons, ketones, ethers and mixtures of these. Further solvents which can be used include 1,2,4-trimethylbenzene, 1,2,3,4-tetramethylbenzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6-fluorotoluene, 2-fluoroanisole, anisole, 2,3-dimethylpyrazine, 4-fluoroanisole, 3-fluoroanisole, 3-trifluoromethylanisole, 2-methylanisole, phenetole, 4-methylanisole, 3-methylanisole, 4-fluoro-3-methylanisole, 2-fluorobenzonitrile, 4-fluoroveratrole, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, 1,4-dioxane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o, m and p isomers, Solvents having relatively low polarity are generally preferred. For inkjet printing, preference is given to solvents having high boiling temperatures and solvent mixtures. For spin-coating, preference is given to alkylated benzenes such as xylene and toluene.

The examples of particularly preferred solvents include, but are not limited to, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 1,1,1-trichloroethane, 1,1,2,2-tetrachloroethane, ethyl acetate, n-butyl acetate, dimethylformamide, dimethylacetamide, dimethyl sulfoxide, tetralin, decalin, indane, methyl benzoate, ethyl benzoate, mesitylene and mixtures of the aforementioned solvents.

The concentration of the polymers in the solution is preferably 0.1% to 10% by weight, more preferably 0.5% to 5% by weight. If necessary, the solution also comprises one or more binders for adjustment of the rheological properties, as described, for example, in WO 2005/055248 A1.

After appropriate mixing and aging, the solutions are classified into one of the following categories: complete solution, borderline solution or insoluble. The contour line is drawn in order to specify the solubility parameter-hydrogen bonding limits that separate solubility and insolubility, "Complete" solvents which fall within the solubility range can be selected from literature values as published in "Crowley, J. D., Teague, G. S. Jr and Lowe, J. W. Jr., Journal of Paint Technology, 38, no. 496, 296 (1966)". Solvent mixtures can likewise be used and can be identified as described in "Solvents, W. H. Ellis, Federation of Societies for Coatings Technology, p. 9-10, 1986". Such a procedure can lead to a mixture of "non-"solvents which dissolves both polymers of the present invention, even though it is desirable when at least one true solvent is present in a mixture.

The polymers according to the present invention can also be used in structured semiconductor layers in the devices as described above and below. For applications in modern microelectronics, it is generally desirable to produce small structures or patterns, in order to reduce costs (more devices/unit area) and energy consumption. The structuring of thin layers containing a polymer according to the present invention can be conducted, for example, by photolithography, electron beam lithography or laser structuring.

For use as thin layers in electronic or electrooptical devices, the polymers, polymer blends or formulations of the present invention can be deposited by any suitable process. Liquid coating of devices is more desirable than vacuum evaporation techniques. Deposition processes from solution are particularly preferred. The formulations of the present invention enable the use of a number of liquid coating techniques. The preferred deposition techniques include, but are not limited to, dip coating, spin coating, inkjet printing, relief printing, screen printing, knife coating, rotary printing, reverse rotary printing, offset lithography printing, flexographic printing, web printing, spray coating, brush coating or pad printing. Inkjet printing is particularly preferred, since it enables the production of high-resolution layers and devices.

Selected formulations of the present invention can be applied by inkjet printing or microdispensing onto prefabricated substrates for devices. Preferably, for application of the organic semiconductor layer to a substrate, it is possible to use industrial scale piezoelectric printheads as supplied by Aprion, Hitachi-Koki, Inkjet Technology. On Target Technology, Picojet, Spectra, Trident, Xaar, but without limitation thereto. It is also possible to use semi-industrial heads such as those manufactured by Brother, Epson, Konica, Seiko Instruments, Toshiba TEC, or single-nozzle microdispensers such as those manufactured by Microdrop and Microfab.

For application by inkjet printing or microdispensing, the polymers should first be dissolved in a suitable solvent. Solvents must meet the above-specified demands and must not have any adverse effect on the printhead chosen. In addition, solvents should have boiling points of >100° C., preferably >140° C. and more preferably >150° C., in order to prevent operating problems caused by drying of the solution in the printhead. As well as the abovementioned solvents, suitable solvents include substituted and unsubstituted xylene derivatives, di-$C_{1-2}$-alkylformamide, substituted and unsubstituted anisoles and other phenol ether derivatives, substituted heterocycles such as substituted pyridines, pyrazines, pyrimidines, pyrrolidinones, substituted and unsubstituted N,N-di-$C_{1-2}$-alkylanilines and other fluorinated or chlorinated aromatics.

A preferred solvent for deposition of a polymer according to the present invention by inkjet printing contains a benzene derivative in which a benzene ring is substituted by one or more substituents, where the total number of carbon atoms in the one or more substituents is at least three. For example, the benzene derivative may be substituted by one propyl group or three methyl groups, with a total of at least three carbon atoms present in both cases. Such a solvent permits the formation of an inkjet ink containing the solvent together with the polymer, which reduces or prevents blockage of the nozzles and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, i.e. a combination of two or more solvents, where each solvent preferably has a boiling point of >100° C., more preferably >140° C. Solvents of this kind also improve film formation in the layer deposited and reduce defects in the layer.

The inkjet ink (i.e. the mixture of solvent, binder and semiconductor compound) preferably has, at 20° C., a viscosity of 1-100 mPa·s, more preferably 1-50 mPa·s and especially preferably 1-30 mPa·s.

The polymers or formulations according to the present invention may additionally comprise one or more further components or additives which are selected for, for example, from surface-active compounds, lubricants, wetting agents, dispersants, hydrophobizing agents, adhesives, flow improvers, defoamers, devolatilizing agents, diluents which may be reactive or non-reactive, auxiliaries, colorants, dyes or pigments, sensitizers, stabilizers, nanoparticles and inhibitors.

The polymers according to the present invention are usable as charge transport materials, semiconductor materials, electrically conductive materials, photoconductive materials or light-emitting materials in optical, electrooptical, electronic, electroluminescent or photoluminescent components or devices. In these devices, the polymers of the present invention are typically applied as thin layers or films.

The present invention therefore further provides for the use of a semiconductive polymer or polymer blend of the invention or of a formulation or layer of the invention in an electronic device. The formulation can be used as semiconductor material with high mobility in various devices and appliances. The formulation can be used, for example, in the form of a semiconductor layer or semiconductor film. Accordingly, the present invention provides, in a further aspect, a semiconductor layer for use in an electronic device, wherein the layer comprises a polymer, a polymer blend or a formulation according to the invention. The layer or film may be less than about 30 microns. For use in various electronic devices, the thickness may be less than about 1 micron. The layer can be deposited by means of any of the aforementioned solution coating or printing techniques, for example on part of an electronic device.

The present invention further provides an electronic device comprising a polymer, a polymer blend, a formulation or an organic semiconductor layer according to the present invention. Particularly preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarization layers, antistatic films, conductive substrates and conductive patterns.

Particularly preferred electronic devices are OFETs, OLEDs, OPV devices and OPD devices, especially OPV devices having a bulk heterojunction ("BHJ"). In an OFET, for example, the active semiconductor channel may contain the layer of the invention between the drain and source. As a further example, in an OLED device, the charge (hole or electron) injection or transport layer may comprise the layer of the invention.

For use in OPV or OPD devices, the polymer of the invention is preferably used in a formulation which comprises or contains a p-type semiconductor (electron donor) and an n-type semiconductor (electron acceptor), more preferably one which consists essentially thereof and very preferably one which consists exclusively thereof. The p-type semiconductor is preferably a polymer of the invention. The n-type semiconductor is, for example, an inorganic material such as zinc oxide ($ZnO_x$), zinc tin oxide (ZTO), titanium oxide ($TiO_x$), molybdenum oxide ($MoO_x$), nickel oxide ($NiO_x$), or cadmium selenide (CdSe), or an organic material such as grapheme, a fullerene or a substituted fullerene, e.g. an indene-$C_{60}$-fullerene bisadduct such as ICBA, or (6,6)-phenylbutyric acid methyl ester-derivatized methano-$C_{60}$-fullerene, also known as "PCBM" or "$C_{60}$PCBM", as disclosed, for example, in G. Yu, J, Gao, J. C. Hummelen, F. Wudl, A. J. Heeger, Science 1995, vol. 270, p. 1789 ff and with the structure shown below, or a structurally analogous compound having, for example, a $C_{70}$-fullerene group ($C_{70}$PCBM) or a polymer (see, for example, Coakley, K. M. and McGehee, M. D. Chem. Mater. 2004, 16, 4533). Polymers of the invention containing an acceptor group, for example a repeat unit of the formula I10 or I11, can also be used as n-type semiconductors.

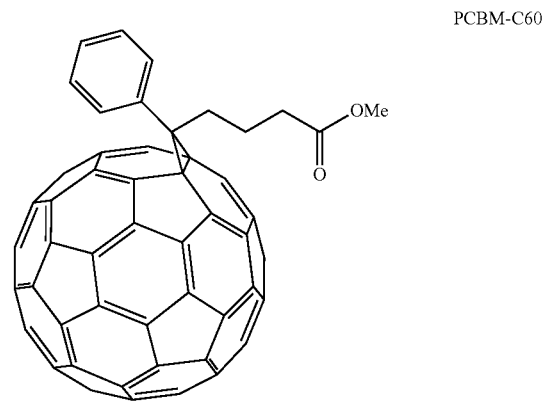

PCBM-C60

In order to form a photoactive layer in an OPD or OPV device of the invention, a polymer of the invention is preferably mixed with a fullerene or a substituted fullerene such as PCBM-$C_{60}$, PCBM-$C_{70}$, bis-PCBM-$C_{60}$, bis-PCBM-$C_{70}$, ICBA (1′,1″,4′,4″-tetrahydrodi[1,4]methanon-aphthaleno[1,2:2′,3′; 56,60:2″,3″][5,6]fullerene-C60-Ih), or with graphene or a metal oxide, for example $ZnO_x$, $TiO_x$, ZTO, $MoO_x$, $NiO_x$.

An OPD or OPV device of the invention preferably comprises, apart from the photoactive layer, a first transparent or semitransparent electrode on a transparent or semitransparent substrate on one side of the photoactive layer, and a second metallic or semitransparent electrode on the other side of the photoactive layer.

In a further preferred embodiment, an OPD or OPV device of the invention comprises, between the photoactive layer and the first and/or second electrode, one or more interlayers or buffer layers which can function as hole transport and/or electron-blocking layer and comprise a material, for example a metal oxide, e.g. ZTO, $MoO_x$, $NiO_x$, a conjugated polymer electrolyte, e.g. PEDOT:PSS, a conjugated polymer, e.g. polytriarylamine (PTAA), or an organic compound, e.g. N,N'-diphenyl-N,N'-bis(1-naphthyl) (1,1'-biphenyl)-4,4'-diamine (NPB), N,N'-diphenyl-N,N'-(3-methylphenyl)-1,1'-biphenyl-4,4'-diamine (TPD), or one or more interlayers or buffer layers which can function as hole-blocking and/or electron transport layer and contain a material, for example a metal oxide, e.g. $ZnO_x$, $TiO_x$, a salt, e.g. LiF, NaF, CsF, a conjugated polymer electrolyte, e.g. poly[3-(6-trimethylammoniohexyl)thiophene], poly(9,9-bis (2-ethylhexyl)-fluorene]-b-poly[3-(6-trimethylammoniohexyl)thiophene], or poly[(9,9-bis(3'-(N,N-dimethylamino) propyl)-2,7-fluorene)-alt-2,7-(9,9-dioctylfluorene)], or an organic compound, e.g. tris(8-quinolinolato)aluminum(III) ($Alq_3$), or 4,7-diphenyl-1,10-phenanthroline.

In a mixture of a polymer or polymer blend of the invention with a fullerene or substituted fullerene, the polymer:fullerene ratio is preferably from 5:1 to 1:5 parts by weight, more preferably from 1:1 to 1:3 pads by weight, most preferably from 1:1 to 1:2 parts by weight. A polymeric binder can also be added, preferably in a concentration of 5% to 95% by weight. Examples of suitable and preferred binders include polystyrene (PS), polypropylene (PP) and polymethylmethacrylate (PMMA).

For production of thin layers in BHJ-OPV devices, the polymers, polymer blends or formulations of the present invention can be deposited by any suitable process. Liquid coating of devices is more desirable than vacuum evaporation techniques. Deposition processes from solution are particularly preferred. The formulations of the present invention enable the use of a number of liquid coating techniques. The preferred deposition techniques include, but are not limited to, dip coating, spin coating, inkjet printing, relief printing, screen printing, knife coating, rotary printing, reverse rotary printing, offset lithography printing, flexographic printing, web printing, slot-dye coating, spray coating, brush coating or pad printing, Inkjet printing is particularly preferred, since it enables the production of high-resolution layers and devices.

For the production of OPV devices and OPV modules, particular preference is given to areal printing methods that are compatible with flexible substrates, for example slot-dye coating or spray coating.

In the selection of suitable solvents for production of BHJ layers from a polymer of the invention and a fullerene, complete dissolution of both components should be ensured, and attention should be paid to the interfacial conditions (e.g. the rheological properties) that result from the printing or coating method chosen.

For this purpose, organic solvents are used. Typical solvents are, for example, aromatic and/or chlorinated solvents. Examples of suitable and preferred solvents include, but are not limited to, chlorobenzene, 1,2-dichlorobenzene, chloroform, 1,2-dichloroethane, dichloromethane, carbon tetrachloride, toluene, cyclohexanone, ethyl acetate, tetrahydrofuran, anisole, morpholine, o-xylene, m-xylene, p-xylene, 1,4-dioxane, acetone, methyl ethyl ketone, 1,2-dichloroethane, 1,1,1-trichloroethane, 1,1,2,2-tetrachloroethane, n-butyl acetate, dimethylformamide, dimethylacetamide, dimethyl sulfoxide, tetralin, decalin, indane, methyl benzoate, ethyl benzoate, mesitylene and mixtures of the aforementioned solvents.

The OPV device may, for example, be of any type known from the literature [see, for example, Waldauf et al., *Appl. Phys. Lett.* 89, 233517 (2006)].

A first preferred OPV device of the invention contains (in the sequence beginning with the side facing the incident light):
  optionally a substrate,
  an electrode with a high work function, preferably containing a metal oxide, for example ITO, as anode,
  optionally a conductive polymer layer or hole transport layer, preferably comprising an organic polymer or polymer blend or an organic compound, for example PEDOT:PSS (poly(3,4-ethylenedioxythiophene):poly (styrenesulfonate)), TBD (N,N'-diphenyl-N—N'-bis(3-methylphenyl)-1,1'-biphenyl-4,4'-diamine) or NBD (N,N'-diphenyl-N—N'-bis(1-naphthylphenyl)-1,1'-biphenyl-4,4'-diamine),
  a layer (also referred to as "active layer" or "photoactive layer") comprising an organic p-type semiconductor and an organic n-type semiconductor, present, for example, in the form of a double layer or two separate layers of a p-type and n-type semiconductor, or as a blend of a p-type or n-type semiconductor, which form a bulk heterojunction (BHJ),
  optionally an electron transport layer comprising, for example, LIF,
  an electrode with a low work function, preferably containing a metal, for example aluminum, as cathode,
  wherein at least one of the electrodes, preferably the anode, is transparent, and
  wherein the p-type semiconductor and/or the n-type semiconductor is a polymer of the invention.

A second preferred OPV device of the invention is an inverted OPV device and contains (in the sequence beginning with the side facing the incident light):
  optionally a substrate,
  an electrode with a high work function, preferably containing a metal oxide, for example ITO, as cathode,
  a hole-blocking layer, preferably comprising a metal oxide, for example $TIO_x$ or $ZnO_x$,
  a layer (also referred to as "active layer" or "photoactive layer") comprising an organic p-type semiconductor and an organic n-type semiconductor, present, for example, in the form of a double layer or two separate layers of a p-type and n-type semiconductor, or as a blend of a p-type or n-type semiconductor, which form a bulk heterojunction (BHJ),
  optionally a conductive polymer layer or hole transport layer, preferably comprising an organic polymer or polymer blend or an organic compound, for example PEDOT:PSS, TBD or NBD,
  an electrode comprising a metal with a high work function, for example silver, as an anode,
  wherein at least one of the electrodes, preferably the cathode, is transparent, and
  wherein the p-type semiconductor and/or the n-type semiconductor is a polymer of the invention.

In the OPV devices of the present invent invention, the p-type and n-type semiconductor materials are preferably selected from the above-described materials, such as the polymer/fullerene systems. If an active layer comprising such a polymer/fullerene system is applied to a substrate, it forms a BHJ which exhibits phase separation in the nanometer range; see, for example, Dennler et al., *Proceedings of the IEEE*, 2005, 93 (8), 1429 or Hoppe et al., *Adv. Func. Mater,* 2004, 14(10), 1005. In some cases, a treatment step may be required to optimize the morphology of the blend and the performance of the OPV device.

A further method of optimizing the performance of the OPV device is the preparation of a formulation for production of OPV(BHJ) devices which comprises high-boiling additives that affect the phase separation and can guide it in the desired direction. For this purpose, it is possible to use, for example, octane-1,8-dithiol, 1,8-diiodooctane, nitrobenzene, chloronaphthalene or other additives in order to produce highly efficient solar cells. Examples of these are described in J. Peet, et al., *Nat. Mater.,* 2007, 6, 497 or Fréchet et al, *J. Am. Chem. Soc.,* 2010, 132, 7595-7597.

The polymers, polymer blends, formulations and layers of the invention are also suitable for use in an OFET as semiconductor channel. Accordingly, the invention also provides an OFET comprising a gate electrode, an insulating (or gate insulator) layer, a source electrode, a drain electrode and an organic semiconductor channel connecting the source and drain electrodes, wherein the organic semiconductor channel comprises a polymer, polymer blend, formulation or organic semiconductor layer according to the present invention. Further features of the OFET are known to those skilled in the art and can be added without exercising inventive skill.

OFETs, in which an organic semiconductor material is disposed as a thin film between a gate dielectric and a drain electrode and a source electrode, are common knowledge and are described, for example, in U.S. Pat. Nos. 5,892,244, 5,998,804 or U.S. Pat. No. 6,723,934. Because of the advantages, such as inexpensive production with exploitation of the solubility properties of the compounds of the invention and hence processibility over large areas, preferred applications of these FETs are those such as integrated circuits, TFT displays and security applications.

The gate, source and drain electrodes and the insulating and semiconductor layers in the OFET device may be arranged in any sequence, provided that the source and drain electrodes are separated from the gate electrode by the insulating layer, the gate electrode and semiconductor layer both have contact with the insulating layer, and the source electrode and drain electrode both have contact with the semiconductor layer.

An OFET device according to the present invention preferably comprises:
a source electrode,
a drain electrode,
a gate electrode,
a semiconductor layer,
one or more gate insulator layers,
optionally a substrate,
wherein the semiconductor layer preferably comprises a polymer, polymer blend or formulation according to the present invention.

The OFET device may be a top gate device or a bottom gate device. Suitable structures and production methods for an OFET device are known to those skilled in the art and are described in the literature, for example in US 2007/0102696 A1.

The gate insulator layer may preferably contain a fluoropolymer, for example the commercially available Cytop 809M® or Cytop 107M® (from Asahi Glass). Preferably, the gate insulator layer is deposited from a formulation comprising an insulator material and one or more solvents having one or more fluorine atoms (fluoro solvents), preferably a perfluoro solvent, for example by spin coating, knife coating, wire doctor coating, spray coating or dip coating or other known methods. A suitable perfluoro solvent is, for example, $FC_{75}$® (from Acros, catalog number 12380). Other suitable fluoropolymers and fluoro solvents are known from the prior art, for example the perfluoropolymers Teflon AF® 1600 or 2400 (from DuPont) or Fluoropel® (from Cytonix) or the perfluoro solvent FC 43® (Acros, no. 12377). Particular preference is given to organic dielectric materials having a low permittivity (or dielectric constant) of 1.0 to 5.0, very preferably of 1.8 to 4.0 ("low-k materials"), as disclosed, for example, in US 2007/0102696 A1 or U.S. Pat. No. 7,095,044.

In security applications, it is possible to use OFETs and other devices comprising semiconductor materials according to the present invention, such as transistors or diodes, for RFID tags or safety labels, in order to authenticate and prevent the forgery of documents of value such as banknotes, credit cards or ID cards, national identity documents, vouchers or any products having monetary value, such as stamps, entry and travel tickets, lottery tickets, shares, checks, etc.

Alternatively, the materials of the invention can be used in OLEDs, for example as active display material in flat screen display applications or as backlighting of a flat screen, for example of a liquid-crystal display. Standard OLEDs are implemented using multilayer structures. In general, an emission layer is disposed between one or more electron transport and/or hole transport layers. Through application of an electrical voltage, electrons and holes as charge carriers move to the emission layer, where recombination thereof leads to excitation and hence luminescence of the luminophore units present in the emission layer. The compounds, materials and films of the invention can be used in one or more of the charge transport layers and/or in the emission layer, in accordance with their electrical and/or optical properties. In addition, use thereof in the emission layer is particularly advantageous when the compounds, materials and films of the invention themselves exhibit electroluminescence properties or contain electroluminescent groups or compounds. The selection, characterization and processing of suitable monomeric, oligomeric and polymeric compounds or materials for use in OLEDs is common knowledge to those skilled in the art see, for example, Müller et aL, *Synth. Metals,* 2000, 111-112, 31-34, Alcala, *J. Appl. Phys.,* 2000, 88, 7124-7128 and the literature cited therein.

In another use, the materials according to this invention, especially those which exhibit photoluminescence properties, can be used as materials for light sources, for example for display devices, as described in EP 0 889 350 A1 or by C. Weder et al., *Science,* 1998, 279, 835-837.

A further aspect of the invention relates both to the oxidized and to the reduced form of the compounds of the invention. Release or acceptance of electrons leads to formation of a highly delocalized ionic form with high conductivity. This can occur through the action of customary dopants. Suitable dopants and methods are known to those skilled in the art, for example from EP 0 528 662, U.S. Pat. No. 5,198,153 or WO 96/21659.

The doping method typically involves the treatment of the semiconductor material with an oxidizing or reducing agent in a redox reaction, such that delocalized ionic sites form in the material, the corresponding counterions originating from the dopants employed. Suitable doping methods include, for example, contact with a doping vapor under atmospheric or reduced pressure, electrochemical doping in a dopant-containing solution, contacting of a dopant with the semiconductor material for thermal diffusion, and ion implantation of the dopant into the semiconductor material.

When electrons are used as carriers, suitable dopants are, for example, halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protic acids, organic acids or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (in which Ln is an element of the lanthanum series), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$ and anions of various sulfonic acids, such as aryl-$SO_3^-$). When holes are used as carriers, illustrative dopants are cations (e.g. $H^+$, $Li^+$, $Na^+$, $K^+$, $Rb^+$ and $Cs^+$), alkali metals (e.g. Li, Na, K, Rb and Cs), alkaline earth metals (e.g. Ca, Sr and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$ (R is an alkyl group), $R_4P^+$ (R is an alkyl group), $R_6As^+$ (R is an alkyl group) and $R_3S^+$ (R is an alkyl group).

The conductive form of the compounds of the present invention can be used as organic "metal" in applications such as charge injection layers and ITO planarization layers in OLEO applications, films for flat display screens and touchscreens, antistatic films, printed conductive substrates, patterns or conductor tracks in electronics applications such as circuit boards and capacitors, for example, without any restriction thereto.

The compounds and formulations according to the present invention may also be suitable for use in organic plasma-emitting diodes (OPEDs), as described, for example, in Koller et al., *Nat. Photonics*, 2008, 2, 684.

In another use, the materials according to the present invention can be used alone or together with other materials in or as orientation layers in LCD or OLED devices, as described, for example, in US 2003/0021913, The use of charge transport compounds according to the present invention can increase the electrical conductivity of the orientation layer. In the case of use in an LCD, this elevated electrical conductivity can lower unfavorable residual DC current effects in the switchable LCD element and suppress baking or, for example, in ferroelectric LCDs, lower the residual charge generated by the switching of the spontaneous polarization charge of the ferroelectric LCs. In the case of use in an OLED device with a light-emitting material mounted on the orientation layer, this elevated electrical conductivity can boost the electroluminescence of the light-emitting material. The compounds or materials according to the present invention having mesogenic or liquid-crystalline properties can form aligned anisotropic films as described above, which are especially suitable as orientation layers for induction or enhancement of orientation in a liquid-crystal medium upon the anisotropic film. The materials according to the present invention can also be combined with photoisomerizable compounds and/or chromophores for use in or as photoorientation layers, as described in US 2003/0021913.

In another use, the materials according to the present invention, especially the water-soluble derivatives (for example with polar or ionic side groups) or ionically doped forms thereof, can be used as chemical sensors or materials for detection and for distinction of DNA sequences. Uses of this kind are described, for example, in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Aced. Sci. U.S.A.*, 2002, 99, 49; N. DiCesare, M. R. Pinot, K. S, Schanze and J. R. Lakowicz, Langmuir, 2002, 18, 7785; D. T. McQuade, A. E. Pullen, T. M. Swager, *Chem. Rev.*, 2000, 100, 2537.

Unless the opposite is clearly apparent from the context, plural forms of the terms used here should be regarded as including the singular form and vice versa.

In the overall description and the claims of this specification, the terms "comprise" and "contain" and variations thereof, for example "containing" and "contains", have the meaning "including but not limited to" and should not be understood such that they exclude other components.

It will be apparent that it is possible to conduct variations of the preceding embodiments of the invention that still fall within the scope of protection of the present invention. Every feature disclosed in this application text can, unless stated otherwise, be replaced by alternative features which serve an identical, equivalent or similar purpose. Unless stated otherwise, every feature disclosed is therefore just an example of a generic series of equivalent or similar features.

All the features disclosed in this application text can be combined with one another in any desired combination, excluding combinations where at least some of these features and/or steps are mutually exclusive. More particularly, the preferred features of the invention are applicable to all aspects of the invention and can be used in any desired combination. It is likewise possible to use features described in non-essential combinations separately from one another as well (i.e. not in combination with one another).

Unless noted otherwise, all percentages above and below are percent by weight, and all temperature values are degrees Celsius. The values for the dielectric constant ε ("permittivity") mean the values ascertained at 20° C. and 1000 Hz.

The invention is now described in more detail with reference to the examples which follow, which are intended to illustrate the invention without limiting it.

Example 1—Synthesis Units

Synthesis of the Polythiophene Unit:

1.1 2-(2-Bromothiophen-3-yl)ethanol

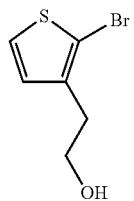

N-Bromosuccinimide (13.9 g, 78.0 mmol, 1.00 equiv.) was added in portions at 0° C. to a solution of 2-(thiophen-3-yl)ethanol (10.0 g, 78.0 mmol, 1.00 equiv.) in tetrahydrofuran (200 mL). The suspension was warmed up gradually to room temperature while stirring overnight. 50 mL of water were added to the reaction mixture, the phases were separated, and the aqueous phase was extracted with chloroform (50 mL). The combined organic phases were washed with an aqueous sodium hydrogencarbonate solution (50 mL) and dried over magnesium sulfate, and the solvent was removed under reduced pressure. The crude product was purified by column chromatography on silica gel with petroleum ether/ethyl acetate (2:1) as eluent. 14.5 g (90%) of the product were obtained as a yellow oil. —$R_f$=0.39 (petroleum ether/ethyl acetate 2:1). —$^1$H-NMR (300 MHz, CDCl$_3$): δ=7.26 (d, $^3$J=5.6 Hz, 1H, H$_{ar}$), 6.90 (d, $^3$J=5.6 Hz, 1H, H$_{ar}$), 3.86 (t, 3J=6.6 Hz, 2H, CH$_2$—OH), 2.89 (t, $^3$J=6.6 Hz, 2H, C$_{ar}$—CH$_2$), 1.75 (s, 1H, OH). $^{13}$C-NMR (75 MHz, CDCl$_3$): δ=138.1 (C$_{ar}$—CH$_2$), 128.7 (C$_{ar}$), 125.8 (C$_{ar}$), 110.5 (C$_{ar}$—Br), 62.2 (CH$_2$—OH), 32.9 (C$_{ar}$—CH$_2$). MS (EI), m/z (%): 208/206 (52/51) [M$^+$], 177/175 (100/91) [(C$_5$H$_4$BrS)$^+$]97 (38).—HRMS (C$_6$H$_7$BrOS): calc. 205.9401, found 205.9402.

1.2 2-(2-Bromo-5-iodothiophen-3-yl)ethyl acetate

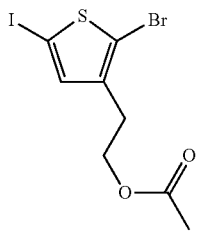

2-(2-Bromothiophen-3-yl)ethanol (9.11 g, 44.0 mmol, 1.00 equiv.) was dissolved in acetic, acid (50 mL). After the addition of n-iodosuccinimide (10.4 g, 46.2 mmol, 1.05 equiv.), the resultant suspension was stirred at 100° C. for 4 h. The reaction mixture was added to water (50 mL), the phases were separated, and the aqueous phase was extracted with dichloromethane (50 mL). The combined organic phases were washed with an aqueous 1 M sodium hydroxide solution (50 mL), 10% sodium thiosulfate solution (50 mL), water (50 mL) and saturated sodium chloride solution (50 mL), and dried over magnesium sulfate, and the solvent was removed under reduced pressure. The crude product was purified by column chromatography on silica gel with petroleum ether/ethyl acetate (3:1) as eluent, 15.4 g (93%) of the product were obtained as an orange oil.

$R_f$=0.54 (petroleum ether/ethyl acetate 3:1). $^1$H-NMR (300 MHz, CDCl$_3$): δ=7.01 (s, 1H, H$_{ar}$), 4.20 (t, $^3$J=6.9 Hz, 2H, CH$_2$—O), 2.88 (t, $^3$J=6.9 Hz, 2H, C$_{ar}$—CH$_2$) 2.05 (s, 3H, CH$_3$).—$^{13}$C-NMR (75 MHz, CDCl$_3$): δ=171.0 (C=O), 140.0 (C$_{ar}$—CH$_2$), 138.1 (C$_{ar}$), 113.7 (C$_{ar}$—Br), 71.7 (C$_{ar}$—I), 63.2 (CH$_2$—O), 28.8 (C$_{ar}$—CH$_2$), 21.2 (CH$_3$).—FTIR: ṽ=2952, 1735, 1363, 1228, 1036 cm$^{-1}$.—MS (EI), m/z (%): 376/374 (15/15) [M$^+$], 316/314 (100/100) [(C$_6$H$_4$BrIS)$^+$], 190/188 (8/9) [(C$_6$H$_5$BrS)$^+$].—HRMS (C$_8$H$_8$BrIO$_2$S): calc. 373.8473, found 373.8463.

1.3 2-(2-Bromo-5-iodothiophen-3-yl)ethanol

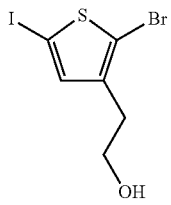

2-(2-Bromo-5-iodothiophen-3-yl)ethyl acetate (17.1 g, 45.7 mmol, 1.00 equiv.) was dissolved in a mixture of tetrahydrofuran (300 mL) and aqueous 1 M sodium hydroxide solution (200 mL), and the mixture was stirred at 70° C. for 4 h. The reaction mixture was diluted with toluene (100 mL) and the organic phase was washed three times with 100 mL each time of water and dried over magnesium sulfate, and the solvent was removed under reduced pressure. The crude product was purified by column chromatography on silica gel with petroleum ether/ethyl acetate (3:1) as eluent. 14.9 g (98%) of the product were obtained as a pale yellow solid.

$R_f$=0.23 (petroleum ether/ethyl acetate 3:1).
$^1$H-NMR (300 MHz, CDCl$_3$): δ=7.06 (s, 1H, H$_{ar}$), 3.82 (t, $^3$J=6.4 Hz, 2H, CH$_2$—OH), 2.82 (t, $^3$J=6.4 Hz, 2H, C$_{ar}$CH$_2$), 1.44 (s, 1H, OH).—$^{13}$C-NMR (75 MHz, CDCl$_3$): δ=140.5 (C$_{ar}$—CH$_2$), 138.4 (C$_{ar}$), 113.4 (C$_{ar}$—Br), 71.8 (C$_{ar}$I), 62.0 (CH$_2$—OH), 32.7 (C$_{ar}$CH$_2$).—FTIR: ṽ=3257, 2952, 999 cm$^{-1}$.—MS (EI), m/z (%): 334/332 (91/94) [M$^+$], 303/301 (100/99) [(C$_5$H$_3$BrIS)$^+$].—HRMS (C$_6$H$_6$BrIOS): calc, 331.8367, found 331.8363.

Synthesis of the Fluorene Unit:

1.4 2,7-Dibromo-9-methylfluorene

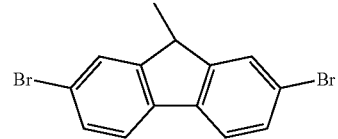

1.54 M n-butyllithium solution (35 mL, 3.42 g, 53.4 mmol, 1.01 equiv.) in hexane was slowly added dropwise to a solution of 2,7-dibromofluorene (17.1 g, 52.9 mmol, 1.00 equiv.) in tetrahydrofuran (300 mL) at −78° C. After five minutes, iodomethane (8.26 g, 58.2 mmol, 1.10 equiv.) was slowly added dropwise. The reaction mixture was stirred for 4 h and then added to dichloromethane/water (2:1, 100 mL), The aqueous phase was extracted further with dichloromethane, the combined organic phases were dried over magnesium sulfate and the solvent was removed under reduced pressure. The residue was recrystallized from petroleum ether. 11.8 g (66%) of the product were obtained as a yellow solid.

1.5
2,7-Dibromo-9-(3-hydroxypropyl)-9-methylfluorene

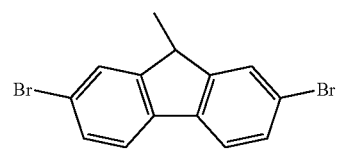 [SMILES: CC1c2cc(Br)ccc2-c2ccc(Br)cc21]

2,7-Dibromo-9-methylfluorene (9.03 g, 26.7 mmol, 1.00 equiv.) was dissolved in dimethyl sulfoxide (150 mL). To this were added potassium hydroxide (1.65 g, 29.4 mmol, 1.10 equiv.), 18-crown-6 (141 mg, 534 µmol, 0.02 equiv.), water (5 mL) and 3-bromopropan-1-ol (3.90 g, 28.0 mmol, 1.05 equiv.). The reaction mixture was stirred at room temperature overnight and then added cautiously to dichloromethane (100 mL). The organic phase was washed with saturated sodium chloride solution (50 mL) and water (50 mL). The organic phase was dried over magnesium sulfate and the solvent was removed under reduced pressure. The crude product was purified by column chromatography on silica gel with dichloromethane as eluent. 5.73 g (54%) of the product were obtained as a yellow solid. —$R_f$=0.40 (dichloromethane).—$^1$H-NMR (300 MHz, CDCl$_3$): δ=7.53 (d, $^3$J=8.1 Hz, 2H, 2×H$_{ar}$), 7.50 (d, $^4$J=1.5 Hz, 2H, 2×H$_{ar}$), 7.45 (d, $^3$J=8.1 Hz, $^4$J=1.5 Hz, 2H, 2×H$_{ar}$), 3.34-3.41 (m, 2H, CH$_2$—OH), 1.98-2.05 (m, 2H, CH$_2$), 1.46 (s, 3H, CH$_3$), 0.83-0.94 (m, 2H, CH$_2$).—$^{13}$C-NMR (75 MHz, CDCl$_3$): δ=153.3 (2×C$_{ar}$), 138.2 (2×C$_{ar}$), 130.5 (2×C$_{ar}$H), 126.3 (2×C$_{ar}$H), 121.7 (2×C$_{ar}$—Br), 121.5 (2×C$_{ar}$H), 62.8 (CH$_2$—OH), 51.0 (CH$_2$), 36.6 (CH$_2$), 27.6 (CH$_3$) 26.6 (CH$_2$).—MS (EI), m/z (%): 398/396/394 (50/99/53) [M$^+$], 339/337/335 (56/100/51) [(C$_{14}$H$_{19}$Br$_2$)$^{30}$ ], 258/256 (76/75) [(C$_{14}$H$_{19}$Br)+], 176 (89).—HRMS (C$_{17}$H$_{16}$Br$_2$O): calc. 393.9568, found 393.9605.

Synthesis of the Carbazole Unit:

1.6 4,4-Dibromo-2-nitrobiphenyl

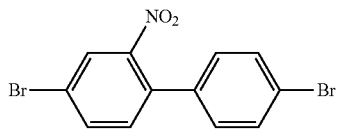 [SMILES: O=[N+]([O-])c1cc(Br)ccc1-c1ccc(Br)cc1]

A mixture of fuming nitric acid (92 mL) and water (8 mL) was added gradually at 100° C. to a solution of 4,4-dibromobiphenyl (20 g, 0.064 mol, 1.00 equiv.) in acetic acid (300 mL). The reaction mixture was stirred at 100° C. for 30 minutes. After cooling to room temperature, the reaction mixture was added to water (100 mL) and extracted with dichloromethane (100 mL). The combined organic phases were dried over magnesium sulfate and the solvent was removed under reduced pressure. The residue was recrystallized from ethanol. 18.1 g (79%) of the product were obtained as a yellow solid. —$^1$H-NMR (300 MHz, CDCl$_3$): δ=8.03 (d, $^4$J=2.0 Hz, 1H, H$_{ar}$), 7.76 (dd, $^3$J=8.3 Hz, $^4$J=2.0 Hz, 1H, H$_{ar}$), 7.56 (d, $^3$J=8.6 Hz, 2H, 2×H$_{ar}$), 7.29 (q, $^3$J=8.3 Hz, 1H, H$_{ar}$), 7.16 (d, $^3$J=8.6 Hz, 2H, 2×H$_{ar}$).—$^{13}$C-NMR (75 MHz, CDCl$_3$): δ=145.8 (C$_{ar}$—NO$_2$), 135.7 (C$_{ar}$H), 135.4 (C$_{ar}$), 134.3 (C$_{ar}$), 133.2 (C$_{ar}$H), 132.2 (2×C$_{ar}$H), 129.6 (2×C$_{ar}$H), 127.4 (C$_{ar}$H), 123.2 (C$_{ar}$—Br), 122.0 (C$_{ar}$—Br),—MS (EI), m/z (%); 359/357/355 (50/100/51) [M$^+$], 232/230 (50/47) [(C$_{12}$H$_7$Br)$^+$], 151 (65) [(C$_{12}$H$_7$)$^+$].—HRMS (C$_{12}$H$_7$Br$_2$NO$_2$): calc. 354.8844, found 354.8846.

1.7 2,7-Dibromocarbazole

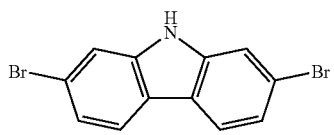 [SMILES: Brc1ccc2c(c1)[nH]c1cc(Br)ccc12]

A mixture of 4,4-dibromo-2-nitrobiphenyl (18.2 g, 51.0 mmol, 1.00 equiv.) and triethyl phosphite (100 mL) was stirred at 160° C. for 18 h. After the cooling to room temperature, the reaction mixture was added to water (100 mL) and extracted with dichloromethane. The combined organic phases were dried over magnesium sulfate and the excess of triethyl phosphite was distilled off at 160° C. The crude product was purified by column chromatography on silica gel with petroleum ether/ethyl acetate (20:1) as eluent. 10.0 g (60%) of the product were obtained as a yellow solid. —$R_f$=0.23 (petroleum ether/ethyl acetate 20:1).—$^1$H-NMR (300 MHz, acetone-d$_6$): δ=10.60 (bs, 1H, NH), 8.06 (d, $^3$J=8.5 Hz, 2H, 2×H$_{ar}$), 7.73 (d, $^4$J=1.7 Hz, 2H, 2×H$_{ar}$), 7.35 (dd, $^3$J=8.5 Hz, $^4$J=1.7 Hz, 2H, 2×H$_{ar}$).—$^{13}$C-NMR (75 MHz, acetone-d$_6$): δ=141.9 (2×C$_{ar}$—NH), 123.3 (2×C$_{ar}$H), 122.6 (2×C$_{ar}$H), 119.9 (2×C$_{ar}$—Br), 114.9 (2×C$_{ar}$), 114.8 (2×C$_{ar}$H).—MS (EI), m/z (%): 327/325/323 (50/100/51) [M$^+$], 246/244 (14/15) [(C$_{12}$H$_7$BrN)$^+$].—HRMS (C$_{12}$H$_7$Br$_2$N): calc. 322.8945, found 322.8927.

Synthesis of the Alcohols for the Imidazole Esters:

1.8 1-Butylcyclopentanol

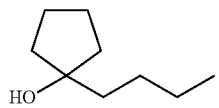

A 1.6 m n-butyllithium solution in hexane (31.3 mL, 3.20 g, 50.0 mmol, 1.00 equiv.) was slowly added dropwise to a solution of cyclopentanone (4.21 g, 50.0 mmol, 1.00 equiv.) and 0.6 M lanthanum chloride bis(lithium chloride) complex solution (40.0 mL, 4.13 g, 12.5 mmol, 0.25 equiv.) in tetrahydrofuran at −78° C. The solution was warmed up gradually to room temperature while stirring overnight. Saturated aqueous ammonium chloride solution (20 mL) was added to the reaction mixture, and the phases were separated and diethyl ether extracted. The combined organic phases were dried over sodium sulfate and the solvent was removed under reduced pressure. The crude product was purified by column chromatography on silica gel with petroleum ether/ethyl acetate (10:1) as eluent, 5.46 g (70%) of the product were obtained as a yellow oil. —$R_f$=0.24 (petroleum ether/ethyl acetate 10:1).—$^1$H-NMR (300 MHz, CDCl$_3$): δ=1.74-1.86 (m, 3H, OH+CH$_2$), 1.52-1.66 (m, 8H, 4×CH$_2$), 1.26-1.43 (m, 4H, 2×CH$_2$), 0.91 (t, $^3$J=7.0 Hz, 3H, CH$_3$).—$^{13}$C-NMR (75 MHz, CDCl$_3$): δ=82.7 (C$_q$—OH), 41.4 (CH$_2$), 39.8 (2×CH$_2$), 27.1 (CH$_2$), 24.0 (2×CH$_2$), 23.5 (CH$_2$), 14.3 (CH$_2$).—FTIR: ṽ=3376, 2954, 2871, 1696, 1634, 988 cm$^{-1}$.—MS (EI), m/z (%): 142 (6) [M$^+$], 113 (57) [(C$_7$H$_{13}$O)$^+$], 110 (23) [(C$_7$H$_{13}$O)$^+$], 85 (100) [(C$_5$H$_9$O)$^+$], 85 (100) [(C$_5$H$_9$O)$^+$], 58 (29).—HRMS (C$_9$H$_{16}$O): calc. 142.1358, found 142.1345.

1.9 2-Methyloct-3-yn-2-ol

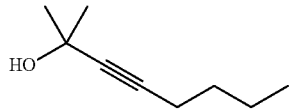

A 1.6 M n-butyllithium solution in hexane (34.4 mL, 3.52 g, 55.0 mmol, 1.10 equiv.) was slowly added dropwise to a solution of 1-hexyne (4.11 g, 50.0 mmol, 1.00 equiv.) in tetrahydrofuran (50 mL) at −78° C. After one hour, the reaction mixture was warmed to room temperature and then cooled back to −78° C. Then acetone (3.49 g, 60.0 mmol, 1.20 equiv.) was slowly added dropwise. The solution was warmed up gradually to room temperature while stirring overnight. Water (20 mL) was added to the reaction mixture, and the organic phase was washed three times with 20 mL each time of water. The combined organic phases were dried over magnesium sulfate and the solvent was removed under reduced pressure. The crude product was purified by column chromatography on silica gel with petroleum ether/ethyl acetate (10:1) as eluent. 5.47 g (78%) of the product were obtained as a clear oil. —$R_f$=0.32 (petroleum ether/ethyl acetate 10:1).—$^1$H-NMR (300 MHz, CDCl$_3$): δ=2.17 (t, $^3$J=6.9 Hz, 2H, CH$_2$), 1.96 (bs, 1H, OH), 1.32-1.52 (m, 4H, 2×CH$_2$), 1.48 (s, 6H, 2×CH$_3$), 0.89 (t, $^3$J=7.0 Hz, 3H, CH$_3$), —$^{13}$C-NMR (75 MHz, CDCl$_3$): δ=85.2 (C$_q$—C), 82.7 (C—CH$_2$), 65.4 (C$_q$—OH), 31.9 (2×CH$_3$), 30.9 (CH$_2$), 22.0 (CH$_2$), 18.03 (CH$_2$), 13.7 (CH$_3$).—FTIR: ṽ=3354, 2978, 2934, 2871, 2235, 1462, 1362, 1238, 1163, 944, 554 cm$^{-1}$.—MS (EI), m/z (%); 140 (1) [M$^+$], 125 (100) [(C$_8$H$_{13}$O)$^+$], 43 (100) [(C$_3$H$_7$)+].—HRMS (C$_9$H$_{16}$O): calc. 140.1201, found 140.1197.

1.10 1-(Hex-1-yn-1-yl)cyclohexanol

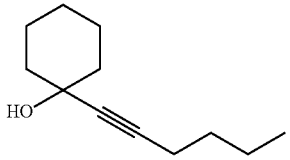

A 1.6 M n-butyllithium solution in hexane (34.4 mL, 3.52 g, 55.0 mmol, 1.10 equiv.) was slowly added dropwise to a solution of 1-hexyne (4.11 g, 50.0 mmol, 1.00 equiv.) in tetrahydrofuran (50 mL) at −78° C. After one hour, the reaction mixture was warmed to room temperature and then cooled back to −78° C. Then cyclohexanone (5.89 g, 60.0 mmol, 1.20 equiv.) was slowly added dropwise. The solution was warmed up gradually to room temperature while stirring overnight. Water (20 mL) was added to the reaction mixture, and the organic phase was washed three times with 20 mL each time of water. The combined organic phases were dried over magnesium sulfate and the solvent was removed under reduced pressure. The crude product was purified by column chromatography on silica gel with petroleum ether/ethyl acetate (10:1) as eluent. 8.21 g (91%) of the product were obtained as a yellow oil. —$R_f$=0.23 (petroleum ether/ethyl acetate 10:1).—$^1$H-NMR (300 MHz, CDCl$_3$): δ=2.21 (t, $^3$J=6.9 Hz, 2H, CH$_2$), 1.80-1.91 (m, 2H, CH$_2$), 1.77 (s, 1H, OH), 1.60-1.72 (m, 2H, CH$_2$), 1.23-1.58 (m, 10H, 5×CH$_2$), 0.90 (t, $^3$J=7.2 Hz, 3H, CH$_3$).—$^{13}$C-NMR (75 MHz, CDCl$_3$): δ=84.8 (C$_q$—C), 84.0 (C—CH$_2$), 68.9 (C$_q$—OH), 40.4 (2×CH$_2$), 31.0 (CH$_2$), 25.4 (CH$_2$), 23.6 (2×CH$_2$), 22.0 (CH$_2$), 18.5 (CH$_2$), 13.7 (CH$_3$).—FTIR: ṽ=3362, 2929, 2859, 1447, 1061, 963 cm$^{-1}$.—MS (EI), m/z (%): 180 (18) [M$^+$], 137 (100) [(C$_9$H$_{13}$O)$^+$].—HRMS (C$_{11}$H$_{18}$O): calc. 180.1514, found 180.1521.

1.11 9-Methylheptadecan-9-ol

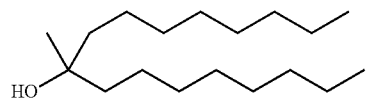 [SMILES: CCCCCCCCC(C)(O)CCCCCCCC]

A solution of 1-bromooctane (19.3 g, 100 mmol, 1.00 equiv.) in tetrahydrofuran (100 mL) was added dropwise to a suspension of magnesium turnings (2.67 g, 110 mmol, 1.10 equiv.) in tetrahydrofuran (10 mL) and then stirred at 80° C. for 6 hours. Thereafter, a solution of ethyl acetate (2.20 g, 50 mmol, 0.50 equiv.) in tetrahydrofuran (80 mL) was added dropwise and the mixture was stirred at 80° C. for a further 5 hours. The reaction mixture was added a saturated ammonium chloride solution (100 mL) and extracted with diethyl ether (30 mL). The combined organic phases were dried over magnesium sulfate and the solvent was removed under reduced pressure. The crude product was purified by column chromatography on silica gel with petroleum ether/ethyl acetate (20:1) as eluent. 5.86 g (44%) of the product were obtained as a yellow oil. —$R_f$=0.18 (petroleum ether/ethyl acetate 20:1).—$^1$H-NMR (300 MHz, CDCl$_3$): δ=1.40-1.46 (m, 4H, 2×CH$_2$), 1.23-1.35 (m, 25H, 12×CH$_2$+OH), 1.14 (s, 3H, CH$_3$), 0.88 (t, $^3$J=6.6 Hz, 6H, 2×CH$_3$).—$^{13}$C-NMR (75 MHz, CDCl$_3$): δ=73.0 (C$_{ar}$—OH), 42.0 (2×CH$_2$), 32.1 (2×CH$_2$), 30.4 (2×CH$_2$), 29.8 (2×CH$_2$), 29.5 (2×CH$_2$), 27.1 (CH$_3$), 24.1 (2×CH$_2$), 22.8 (2×CH$_2$), 14.3 (2×CH$_3$).—MS (EI), m/z (%): 270 (1) [M$^+$], 255 (50) [(C$_{17}$H$_{35}$O)$^+$], 157 (100) [(C$_{10}$H$_{21}$O)$^+$].—HRMS (C$_{18}$H$_{38}$O): calc. 270.2923, found 270.2894.

Synthesis of the Imidazole Esters:

General Procedure for Preparation of Imidazole Esters (GP 1):

A suspension of the corresponding alcohol (1.00 equiv.), 1,1-carbonyldiimidazole (1.10 equiv.) and potassium hydroxide (0.01 equiv.) in toluene (5.0 mL/mmol alcohol) was stirred at 60° C. for 18 h. The solvent was removed under reduced pressure and the remaining residue was taken up again with dichloromethane (50 The organic phase was washed three times with 50 mL each time of water and dried over magnesium sulfate, and the solvent was removed under reduced pressure. The crude product was purified by column chromatography on silica gel with petroleum ether/ethyl acetate mixtures as eluent.

1.12 2-Methylhexan-2-yl 1H-Imidazole-1-carboxylate

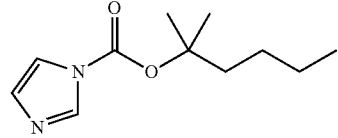

The synthesis was conducted proceeding from 2-methylhexan-2-ol (9.30 g, 80.0 mmol, 1.00 equiv.), 1,1-carbonyldiimidazole (15.7 g, 88.0 mmol, 1.10 equiv.) and potassium hydroxide (45.0 mg, 800 μmol, 0.01 equiv.) according to GP 1. After purification by column chromatography (silica gel, petroleum ether/ethyl acetate 5:1), 11.7 g (70%) of the imidazole ester were obtained as a clear liquid. —$R_f$=0.18

(petroleum ether/ethyl acetate 5:1).—$^1$H-NMR (300 MHz, CDCl$_3$): δ=8.04 (s, 1H, H$_{ar}$), 7.34 (s, 1H, H$_{ar}$), 7.01 (s, 1H, H$_{ar}$), 1.83-1.89 (m, 2H, CH$_2$), 1.58 (s, 6H, 2×CH$_3$), 1.30-1.38 (m, 4H, 2×CH$_2$), 0.89-0.92 (m, 3H, CH$_3$).—$^{13}$C-NMR (75 MHz, CDCl$_3$): δ=147.1 (C=O), 137.2 (C$_{ar}$H), 130.4 (C$_{ar}$H), 117.2 (C$_{ar}$H), 88.1 (O—C$_q$), 40.6 (CH$_2$), 26.2 (CH$_2$), 25.9 (2×CH$_3$), 22.6 (CH$_2$), 14.0 (CH$_3$).—FTIR: $\tilde{v}$=1752 cm$^{-1}$.—MS (EI), m/z (%): 210 (10) [M$^+$], 153 (18) [(C$_7$H$_9$N$_2$O$_2$)$^+$], 99 (100) [(C$_7$H$_{15}$)$^+$], 95 (45) [(C$_4$H$_3$N$_2$O)$^+$].—HRMS (C$_{11}$H$_{18}$N$_2$O$_2$): calc. 210.1368, found 210.1355.

1.13 1-Butylcyclopentyl 1H-imidazole-1-carboxylate

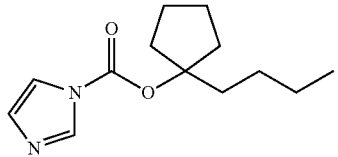 [SMILES: CCCCC1(OC(=O)n2ccnc2)CCCC1]

The synthesis was conducted proceeding from 1-butylcyclopentanol (2.13 g, 15.0 mmol, 1.00 equiv.), 1,1-carbonyldiimidazole (3.80 g, 18.8 mmol, 1.10 equiv.) and potassium hydroxide (8.00 mg, 150 μmol, 0.01 equiv.) according to GP 1. After purification by column chromatography (silica gel, petroleum ether/ethyl acetate 5:1), 1.04 g (29%) of the imidazole ester were obtained as a clear liquid. —R$_f$=0.19 (petroleum ether/ethyl acetate 5:1).—$^1$H-NMR (300 MHz, CDCl$_3$): δ=8.07 (s, 1H, C$_{ar}$H), 7.37 (s, 1H, C$_{ar}$H), 7.04 (s, 1H, C$_{ar}$H), 2.23-2.34 (m, 2H, CH$_2$), 2.04-2.10 (m, 2H, CH$_2$), 1.66-1.84 (m, 6H, 3×CH$_2$), 1.27-1.37 (m, 4H, 2×CH$_2$), 0.89 (t, $^3$J=7.1 Hz, 3H, CH$_3$).—$^{13}$C-NMR (75 MHz, CDCl$_3$): δ=145.4 (C=O), 137.2 (C$_{ar}$H), 130.5 (C$_{ar}$H), 117.2 (C$_{ar}$H), 98.8 (O—C$_q$), 37.6 (2×CH$_2$), 36.8 (CH$_2$), 26.8 (CH$_2$), 24.0 (2×CH$_2$), 23.0 (CH$_2$), 14.1 (CH$_3$).—FTIR: $\tilde{v}$=2959, 2872, 1752, 1469, 1382, 1286, 1239, 1171, 999, 772 cm$^{-1}$.—MS (ESI), m/z (%): 275 [(M+K)$^+$], 259 [(M+Na)$^+$], 236 [M$^+$].—HRMS (C$_{13}$H$_{20}$N$_2$O$_2$Na): calc. 259.1422, found 259.1419.—HRMS (C$_{13}$H$_{20}$N$_2$K): calc. 275.1162, found 275.1159.

1.14 2-Methyloct-3-yn-2-yl 1H-imidazole-1-carboxylate

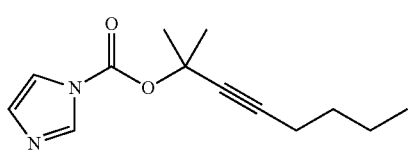 [SMILES: CCCCC#CC(C)(C)OC(=O)n1ccnc1]

The synthesis was conducted proceeding from 2-methyloct-3-yn-2-ol (1.01 g, 7.20 mmol, 1.00 equiv.), 1,1-carbonyldiimidazole (1.41 g, 7.92 mmol, 1.10 equiv.) and potassium hydroxide (4.00 mg, 72.0 μmol, 0.01 equiv.) according to GP 1. After purification by column chromatography (silica gel, petroleum ether/ethyl acetate 10:1), 1.25 g (74%) of the imidazole ester were obtained as a clear liquid. —R$_f$=0.14 (petroleum ether/ethyl acetate 10:1).—$^1$H-NMR (300 MHz, CDCl$_3$): δ=8.08 (s, 1H, H$_{ar}$), 7.38 (s, 1H, H$_{ar}$), 7.03 (s, 1H, H$_{ar}$), 2.21 (t, $^3$J=7.0 Hz, 2H, CH$_2$), 1.79 (s, 6H, 2×CH$_3$), 1.32-1.53 (m, 4H, 2×CH$_2$), 0.89 (t, $^3$J=7.2 Hz, 3H, CH$_3$).—$^{13}$C-NMR (75 MHz, CDCl$_3$): δ=146.7 (C=O), 137.3 (C$_{ar}$H), 130.5 (C$_{ar}$H), 117.3 (C$_{ar}$H), 87.3 (C$_q$—C), 79.8 (C—CH$_2$), 77.7 (O—C$_q$), 30.6 (CH$_2$), 29.5 (2×CH$_3$), 22.0 (CH$_2$), 18.5 (CH$_2$), 13.7 (CH$_3$).—FTIR: $\tilde{v}$=2989, 2933, 2689, 2247, 163, 1468, 1379, 1291, 1241, 1125, 1091, 998, 839, 769, 649 cm$^{-1}$.—MS (EI), m/z (%): 234 (4) [M$^+$], 123 (100) [(C$_9$H$_{15}$)$^+$], 81 (71) [(C$_6$H$_9$)$^+$].—HRMS (C$_{13}$H$_{18}$N$_2$O$_2$): calc. 234.1368, found 234.1366.

1.15 1-(Hex-1-yn-1yl)cyclohexyl 1H-imidazole-1-carboxylate

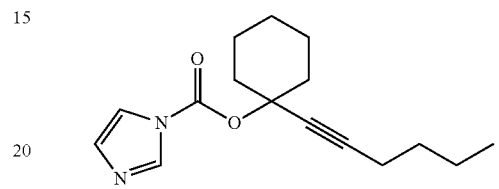

The synthesis was conducted proceeding from 1-(hex-1-yn-1-yl)cyclohexanol (4.06 g, 22.5 mmol, 1.00 equiv.), 1,1-carbonyldiimidazole (4.41 g, 24.8 mmol, 1.10 equiv.) and potassium hydroxide (13.0 mg, 225 μmol, 0.01 equiv.) according to GP 1. After purification by column chromatography (silica gel, petroleum ether/ethyl acetate 5:1), 5.24 g (85%) of the imidazole ester were obtained as a colorless solid. —R$_f$=0.16 (petroleum ether/ethyl acetate 5:1).—$^1$H-NMR (300 MHz, CDCl$_3$): δ=8.10 (s, 1H, H$_{ar}$), 7.40 (s, 1H, H$_{ar}$), 7.04 (s, 1H, H$_{ar}$), 2.17-2.28 (m, 4H, 2×CH$_2$), 1.94-2.04 (m, 2H, CH$_2$), 1.30-1.71 (m, 10H, 5×CH$_2$), 0.90 (t, $^3$J=7.2 Hz, 3H, CH$_3$).—$^{13}$C-NMR (75 MHz, CDCl$_3$): δ=146.3 (C=O), 137.2 (C$_{ar}$H), 130.4 (C$_{ar}$H), 117.2 (C$_{ar}$H), 89.0 (C$_q$—C), 81.2 (C—C), 78.5 (C$_q$), 37.5 (2×CH$_2$), 30.6 (CH$_2$), 25.0 (CH$_2$), 22.9 (2×CH$_2$), 22.0 (CH$_2$), 18.5 (CH$_2$), 13.6 (CH$_3$).—FTIR: $\tilde{v}$=2934, 2860, 2240, 1763, 1467, 1378, 1283, 1234, 1167, 1092, 996, 893, 830, 765, 742, 649 cm$^{-1}$.—MS (ESI), m/z (%): 313 [(M+K)$^+$], 297 [(M+Na)$^+$].—HRMS (C$_{16}$H$_{22}$N$_2$O$_2$Na): calc. 297.1579, found 297.1574.

1.16 9-Methylheptadecan-9-yl 1H-imidazole-1-carboxylate

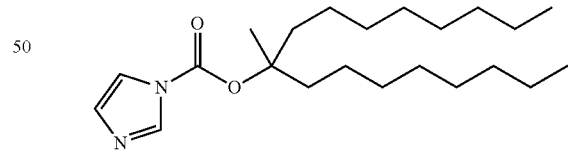

The synthesis was conducted proceeding from 9-methylheptadecan-9-ol (5.82 g, 21.5 mmol, 1.00 equiv.), 1,1-carbonyldiimidazole (5.45 g, 26.9 mmol, 1.10 equiv.) and potassium hydroxide (12.0 mg, 215 μmol, 0.01 equiv.) according to GP 1. After purification by column chromatography (silica gel, petroleum ether/ethyl acetate 10:1), 6.71 g (86%) of the imidazole ester were obtained as a clear liquid. —R$_f$=0.09 (petroleum ether/ethyl acetate 10:1).—$^1$H-NMR (300 MHz, CDCl$_3$): δ8.05 (s, 1H, H$_{ar}$), 7.35 (s, 1H, H$_{ar}$), 7.03 (s, 1H, H$_{ar}$), 1.79-1.99 (m, 4H, 2×CH$_2$), 1.56 (s, 3H, CH$_3$), 1.23-1.36 (m, 24H, 12×CH$_2$), 0.87 (t, $^3$J=6.7 Hz, 6H, 2×CH$_3$), —$^{13}$C-NMR (75 MHz, CDCl$_3$): δ=147.1

(C=O), 137.2 (C$_{ar}$H), 130.4 (C$_{ar}$H), 117.2 (C$_{ar}$H), 90.8 (C$_q$) 38.3 (2×CH$_2$), 31.9 (2×CH$_2$), 30.0 (2×CH$_2$), 29.6 (2×CH$_2$), 29.3 (2×CH$_2$), 23.8 (2×CH$_2$), 23.7 (CH$_3$), 22.8 (2×CH$_2$), 14.2 (2×CH$_3$).—FTIR: $\tilde{v}$=2925, 2854, 1753, 1466, 1380, 1317, 1281, 1237, 1187, 1091, 999, 835, 771, 742, 649 cm$^{-1}$.—MS (ESI), m/z (%): 730 [(M–H–M)$^+$], 403 [(M+K)$^+$], 387 [(M+Na)$^+$].—HRMS (C$_{22}$H$_{40}$N$_2$O$_2$Na): calc. 387.2987, found 387.2987.

Synthesis of the benzo[lmn][3,8]phenanthroline-1,3, 6,8-tetraone-4,9-diyl Unit 1.17
2,7-Dibromonaphthalene-1,8:4,5-tetracarboxylic dianhydride

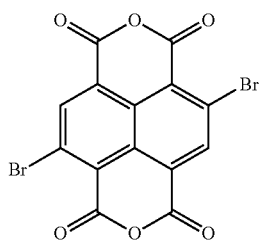

(1.17)

Naphthalene-1,4,5,8-tetracarboxylic dianhydride (20 mmol, 1 eq) was dissolved in conc. H$_2$SO$_4$ (97%, 250 mL). Dibromoisocyanuric acid (40 mmol, 2 eq) was added. The setup was covered with aluminum foil and stirred at room temperature for 7 days. The reaction solution was poured cautiously under 1.5 kg of ice and stirred at room temperature for 1 hour. The suspension was left to stand for one hour, and the precipitate was removed by means of centrifugation, washed three times each with water and methanol and dried under reduced pressure. The solid obtained was suspended in fresh acetic anhydride and stirred under argon at 120° C. for 5 hours. The mixture was cooled down to room temperature and stored in a refrigerator overnight. The precipitate was filtered off, washed with methanol and dried under reduced pressure. 4.80 g (56%) of a yellow solid were obtained. It was apparent from derivatization reactions that this crude product has roughly a strength of 50%.

IR (v in cm$^{-1}$): 1778 (s, O—C=O), 1747 (vs, O—C=O), 1568 (m).—MS (EI$^+$), m/z: 268.0 [(C$_{14}$H$_4$O$_6$)$^+$], 345.9 [(C$_{14}$H$_3$$^{79}$BrO$_6$)$^+$], 423.8 [(C$_{14}$H$_2$$^{79}$Br$_2$O$_6$)$^+$], 501.7 [(C$_{14}$H$_1$$^{79}$Br$_3$O$_6$)$^+$].

1.18
2,7-Dibromonaphthalene-1,8:4,5-tetracarboximide N,N-bis(hexane-6,1-diyl) dipropionate

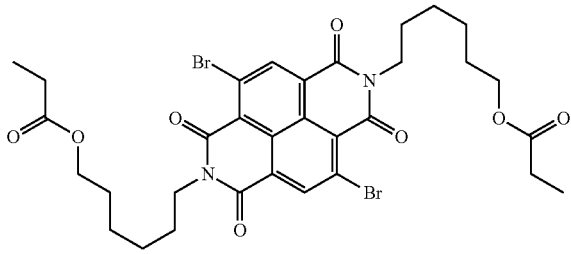

(1.18)

2,7-Dibromonaphthalene-1,8:4,5-tetracarboxylic dianhydride (2.13 g of crude product, 5 mmol) and 6-aminohexanol (1.46 g, 12.5 mmol) were suspended in 25 mL of a mixture of propionic acid and o-xylene (1:1, v:v) and heated under reflux overnight. The reaction mixture was cooled down very gradually to room temperature. The precipitate was filtered off and washed with acetic acid. The solid obtained was then recrystallized from 30 mL of propionic acid:o-xylene (1:1, v:v). The precipitate was filtered off, washed with acetic acid and methanol, and dried under reduced pressure. The crude product was purified by column chromatography on silica gel with a mixture of chloroform and toluene (1:1, v:v) with 3% THF as eluent. 1.13 g (30% of theory for 100% pure reactant) of the product were obtained as a yellow solid. —R$_f$=0.32 (chloroform:toluene (1:1) 3% THF).—$^1$H-NMR (300 MHz, CDCl$_3$): δ=8.99 (s, 2H, 2×CH$_{ar}$), 4.19 (t, $^3$J=7.7 Hz, 4H, 2×N—CH$_2$), 4.06 (t, $^3$J=6.6 Hz, 4H, 2×O—CH$_2$), 2.32 (q, $^3$J=7.6 Hz, 4H, (C=O)CH$_2$), 1.70-1.80 (m, 4H, CH$_2$), 1.65 (m, 4H, CH$_2$), 1.40-1.50 (m, 8H, CH$_2$), 1.13 (t, $^3$J=7.6 Hz, 6H, CH$_3$).—$^{13}$C-NMR (75 MHz, CDCl$_3$): δ=174.6 (2×O—C=O), 160.7 (2×N—C=O), 160.6 (2×N—C=O), 139.1 (2×C$_{ar}$H), 128.3 (2×C$_{q-ar}$), 127.7 (2×C$_{q-ar}$), 124.0 (2×C$_{q-ar}$), 64.2 (CH$_2$—O), 41.4 (CH$_2$—N), 28.5 (CH$_2$), 27.8 (CH$_2$), 27.6 ((C=O)—CH$_2$), 26.6 (CH$_2$), 25.6 (CH$_2$), 9.2 (CH$_3$).—HR-MS (DART, NH$_4$$^+$-adduct, [C$_{32}$H$_{40}$Br$_2$N$_3$O$_8$]$^+$): calc. 752.1177, found 752.1166.—IR: (v in cm$^{-1}$): 1732 (s, O—C=O), 1701 (s, N—C=O), 1649 (vs, N—C=O), 1559 (m).

1.19 2,7-Bis(2'-thiophenyl)naphthalene-1,8:4,5-tetracarboximide[N,N]-bis(hexane-6,1-diyl) dipropionate

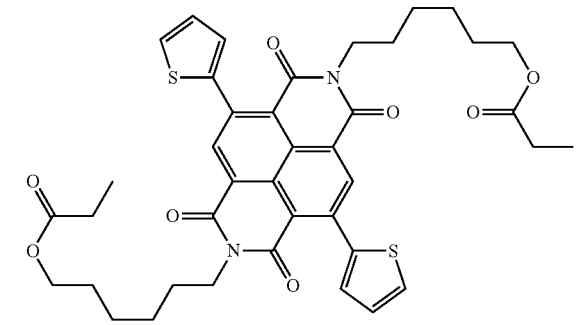

(1.19)

2,7-Dibromonaphthalene-1,8:4,5-tetracarboximide[N,N]-bis(hexane-6,1-diyl) dipropionate (368 mg, 0.5 mmol) and 2-(tributylstannyl)thiophene (560 mg, 1.5 mmol) were dissolved in 2.5 mL of dry DMF and freed of oxygen by means of vacuum degassing three times.

Tetrakis(triphenylphosphine)palladium(0) (29 mg, 0.05 eq) was added in an argon counterflow and the reaction solution was stirred at 100° C. for 14 hours. The reaction solution was cooled down to room temperature and then diluted with 35 mL of methanol and stirred for 2 hours. Precipitates were filtered off, washed with MeOH and dried under reduced pressure. The crude product was purified by column chromatography on silica gel with a mixture of chloroform and toluene (1:1, v:v) with 3% THF as eluent. 330 mg (90% of theory) of the product were obtained as a red solid.

—$R_f$=0.33 (chloroform:toluene (1:1)+3% THF).—$^1$H-NMR (300 MHz, CDCl$_3$): δ=8.75 (a, 2H, 2×CH$_{ar}$), 7.58 (dd, $^3$J=5.1 Hz, $^4$J=1.2 Hz, 2H, CH$_{ar}$), 7.29 (dd, $^3$J=3.6 Hz, $^4$J=1.2 Hz, 2H, CH$_{ar}$), 7.21 (dd, $^3$J=5.1 Hz, $^3$J=3.6 Hz, 2H, CH$_{ar}$), 4.11 (t, $^3$J=7.7 Hz, 4H, 2×N—CH$_2$), 4.04 (t, $^3$J=6.6 Hz, 4H, 2×O—CH$_2$), 2.32 (q, $^3$J=7.6 Hz, 4H, (C=O)CH$_2$), 1.58-1.73 (m, 8H, CH$_2$), 1.36-1.43 (m, 8H, CH$_2$), 1.12 (t, $^3$J=7.6 Hz, 6H, CH$_3$). —$^{13}$C-NMR (75 MHz, CDCl$_3$): δ=174.6 (2×O—C=O), 162.1 (2×N—C=O), 161.9 (2×N—C=O), 140.6 (2×C$_q$—S), 140.3 (2×C$_q$), 136.7 (2×C$_{ar}$H), 128.2 (2×S—CH$_{ar}$), 128.0 (2×C$_{ar}$H), 127.5 (2×C$_q$), 127.4 (2×C$_{ar}$H), 125.3 (2×(C=O)—C$_{q-ar}$), 123.4 (2×(C=O)—C$_{q-ar}$), 64.2 (CH$_2$—O), 40.9 (CH$_2$—N), 28.5 (CH$_2$), 27.8 (CH$_2$), 27.6 ((C=O)—CH$_2$), 26.6 (CH$_2$), 25.6 (CH$_2$), 9.1 (CH$_3$).—HR-MS (DART, NH$_4^+$-adduct, [C$_{40}$H$_{46}$N$_3$O$_8$S$_2$]$^+$): calc. 760.2721, found 760.2723.

1.20 2,7-Bis(4'-hexyl-2'-thiophenyl)naphthalene-1,8: 4,5-tetracarboximide[N,N]-bis(hexane-6,1-diyl) dipropionate (1.20)

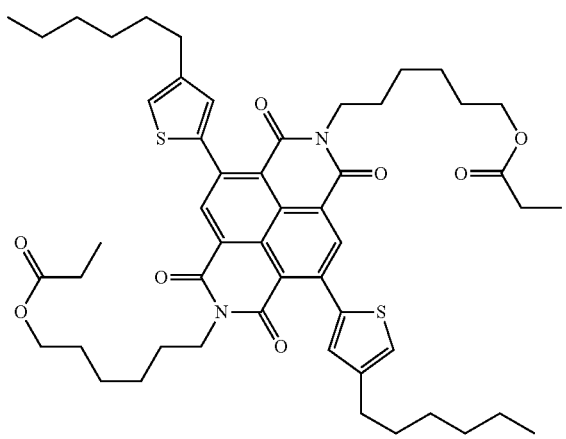

2,7-Dibromonaphthalene-1,8:4,5-tetracarboximide[N,N]-bis(hexane-6,1-diyl) dipropionate (368 mg, 0.5 mmol) and 2-(tributylstannyl)-4-hexylthiophene (1.2 g, 5 mmol, 60% strength) were dissolved in 5 mL of dry DMF and freed of oxygen by means of vacuum degassing three times. Tetrakis(triphenylphosphine)palladium(0) (46 mg, 0.08 eq) was added in an argon counterflow and the reaction solution was stirred at 100° C. for 2 hours. The reaction solution was cooled down to room temperature and then diluted with 50 mL of methanol, stirred vigorously for 3 hours and then stored in a refrigerator overnight. Precipitates were filtered off, washed with MeOH and dried under reduced pressure. The crude product was purified by column chromatography on silica gel with a mixture of Chloroform and toluene (1:1, v:v) with 3% THF as eluent. 349 mg (77% of theory) of the product were obtained as a red solid.

—$R_f$=0.35 (chloroform:toluene (1:1)+3% THF), —$^1$H-NMR (300 MHz, CDCl$_3$): δ=8.74 (s, 2H, 2×CH$_{ar}$), 7.16 (s, 2H, CH$_{ar}$), 7.13 (s, 2H, CH$_{ar}$), 4.11 (t, $^3$J=7.7 Hz, 4H, 2×N—CH$_2$), 4.04 (t, $^3$J=6.6 Hz, 4H, 2×O—CH$_2$), 2.69 (t, $^3$J=7.7 Hz, 4H, 2×C$_q$—CH$_2$), 2.30 (q, $^3$J=7.6 Hz, 4H, (C=O)CH$_2$), 1.66-1.72 (m, 8H, CH$_2$), 1.59-1.64 (m, 6H, CH$_2$), 1.36-1.43 (m, 10H, CH$_2$), 1.30-1.36 (m, 8H, CH$_2$), 1.12 (t, $^3$J=7.6 Hz, 6H, CH$_3$), 0.91 (t, $^3$J=6.9 Hz, 6H, CH$_3$).—$^{13}$C-NMR (75 MHz, CDCl$_3$): δ=174.6 (2×O—C=O), 162.2 (2×N—C=O), 162.0 (2×N—C=O), 143.7 (2×C$_q$), 140.6 (2×C$_{q\ S}$), 140.3 (2×C$_q$), 136.7 (2×CH$_{ar}$), 129.7 (2×CH$_{ar}$), 127.3 (2×C$_q$), 125.2 (2×(C=O)—C$_{q-ar}$), 123.0 (2×(C=O)—C$_{q-ar}$), 122.8 (2×CH$_{ar}$), 64.2 (CH$_2$—O), 40.9 (CH$_2$—N), 31.7 (C$_q$—CH$_2$), 30.5 (CH$_2$), 30.3 (CH$_2$), 29.0 (CH$_2$), 28.5 (CH$_2$), 27.8 (CH$_2$), 27.6 ((C=O)—CH$_2$), 26.6 (CH$_2$), 25.6 (CH$_2$), 22.6 (CH$_2$), 14.1 (CH$_3$), 9.1 (CH$_3$).—HR-MS (ESI, Na$^+$-adduct, [C$_{52}$H$_{66}$N$_2$NaO$_8$S$_2$]$^+$): calc. 933.4152, found 933.4160.

1.21 2,7-Bis(5'-bromo-2'-thiophenyl)naphthalene-1, 8:4,5-tetracarboximide[N,N]-bis(hexane-6,1-diyl) dipropionate (1.21)

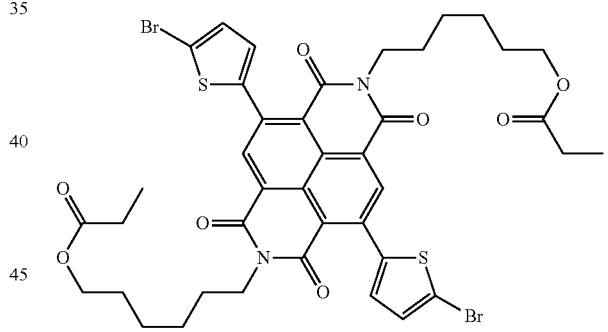

2,7-Bis(2'-thiophenyl)naphthalene-1,8:4,5-tetracarboximide[N,N]-bis(hexane-6,1-diyl) dipropionate (330 mg, 0.44 mmol) was initially charged in a dry 50 mL Schlenk flask and an argon atmosphere was generated, 22 mL of dry N,N-dimethylformamide and N-bromosuccinimide (190 mg, 1.07 mmol) were added and the reaction mixture was stirred in the dark at room temperature for 5 days. The solvent was then removed under reduced pressure and the residue was dissolved in 5 mL of chloroform. 30 mL of MeOH were added and the mixture was stirred vigorously for 3 hours. Precipitates were filtered off, washed with MeOH and dried under reduced pressure. The crude product was purified by column chromatography on silica gel with a mixture of chloroform and toluene (1:1, v:v) with 2.5% THF as eluent. 372 mg (93% of theory) of the product were obtained as a red solid. —$R_f$=0.30 (chloroform:toluene (1:1)+3% THF).—$^1$H-NMR (300 MHz, CDCl$_3$): δ=8.71 (s, 2H, 2×CH$_{ar}$), 7.16 (d, $^3$J=3.8 Hz, 2H, CH$_{ar}$), 7.07 (d, $^3$J=3.8 Hz, 2H, CH$_{ar}$), 4.12 (t, $^3$J=7.7 Hz, 4H, 2×N—CH$_2$), 4.05 (t, $^3$J=6.6 Hz, 4H, 2×O—CH$_2$), 2.30 (q, $^3$J=7.6 Hz, 4H, (C=O)CH$_2$), 1.58-1.73 (m, 8H, CH$_2$), 1.36-1.43 (m, 8H, CH$_2$), 1.12 (t, $^3$J=7.6 Hz, 6H, CH$_3$), $^{13}$C-NMR (75 MHz, CDCl$_3$): δ=174.6 (2×O—C=O), 161.9 (2×N—C=O), 161.8 (2×N—C=O), 141.9 (2×C$_q$—S), 139.1 (2×C$_q$), 136.5 (2×C$_{ar}$H), 130.2 (2×S—CH$_{ar}$), 128.8 (2×C$_{ar}$H), 127.5 (2×C$_q$), 125.6 (2×(C=O)—C$_{q-ar}$), 123.2 (2×(C=O)—C$_{q-ar}$), 115.4 (C$_{q-ar}$Br), 64.2 (CH$_2$—O), 41.0 (CH$_2$—N), 28.5 (CH$_2$), 27.8 (CH$_2$), 27.6 ((C=O)—CH$_2$), 26.6 (CH$_2$), 25.6 (CH$_2$), 9.1 (CH$_3$), —HR-MS (DART, NH$_4^+$-adduct, [C$_{40}$H$_{44}$Br$_2$N$_3$O$_8$S$_2$]$^+$): calc. 916.0931, found 916.0915.

1.22 2,7-Bis(5'-bromo-4'-hexyl-2'-thiophenyl)naphthalene-1,8:4,5-tetracarboximide[N,N]-bis(hexane-6,1-diyl) dipropionate

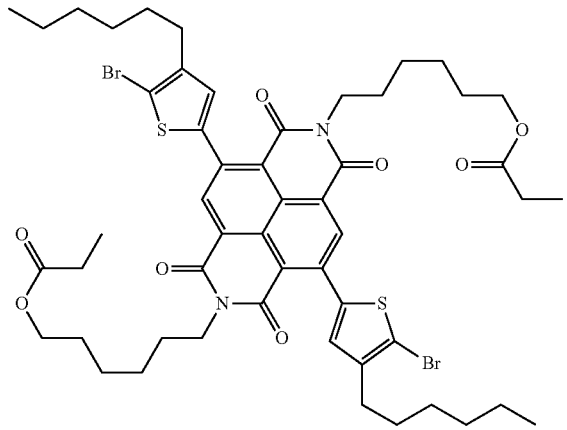

(1.22)

2,7-Bis(4'-hexyl-2'-thiophenyl)naphthalene-1,8:4,5-tetracarboximide[N,N]-bis(hexane-6,1-diyl) dipropionate (328 mg, 0.36 mmol) and N-bromosuccinimide (225 mg, 1.44 mmol) were initially charged in a dry 25 mL Schlenk flask and an argon atmosphere was generated. 15 mL of dry tetrahydrofuran were added and the reaction mixture was stirred in the dark at room temperature for 4 days. The solvent was then removed under reduced pressure, and the residue was dissolved in 5 mL of dichloromethane, applied to a short DCM-equilibrated silica gel column and washed cautiously with pure dichloromethane. The product was eluted with a solvent mixture of dichloromethane and tetrahydrofuran (100:2, v:v). Dark red fractions were combined and the solvent was removed. The crude product thus obtained was recrystallized twice from MeOH. 375 mg (97% of theory) of the product were obtained as a violet solid. —$R_f$=0.37 (chloroform:toluene (1:1)+3% THF).—$^1$H-NMR (300 MHz, CDCl$_3$): δ=8.71 (s, 2H, 2×CH$_{ar}$), 7.03 (s, 2H, CH$_{ar}$), 4.12 (t, $^3$J=7.7 Hz, 4H, 2×N—CH$_2$), 4.05 (t, 3 J=6.6 Hz, 4H, 2×O—CH$_2$), 2.64 (t, $^3$J=7.7 Hz, 4H, 2×C$_q$—CH$_2$), 2.30 (q, $^3$J=7.6 Hz, 4H, (C=O)CH$_2$), 1.60-1.71 (m, 14H, CH$_2$), 1.41 (s, 10H, CH$_2$), 1.34 (m, 8H, CH$_2$), 1.12 (t, $^3$J=7.6 Hz, 6H, CH$_3$), 0.91 (t, $^3$J=6.9 Hz, 6H, CH$_3$).—$^{13}$C-NMR (75 MHz, CDCl$_3$): δ=174.6 (2×O—C=O), 162.1 (2×N—C=O), 162.0 (2×N—C=O), 142.5 (2×C$_q$), 140.0 (2×C$_q$), 139.5 (2×C$_q$), 136.4 (2×CH$_{ar}$), 129.6 (2×CH$_{ar}$), 127.4 (2×C$_q$), 125.4 (2×(C=O)—C$_{q-ar}$), 122.9 (2×(C=O)—C$_q$), 112.5 (2×C$_{q-ar}$Br), 64.2 (CH$_2$—O), 41.0 (CH$_2$—N), 31.6 (C$_q$—CH$_2$), 29.7 (CH$_2$), 29.0 (CH$_2$), 28.5 (CH$_2$), 27.8 (CH$_2$), 27.6 ((C=O)—CH$_2$), 26.6 (CH$_2$), 25.6 (CH$_2$), 22.6 (CH$_2$), 14.1 (CH$_3$), 9.1 (CH$_3$).—HR-MS (ESI, Na$^+$-adduct, [C$_{52}$H$_{64}$Br$_2$N$_2$NaO$_8$S$_2$]$^+$): calc. 1089.2363, found 1089.2371.

1.23 2,7-Bis(5'-bromo-2'-thiophenyl)-[N,N]-bis(hexan-1-yl-6-ol)naphthalene-1,8:4,5-tetracarboximide

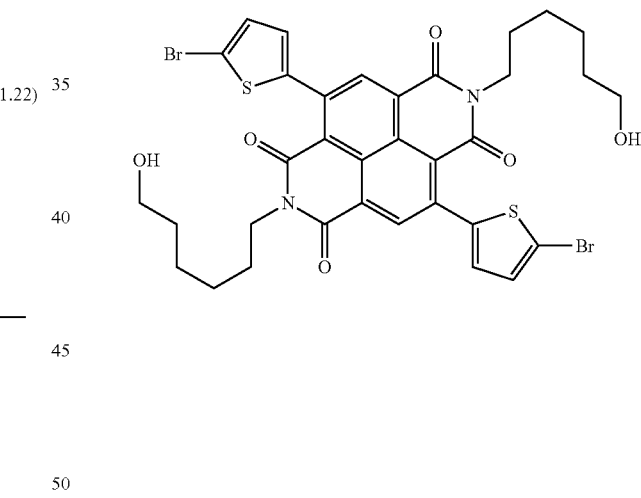

(1.23)

2,7-Bis(5'-bromo-4'-hexyl-2'-thiophenyl)naphthalene-1,8:4,5-tetracarboximide [N,N]-bis(hexane-6,1-diyl) dipropionate (360 mg, 0.4 mmol) was dissolved in a mixture of 16 mL of chloroform and 4 mL of MeOH, and 100 μL of concentrated hydrochloric acid were added. The apparatus was degassed and heated under reflux under argon for 18 hours, then cooled down gradually to room temperature and stored in a refrigerator for 3 hours. The precipitate was isolated and washed successively with a cold mixture of chloroform and methanol (1:1, v:v) and pure methanol. After drying under reduced pressure, 276 mg of a violet solid were obtained, which, because of its insolubility, was not purified any further (88% of theory).—M.p.: 226° C.—IR: (v in cm$^{-1}$): 3100-3300 (vbs, OH), 1698 (s, N—C=O), 1659 (vs, N—C=O), 1571 (m). HR-MS (MALI, DCTB matrix, [C$_{34}$H$_{33}$Br$_2$N$_2$O$_6$S$_2$]$^+$): calc. 787.01413, found 787.01419.

1.24 2,7-Bis(5'-bromo-4'-hexyl-2'-thiophenyl)-[N,N]-bis(hexan-1yl-6-ol)naphthalene-1,8:4,5-tetracarboximide

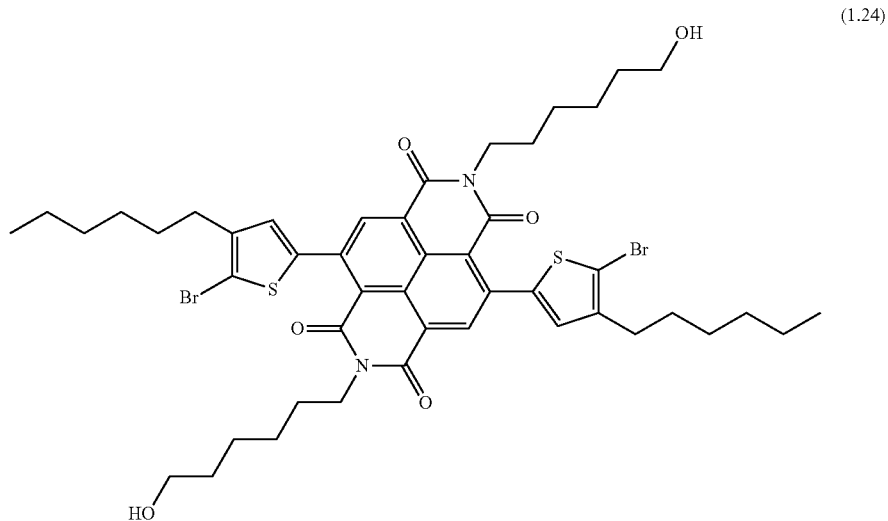 [SMILES: CCCCCCc1cc(-c2cc3c4c(c(-c5cc(CCCCCC)c(Br)s5)cc5c4c2C(=O)N(CCCCCCO)C5=O)C(=O)N(CCCCCCO)C3=O)sc1Br]

(1.24)

2,7-Bis(5'-bromo-4'-hexyl-2'-thiophenyl)naphthalene-1,8:4,5-tetracarboximide[N,N]-bis(hexane-6,1-diyl) dipropionate (374 mg, 0.35 mmol) was dissolved in a mixture of 16 mL of chloroform and 4 mL of MeOH, and 100 μL of concentrated hydrochloric acid were added. The apparatus was degassed, heated under reflux under argon for 8 hours and then cooled down gradually to room temperature. The solvent was removed under reduced pressure. The residue was suspended in 15 mL of MeOH, and the solids were filtered off and washed with MeOH. The violet solid was again partly dissolved in chloroform and the solvent was removed under reduced pressure. The crude product was purified by column chromatography on silica gel with a mixture of chloroform and toluene (1:1, v:v) with 5% ethanol as eluent. 330 mg (99% of theory) of the product were obtained as a violet solid. —$R_f$=0.14 (chloroform:toluene (1:1)+5% EtOH). —$^1$H-NMR (300 MHz, CDCl$_3$): δ=8.70 (s, 2H, 2×CH$_{ar}$), 7.03 (s, 2H, CH$_{ar}$), 4.12 (t, J=7.7 Hz, 4H, 2×N—CH$_2$), 3.63 (t, 3J=6.6 Hz, 4H, 2×O—CH$_2$), 2.64 (t, $^3$J=7.7 Hz, 4H, 2×C$_q$—CH$_2$), 1.60-1.73 (Ml, 8H, CH$_2$), 1.57 (m, 4H, CH$_2$), 1.37-1.44 (m, 12H, CH$_2$), 1.32-1.37 (m, 10H, CH$_2$), 0.91 (t, $^3$J=6.9 Hz, 6H, CH$_3$). $^{13}$C-NMR (75 MHz, CDCl$_3$): δ=162.1 (2×N—C=O), 162.0 (2×N—C=O), 142.5 (2×C$_q$), 140.0 (2×C$_q$), 139.5 (2×C$_q$), 136.4 (2×CH$_{ar}$), 129.6 (2×CH$_{ar}$), 127.4 (2×C$_q$), 125.4 (2 (C=O)—C$_{q-ar}$), 122.9 (2×(C=O)—C$_q$), 112.5 (2×C$_{qar}$Br), 62.8 (CH$_2$—O), 41.0 (CH$_2$—N), 32.6 (CH$_2$), 31.6 (C$_q$—CH$_2$), 29.7 (CH$_2$), 29.0 (CH$_2$), 27.9 (CH$_2$), 26.7 (CH$_2$), 25.3 (CH$_2$), 22.6 (CH$_2$), 14.1 (CH$_3$).—HR-MS (ESI, H$^+$-Addukt, [C$_{46}$H$_{57}$Br$_2$N$_2$O$_6$S$_2$]$^+$): calc. 955.2019, found 955.2025.

1.25 Bis(2-methylhexan-2-yl) dicarbonate

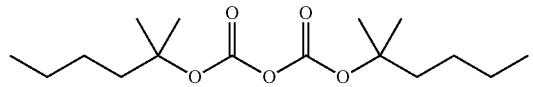

(1.25)

To a solution of 2-methyl-2-hexanol (15.1 g, 1.0 eq, 130 mmol) in 260 mL of a mixture of dry toluene and tetrahydrofuran in a ratio of 2:1 (v:v) were added stepwise, while cooling with ice, in a protective gas counterflow, 3.14 g of pulverulent sodium hydride (1.05 eq, 136 mmol). The reaction mixture was heated under reflux for 18 hours, in the course of which a majority of the solids dissolved. After cooling down to room temperature, the slightly cloudy solution was cooled to −78° C. and transferred gradually under protective gas into a large excess of solid CO$_2$ at about −100° C. The reaction mixture was warmed gradually to room temperature. For a further 2 hours, dry CO$_2$ was passed through the viscous reaction mixture. Subsequently, the reaction mixture was cooled back to 0° C. and catalytic amounts of DMF (51 μL, 0.005 eq, 0.6 mmol) were added, followed by oxalyl chloride (5.6 mL, 0.5 eq, 65 mmol) and catalytic amounts of benzyltrimethylammonium chloride (338 mg, 0.014 eq, 1.8 mmol) and pyridine (315 μL, 0.03 eq, 3.9 mmol). After the evolution of gas had ended, the reaction mixture was warmed to room temperature and stirred for 2 days. Subsequently, 35 mL of a one percent aqueous sulfuric acid solution were added. The organic phase was removed and washed with water. The aqueous phase was extracted three times with diethyl ether. The combined organic extracts were combined, dried with saturated sodium chloride solution and MgSO$_4$, and concentrated. The crude product was purified by column chromatography on silica with an eluent mixture of petroleum ether and ethyl acetate 20:1 (v:v). 7.01 g (37% of theory) of the desired product were kept as a colorless oil.—Rf=0.45 (petroleum ether/ethyl acetate 20:1).—$^1$H-NMR (300 MHz, CDCl$_3$): δ=1.82-1.75 (m, 4H, C$_q$—CH$_2$), 1.50 (s, 12H, C$_q$—CH$_3$), 1.36-1.28 (m, 8H, CH$_2$), 0.91 (t, 6H, C$_s$—CH$_3$).—$^{13}$C-NMR (75 MHz, CDCl$_3$): δ=146.7 (O—(C=O)—O), 87.5 (C$_q$), 40.0 (C$_q$—CH$_3$), 25.6 (CH$_2$), 25.2 (CH$_2$), 22.8 (CH$_2$), 13.9 (CH$_3$).—Elemental analysis: theory: C: 63.55, H: 10.00; found: C: 63.80, H: 9.98.

1.26 Tetrabutyl 2,7-bis(4'-hexylthiophen-2'-yl)naphthalene-1,4,5,8-tetracarboxylate

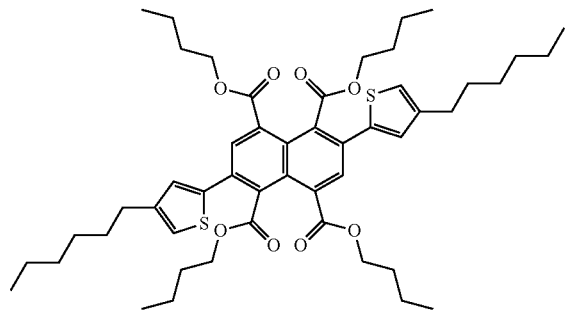

(1.26)

Tetrabutyl 2,7-dibromonaphthalene-1,4,5,8-tetracarboxylate (1.506 g, 2.2 mmol, 1.00 eq) and 4-hexyl-2-(tributylstannyl)thiophene (3.02 g, 6.6 mmol, 3 eq) were dissolved in 12 mL of dry N,N-dimethylformamide and degassed by the freeze-pump-thaw method three times.

Tetrakis(triphenylphosphine)palladium (114 mg, 0.1 mmol, 0.045 eq) was added and the reaction mixture was stirred at 105° C. for five hours under protective gas. To the mixture were added 45 mL of a 20 percent aqueous potassium fluoride solution, and the aqueous phase was extracted three times with 40 mL each time of methyl tert-butyl ether. The combined organic extracts were washed twice with water, dried with saturated sodium chloride solution and MgSO$_4$, and concentrated. The crude product was purified by column chromatography on silica with an eluent mixture of petroleum ether and dichloromethane in a ratio of 9:1→1:1→1:5 (v:v), 1.53 g (72% of theory) of the target substance were obtained as a viscous yellow oil. —Rf=0.34 (petroleum ether/ethyl acetate 15:1)—$^1$H-NMR (300.51 MHz, CDCl$_3$): δ [ppm]=7.95 (s, 2H, H$_{ar}$), 7.01 (d, $^4$J=1.1 Hz, 2H, H$_{ar}$), 6.89 (d, $^4$J=1.3 Hz, 2H, H$_{ar}$), 4.29 (t, $^3$J=6.8 Hz, 4H, CH$_2$), 4.02 (t, $^3$J=6.8 Hz, 4H, CH$_2$), 2.59 (t, $^3$J=7.8 Hz, 4H, CH$_2$), 1.77 (p, $^3$J=7.8 Hz, 4H, CH$_2$), 1.61-1.67 (m, 4H, CH$_2$), 1.26-1.53 (m, 20H, CH$_2$), 1.16 (m, 4H, CH$_2$) 0.97 (t, $^3$J=7.3 Hz, 6H, CH$_3$), 0.92 (t, $^3$J=8.0 Hz, 6H, CH$_3$), 0.82 (t, $^3$J=7.3 Hz, 6H, CH$_3$) APCI$^+$-MS: [M–BuO$^-$]$^+$ calc. m/z=787.37, found: 787.32.

1.27 Tetrabutyl 2,7-bis(5'-bromo-4'-hexylthiophen-2'-yl)naphthalene-1,4,5,8-tetracarboxylate

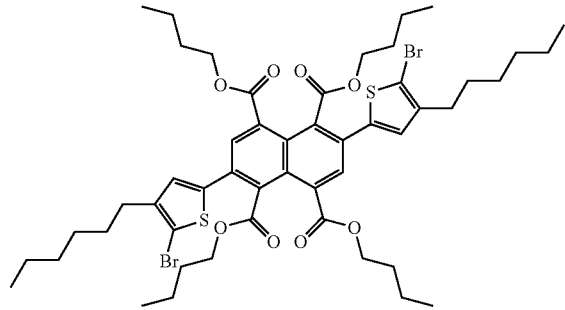

(1.27)

To a solution of 1.52 g of tetrabutyl 2,7-bis(4'-hexylthiophen-2'-yl)naphthalene-1,4,5,8-tetracarboxylate (1.77 mmol, 1.00 eq) in 95 mL of dry tetrahydrofuran were added 1.26 g of N-bromosuccinimide (7.08 mmol, 4.00 eq) under protective gas. The reaction solution was stirred with exclusion of light for two days. The solvent was removed under reduced pressure and the crude product was purified by column chromatography on silica with an eluent mixture of petroleum ether and dichloromethane in a ratio of 9:1→1:1→1:5 (v:v). 1.80 g (99% of theory) of the target substance were obtained as a yellow solid. —Rf=0.35 (petroleum ether:ethyl acetate 15:1)—$^1$H-NMR (300.51 MHz, CDCl$_3$): δ [ppm]=7.95 (s, 2H, H$_{ar}$), 7.01 (d, $^4$J=1.1 Hz, 2H, H$_{ar}$), 6.89 (d, $^4$J=1.3 Hz, 2H, H$_{ar}$), 4.29 (t, $^3$J=6.8 Hz, 4H, CH$_2$), 4.02 (t, $^3$J=6.8 Hz, 4H, CH$_2$), 2.59 (t, $^3$J=7.8 Hz, 4H, CH$_2$), 1.77 (p, $^3$J=7.8 Hz, 4H, CH$_2$), 1.61-1.67 (m, 4H, CH$_2$), 1.26-1.53 (m, 20H, CH$_2$), 1.16 (m, 4H, CH$_2$) 0.97 (t, $^3$J=7.3 Hz, 6H, CH$_3$), 0.92 (t, $^3$J=8.0 Hz, 6H, CH$_3$), 0.82 (t, $^3$J=7.3 Hz, 6H, CH$_3$). APCI$^+$-MS: [M–BuO$^-$]$^+$, C$_{46}$H$_{57}$Br$_2$O$_7$S$_2$$^+$, calculated: m/z=943.19:945.19:947.19 (1:2:1), found: 943.12: 945.08:947.03 (1:2:1).

1.28 2,7-bis(5'-bromo-4'-hexylthiophen-2'-yl)naphthalene-1,4,5,8-tetracarboxylic dianhydride

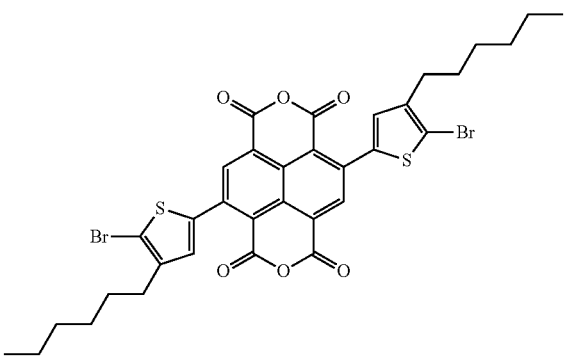

(1.28)

Tetrabutyl 2,7-bis(5'-bromo-4'-hexylthiophen-2'-yl)naphthalene-1,4,5,8-tetracarboxylate (1.80 g, 1.77 mmol, 1.00 eq) was suspended in 72 mL of ethanol, and a solution of 1.49 g of sodium hydroxide (15 mmol, 21.0 eq) in 4 mL of water was added. The reaction apparatus was purged with protective gas and heated under reflux for 20 hours. After cooling to room temperature, the mixture was cooled to 0° C., 4.5 mL of concentrated hydrochloric acid were added and the mixture was stirred for a further 20 minutes. The reaction mixture was concentrated under reduced pressure and the residue was suspended in petroleum ether. The solid obtained was removed by centrifugation, washed twice more with petroleum ether and finally taken up in 50 mL of acetone. The colorless solid remaining was removed by filtration and washed with a further 100 mL of acetone, and the filtrate was collected. Removal of the solvent gave a red-brown solid which was dried under reduced pressure and transferred into a 100 mL flask. Under a protective gas atmosphere, 35 mL of acetic anhydride were added and the suspension was stirred at 110° C. for 5 hours. After cooling to room temperature, the reaction mixture was stored in a refrigerator at 6° C. overnight. The solids were removed and washed with 50 mL each of acetic anhydride and mL of methyl tert-butyl ether. The residue was dried under reduced pressure, and 966 mg (72% of theory) of the desired product were obtained as a deep violet solid.—$^1$H-NMR (600.24 MHz, o-C$_6$D$_4$Cl$_2$): δ [ppm]=8.60 (s, 2H, CH$_{ar}$), 7.28 (s, 2H, CH$_{ar}$), 2.56 (t, $^3$J=7.7 Hz, 4H, CH$_2$), 1.57 (m, 4H, CH$_2$), 1.37 (m, 4H, CH$_2$), 1.28-1.19 (m, 8H, CH$_2$), 0.86 (t, 6H, CH$_3$)—$^{13}$C-NMR (150.9 MHz, o-C$_6$D$_4$Cl$_2$): 158.1 (C=O), 157.0 (C=O), 143.9 (C$_q$), 140.8 (C$_q$), 137.9 (C$_q$), 137.5 (CH$_{ar}$), 132.2 (CH$_{ar}$), 129.1 (C$_q$), 122.9 (C$_q$), 119.5 (C$_q$), 115.2 (C$_q$), 32.1 (CH$_2$), 30.1 (CH$_2$), 30.0 (CH$_2$), 29.4 (CH$_2$), 23.1 (CH$_2$), 14.5 (CH$_3$) HR-FAB-MS: [M+H]$^+$ C$_{34}$H$_{31}$O$_6$S$_2$$^{79}$Br$_2$, calc: m/z=756.9923, found: m/z=756.9929-FTIR: ν [cm$^{-1}$]=2950 (w, CH$_2$), 2920 (m, CH$_2$), 2848 (w, CH$_2$), 1767 (s, O(C=O)$_2$), 1729 (s, O(C=O)$_2$), 1567 (m).

1.29 2,7-Bis(5'-bromo-4'-hexylthiophen-2'-yl)naphthalene-1,4,5,8-tetracarboximide

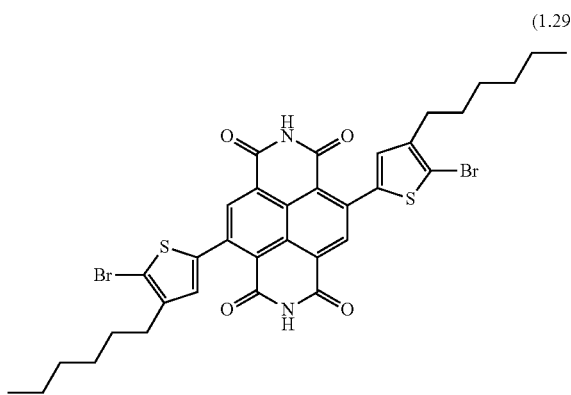

(1.29)

To 2,7-bis(5'-bromo-4'-hexylthiophen-2'-yl)naphthalene-1,4,5,8-tetracarboxylic dianhydride (0.933 g, 1.23 mmol, 1.0 eq) and dry ammonium acetate (1.89 g, 24.6 mmol, 20 eq) were added 13 mL of glacial acetic acid, and the mixture was degassed and heated under reflux for 2 hours. After cooling, the reaction mixture was stored in a refrigerator at 6° C. overnight. The viscous reaction mixture was diluted with 10 mL of acetic acid and the solids were removed via centrifugation. The solids thus obtained were washed twice each with 35 mL each of acetic acid, methyl tert-butyl ether and dichloromethane. After drying, 865 mg (93% of theory) of the desired product were obtained as a deep violet solid. —HR-MALDI-MS: Matrix: DCTB, [M+H]$^+$, C$_{34}$H$_{33}$N$_2$O$_4$S$_2$$^{79}$Br$_2$, calc.: m/z=757.0223, found: m/z=757.0233-FT-IR: ν [cm$^{-1}$]=3171 (m, N—H), 3061 (m, N—H), 2951 (w, CH$_2$) 2925 (m, CH$_2$), 2852 (w, CH$_2$), 1703 (s, O(C=O)$_2$), 1674 (s, O(C=O)$_2$), 1576 (m).

Example 2—Monomers 2.1 4,7-Bis(4,4,5,5-tetramethyl-1,3,2-dioxaborolan-2-yl)benzo[c][1,2,5]thiadiazole

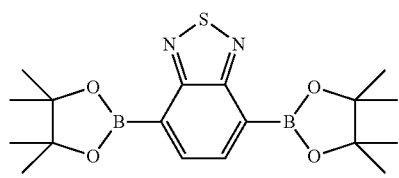

(2.1)

[1,1-Bis(diphenylphosphine)ferrocene]dichloropalladium (II) (307 mg, 420 μmol, 0.02 equiv.) was added to a mixture of 4,7-dibromobenzo[c][1,2,5]thiadiazole (6.17 g, 22.0 mmol, 1.00 equiv.), bis(pinacolato)diboron (11.7 g, 46.2 mmol, 2.20 equiv.) and potassium acetate (12.4 g, 126 mmol, 6.00 equiv.) in 1,4-dioxane (100 mL). The reaction mixture was stirred at 80° C. for 18 h. After cooling to room temperature, the reaction mixture was added to water (30 mL) and extracted with ethyl acetate (50 mL). The combined organic phases were washed with saturated sodium chloride solution (50 mL) and dried over magnesium sulfate, and the solvent was removed under reduced pressure. The crude product was purified by column chromatography on silica gel with petroleum ether/ethyl acetate (1:1) as eluent. 4.05 g (50%) of the product were obtained as a yellow solid. —Rf=0.80 (petroleum ether/ethyl acetate 1:1).—$^1$H-NMR (300 MHz, CDCl$_3$): δ=8.12 (s, 2H, H$_{ar}$), 1.44 (s, 24H, 8×CH$_3$).—$^{13}$C-NMR (75 MHz, CDCl$_3$): δ=157.1 (2×C—N), 137.9 (2×C$_{ar}$H), 84.5 (4×C$_q$), 25.0 (8×CH$_3$).—MS (EI), m/z (%): 388 (23) [M$^+$], 330 (100) [(C$_{18}$H$_{28}$B$_2$O$_4$)$^+$].—HRMS (C$_{14}$H$_{18}$BrIO$_3$S): calc. 388.1799, found 388.1823.

General Procedure for Preparation of the Carbonates (GP 2):

A solution of the appropriate alcohol (1.00 equiv.) in tetrahydrofuran was slowly added dropwise at 60° C. to a solution of the appropriate imidazole ester (1.10 equiv.) and potassium hydroxide (0.01 equiv.) in tetrahydrofuran (4.0 mL/mmol of alcohol), and the mixture was stirred at 60° C. over 18 h. The solvent was removed under reduced pressure and the remaining residue was taken up again with dichloromethane (50 mL). The organic phase was washed three times with 50 mL each time of water and dried over magnesium sulfate, and the solvent was removed under reduced pressure. The crude product was purified by column chromatography on silica gel with petroleum ether/ethyl acetate mixtures as eluent.

2.2 2-(2-Bromo-5-iodothiophen-3-yl)ethyl 2-methylhexan-2-yl carbonate

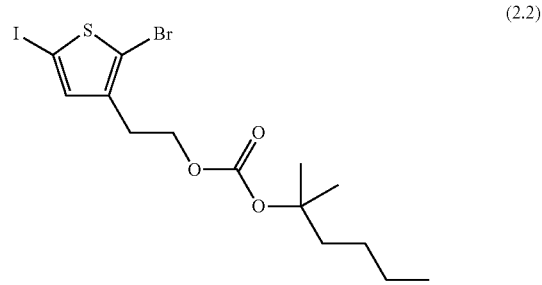 [SMILES: CCCCC(C)(C)OC(=O)OCCc1cc(I)sc1Br]

(2.2)

The synthesis was conducted proceeding from 2-(2-bromo-5-iodothiophen-3-yl)ethanol (1.00 g, 3.00 mmol, 1.00 equiv,), 2-methylhexan-2-yl 1H-imidazole-1-carboxylate (694 mg, 3.30 mmol, 1.10 equiv.) and potassium hydroxide (2.00 mg, 30.0 μmol, 0.01 equiv.) according to GP 2, After purification by column chromatography (silica gel, petroleum ether/ethyl acetate 10:1), 1.23 g (86%) of the carbonate were obtained as a clear oil.—R$_f$=0.55 (petroleum ether/ethyl acetate 5:1).—$^1$H-NMR (300 MHz, CDCl$_3$): δ=7.02 (s, 1H, H$_{ar}$), 4.20 (t, $^3$J=6.9 Hz, 2H, CH$_2$—O), 2.91 (t, $^3$J=6.9 Hz, 2H, C$_{ar}$CH$_2$), 1.73-1.78 (m, 2H, C$_q$—CH$_2$), 1.45 (s, 6H, 2×CH$_3$), 1.26-1.35 (m, 4H, 2×CH$_2$), 0.91

(t, $^3J$=6.7 Hz, 3H, CH$_3$). $^{13}$C-NMR (75 MHz, CDCl$_3$): δ=153.4 (C=O), 139.3 (C$_{ar}$—CH$_2$), 138.2 (C$_{ar}$), 113.7 (C$_{ar}$Br), 84.7 (O—C$_q$), 71.7 (C$_{ar}$—I), 65.3 (CH$_2$—O), 40.4 (C$_q$—CH$_2$), 28.9 (C$_{ar}$—CH$_2$), 26.2 (CH$_2$), 25.8 (2×CH$_2$), 23.1 (CH$_2$), 14.2 (CH$_3$).—FTIR: ṽ=2955, 1734, 1250 cm$^{-1}$.—MS (EI), m/z (%): 476/474 (9/9) [M$^+$], 316/314 (100/94) [(C$_6$H$_4$BrIS)$^+$].—HRMS (C$_{14}$H$_{20}$BrIO$_3$S): calc. 473.9361, found 473.9370.—Detachment temperature: T$_{on}$ (onset temperature)=190° C.

2.3 2-(2-Bromo-5-iodothiophen-3-yl)ethyl 1-butylcyclopentyl carbonate

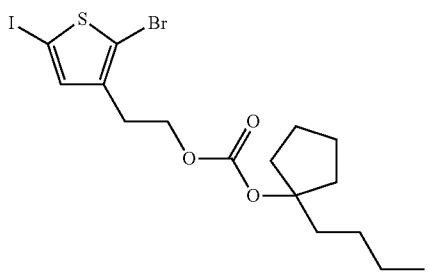

(2.3)

The synthesis was conducted proceeding from 2-(2-bromo-5-iodothiophen-3-yl)ethanol (1.30 g, 3.90 mmol, 1.00 equiv.), 1-butylcyclopentyl 1H-imidazole-1-carboxylate (1.01 g, 4.29 mmol, 1.10 equiv.) and potassium hydroxide (2.00 mg, 39.0 μmol, 0.01 equiv.) according to GP 2. After purification by column chromatography (silica gel, petroleum ether/ethyl acetate 10:1), 1.77 g (91%) of the carbonate were obtained as a yellow oil. —R$_f$=0.73 (petroleum ether/ethyl acetate 10:1). —$^1$H-NMR (300 MHz, CDCl$_3$): δ=7.02 (s, 1H, H$_{ar}$), 4.21 (t, $^3J$=6.7 Hz, 2H, CH$_2$—O), 2.91 (t, $^3J$=6.7 Hz, 2H, C$_{ar}$—CH$_2$), 2.07-2.18 (m, 2H, C$_q$—CH$_2$), 1.89-1.97 (m, 2H, CH$_2$), 1.57-1.79 (m, 6H, 3×CH$_2$), 1.25-1.35 (m, 4H, 2×CH$_2$), 0.90 (t, $^3J$=6.9 Hz, 3H, CH$_3$).—$^{13}$C-NMR (75 MHz, CDCl$_3$): δ=153.5 (C=O), 139.3 (C$_{ar}$CH$_2$), 138.2 (C$_{ar}$H), 113.7 (C$_{ar}$—Br), 95.5 (O—C$_q$), 71.8 (C$_{ar}$—I), 65.4 (CH$_2$—O), 37.5 (2×CH$_2$), 36.7 (CH$_2$), 29.0 (CH$_2$), 27.1 (CH$_2$), 24.1 (2×CH$_2$), 23.1 (CH$_2$), 14.2 (CH$_3$), —FTIR: ṽ=2959, 2870, 1735, 1453, 1388, 1251, 1172, 1102, 965, 792 cm$^{-1}$.—MS (Fab), m/z (%): 502/500 [M$^+$].—HRMS (C$_{16}$H$_{22}$BrIO$_3$S): calc. 499.9518, found 499.9489.—Detachment temperature: T$_{on}$=158° C.

2.4 2-(2-Bromo-5-iodothiophen-3-yl)ethyl 2-methyloct-3-yn-2-yl Carbonate

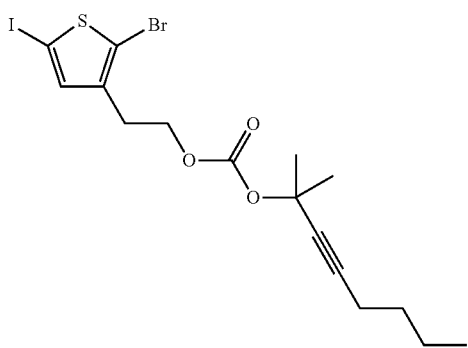

(2.4)

The synthesis was conducted proceeding from 2-(2-bromo-5-iodothiophen-3-yl)ethanol (1.67 g, 5.00 mmol, 1.00 equiv.), 2-methyloct-3-yn-2-yl 1H-imidazole-1-carboxylate (1.29 g, 5.50 mmol, 1.10 equiv.) and potassium hydroxide (3.00 mg, 50.0 μmol, 0.01 equiv.) according to GP 2. After purification by column chromatography (silica gel, petroleum ether/ethyl acetate 10:1), 1.77 g (91%) of the carbonate were obtained as a clear oil. —R$_f$=0.69 (petroleum ether/ethyl acetate 10:1), —$^1$H-NMR (300 MHz, CDCl$_3$): δ=7.03 (s, 1H, H$_{ar}$), 4.23 (t, $^3J$=6.9 Hz, 2H, CH$_2$—O), 2.92 (t, $^3J$=6.9 Hz, 2H, C$_{ar}$CH$_2$), 2.21 (t, $^3J$=6.9 Hz, 2H, C—CH$_2$), 1.67 (s, 6H, 2×CH$_3$), 1.33-1.53 (m, 4H, 2×CH$_2$), 0.90 (t, $^3J$=7.1 Hz, 3H, CH$_3$).—$^{13}$C-NMR (75 MHz, CDCl$_3$): δ=152.9 (C=O), 139.3 (C$_{ar}$—CH$_2$), 138.2 (C$_{ar}$H), 113.7 (C$_{ar}$—Br), 85.6 (C—CH$_2$), 80.7 (C—C$_q$), 75.3 (O—C$_q$), 71.7 (C$_{ar}$—I), 65.7 (CH$_2$—O), 30.7 (CH$_2$), 29.3 (2×CH$_3$), 28.9 (CH$_2$), 22.0 (CH$_2$), 18.5 (CH$_2$), 13.7 (CH$_3$) .—FTIR: ṽ=2958, 2930, 2867, 2245, 1748, 1463, 1384, 1250, 1194, 1132, 1100, 790 cm$^{-1}$.—MS (EI), m/z (%): 500/498 (12/12) [M$^+$], 316/314 (100/95) [(C$_6$H$_4$BrIS)$^+$], 236 (25) [(C$_6$H$_5$IS)$^+$], 123 (61) [(C$_9$H$_{15}$)$^+$].—HRMS (C$_{16}$H$_{20}$BrIO$_3$S): calc. 497.9361, found 497.9385.—Detachment temperature: T$_{on}$=186° C.

2-5 2-(2-Bromo-5-iodothiophen-3-yl)ethyl 1-(hex-1-yn-1-yl)cyclohexyl carbonate

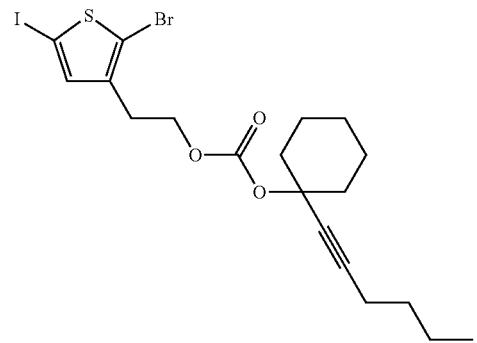

(2.5)

The synthesis was conducted proceeding from 2-(2-bromo-5-iodothiophen-3-yl)ethanol (1.67 g, 5.00 mmol, 1.00 equiv.), 1-(hex-1-yn-1-yl)cyclohexyl 1H-imidazole-1-carboxylate (1.51 g, 5.50 mmol, 1.10 equiv.) and potassium hydroxide (3.00 mg, 50.0 μmol, 0.01 equiv.) according to GP 2. After purification by column chromatography (silica gel, petroleum ether/ethyl acetate 20:1, 5% triethylamine), 2.17 g (80%) of the carbonate were obtained as a yellow oil. —R$_f$=0.50 (petroleum ether/ethyl acetate 20:1, TEA).—$^1$H-NMR (300 MHz, CDCl$_3$): δ=7.03 (s, 1H, H$_{ar}$), 4.24 (t, $^3J$=7.2 Hz, 2H, CH$_2$—O), 2.93 (t, $^3J$=7.2 Hz, 2H, C$_{ar}$—CH$_2$), 2.25 (t, $^3J$=7.2 Hz, 2H, C—CH$_2$), 2.09-2.17 (m, 2H, CH$_2$), 1.77-1.86 (m, 2H, CH$_2$), 1.60-1.68 (m, 4H, 2×CH$_2$), 1.39-1.45 (m, 6H, 3×CH$_2$), 0.91 (t, $^3J$=7.2 Hz, 3H, CH$_3$).— $^{13}$C-NMR (75 MHz, CDCl$_3$): δ=152.8 (C=O), 139.3 (C$_{ar}$CH$_2$), 138.2 (C$_{ar}$H), 113.7 (C$_{ar}$—Br), 87.9 (C—CH$_2$), 79.5 (C—C$_q$), 79.0 (O—C$_q$), 71.9 (C$_{ar}$—I), 65.7 (CH$_2$—O), 37.5 (2×CH$_2$), 30.9 (CH$_2$), 27.1 (CH$_2$), 25.3 (2×CH$_2$), 23.1 (CH$_2$), 22.1 (CH$_2$), 18.7 (CH$_2$), 13.8 (CH$_3$).—FTIR: ṽ=2930, 2857, 2240, 1745, 1447, 1267, 1231, 1182, 1125, 1014, 917, 782 cm$^{-1}$. —MS (FAB), m/z (%): 541/539 (67/100) [(M+H)$^+$], 540/538 (50/47) [M$^+$].—HRMS

2.6 3-(2,7-Dibromo-9-methylfluoren-9-yl)propyl 2-methylhexan-2-yl carbonate

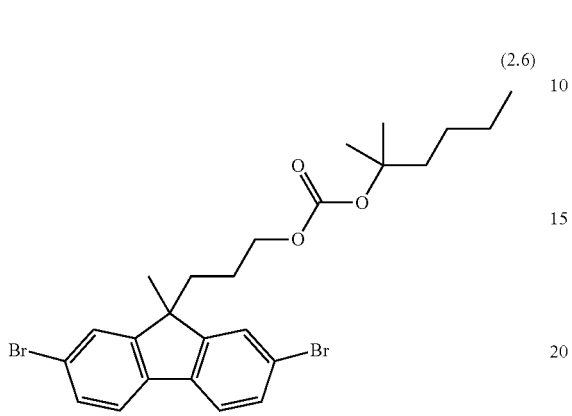
(2.6)

The synthesis was conducted proceeding from 2,7-dibromo-9-(3-hydroxypropyl)-9-methylfluorene (3.17 g, 8.00 mmol, 1.00 equiv.), 2-methylhexan-2-yl 1H-imidazole-1-carboxylate (1.85 g, 8.80 mmol, 1.10 equiv.) and potassium hydroxide (4.00 mg, 80.0 µmol, 0.01 equiv.) according to GP 2. After purification by column chromatography (silica gel, petroleum ether/ethyl acetate 20:1), 3.70 g (86%) of the carbonate were obtained as a clear oil. —$R_f$=0.40 (petroleum ether/ethyl acetate 20:1). —$^1$H-NMR (300 MHz, CDCl$_3$): δ=7.53 (d, $^3$J=8.0 Hz, 2H, 2×H$_{ar}$), 7.49 (d, $^4$J=1.8 Hz, 2H, 2×H$_{ar}$), 7.46 (d, $^3$J=8.0 Hz, $^4$J=1.8 Hz, 2H, 2×H$_{ar}$), 3.82 (t, $^3$J=6.7 Hz, 2H, CH$_2$—O), 1.99-2.06 (m, 2H, CH$_2$), 1.69-1.76 (m, 2H, CH$_2$—C$_q$), 1.47 (s, 3H, CH$_3$), 1.42 (s, 6H, 2×CH$_3$), 1.25-1.32 (m, 4H, 2×CH$_2$), 0.94-1.04 (m, 2H, CH$_2$), 0.86-0.92 (m, 3H, CH$_3$). —$^{13}$C-NMR (75 MHz, CDCl$_3$): δ=153.5 (C=O), 153.2 (2×C$_{ar}$), 138.3 (2×C$_{ar}$), 130.7 (2×C$_{ar}$H), 126.3 (2×C$_{ar}$H), 121.8 (2×C$_{ar}$—Br), 121.5 (2×C$_{ar}$H), 84.4 (C$_q$), 66.9 (CH$_2$—O), 51.0 (CH$_2$), 40.3 (CH$_2$—C$_q$), 36.6 (CH$_2$), 26.5 (CH$_2$), 26.2 (CH$_3$), 25.8 (2×CH$_3$), 23.9 (CH$_2$), 23.1 (CH$_2$), 14.1 (CH$_3$). —FTIR: ṽ=2959, 2927, 2858, 1735, 1449, 1250 cm$^{-1}$. —MS (EI), m/z (%): 540/538/536 (47/92/48) [M$^+$], 442/440/438 (34/63/33) [(C$_{18}$H$_{16}$Br$_2$O$_3$)$^+$], 339/337/335 (52/100/52) [(C$_{14}$H$_9$Br$_2$)$^+$], 258/256 (44/46) [(C$_{14}$H$_9$Br)$^+$]. —HRMS (C$_{17}$H$_{16}$BR$_2$O): calc. 536.0562, found 536.0568.

2.7 3-(2,7-Dibromo-9-methyl-9H-fluoren-9-yl)propyl 1-(hex-1-yn-1-yl)cyclohexyl carbonate

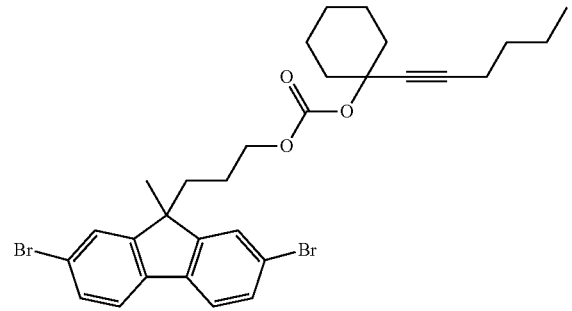
(2.7)

The synthesis was conducted proceeding from 2,7-dibromo-9-(3-hydroxypropyl)-9-methylfluorene (792 mg, 28.00 mmol, 1.00 equiv.), 1-(hex-1-yn-1-yl)cyclohexyl 1H-imidazole-1-carboxylate (604 mg, 2.20 mmol, 1.10 equiv.) and potassium hydroxide (1.00 mg, 20.0 µmol, 0.01 equiv.) according to GP 2. After purification by column chromatography (silica gel, petroleum ether/ethyl acetate 10:1, 5% triethylamine), 895 mg (74%) of the carbonate were obtained as a clear oil. —$R_f$=0.63 (petroleum ether/ethyl acetate 10:1, TEA).—$^1$H-NMR (300 MHz, CDCl$_3$): δ=7.53 (d, $^3$J=8.1 Hz, 2H, 2×H$_{ar}$), 7.49 (d, $^4$J=1.7 Hz, 2H, 2×H$_{ar}$), 7.46 (d, $^3$J=8.1 Hz, $^4$J=1.7 Hz, 2H, 2×H$_{ar}$), 3.88 (t, $^3$J=6.6 Hz, 2H, CH$_2$—O), 2.22 ($^3$J=6.9 Hz, 2H, C$_q$—CH$_2$), 2.01-2.14 (m, 4H, 2×CH$_2$), 1.73-1.84 (m, 2H, CH$_2$—C$_q$), 1.55-1.67 (m, 4H, 2×CH$_2$), 1.40-1.51 (m, 9H, 3×CH$_2$+CH$_3$), 0.95-1.05 (m, 2H, CH$_2$), 0.89 (t, $^3$J=7.1 Hz, 3H, CH$_3$).—$^{13}$C-NMR (75 MHz, CDCl$_3$): δ=153.2 (2×C$_{ar}$), 152.8 (C=O), 138.3 (2×C$_{ar}$), 130.7 (2×C$_{ar}$H), 126.4 (2×C$_{ar}$H), 121.9 (2×C$_{ar}$—Br), 121.6 (2×C$_{ar}$H), 87.6 (C—CH$_2$), 79.5 (C—C$_q$), 78.6 (C$_q$), 67.2 (CH$_2$—O), 51.0 (C$_q$—CH$_3$), 37.5 (2×CH$_2$), 36.7 (CH$_2$—C$_q$), 30.8 (CH$_2$), 27.1 (CH$_2$), 26.5 (CH$_2$), 23.9 (CH$_2$), 23.0 (2×CH$_2$), 22.0 (CH$_2$), 18.6 (CH$_2$), 13.8 (CH$_3$).—FTIR: ṽ=2931, 2857, 1744, 1447, 1414, 1268, 1236, 1181, 1013, 917, 812 cm$^{-1}$.—MS (FAB), m/z (%): 604/602/600 (60/100/53) [M$^+$].—HRMS (C$_{30}$H$_{34}$Br$_2$O$_3$): calc. 600.0875, found 600.0858.

2.8 2,7-Bis(5'-bromo-2'-thiophenyl)-[N,N]-bis(Hexan-1-yl-6-(2-methylhexan-2-yl)carbonate)naphthalene-1,8:4,5-tetracarboximide

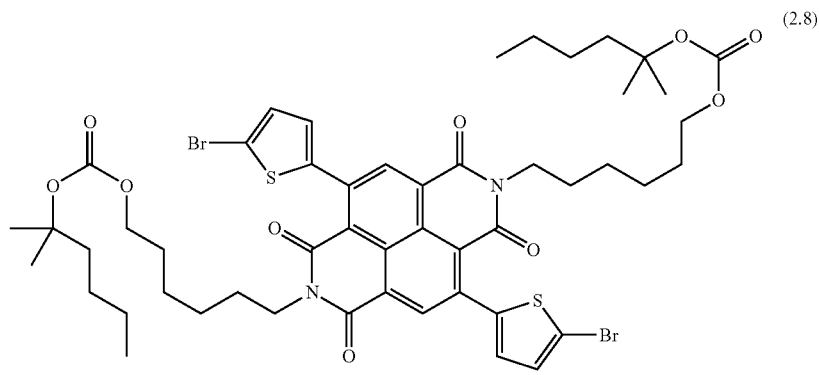 [SMILES: CCCCC(C)(C)OC(=O)OCCCCCCN1C(=O)c2cc(-c3ccc(Br)s3)c3c4c(cc(-c5ccc(Br)s5)c(c24)C1=O)C(=O)N(CCCCCCOC(=O)OC(C)(C)CCCC)C3=O]
(2.8)

In a dry Schlenk flask, 2,7-bis(5'-bromo-2'-thiophenyl)-[N,N]-bis(hexan-1-yl-6-ol)naphthalene-1,8:4,5-tetracarboximide (213 mg, 270 mmol) and 2-methylhexan-2-yl-1-carbonylimidazole (227 mg, 1.08 mmol) were dissolved in 6 mL of dry DMF. Catalytic amounts of KOH (8 mg, 0.14 mmol) were added and the reaction mixture was stirred at room temperature. After two hours, 10 mL of aqueous NH$_4$Cl solution were added. The suspension obtained was stirred vigorously for 1 hour. The aqueous phase was removed and the residue was dissolved in dichloromethane, washed with saturated NaCl solution and dried with MgSO$_4$. The crude product was purified by column chromatography on silica gel with a mixture of chloroform and toluene (1:1, v:v) with 2% THF as eluent and then recrystallized repeatedly from MeOH, 140 mg (48% of theory) of the product were obtained as a red solid. —R$_f$=0.32 (chloroform:toluene (1:1)+3% THF).—$^1$H-NMR (300 MHz, CDCl$_3$): δ=8.71 (s, 2H, 2×CH$_{ar}$), 7.15 (d, $^3$J=3.8 Hz, 2H, CH$_{ar}$), 7.07 (d, 3J=3.8 Hz, 2H, CH$_{ar}$), 4.11 (t, $^3$J=7.7 Hz, 4H, 2×N—CH$_2$), 4.03 (t, $^3$J=6.6 Hz, 4H, 2×O—CH$_2$), 1.62-1.77 (m, 12H, CH$_2$), 1.39-1.46 (m, 8H, CH$_2$), 1.44 (s, 12H, C$_q$—CH$_3$), 1.24-1.32 (m, 8H, CH$_2$), 1.12 (t, $^3$J=7.6 Hz, 6H, CH$_3$). —$^{13}$C-NMR (75 MHz, CDCl$_3$): —IR: (v in cm$^{-1}$): 1730 (vs, O—(C=O)—O), 1705 (s, N—C=O), 1662 (vs, N—C=O), 1578 (m). MS (APCI$^-$), m/z: 1070.3 [(C$_{50}$H$_{60}$$^{79}$Br$_2$N$_2$O$_{10}$S$_2$)$^-$], 1072.3 [(C$_{50}$H$_{60}$$^{79}$Br$^{81}$Br N$_2$O$_{10}$S$_2$)$^-$], 1074.3 [(C$_{50}$H$_{60}$$^{81}$Br$_2$N$_2$O$_{10}$S$_2$)$^-$].

2.9 2,7-Bis(5'-bromo-4'-hexyl-2'-thiophenyl)-[N,N]-bis(hexan-1-yl-6-(2-methylhexan-2-yl)carbonate)naphthalene-1,8:4,5-tetracarboximide

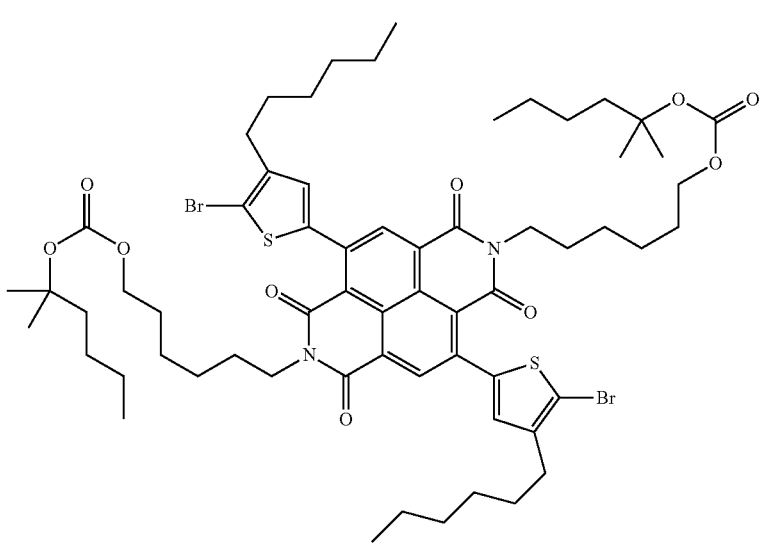

(2.9)

In a dry, argon-filled Schlenk flask, 2,7-bis(5'-bromo-4'-hexyl-2'-thiophenyl)-[N,N]-bis(hexan-1-yl-6-ol)naphthalene-1,8:4,5-tetracarboximide (248 mg, 0.26 mmol) and 2-methylhexan-2-yl 1H-imidazole-1-carboxylate (219 mg, 1.04 mmol) were dissolved in 5 mL of dry DMF. The suspension was cooled to 0° C. and catalytic amounts of KOH (7 mg, 0.13 mmol) were added and the mixture was stirred at 0° C. for 3 hours. Subsequently, 10 mL of aqueous NH$_4$Cl solution were added and the mixture was stirred for a further hour. The precipitate was filtered off, washed with water and extracted again with dichloromethane. The organic phase was washed with sat. NaCl and dried over MgSO$_4$. The crude product was purified by column chromatography on silica gel with a mixture of chloroform and toluene (1:1, v:v) with 2% THF as eluent and then recrystallized repeatedly from MeOH. 180 mg (56% of theory) of the product were obtained as a violet solid.—$^1$H-NMR (300 MHz, CDCl$_3$): δ=8.70 (s, 2H, 2×CH$_{ar}$), 7.03 (s, 2H, CH$_{ar}$), 4.12 (t, $^3$J=7.7 Hz, 4H, 2×N—CH$_2$), 4.03 (t, 3J=6.6 Hz, 4H, 2×O—CH$_2$), 2.64 (t, $^3$J=7.7 Hz, 4H, 2×C$_q$—CH$_2$), 1.73-1.76 (m, 4H, C$_q$—CH$_2$), 1.60-1.73 (m, 12H, CH$_2$), 1.43 (s, 12H, C$_q$—CH$_3$), 1.37-1.44 (m, 12H, CH$_2$), 1.32-1.37 (m, 8H, CH$_2$), 1.27-1.32 (m, 8H, CH$_2$), 0.91 (t, $^3$J=6.9 Hz, 6H, CH$_3$), 0.89 (t, $^3$J=6.9 Hz, 6H, CH$_3$).—$^{13}$C-NMR (75 MHz, CDCl$_3$): δ=162.1 (2×N—C=O), 162.0 (2×N—C=O), 153.6 (O—(C=O)—O), 142.5 (2×C$_q$), 140.0 (2×C$_q$), 139.5

(2×$C_q$), 136.4 (2×$CH_{ar}$), 129.6 (2×$CH_{ar}$), 127.4 (2×$C_1$), 125.4 (2×(C=O)—$C_{q\text{-}ar}$), 122.9 (2×(C=O)—$C_q$), 112.5 (2×$C_{q\text{-}ar}$Br), 84.1 ($CH_2$—$C_q$), 66.9 ($CH_2$—O), 41.0 ($CH_2$—N), 40.2 ($CH_2$), 31.6 ($C_q$—$CH_2$), 29.7 ($CH_2$), 29.0 ($CH_2$), 28.6 ($CH_2$), 27.9 ($CH_2$), 26.7 ($CH_2$), 26.0 ($CH_2$), 25.7 ($CH_3$), 25.5 ($CH_2$), 22.9 ($CH_2$), 22.6 ($CH_2$), 14.1 ($CH_3$), 14.0 ($CH_3$). —HR-MS (ESI, $Na^+$-adduct, $[C_{62}H_{84}Br_2N_2NaO_{10}S_2]^+$): calc. 1261.3826, found 12613831. —IR: ($\tilde{v}$ in $cm^{-1}$): 1737 (vs, O—(C=O)—O), 1704 (s, N—C=O), 1667 (vs, N—C=O), 1574 (m).—TGA/DSC: m.p.: 78.7° C., pyrolysis onset: 150° C., pyrolysis midpoint: 223° C. Weight loss: 22.4% (calc. 22.9%).

2.10 2-Methylhexan-2-yl 2,7-dibromo-9H-carbazole-9-carboxylate

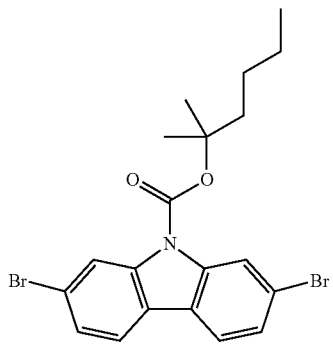

(2.10)

To a solution of 2,7-dibromocarbazole (2.28 g, 7.00 mmol, 1.00 equiv.) in acetonitrile/tetrahydrofuran (4:1, 25 mL) were added, at room temperature, 2-methylhexan-2-yl 1H-imidazole-1-carboxylate (1.62 g, 7.70 mmol, 1.10 equiv.) and 1,8-diazabicyclo[5.4.0]undec-7-ene (213 mg, 1.40 mmol, 0.20 equiv.). The reaction mixture was stirred at room temperature overnight and then admixed with 1 M hydrochloric acid (5 mL) and extracted with ethyl acetate (20 mL). The combined organic phases were washed with saturated sodium chloride solution and dried over magnesium sulfate, and the solvent was removed under reduced pressure, After purification by column chromatography (silica gel, petroleum ether/ethyl acetate 30:1), 2.73 g (84%) of the carbonate were obtained as a yellow solid. —$R_f$=0.66 (petroleum ether/ethyl acetate 30:1).—$^1$H-NMR (300 MHz, CDCl$_3$): δ=8.48 (s, 2H, 2×$H_{ar}$), 7.77 (d, $^3$J=8.3 Hz, 2H, 2×$H_{ar}$), 7.47 (d, 8.3 Hz, 2H, 2×$H_{ar}$), 2.05 (t, $^3$J=7.2 Hz, 2H, $CH_2$), 1.74 (s, 6H, 2×$CH_3$), 1.40-1.53 (m, 4H, 2×$CH_2$), 0.96 (t, $^3$J=6.9 Hz, 3H, $CH_3$).—$^{13}$C-NMR (75 MHz, CDCl$_3$): δ=150.6 (C=O), 139.4 (2×$C_{ar}$—N), 126.7 (2×$C_{ar}$H), 124.1 (2×$C_{ar}$), 121.2 (2×$C_{ar}$—Br), 120.8 (2×$C_{ar}$H), 119.9 (2×$C_{ar}$H), 87.9 ($C_q$), 41.1 ($CH_2$), 26.4 ($CH_2$), 26.3 (2×$CH_3$), 23.3 ($CH_2$), 14.3 ($CH_3$).—FTIR: $\tilde{v}$=2955, 2867, 1729, 1590, 1439, 1406, 1347, 1326, 1277, 1207, 1150, 797 $cm^{-1}$.—MS (DART), m/z (%): 469/467/465 (15/30/15) [M$^+$].—HRMS ($C_{20}H_{21}Br_2NO_2$): calc. 464.9939, found 464.9922.—Detachment temperature: $T_{on}$=159° C.

2.11 9-methylheptadecan-9-yl 2,7-dibromo-9H-carbazole-9-carboxylate

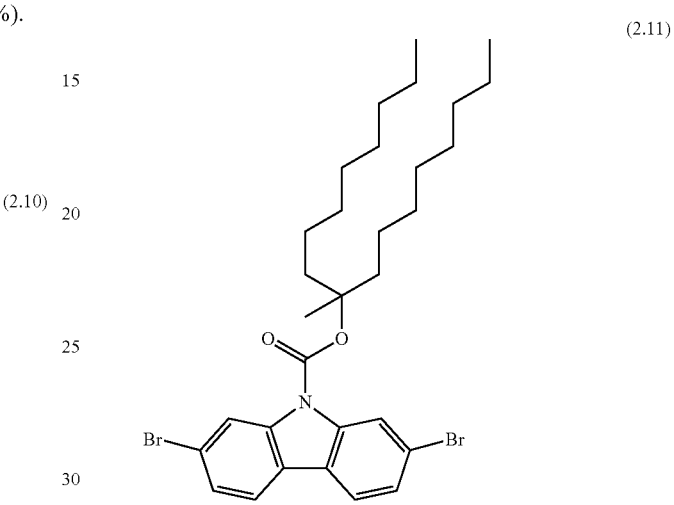

(2.11)

To a solution of 2,7-dibromocarbazole (1.95 g, 6.00 mmol, 1.00 equiv.) in acetonitrile/tetrahydrofuran (4:1, 25 mL) were added, at room temperature, 9-methylheptadecan-9-yl 1H-imidazole-1-carboxylate (2.41 g, 6.60 mmol, 1.10 equiv.) and 1,8-diazabicyclo[5.4.0]undec-7-ene (183 mg, 1.20 mmol, 0.20 equiv.). The reaction mixture was stirred at room temperature overnight and then admixed with 1 M hydrochloric acid (5 mL) and extracted with ethyl acetate (20 mL). The combined organic phases were washed with saturated sodium chloride solution and dried over magnesium sulfate, and the solvent was removed under reduced pressure. After purification by column chromatography (silica gel, petroleum ether/ethyl acetate 40:1), 3.07 g (82%) of the carbonate were obtained as a yellow solid. —$R_f$=0.81 (petroleum ether/ethyl acetate 40:1), —$^1$H-NMR (300 MHz, CDCl$_3$): δ=8.48 (s, 2H, 2×$H_{ar}$), 7.78 (d, $^3$J=8.3 Hz, 2H, 2×$H_{ar}$), 7.47 (d, $^3$J=8.3 Hz, $^4$J=1.7 Hz, 2H, 2×$H_{ar}$), 1.95-2.18 (m, 4H, 2×$CH_2$), 1.71 (s, 3H, $CH_3$), 1.23-1.49 (m, 24H, 12×$CH_2$), 0.84-0.89 (m, 6H, 2×$CH_3$).—$^{13}$C-NMR (75 MHz, CDCl$_3$): δ=150.4 (C=O), 139.4 (2×$C_{ar}$—N), 126.6 (2×$C_{ar}$H), 124.1 (2×$C_{ar}$), 121.2 (2×$C_{ar}$—Br), 120.7 (2×$C_{ar}$H), 119.8 (2×$C_{ar}$H), 90.6 ($C_q$), 38.7 (2×$CH_2$), 32.0 (2×$CH_2$), 30.2 (2×$CH_2$), 29.7 (2×$CH_2$), 29.4 (2×$CH_2$), 24.1 ($CH_3$), 24.0 (2×$CH_2$), 22.8 (2×$CH_2$), 14.3 ($CH_3$).—FTIR $\tilde{v}$=2924, 2852, 1730, 1588, 1438, 1348, 1323, 1278, 1208, 1123, 973, 799 $cm^{-1}$.—MS (DART), m/z (%): 623/621/619 (7/15/7) [M$^+$].—HRMS ($C_{31}H_{43}Br_2NO_2$): calc. 619.1661, found 619.1673.—Detachment temperature: $T_{on}$=151° C.

2.12 Bis(2-methylhexan-2-yl) 2,7-bis(5'-bromo-4'-hexylthiophen-2'-yl)naphthalene-1,4,5,8-tetracarboximide-[N,N]-dicarboxylate

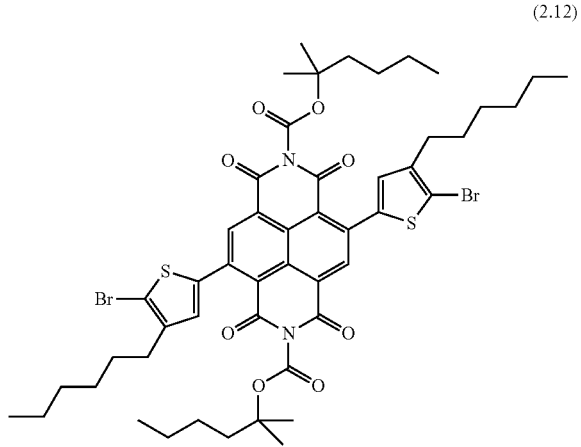 [SMILES: CCCCCCc1cc(-c2cc3c4c(c(-c5cc(CCCCCC)c(Br)s5)cc5c4c2C(=O)N(C(=O)OC(C)(C)CCCC)C5=O)C(=O)N(C(=O)OC(C)(C)CCCC)C3=O)sc1Br]

(2.12)

Bis(2-methylhexan-2-yl) dicarbonate (0.404 g, 1.34 mmol, 4.00 eq) was added under a protective gas atmosphere to a suspension of 2,7-bis(5'-bromo-4'-hexylthiophen-2'-yl)naphthalene-1,4,5,8-tetracarboximide (0.200 g, 0.334 mmol, 1.00 eq) and DMAP (0.100 g, 0.835 mmol, 2.50 eq) in 2.5 mL of dry tetrahydrofuran. The reaction mixture was stirred at room temperature for 4.5 hours, then diluted with 30 mL of chloroform and added to 25 mL of a saturated aqueous ammonium chloride solution. The organic phase was removed and the aqueous phase was extracted twice with 35 mL each time of chloroform. The combined organic phases were dried with saturated sodium chloride solution and $Na_2SO_4$, and concentrated. The solid obtained was purified by column chromatography on silica gel with a solvent mixture of chloroform, petroleum ether, toluene and triethylamine (50:32:15:3, v:v), and recrystallized five times from a mixture of dichloromethane and methanol. 98 mg (31% of theory) of the desired product was obtained, —$R_f$=0.53 (chloroform/petroleum ether/toluene 50:35:15+ 3% triethylamine)—$^1$H-NMR (500 MHz, $CDCl_3$): δ [ppm] =8.76 (s, 1H, $H_{ar}$), 7.12 (s, 2H, $H_{ar}$), 2.63 (t, $^3J$=7.6 Hz, 4H, $CH_2$), 1.88 (m, 4H, $C_2$), 1.64 (t, $^3J$=7.5 Hz, 4H, $CH_2$), 1.63 (s, 12H, $CH_3$), 1.33-1.45 (m, 20H, $CH_2$), 0.91-0.92 (m, 12H, $CH_3$)—$^{13}$C-NMR (125 MHz, $CDCl_3$): δ [ppm]=159.8 ($C_q$), 159.7 ($C_q$), 147.5 ($C_q$), 142.7 ($C_q$), 140.0 ($C_q$), 136.7 ($CH_{ar}$), 136.5 ($C_q$), 130.9 ($CH_{ar}$), 128.1 ($C_q$), 125.4 ($C_q$), 122.3 (C—Br), 113.6 ($C_q$), 90.3 ($C_q$), 40.2 ($C_q$—$CH_2$), 31.6 ($CH_2$), 29.7 ($CH_2$), 29.6 ($CH_2$), 28.9 ($CH_2$), 25.7 ($CH_2$), 25.4 ($CH_3$), 22.9 ($CH_2$), 22.6 ($CH_2$), 14.1 ($CH_3$), 14.0 ($CH_3$)—FT-IR: ṽ[$cm^{-1}$]=2953 (w, $CH_2$), 2923 (m, $CH_2$), 2856 (w, $CH_2$), 1775 (s, C=O), 1713 (s, N(C=O)$_2$), 1683 (s, N(C=O)$_2$), 1589 (w)-UV/Vis ($CHCl_3$): $\lambda_{max}$ (ε)=536 nm (1.23·10$^5$ l mol$^{-1}$)—HR-ESI-MS ($C_{50}H_{60}KN_2O_8S_2{}^{79}Br^{81}Br$): calc. 1079.177 (exp. 1079.179), ($C_{50}H_{60}NaN_2O_8S_2{}^{79}Br^{81}Br$) calc. 1063.203 (exp. 1063.205).

2.13 2,7-Bis(5'-bromo-2'-thiophenyl)-[N,N]-bis(hexan-1-yl-6-(9-methylheptadecan-9-yl)carbonate)naphthalene-1,8:4,5-tetracarboximide

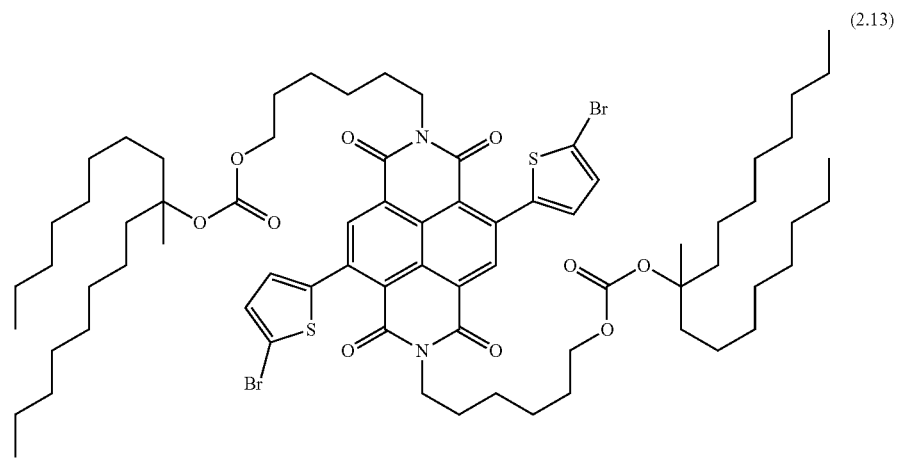 [SMILES: CCCCCCCCC(C)(CCCCCCCC)OC(=O)OCCCCCCN1C(=O)c2cc(-c3ccc(Br)s3)c3c4c(cc(-c5ccc(Br)s5)c(c24)C1=O)C(=O)N(CCCCCCOC(=O)OC(C)(CCCCCCCC)CCCCCCCC)C3=O]

(2.13)

In a dry Schlenk flask, 2,7-bis(5'-bromo-2'-thiophenyl)-[N,N]-bis(hexan-1-yl-6-ol)naphthalene-1,8:4,5-tetracarboximide (434 mg, 550 mmol) and 9-methylheptadecan-9-yl 1H-imidazole-1-carboxylate (802 mg, 2.2 mmol) were dissolved in 11 mL of dry DMF. Catalytic amounts of KOH (15 mg, 0.28 mmol) were added and the reaction mixture was stirred at room temperature. After 18 hours, 200 mL of aqueous NH$_4$Cl solution were added. The suspension obtained was stirred vigorously for 1 hour. The deep red organic precipitate was removed and dissolved in dichloromethane, washed with water and saturated sodium chloride solution, dried with MgSO$_4$ and concentrated. The crude product was purified by column chromatography on silica gel with a mixture of chloroform, toluene and petroleum ether (3:4:3, v:v) with 2% THF as eluent and then recrystallized repeatedly from MeOH and acetonitrile. 228 mg (30% of theory) of the product were obtained as a red solid. —UPLC purity: 98.6%. —$R_f$=0.32 (chloroform:toluene:petroleum ether (3:4:3, v:v)+2% THF).—$^1$H-NMR (500 MHz, CDCl$_3$): δ=8.71 (s, 2H, CH$_{ar}$), 7.15 (d, $^3$J=3.8 Hz, 2H, CH$_{ar}$), 7.07 (d, $^3$J=3.8 Hz, 2H, CH$_{ar}$), 4.11 (t, 3J=7.7 Hz, 4H, N—CH$_2$), 4.03 (t, sJ=6.6 Hz, 4H, O—CH$_2$), 1.62-1.82 (m, 16H, CH$_2$), 1.39-1.41 (m, 14H, CH$_2$), 1.21-1.31 (m, 48H, CH$_2$), 1.12 (t, $^3$J=7.6 Hz, 12H, CH$_3$).—$^{13}$C-NMR (125 MHz, CDCl$_3$): 161.9 (C$_q$), 161.8 (C$_q$), 153.5 (C$_q$), 141.9 (C$_q$), 139.1 (C$_q$), 136.5 (CH$_{ar}$), 130.2 (CH$_{ar}$), 128.8 (C$_q$), 127.5 (C$_q$), 125.6 (C$_q$), 123.2 (C—Br), 115.4 (C$_q$), 86.6 (CH$_2$), 66.9 (CH$_2$), 41.0, 38.0, 31.8, 29.9, 29.5, 29.2, 28.6, 27.8, 26.7, 25.5, 23.6, 23.5, 22.6, 14.1. —HR-ESI-MS: [M+NH$_4$]$^+$, (C$_{72}$H$_{108}$$^{79}$Br$_2$N$_3$O$_{10}$S$_2$): calc. 1396.584 (exp. 1396.585).

Example 3—Synthesis of the Polymers

Synthesis According to Yokozawa:
General Procedure for Preparation of Polythiophenes (GP 3):

A 2.0 M isopropylmagnesium chloride solution (1.00 equiv.) in tetrahydrofuran was added at 0° C. to a solution of the corresponding carbonate (1.00 equiv.) in tetrahydrofuran (5.0 mL/mmol of carbonate) and the mixture was stirred at this temperature for 1 h. To this was added a suspension of [1,3-bis(diphenylphosphine)propane]nickel chloride (0.005 equiv.) in tetrahydrofuran (5 mL). The reaction mixture was stirred at room temperature for 24 h. After adding 5 M hydrochloric acid (10 mL), the reaction mixture was extracted with chloroform. The organic phase was washed with water and dried over magnesium sulfate, and the solvent was removed under reduced pressure. The residue was then added to methanol (250 mL) and the insoluble material was fractionated in a Soxhlet apparatus with methanol, acetone and chloroform.

3.1 Poly(2-(thiophen-3-yl)ethyl 2-methylhexan-2-yl carbonate)

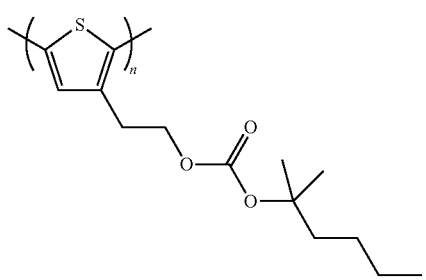

(3.1)

The synthesis was conducted proceeding from 2-(2-bromo-5-iodothiophen-3-yl)ethyl 2-methylhexan-2-yl carbonate (4.66 g, 9.80 mmol, 1.00 equiv.), isopropylmagnesium chloride solution (4.9 ml, 9.80 mmol, 1.00 equiv.) and [1,3-bis(diphenylphosphine)propane]nickel chloride (27.0 mg, 49.0 μmol, 0.005 equiv.) according to GP 3. After fractional purification by means of Soxhlet apparatus (methanol, acetone, chloroform), 1.02 g (39%) were obtained in the acetone fraction and 382 mg (15%) in the chloroform fraction of the polymer as a dark red solid.—Acetone: $M_n$=15.3 kDa, $M_w$=24.6 kDa, PDI=1.61; chloroform: $M_n$=41.0 kDa, $M_w$=45.6 kDa, PDI=1.11.—Detachment temperature: $T_{on}$=180° C.

Synthesis According to Yamamoto:
General Procedure for Preparation of Homopolymers (Polyfluorenes and Polycarbazoles) (GP 4):

A mixture of bis(1,5-cyclooctadiene)nickel (2.25 equiv.), cyclooctadiene (2.25 equiv.) and 2,2-bipyridine (2.25 equiv.) in N,N-dimethylformamide (5 mL) was stirred at 50° C. for 30 minutes. To this was added a solution of the appropriate monomer (1.00 equiv.) in tetrahydrofuran (10 mL/mmol of monomer). The reaction mixture was stirred at 70° C. for two days. To this was added the end-capper (1.00 equiv.), and the mixture was stirred at the same temperature for a further 12 h. After cooling, the reaction mixture was added to a mixture of methanol/hydrochloric acid (2:1, 300 mL) and the insoluble material was fractionated in a Soxhlet apparatus with methanol, acetone and chloroform.

3.2 Poly(2,7-(3-(9-methylfluoren-9-yl)propyl) 2-methylhexan-2-yl Carbonate)

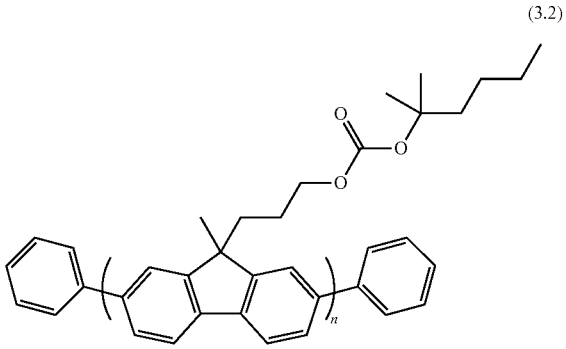

(3.2)

The synthesis was conducted proceeding from 3-(2,7-dibromo-9-methylfluoren-9-yl)propyl 2-methylhexan-2-yl carbonate (807 mg, 1.50 mmol, 1.00 equiv.), bis(1,5-cyclooctadiene)nickel (928 mg, 3.38 mmol, 2.25 equiv.), cyclooctadiene (365 mg, 3.38 mmol, 2.25 equiv.), 2,2-bipyridine (527 mg, 3.38 mmol, 2.25 equiv.) and bromobenzene (236 mg, 1.50 mmol, 1.00 equiv.) according to GP 4. After fractional purification by means of Soxhlet apparatus (methanol, acetone, chloroform), 471 mg (80%) were obtained in the chloroform fraction of the polymer as a yellow solid. —Chloroform: $M_n$=167 kDa, $M_w$=577 kDa, PDI=3.46.—Detachment temperature: $T_{on}$=200° C.

3.3 Poly-[5',5']-2,7-bis(2'-thiophenyl)-[N,N]-bis(hexan-1-yl-6-(2-methylhexan-2-yl)carbonate)naphthalene-1,8:4,5-tetracarboximide

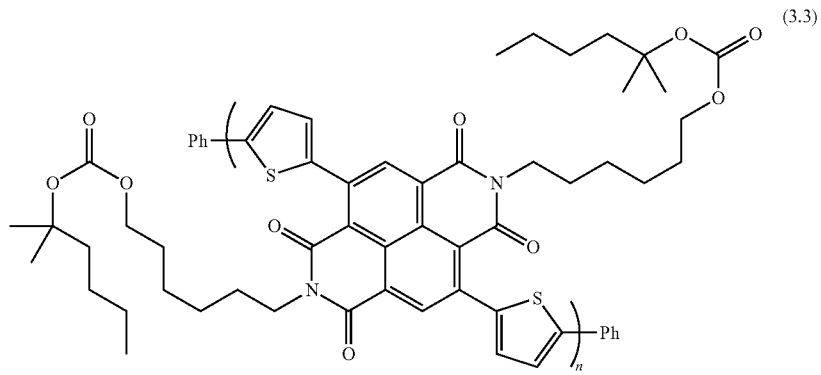

(3.3)

In a glovebox, bis(1,5-cyclooctadiene)nickel(0) (75 mg, 0.27 mmol), 1,5-cyclooctadiene (29 mg, 0.27 mmol) and 2,2'-bipyridine (42 mg, 0.27 mmol) were admixed with 3 mL of dry and degassed tetrahydrofuran, and the mixture was heated to 70° C. for 30 min. 2,7-Bis(5'-bromo-2'-thiophenyl)-[N,N]-bis(hexan-1-yl-6-(2-methylhexan-2-yl)carbonate)naphthalene-1,8:4,5-tetracarboximide (91 mg, 0.85 mmol) was dissolved in 7 mL of dry and degassed tetrahydrofuran, added to the nickel solution which had been cooled down to 10° C., and stirred at 10° C. for 120 min. Subsequently, 100 μL of bromobenzene were added and the mixture was stirred at 60° C. for 4 hours. After it had been cooled down to room temperature, the reaction suspension was added to a stirred mixture of 100 mL of MeOH and 50 mL of conc. hydrochloric acid. The mixture was stirred for one hour, and the precipitates were filtered off and washed with MeOH. The residue was extracted with 200 mL of chloroform, leaving a large proportion undissolved. The extract was concentrated to 3 mL and slowly added dropwise to 50 mL of MeOH. After stirring for three hours, the mixture was filtered and the residue was washed with MeOH. This operation was repeated twice in total, first using MeOH again, then n-hexane. The violet solid obtained was dried under reduced pressure, extracted with 10 mL of benzene for 2 hours, solids were filtered off and the liquid was lyophilized. 23 mg (30% of theory) of a violet polymer foam were obtained.

—GPC: Mn: 10 kD, Mw: 21 kD, PDI: 2.1. —IR: (ν in $cm^{-1}$): 2927 (m, $CH_2$), 2858 (m, $CH_2$), 1735 (s, O—C=O)—O), 1703 (s, N—C=O), 1664 (vs, N—C=O), 1570 (m).—Detachment temperature: $T_{on}$=155° C.

3.4 Poly-[5',5']-2,7-bis(4'-hexyl-2'-thiophenyl)-[N,N]-bis(hexan-1-yl-6-(2-methylhexan-2-yl)carbonate)naphthalene-1,8:4,5-tetracarboximide

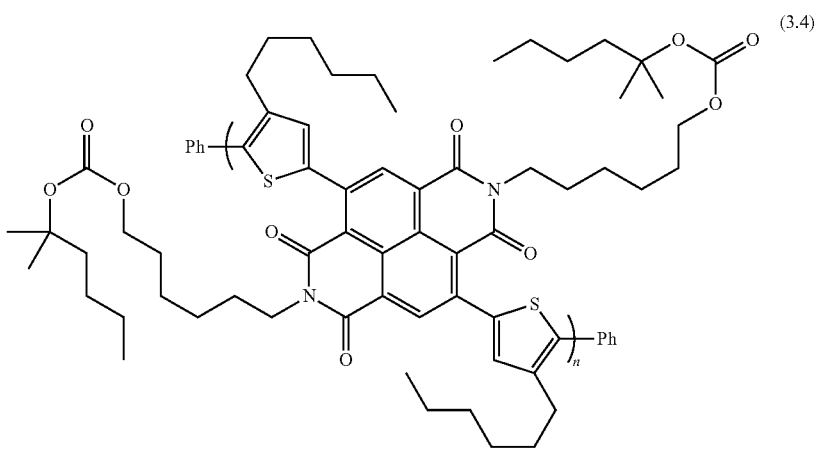

(3.4)

In a glovebox, bis(1,5-cyclooctadiene)nickel(0) (81 mg, 0.29 mmol), 1,5-cyclooctadiene (32 mg, 0.29 mmol) and 2,2'-bipyridine (46 mg, 0.29 mmol) were suspended in 3 mL of dry and degassed tetrahydrofuran, and the mixture was heated to 70° C. for 30 min, 2,7-Bis(5'-bromo-4'-hexyl-2'-thiophenyl). [N,N]-bis(hexan-1-yl-6-(2-methylhexan-2-yl) carbonate)naphthalene-1,8:4,5-tetracarboximide (114 mg, 0.09 mmol) was dissolved in 9 mL of dry and degassed tetrahydrofuran, added to the nickel solution which had been cooled down to room temperature (25° C.), and stirred at room temperature for 4 hours. To the reaction was added 100 µL. of bromobenzene (0.64 mmol), and the mixture was heated to 65° C. for a further 3 hours, cooled down to room temperature and then added to a stirred mixture of 100 mL of MeOH and 50 mL of conc. HCl. The suspension was stirred for one hour, and the precipitates were filtered off and washed with MeOH. The residue was extracted with chloroform, concentrated to 3 mL and slowly added dropwise to 100 mL of MeOH. After stirring for one hour, the mixture was filtered and the residue was washed with MeOH. This operation was repeated a total of three times, first using MeOH again, then a mixture of MeOH and acetone (2:1, v:v) and finally n-hexane. The violet solid obtained was dried under reduced pressure and lyophilized from benzene. 58 mg (58% of theory) of a violet polymer foam were obtained.

—GPC: Mn: 30 kD, Mw: 130 kD, PDI: 4.1. —IR: (v in cm$^{-1}$): 1735 (vs, O—C=O)—O), 1705 (s, N—C=O), 1663 (vs, N—C=O), 1572 (m). Detachment temperature: $T_{on}$=157° C.

Synthesis According to Suzuki:

General Procedure for Preparation of Copolymers (GP 5):

A mixture of the appropriate monomers (1.00 equiv. of each), tetrakis(triphenylphosphine)palladium (0.05 equiv.), potassium carbonate (2.50 equiv.), Aliquat 336 (0.01 equiv.) and water (5 mL) in toluene (5 mL/mmol of monomer) was stirred at 120° C. for 3 days. To this were added the end-cappers (1.00 equiv. of each), and the mixture was stirred at the same temperature for a further 12 h in each case. After cooling, the reaction mixture was added to a mixture of methanol/hydrochloric acid (2:1, 300 mL) and the insoluble material was fractionated in a Soxhlet apparatus with methanol, acetone and chloroform.

3.5 Poly[2,7-(3-(9-methylfluoren-9-yl)propyl 2-methylhexan-2-yl carbonate)-4,7-(benzo[c][1,2,5] thiadiazole)]

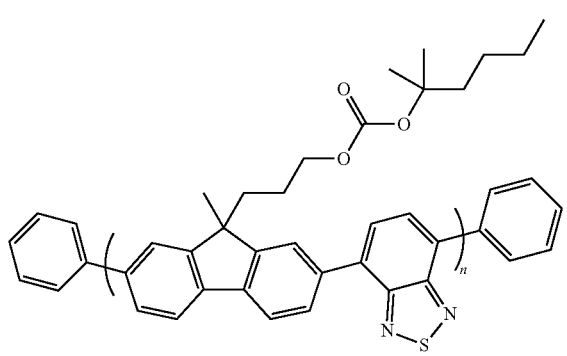

(3.5)

The synthesis was conducted proceeding from 3-(2,7-dibromo-9-methylfluoren-9-yl)propyl 2-methylhexan-2-yl carbonate (1.35 g, 2.50 mmol, 1.00 equiv.), 4,7-bis(4,4,5,5-tetramethyl-1,3,2-dioxaborolan-2-yl)benzo[c][1,2,5]thiadiazole (970 mg, 2.50 mmol, 1.00 equiv.), tetrakis(triphenylphosphine)palladium (144 mg, 125 µmol, 0.05 equiv.), potassium carbonate (864 mg, 6.25 mmol, 2.50 equiv.), Aliquat 336 (10.0 mg, 25.0 mmol, 2.50 equiv.), phenylboronic acid (305 mg, 2.50 mmol, 1.00 equiv.) and bromobenzene (393 mg, 2.50 mmol, 1.00 equiv.) according to GP 4. After fractional purification by means of Soxhlet apparatus (methanol, acetone, chloroform), 1.07 g (83%) were obtained in the chloroform fraction of the polymer as a yellow solid.

—Chloroform: $M_n$=25.8 kDa, $M_w$=55.8 kDa, PDI=2.28.—Detachment temperature: $T_{on}$=204° C.

Synthesis According to Yamamoto:

3.6 Poly(9-methylheptadecan-9-yl 2,7-dibromo-9H-carbazole-9-carboxylate

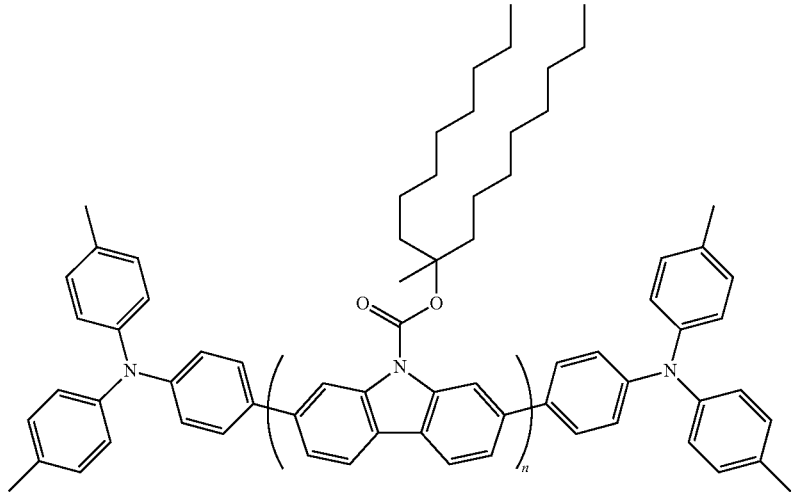

(3.6)

The synthesis was conducted proceeding from 9-methylheptadecan-9-yl 2,7-dibromo-9H-carbazole-9-carboxylate (932 mg, 1.50 mmol, 1.00 equiv.), bis(1,5-cyclooctadiene) nickel (928 mg, 3.38 mmol, 2.25 equiv.), cyclooctadiene (365 mg, 3.38 mmol, 2.25 equiv.), 2,2-bipyridine (527 mg, 3.38 mmol, 2.25 equiv,) and 4-bromo-N,N-di-p-tolylaniline (5.00 mg, 15.0 μmol, 0.01 equiv,) according to GP 4. After fractional purification by means of Soxhlet apparatus (methanol, acetone, chloroform), 661 mg (95%) were obtained in the chloroform fraction of the polymer as a gray solid.

—Chloroform: $M_n$=95.9 kDa, $M_w$=370 kDa, PDI=3.86.—Detachment temperature: $T_{on}$=160'C.

3.7 Poly-[5'-5']-2,7-bis(4'-hexylthiophene)-[N,N]-bis(2-methylhexan-2-yl)naphthalene-1,4,5,8-tetracarboxylic dicarbamate

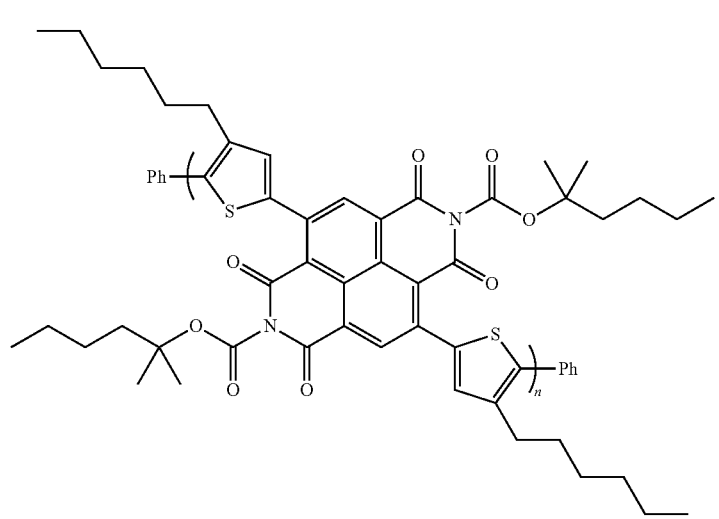

(3.7)

In a glovebox, bis(1,5-cyclooctadiene)nickel(0) (81 mg, 0.29 mmol), 1,5-cyclooctadiene (32 mg, 0.29 mmol) and 2,2'-bipyridine (46 mg, 0.29 mmol) were admixed with 3 mL of dry and degassed tetrahydrofuran, and the mixture was heated to 70° C. for 30 min. Bis(2-methylhexan-2-yl)-2,7-bis(5'-bromo-4'-hexylthiophen-2'-yl)naphthalene-1,4,5,8-tetracarboximide-[N,N]-dicarboxylate (96 mg, 0.09 mmol) was dissolved in 9 mL of dry and degassed tetrahydrofuran, added to the nickel solution which had been cooled down to room temperature (25° C.), and stirred at room temperature for 3.5 hours. To the reaction was added 100 μL of bromobenzene (0.64 mmol), and the mixture was heated to 65° C. for a further 3 hours, cooled down to room temperature and then added to a stirred mixture of 100 mL of MeOH and 50 mL of concentrated hydrochloric acid. The mixture was stirred for one hour, and the precipitates were filtered off and washed with MeOH. The residue was extracted with chloroform, concentrated to 3 mL and slowly added dropwise to 100 mL of MeOH. After stirring for one hour, the mixture was filtered and the residue was washed with MeOH. This operation was repeated three times in total, first using MeOH again, then twice using n-hexane. The violet solid obtained was dried under reduced pressure and lyophilized from benzene. 48 mg (59% of theory) of a violet polymer foam were obtained.

—GPC: Mn: 12.7 kD, Mw: 26 kD, PDI: 2.1.—FT-IR: (v in cm$^{-1}$): 2926 (m, $CH_2$), 2856 (m, $CH_2$), 1783 (vs, N—C=O)—O), 1712 (s, N—C=O), 1684 (vs, N—C=O), 1576 (m). Detachment temperature: $T_{on}$=103° C.

3.8 Poly-[5',5']-2,7-bis(2'-thiophenyl)-[N,N]-bis(hexan-1-yl-6-(9-methylheptadecan-9-yl)carbonate)carbonate)naphthalene-1,8:4,5-tetracarboximide

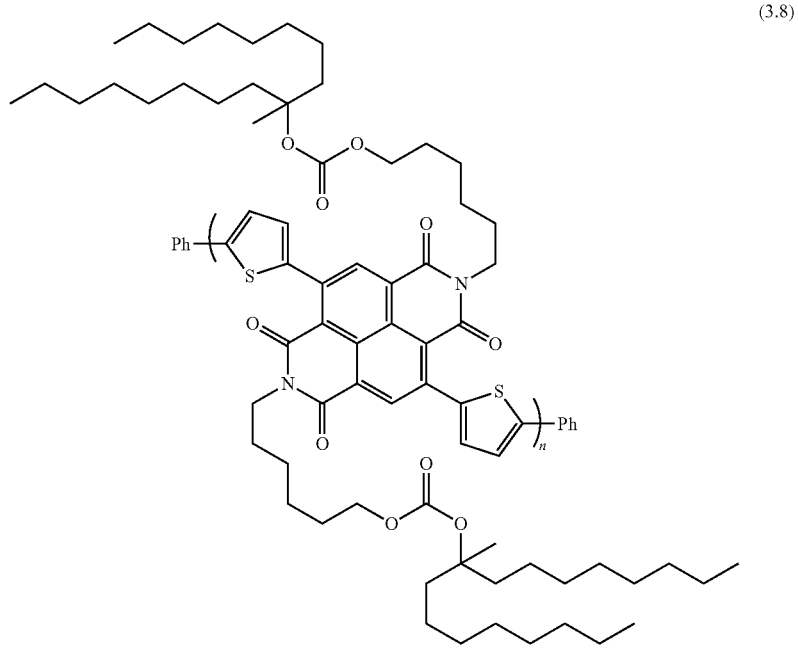

(3.8)

In a glovebox, bis(1,5-cyclooctadiene)nickel(0) (66 mg, 0.24 mmol), 1,5-cyclooctadiene (26 mg, 0.24 mmol) and 2,2'-bipyridine (37 mg, 0.24 mmol) were admixed with 3 mL of dry and degassed tetrahydrofuran, and the mixture was heated to 70'C for 30 min. 2,7-Bis(5'-bromo-2'-thiophenyl)-[N,N]bis(hexan-1-yl-6-(9-methylheptadecan-9-yl)carbonate)naphthalene-1,8:4,5-tetracarboximide (104 mg, 0.075 mmol) was dissolved in 6 mL of dry and degassed tetrahydrofuran, added to the nickel solution which had been cooled down to 10° C., and stirred at 10° C. for 110 min, Subsequently, 200 μL of bromobenzene were added and the mixture was stirred at 60° C. for 3 hours, After it had been cooled down to room temperature, the reaction solution was added to a stirred mixture of 100 mL of MeOH and 50 mL of conc. HCl. The mixture was stirred for one hour, and the precipitates were filtered off and washed with MeOH. The residue was taken up in chloroform, concentrated to 3 mL and slowly added to 150 mL of MeOH. After stirring for three hours, the mixture was filtered and the residue was washed with MeOH. This operation was repeated once. The violet solid obtained was dried under reduced pressure and lyophilized from benzene. The polymer foam thus obtained was then washed with n-pentane in a Soxhlet apparatus for 3 hours. This operation was repeated once. 66 mg (72% of theory) of a violet polymer foam were obtained.—GPC: Mn: 12 kD, Mw: 39 kD, PDI: 3.1.—FT-IR: (v in cm$^{-1}$): 2922 (m, CH$_2$), 2853 (m, CH$_2$), 1735 (s, O—(C=O)—O), 1704 (s, N—C=O), 1664 (vs, N—C=O), 1572 (m). Detachment temperature: $T_{on}$=175° C.

Example 4—Devices

4.1-4.4 Solar Cells Comprising Polymer 3.1 and PCBM-C60

BHJ solar cells were produced as follows:

All organic solar cells were applied to indium tin oxide-coated glass (R☐≈13Ω/☐). The latter was structured beforehand by means of hydrochloric acid and then cleaned in acetone and isopropanol for 15 min each; the last organic residues were removed by means of an oxygen plasma.

The organic layers were deposited by means of spin-coating under a protective gas atmosphere (N$_2$).

The hole injection layer consisting of poly(3,4-ethylenedioxythiophene):poly(styrenesulfonate) (PEDOT:PSS) was diluted with water in a ratio of 1:1 and deposited at 4000 rpm. In order to remove last residues of water, the samples were dried in a vacuum oven at 120° C. for 10 minutes.

The absorber consisting of the mixed system of polymer 3.1 and PC$_{60}$BM (1:0.75) was dissolved in a concentration of 40 mg/mL (dichlorobenzene). Subsequently, the mixed system was spun on at 800 rpm for 120 s, followed by a 10-minute baking step at 200° C. for thermal detachment of the solubility-imparting groups. Likewise constructed as a reference were solar cells without this baking step; these reference solar cells were heated only to 150° C. to evaporate solvent residues, and so the side groups were not detached.

The electrodes deposited by means of thermal sublimation were 20 nm of calcium followed by 20 nm of aluminum.

The voltage-current density (J-V) characteristic was recorded by means of a "Source Measurement Unit" (SMU for short, Keithley 238). On the basis of the voltage and current values thus ascertained, it was possible to calculate the fill factors and efficiencies.

The photoactive layer contains a mixture of polymer 3.1 as donor and $PC_{60}BM$ as acceptor.

Figure 6:
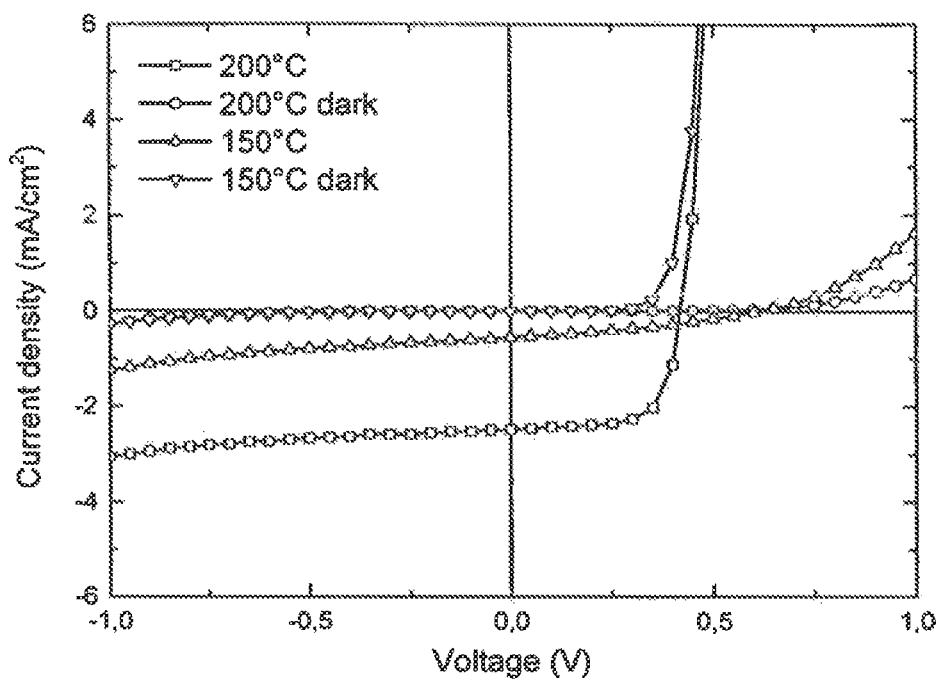
FIG. 6 shows the UI characteristic of an organic solar cell having a photoactive layer comprising a mixture of a polymer according to example 3.1 as donor and PC$_{60}$BM as acceptor.

The UJ characteristic in FIG. 6 shows an increase in the photocurrent after detachment of the side groups and a simultaneous decrease in the serial resistance of the solar cell (inverse slope of the characteristic toward high forward voltages). The detachment of the side groups on heating of the layer leads to a shrinkage in volume, as a result of which the polymer chains are reorganized and the distance between the polymer chains decreases. This reduction in the distance leads to better photogeneration of charge carriers and better intermolecular charge transfer ("better conductivity").

The characteristics for the OPV device are shown in table 1.

TABLE 1

| Ex. | Photoactive layer | $J_{sc}$ [mA/cm$^2$] | $V_{oc}$ [V] | FF [%] | η [%] | $R_s$ [Ω] |
|---|---|---|---|---|---|---|
| 4.1 | Polymer 3.1/ PCBM baking temp. 150° C. | 0.6 | 0.62 | 34 | 0.12 | 1.5 |
| 4.2 | Polymer 3.1/ PCBM baking temp. 200° C. | 2.5 | 0.42 | 68 | 0.71 | 0.1 |

In this table:
$J_{sc}$ = short-circuit current
$V_{oc}$ = open-circuit voltage
FF = fill factor
η = power conversion efficiency (PCE)
$R_s$ = serial resistance 4.5-4.6 OLEDs with an Emitter Layer Comprising Polymer 3.2 or 3.3

OLEDs were produced as follows:

All OLEDs were deposited on indium tin oxide-coated glass (R☐≈13Ω/☐). The latter was structured beforehand by means of hydrochloric acid and then cleaned in acetone and isopropanol for 15 min each; the last organic residues were removed by means of an oxygen plasma.

The organic layers were deposited by means of spin-coating under a protective gas atmosphere ($N_2$).

The hole injection layer consisting of poly(3,4-ethylenedioxythiophene):poly(styrenesulfonate) (PEDOT:PSS) was diluted with water in a ratio of 1:1 and deposited at 4000 rpm. In order to remove last residues of water, the samples were put in a vacuum oven at 120° C. for 10 minutes.

The emitter consisting of polymer 3.2 was dissolved in a concentration of 8 g/L in toluene and deposited at 1000 rpm, followed by a baking step at 200° C. over a period of 10 min for thermal detachment of the solubility-imparting groups. Likewise constructed as a reference were OLEDs without this baking step.

The electrodes deposited by means of thermal sublimation were 0.7 nm of lithium fluoride, followed by 20 nm of aluminum.

The voltage-current density (J-V) characteristic was recorded by means of a "Source Measurement Unit" (SMU for short, Keithley 238). By means of the current and voltage values thus obtained and the luminance calculated from the spectrum, it was ultimately possible to calculate the performance and power efficiency.

The spectrometer had been calibrated beforehand with a halogen standard (Philips FEL-1000W), Performance and power efficiency were calculated assuming Lambertian reflectance.

Polymer 3.2 is a blue-emitting polymer. The solubility group can, as mentioned above, be detached by supplying thermal energy (200° C.) over a period of 10 min. Solubility tests before and after the detachment have shown that the loss of layer thickness is about 10 nm, proceeding from a starting layer thickness of ~80 nm. This decrease corresponds to a loss of mass resulting from the evaporation of the carboxyl and 1,1-dimethylpentyl groups.

For characterization of the surface, atomic force microscope (AFM) studies were conducted.

Figure 1B:
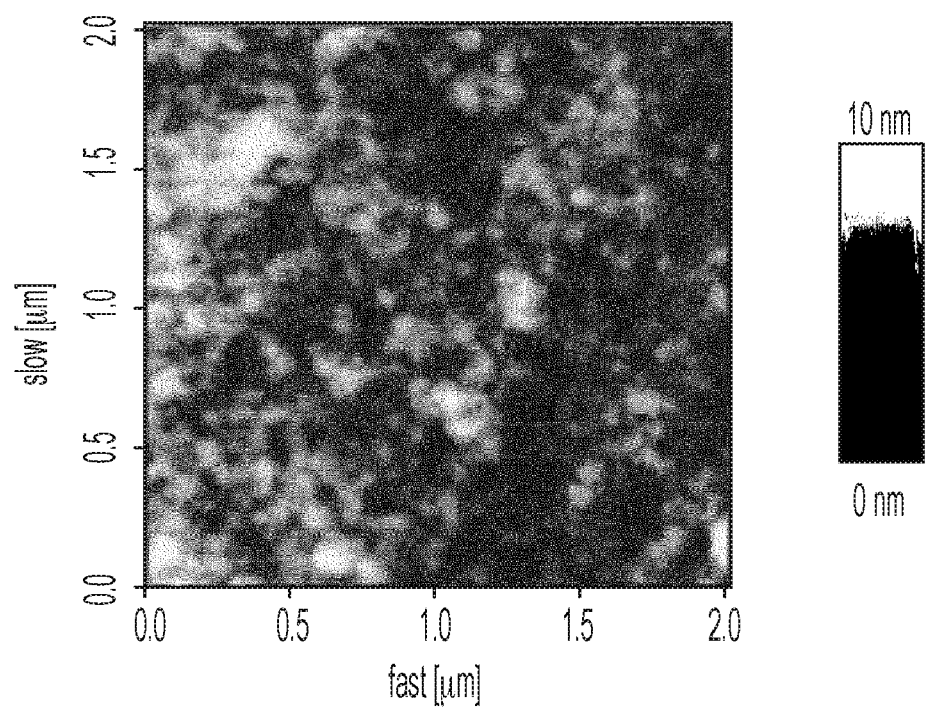
Figure 1C:
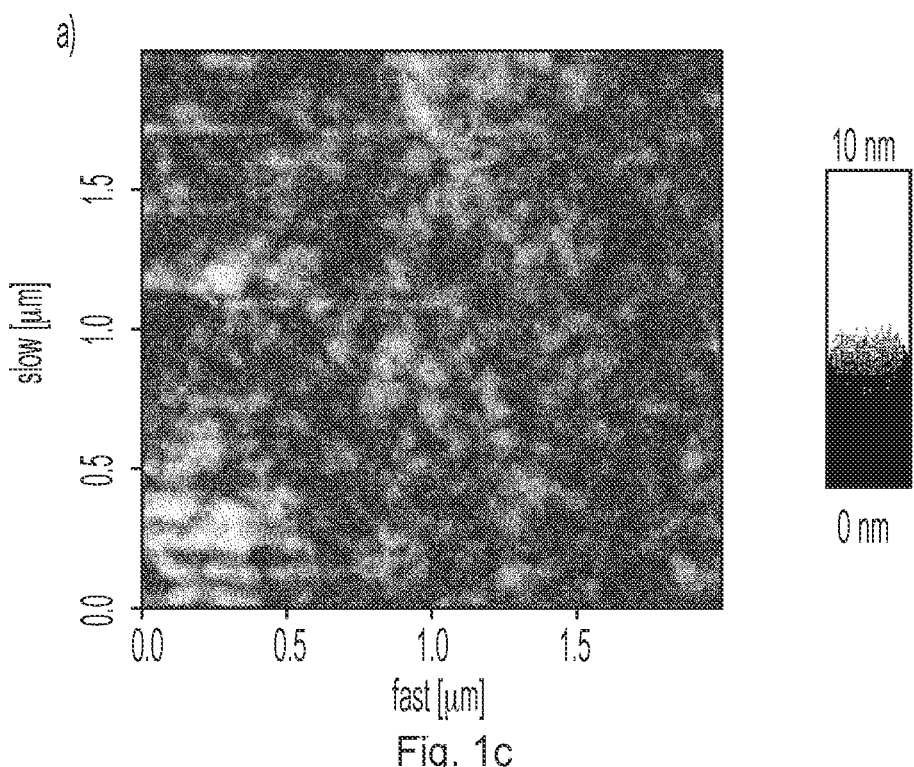

FIGS. 1a-c shows AFM images of the topography of a) an untreated, b) a thermally treated (200° C., 10 min) and c) a thermally treated and toluene-rinsed polymer 3.2 layer.

FIG. 1a shows the topography of a polymer 3.2 layer which has not been treated thermally. The AFM image clearly shows holes in the layer. These defects can be "healed" by the thermal aftertreatment, as apparent in FIG. 1b. The temperature needed to detach the side groups is accordingly high enough (above the glass transition temperature of the polymer) to enable reorganization of the polymer film and to close the holes. Even after the thermally treated layer has been rinsed off with the toluene used for layer deposition, polymer 3.2 forms a continuous film (FIG. 1c).

Figure 2A:
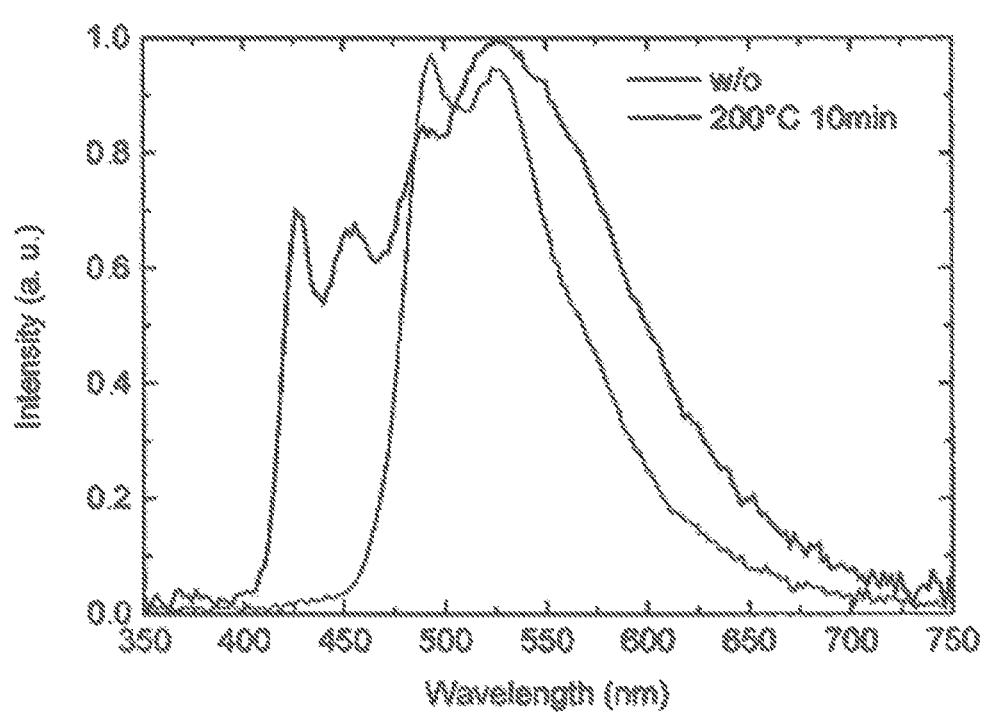
Figure 2B:
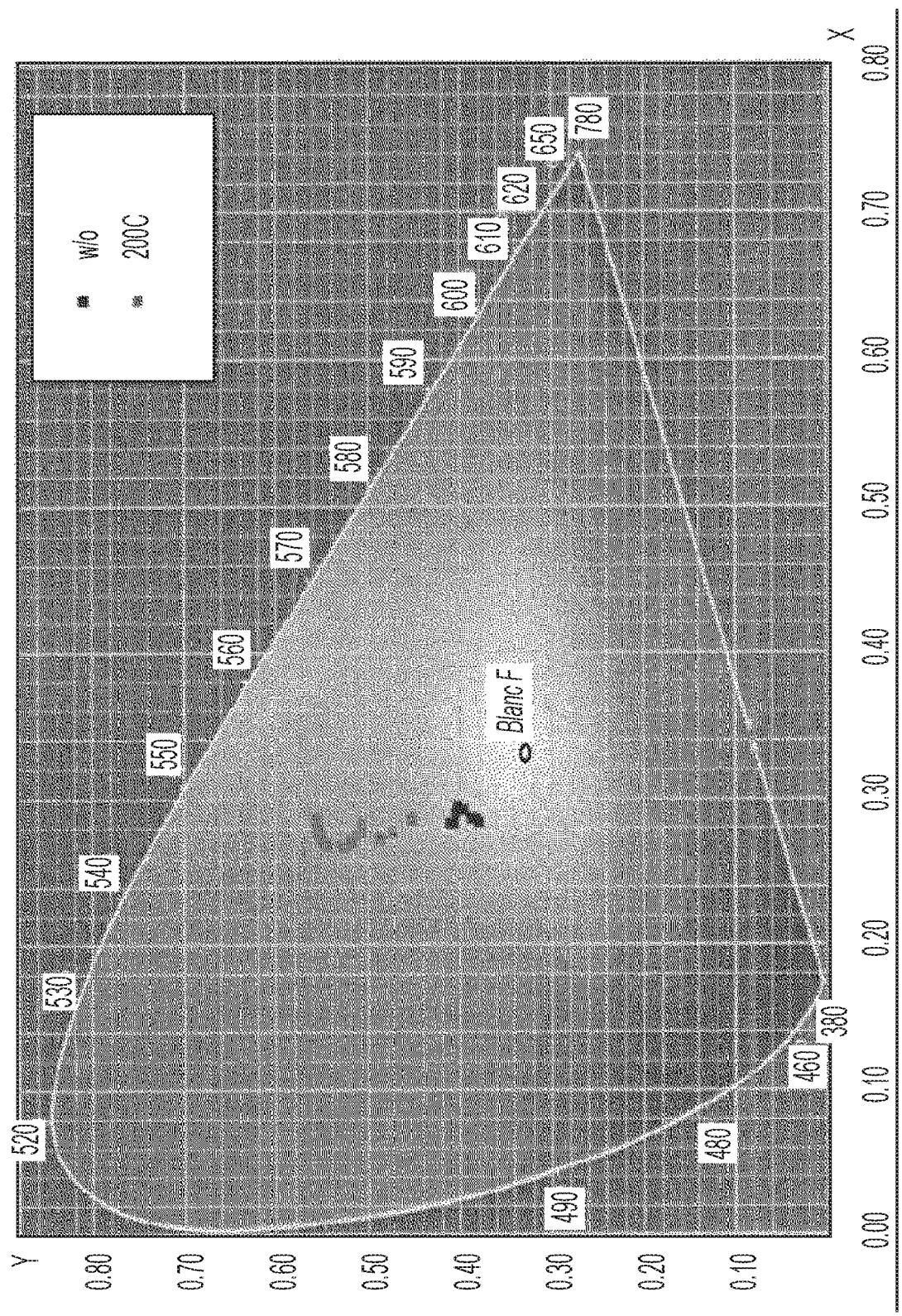
Figure 3A:
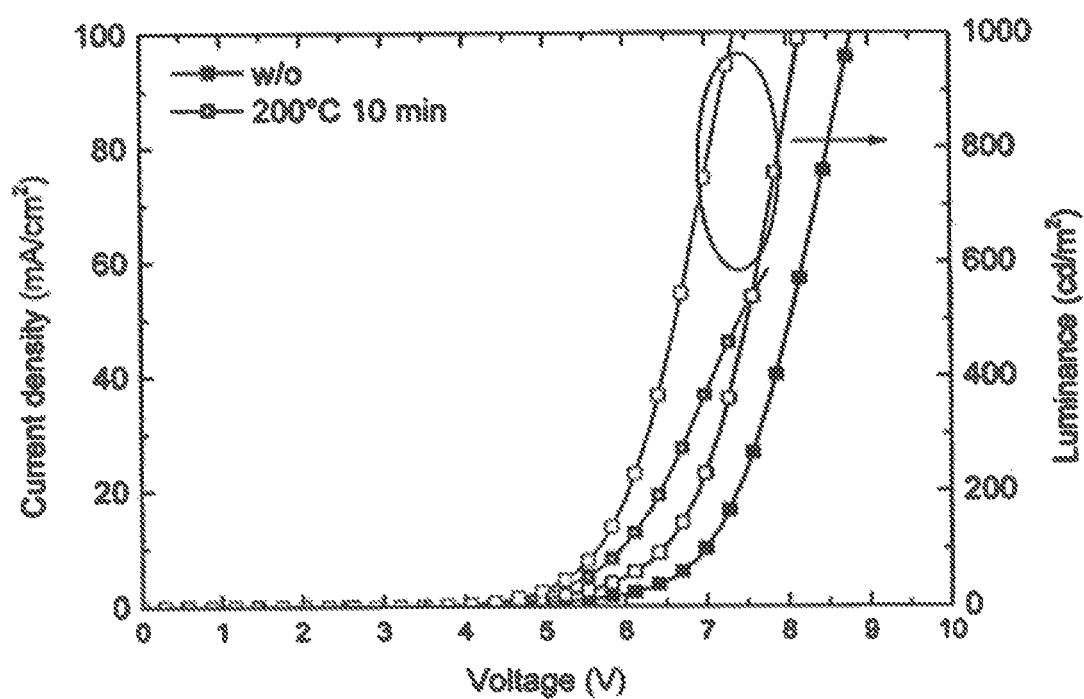
Figure 3B:
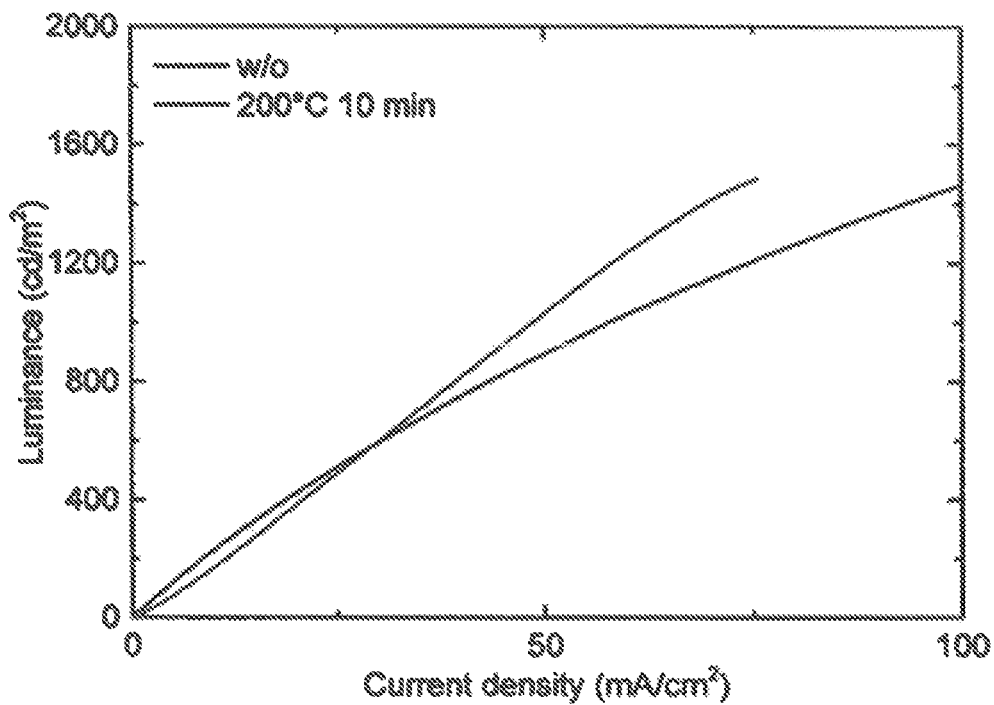
Figure 3C:
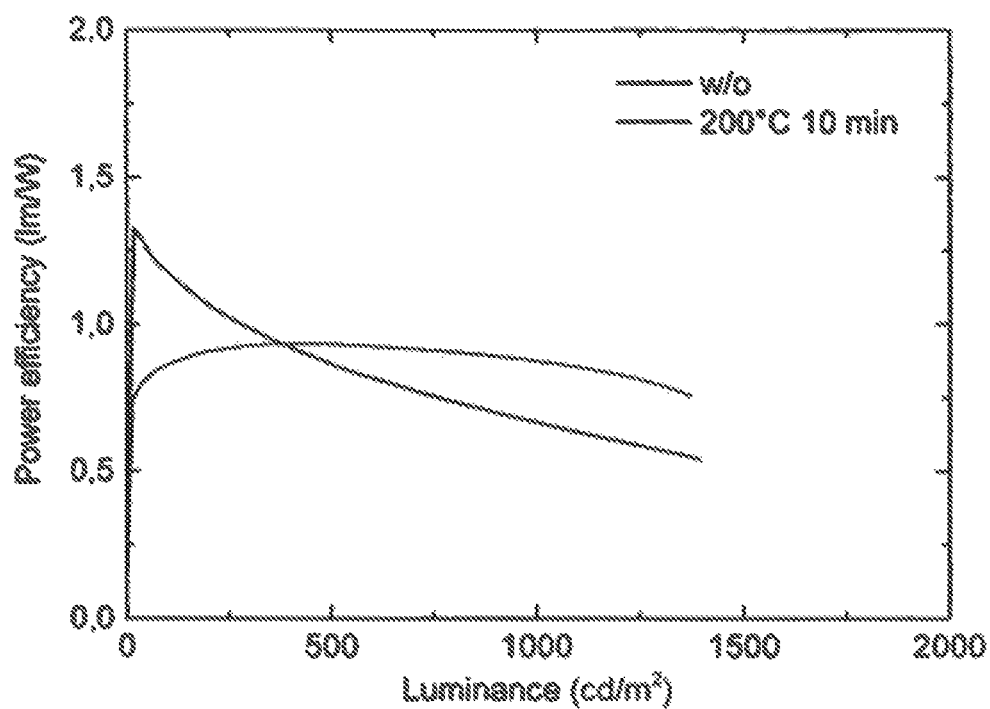
Figure 3D:
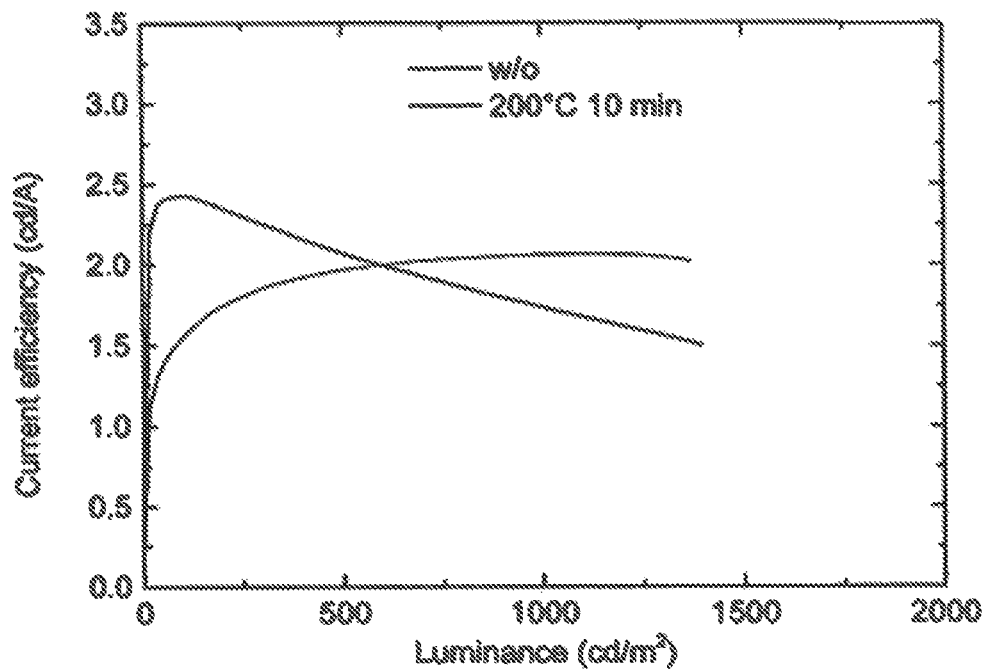

Important conclusions about the emitter can generally be obtained from the emission spectrum. FIGS. 2a-b show the emission spectrum and the color locus of an OLED comprising polymer 3.2 before and after thermal aftertreatment. The electroluminescence spectrum of polymer 3.2 before and after the thermal treatment at 200° C. shows differences (FIG. 2a). This observation is probably direct evidence of the detachment of the side groups in the thermally treated film.

In accordance with the change in the spectral emission, there is also a change in the color coordinates of the OLEDs with the thermal treatment (FIG. 2b). The color coordinates move from close to the white point (CRI: ~65) toward a green emission.

FIGS. 3a-d show the optoelectronic characteristics of an OLED with polymer 3.2 emitter. It was possible to lower the use voltage from 3.9 V to 3.6 V and distinctly reduce the roll-off of the efficiencies.

The optoelectronic characterization (FIG. 3) of the polymer 3.2 emitter shows, inter alia, that the use voltage drops from about 3.9 V to 3.6 V as a result of the thermal treatment. The baking additionally distinctly reduced the roll-off of the efficiencies toward higher luminances, and achieved efficiencies of ~0.9 lm/W and ~2.1 cd/A at 1000 cd/m$^2$.

Figure 4A:
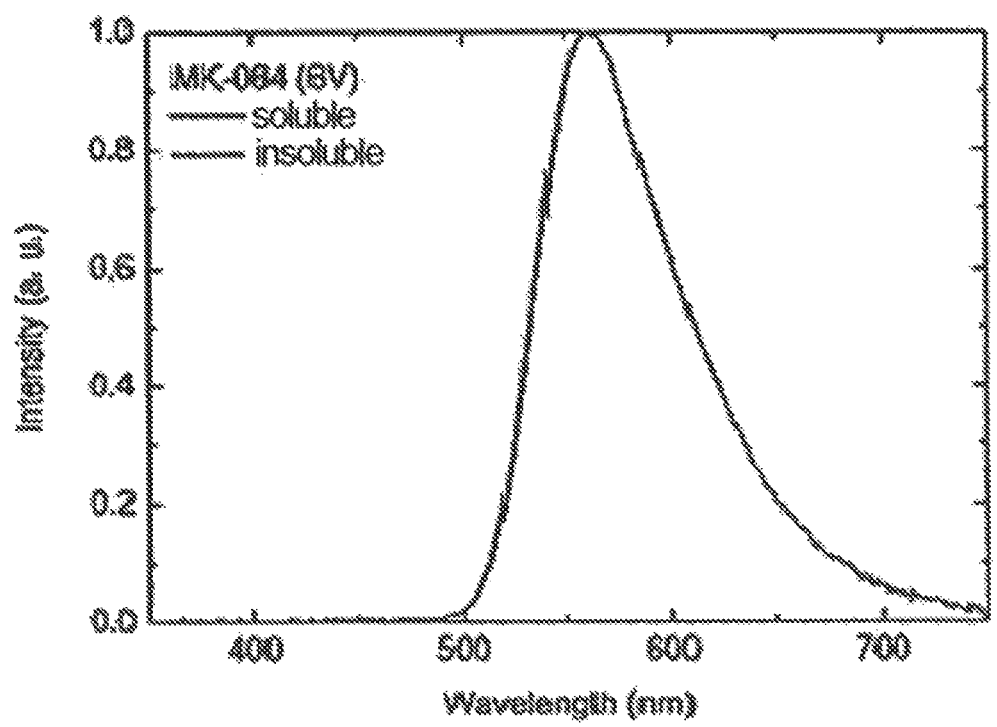
FIG. 4 shows the comparison of the electroluminescence spectra of a polymer according to example 3.3 at a voltage of 6 V before (soluble) and after (insoluble) thermal treatment.

FIG. 4a shows, for polymer 3.3, the comparison of the electroluminescence spectra at a voltage of 6 V before (soluble) and after (insoluble) thermal treatment.

Compared to polymer 3.2 examined previously, polymer 3.3 contains thiobenzodiazole acceptor units. The emission spectrum of polymer 3.3 (FIG. 4a), by contrast with polymer 3.2, no longer shows any spectral shift. The additional acceptor units in the polymer increase the acceptor strength thereof overall, such that the interaction with the carboxyl side groups can be quite different, Here too, further spectroscopic, studies have to be conducted in order to more closely examine the interaction of the carboxyl side groups with the π system of the polymer.

Figure 4B:
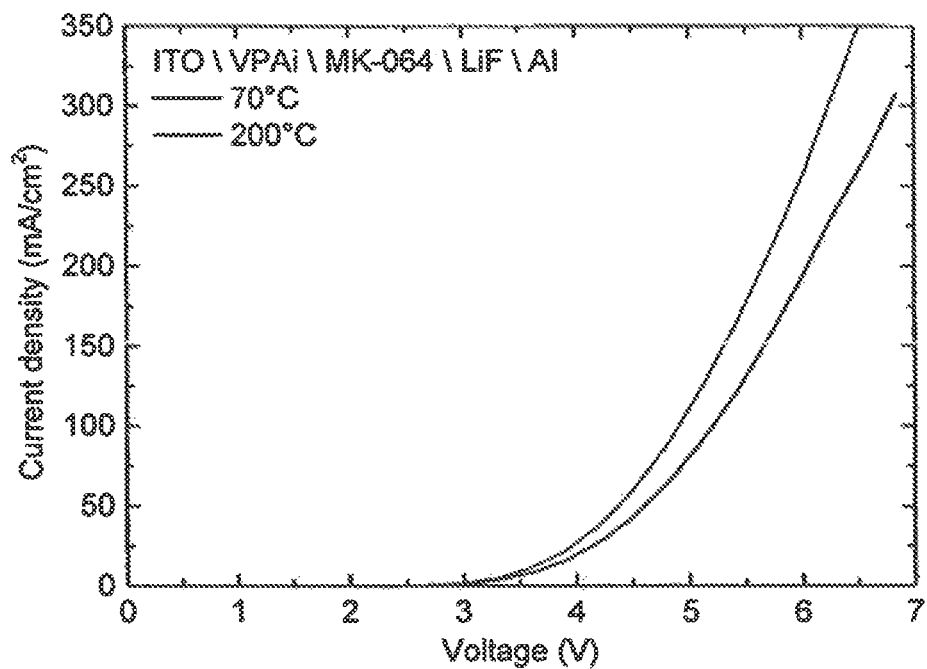

FIG. 4b shows the optoelectronic characteristics of an OLED with polymer 3.3 emitter. The use voltage is ~3.2 V. Luminances of up to 5500 cd/m² were achieved. The efficiencies have only a low roll-off.

Figure 4C:
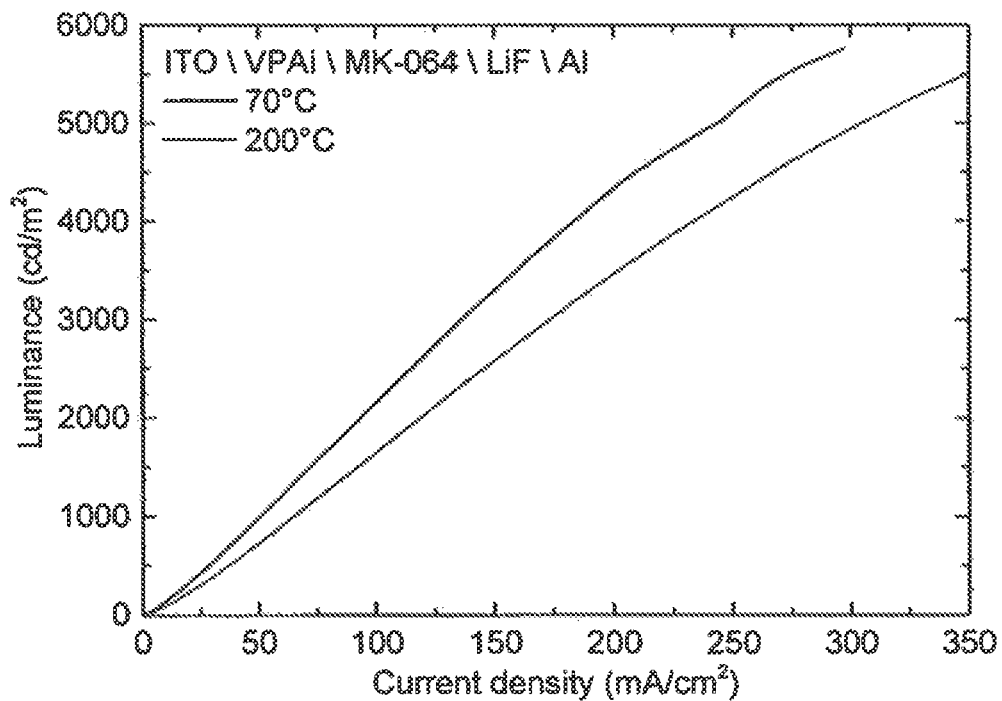
Figure 5A:
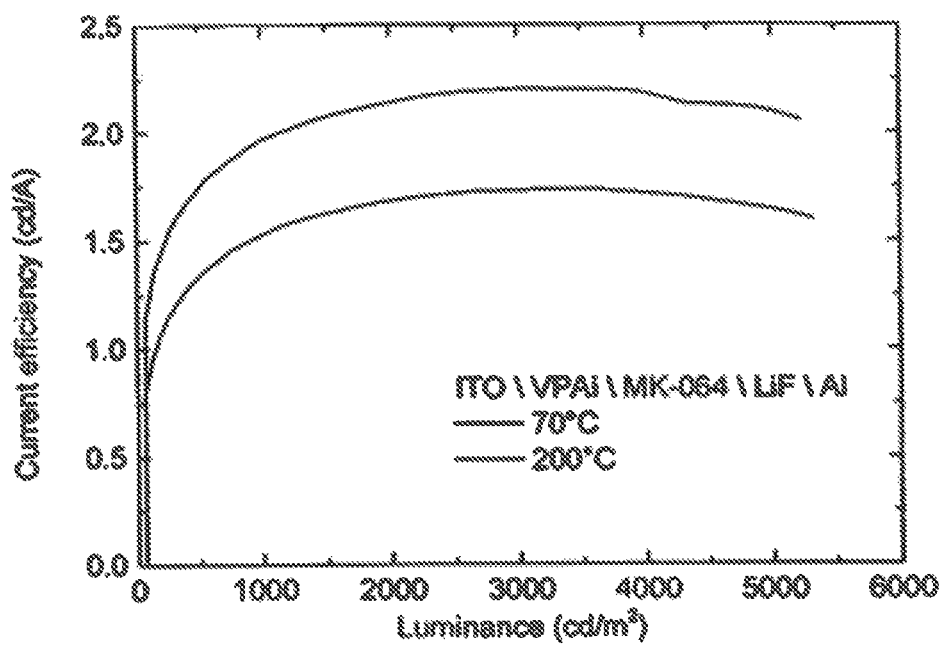
FIG. 5 shows the optoelectronic characteristics of an OLED comprising a polymer according to example 3.3 as emitter.
Figure 5B:
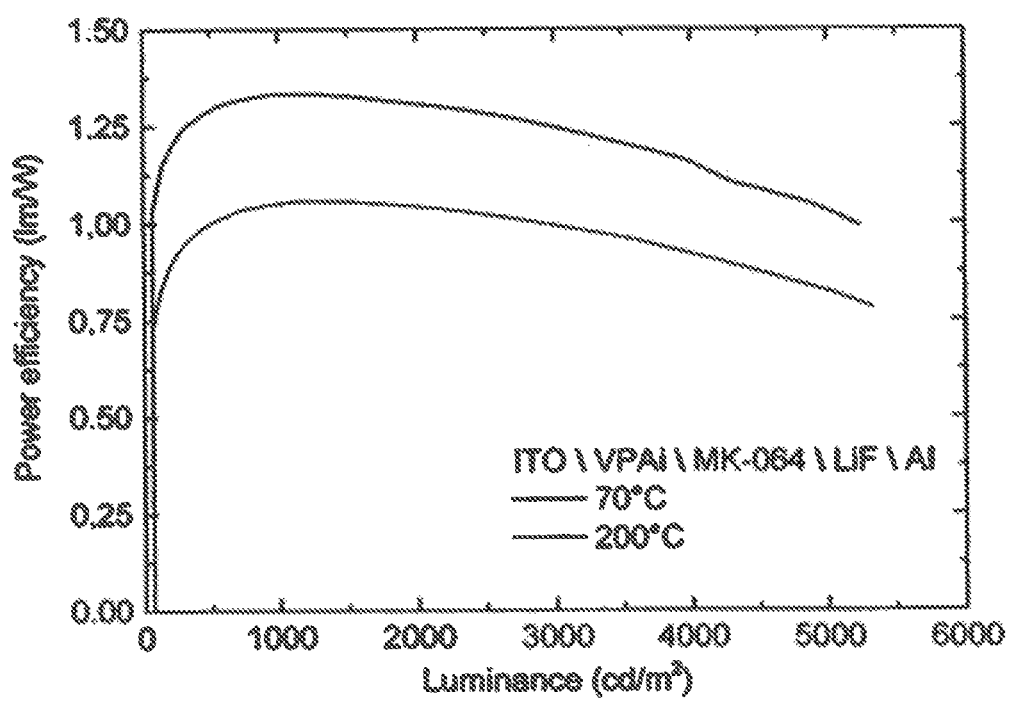

The optoelectronic characteristics (FIGS. 4b-d) of polymer 3.3 OLEDs exhibit a use voltage of 3.2 V. The efficiencies decrease minimally after the detachment of the solubility groups. Both components have only a low roll-off in the efficiencies. The efficiencies are 1000 cd/m² at about 1.5 cd/A and 1.0 lm/W. The maximum luminance achieved is ~5500 cd/m² at a current of 300 mA/cm².

The switchability of the solubility of the polymers can be utilized in order to deposit further functional layers, for example a hole-blocking layer, on the emitters. This generally has a very positive effect on the charge carrier equilibrium and should thus further increase the efficiency of the components.

4.7-4.9 OFETs with an Active Semiconductor Laser Comprising Polymer 3.4, 3.7 or 3.8

Organic field-effect transistors (OFETs) were produced as follows:

All OFETs were produced on glass substrates which had been cleaned beforehand in acetone and isopropanol in an ultrasound bath for 15 min each. The source and drain electrodes composed of gold with a height of 50 nm were applied in a structured manner by thermal evaporation through a shadowmask under high vacuum. The dimensions of the individual OFETs were: channel length: 50 μm, channel width: 1000 μm, electrode height: 50 nm.

Figure 7:
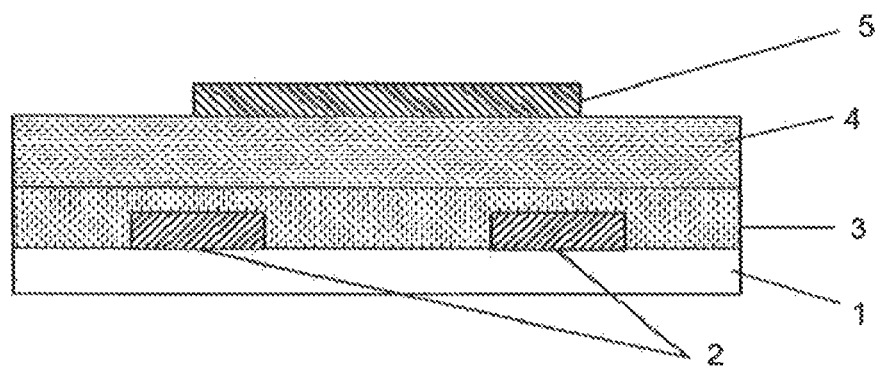
FIG. 7 shows, by way of example, the schematic structure of the top gate/bottom contact OFETs according to examples 4.7 to 4.9.

FIG. 7 shows the structure of a top gate/bottom contact OFET used here. The carrier material used was glass substrates (1). The source (S) and drain (D) electrodes (2) composed of silver were applied through a shadowmask under high vacuum and have a thickness of about 50 nm. The active layer (3) was deposited by means of spin-coating under a protective gas atmosphere ($N_2$).

For deposition of the active semiconductor layer (3) with a layer thickness between 80 and 130 nm, a solution of 5-10 mg/L of polymer 3.4, 3.7 or 3.8 in chlorobenzene was deposited at 1000 rpm with an acceleration of 500 rpm/s and a total duration of 60 s. In order to remove solvent residues, the samples were then heat-treated at 100'C for 180 s. For thermal detachment of the solubility-imparting groups, baking was effected at 180'C to 220° C. for 3-5 min. Likewise produced as a reference were OFETs without this baking step.

As dielectric (4), 300 nm of Parylene C were applied to the entire substrate by gas phase deposition by means of the PDS2010 instrument from "Special Coatings Systems", in order to minimize external influences on the semiconductor layer.

The gate electrodes (5) composed of silver were applied by vapor deposition through a shadowmask under high vacuum.

Thin-film transistor (TFT) transfer measurements were conducted at room temperature under ambient air with a "Semiconductor Parameter Analyzer" (Agilent 4155C). By means of the TFT transfer characteristics thus obtained, it was ultimately possible to determine the mobility of the semiconductive polymer in this construction.

Polymers 3.4 and 3.8 are semiconductive polymers having n-channel character (electron conduction). The solubility-imparting group can, as mentioned above, be detached by supplying thermal energy (200-220° C.) over a period of 5 min. Solubility tests before and after the detachment showed that there is a distinct decrease in solubility after the pyrolysis. The loss of layer thickness during the pyrolysis is between 20% and 35%, proceeding from an initial layer thickness between 25 and 40 nm. This decrease corresponds to the loss of mass resulting from evaporation of the carboxyl and alkyl groups and a small degree of compaction of the layer.

Polymer 3.7 is likewise a semiconductive polymer having n-channel character (electron conduction). The solubility-imparting group can be detached by supplying thermal energy (180-200° C.) over a period of 5 min, After the thermal treatment, the layer exhibits very good solvent stability.

Figure 8A:
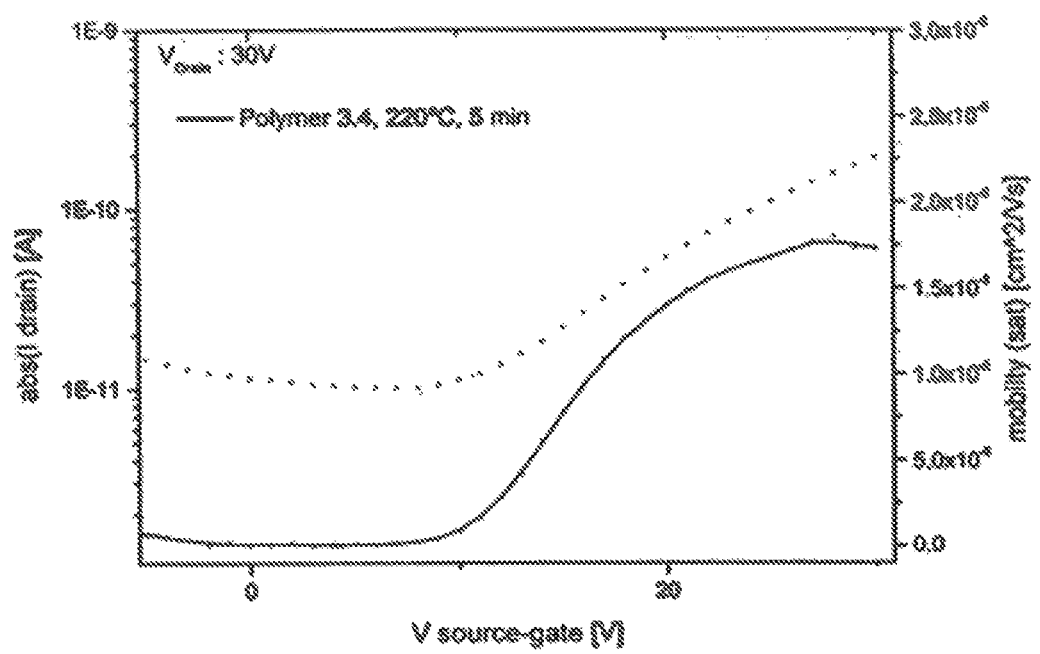
FIGS. 8a, 8b, 9a, 9b, 10a and 10b show the TFT transfer characteristics of OFETs according to examples 4.7 to 4.9.

FIG. 8a shows the TFT transfer characteristic of an OFET (source-drain voltage 30 V) in the saturated regime with polymer 3.4 as semiconductor after a thermal treatment of 220° C. for 5 min. It can be inferred from the characteristic that the phenomenon observed is electron conduction. The highest mobility was measured at a source-gate voltage of 35 V; it is $\mu_e=1.7*10^{-5}$ cm²/Vs. The on/off ratio of the transistor was determined as 1:20.

Figure 8B:
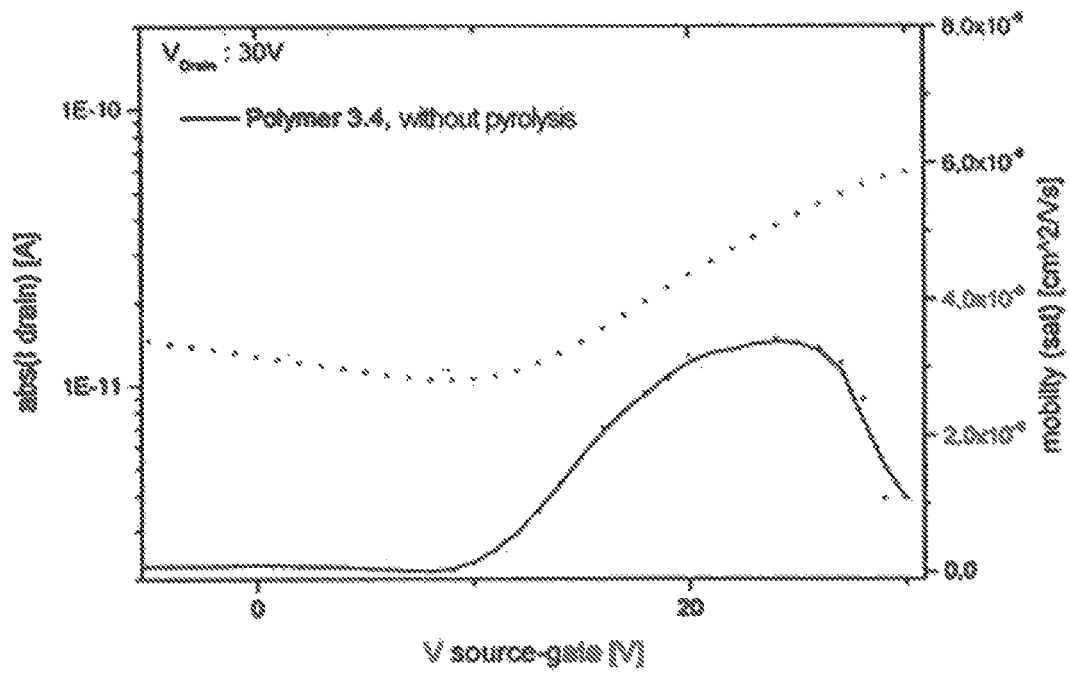

FIG. 8b shows the TFT transfer characteristic of an OFET (source-drain voltage 30 V) in the saturated regime with polymer 3.4 as semiconductor without thermal treatment. It can be inferred from the characteristic that polymer 3.4 even without detachment of the solubility groups already has electron-conducting character. The maximum mobility determined in this case is $\mu_e=3.3*10^{-6}$ cm²/Vs, and the on/off ratio was determined as 1:4. These values are thus well below what has been determined for the same polymer after the thermal treatment.

Figure 9A:
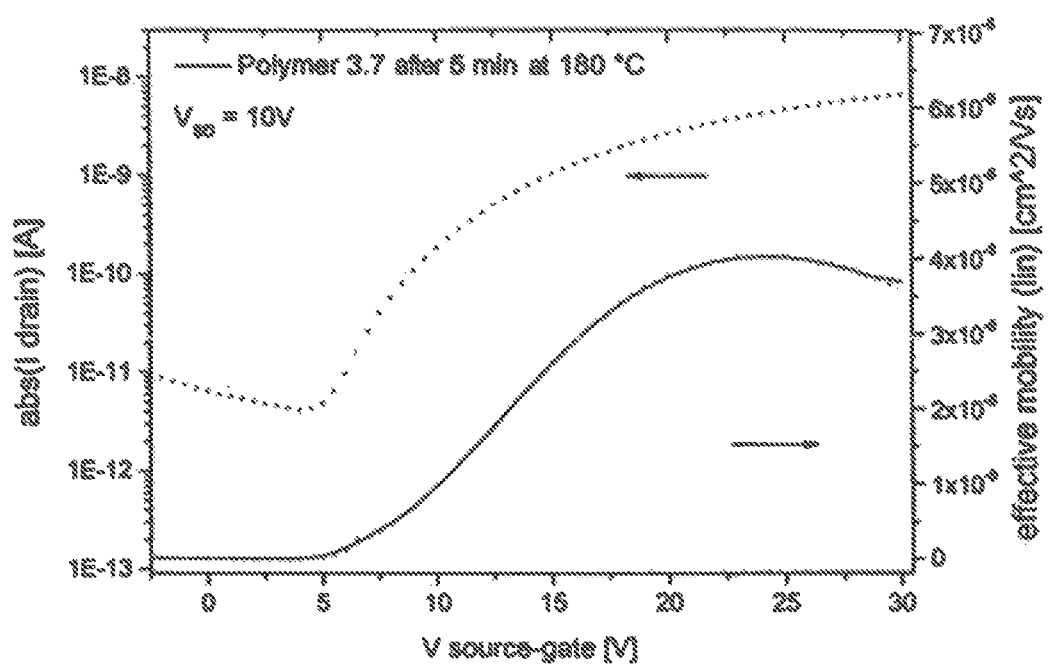

FIG. 9a shows the TFT transfer characteristic of an OFET (source-drain voltage 10 V) in the linear regime with polymer 3.7 as semiconductor after a thermal treatment of 180° C. for 5 min. It can be inferred from the characteristic that the phenomenon observed is electron conduction. The highest effective mobility was measured at a source-gate voltage of 23 V; it is $\mu_e=4*10^{-5}$ cm²/Vs. The on/off ratio of the transistor was determined as $10^3$.

Figure 9B:
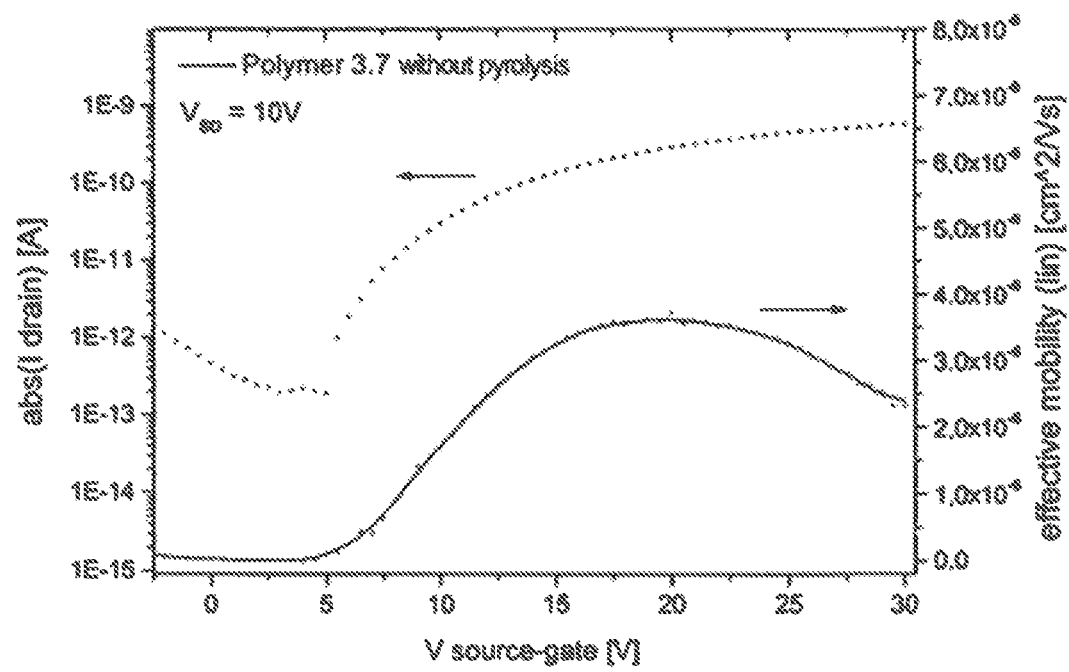

FIG. 9b shows the TFT transfer characteristic of an OFET (source-drain voltage 10 V) in the linear regime with polymer 3.7 as semiconductor without thermal treatment. It can be inferred from the characteristic that polymer 3.7 even before the detachment of the solubility groups already has electron-conducting character. The maximum effective mobility determined in this case is $\mu_e=3.5*10^{-6}$ cm²/Vs, and the on/off ratio was determined as $10^3$. The effective mobility of the uncleaved material is thus about one order of magnitude below that after the cleavage, with the on/off ratio remaining comparable.

Figure 10A:
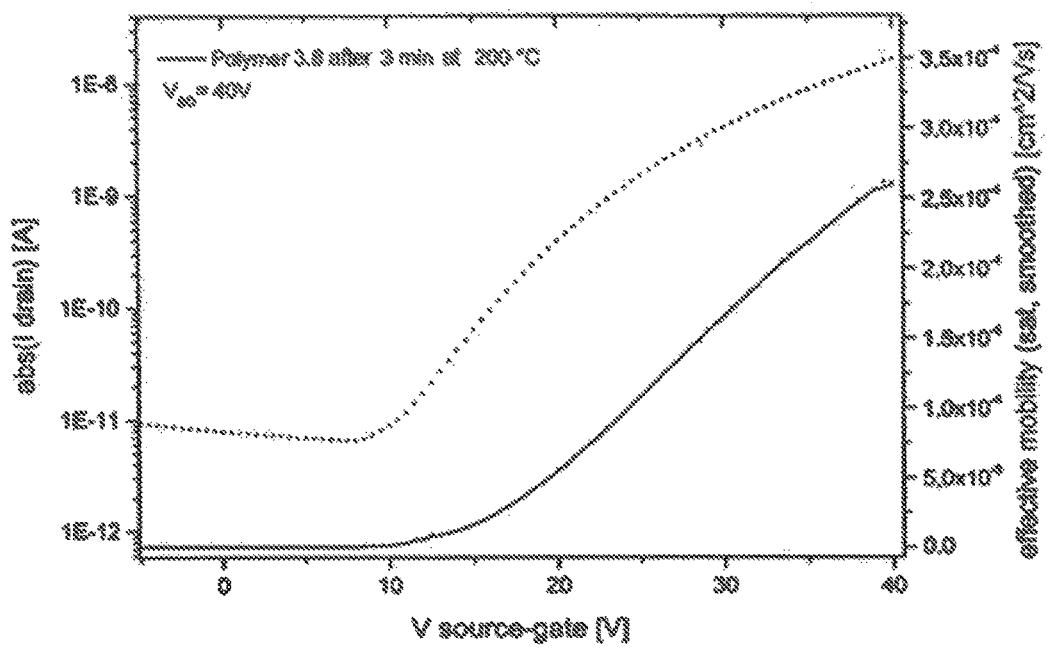

FIG. 10a shows the TFT transfer characteristic of an OFET (source-drain voltage 40 V) in the saturated regime with polymer 3.8 as semiconductor after a thermal treatment of 200° C. for 3 min. It can be inferred from the characteristic that the phenomenon observed is electron conduction. The highest effective mobility was measured at a source-gate voltage of 40 V; it is $\mu_e=2.6*10^{-4}$ cm²/Vs. The on/off ratio of the transistor was determined as $10^4$.

Figure 10B:
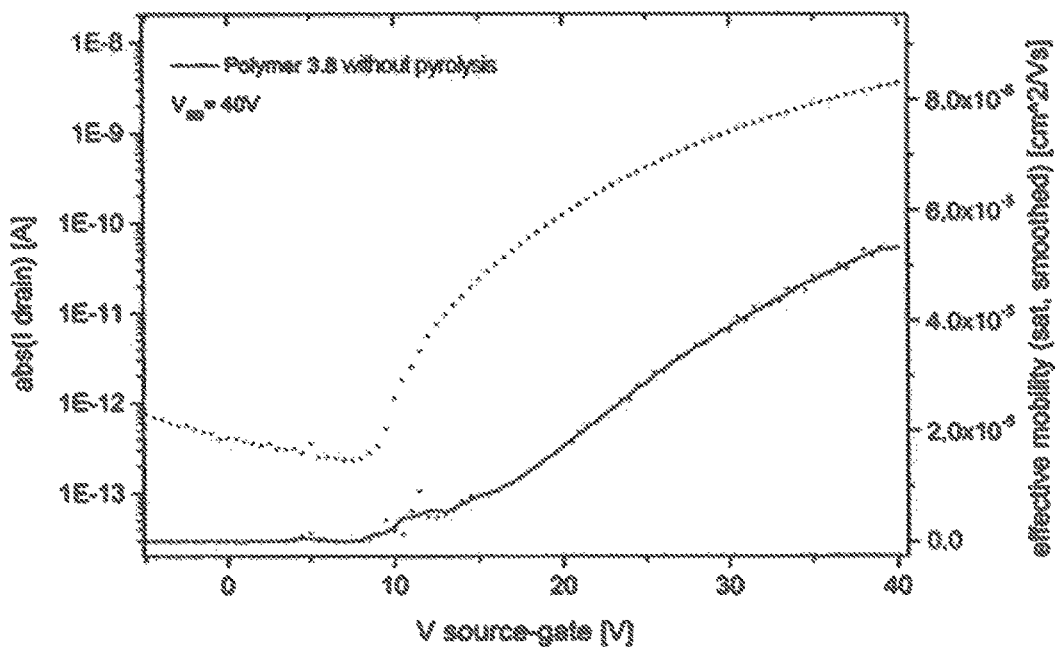

FIG. 10b shows the TFT transfer characteristic of an OFET (source-drain voltage 40 V) in the saturated regime with polymer 3.8 as semiconductor without thermal treatment. It can be inferred from the characteristic that polymer 3.8 even before the detachment of the solubility groups already has electron-conducting character. The maximum effective mobility determined in this case is $\mu_e=5.3*10^{-5}$ cm$^2$/Vs, and the on/off ratio was determined as $10^4$. The effective mobility of the uncleaved material is thus about one order of magnitude below that after the cleavage, with the on/off ratio remaining comparable.

The switchability of the solubility of the polymers can be utilized in order to deposit further functional layers, for example solution-processed dielectrics and electrodes, on the semiconductor layer. The more successive process steps are based on solvent-based deposition techniques, the more efficient it is possible to make the production of the OFET components.

The invention claimed is:

1. A process for partially or fully detaching the carbonate or carbamate groups in a conjugated polymer comprising heating the polymer or a layer comprising the polymer to a temperature in the range of from 150° C. to 200° C., wherein the conjugated polymer comprises one or more identical or different repeat units of formula (I):

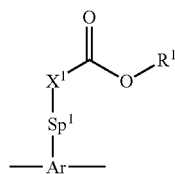
I wherein:
Ar is a mono- or polycyclic aryl or heteroaryl radical which is optionally substituted at one or more positions;
Sp$^1$ is a single bond or alkylene radical having 1 to 20 carbon atoms and is unsubstituted or mono- or polysubstituted by F, Cl, Br, I or CN, and wherein one or more nonadjacent CH$_2$ groups are each optionally independently replaced by —O—, —S—, —NH—, —NR$^0$—, —SiR$^0$R$^{00}$—, —CO—, —COO—, —OCO—, —OCO—O—, —S—CO—, —CO—S—, —CR$^0$=CR$^{00}$—, or —C≡C— such that no oxygen and/or sulfur atoms are directly bonded to one another;
X$^1$ is NR$^0$ or O;
wherein, if the Sp$^1$-X$^1$—C(O)—OR$^1$ radical is bonded to a nitrogen atom in the Ar radical, the Sp$^1$-X$^1$ radical may also be a single bond,
R$^0$ and R$^0$
are each independently H or an alkyl group having 1 to 12 carbon atoms; and
R$^1$ is a hydrocarbyl radical having 1 to 40 carbon atoms, with the proviso that the repeat units of the formula (I) excludes
repeat units wherein Ar is a phenylene radical that is mono-or polysubstituted by —NH—C(O)—OR$^1$ and wherein, in the polymer backbone, is directly adjacent to an optionally substituted benzo[lmn][3,8]phenanthroline-1,3,6,8-tetraone-4,9-diyl unit, and
repeat units wherein Ar is pyrrolo[3,4-c]pyrrole-1,4-dione-3,6-diyl, wherein both nitrogen atoms are substituted by —C(O)—OR$^1$.

2. The process of claim 1, wherein the repeat units of formula (I) are selected from the group consisting of formulae (I1) through (I11):

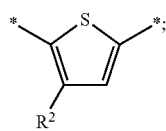
(I1)

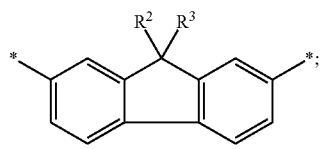
(I2)

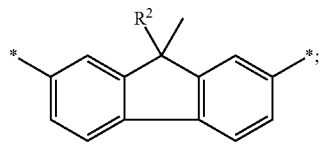
(I3)

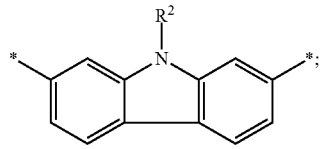
(I4)

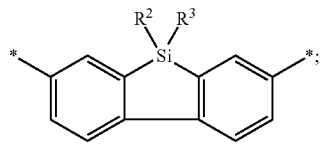
(I5)

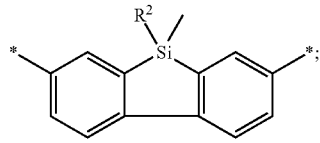
(I6)

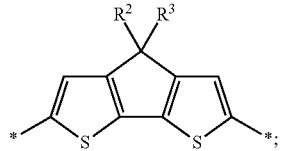
(I7)

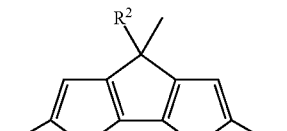
(I8)

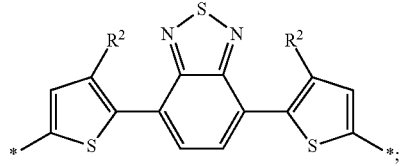
(I9)

-continued

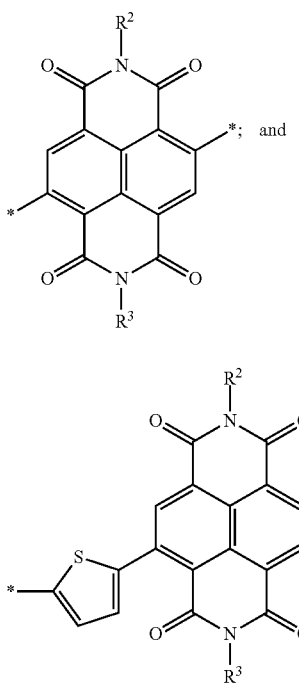
(I10)

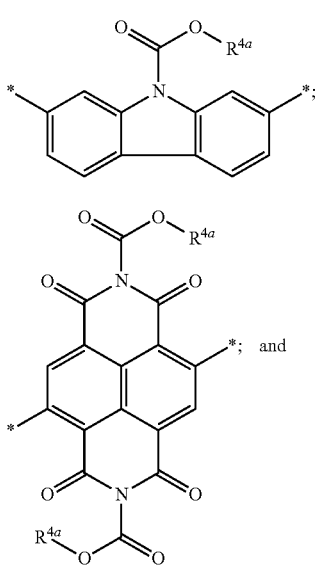
(I11)

wherein

R² and R³
are the same or different in each instance and are each independently a —Sp¹-X¹—C(O)—O—R¹ radical; and R⁴ is the same or different in each instance and is a straight-chain or branched alkyl radical having 1 to 25 carbon atoms.

3. The process of claim 2, wherein the repeat units are selected from the group consisting of formulae (I4a), (I10a), and (I11a):

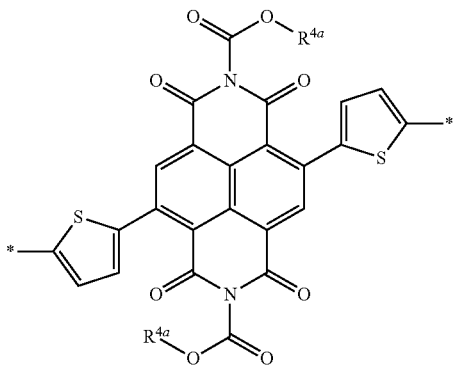
(I4a)

(I10a)

(I11a)

wherein
R⁴ᵃ is a straight-chain or branched alkyl radical having 1 to 25 carbon atoms.

4. The process of claim 1, wherein the Sp¹ radical is an alkylene radical having 1 to 20 carbon atoms.

5. The process of claim 1, wherein the R¹ radical is a straight-chain, branched, or cyclic alkyl radical having 1 to 25 carbon atoms and is unsubstituted or mono- or polysubstituted by F, Cl, Br, I or CN, and wherein one or more nonadjacent CH₂ groups are each optionally independently replaced by —O—, —S—, —C(O)—, —C(S)—, —C(O)—O—, —O—C(O)—, —NR⁰—, —SiR⁰R⁰⁰—, —CF₂—, —CHR⁰=CR⁰⁰—, —CY¹=CY²— or —C≡C— in such a way that no oxygen and/or sulfur atoms are joined directly to one another.

6. The process of claim 1, wherein the X¹ radical is O or NH.

7. The process of claim 1, wherein the -Sp¹-X¹—C(O)—O—R¹ radical is a radical of formula (S):

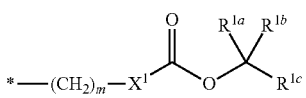
(S)

wherein
R¹ᵃ, R¹ᵇ, and R¹ᶜ
are each independently H or a straight-chain, branched, or cyclic alkyl radical having 1 to 25 carbon atoms or a straight-chain, branched, or cyclic alkenyl radical or alkynyl radical each having 2 to 25 carbon atoms, wherein two of the R¹ᵃ, R¹ᵇ, and R¹ᶜ radicals together optionally define a cyclic alkyl radical, alkenyl radical, or alkynyl radical each having 5 to 12 carbon atoms;
m is 0 or an integer from 1 to 12; and
* denotes the linkage to the Ar radical.

8. The process of claim 7, wherein the radical of formula (S) is selected from the group consisting of formulae (S1) through (S2):

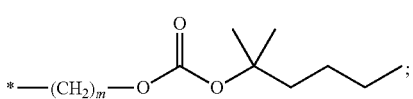
(S1)

-continued

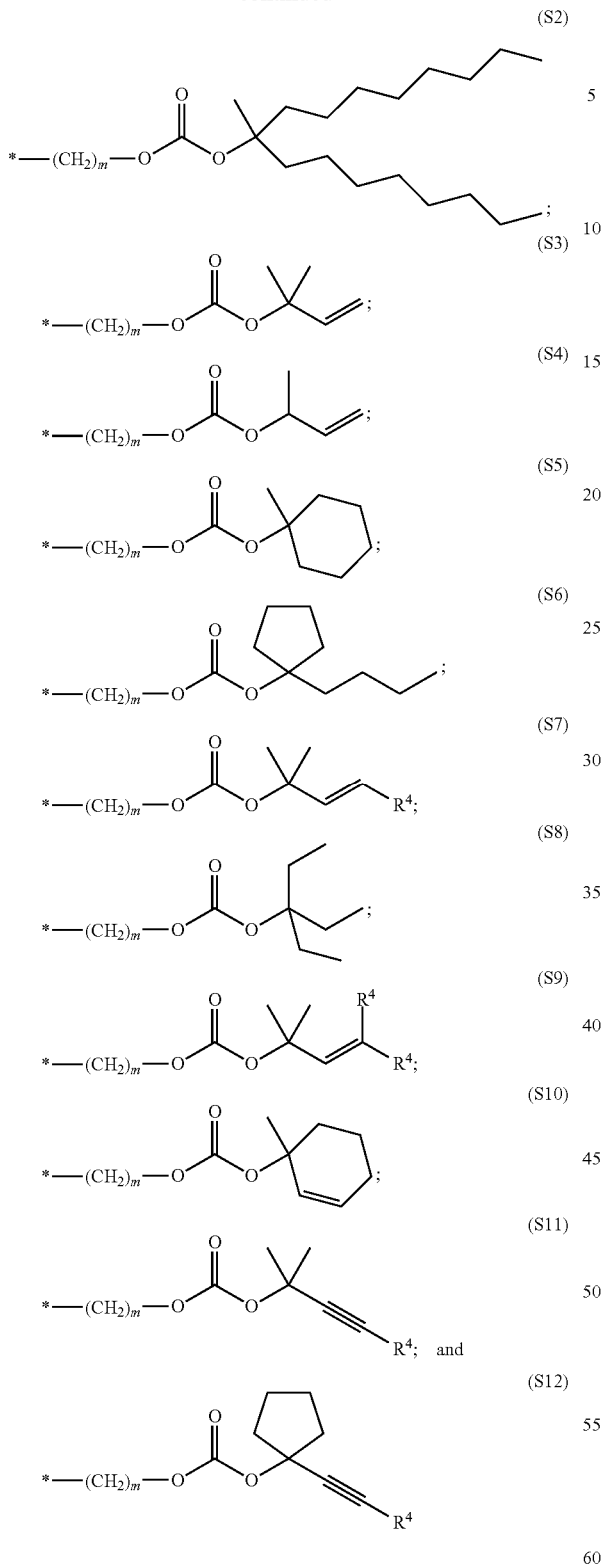

wherein
R⁴ is the same or different at each instance and is 1H or a straight-chain or branched alkyl radical having 1 to 25 carbon atoms;
m is an integer from 1 to 12; and
* denotes the linkage to the Ar radical.

9. The process of claim 1, wherein the Ar radical comprises one or more nitrogen atoms, the $Sp^1$-$X^1$—C(O)—O—$R^1$ radical is bonded to one of the nitrogen atoms in the Ar radical, and the $Sp^1$-$X^1$ radical is a single bond.

10. The process of claim 1, wherein the conjugated polymer comprises one or more repeat units of formulae (IIa) or (IIb):

$$—[(Ar^1)_a—(U)_b—(Ar^2)_c—(Ar^3)_d]—$$ (Ia);

$$—[(U)_b—(Ar^1)_a—(U)_b—(Ar^2)_c—(Ar)_d]—$$ (Ib);

wherein
U is a unit of formula (I) or a unit selected from the group consisting of units of formulae (I1) through (I11):

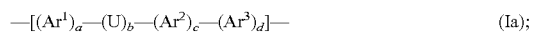
(I1)

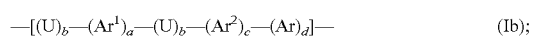
(I2)

(I3)

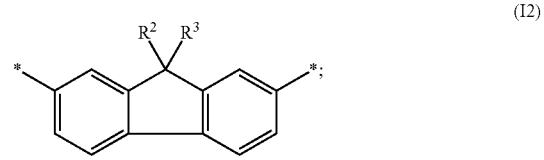
(I4)

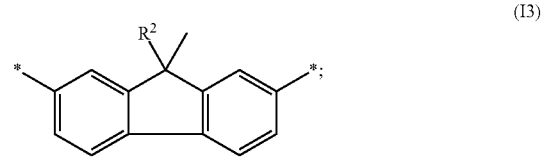
(I5)

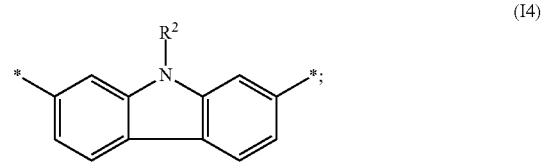
(I6)

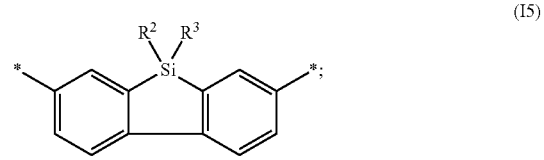
(I7)

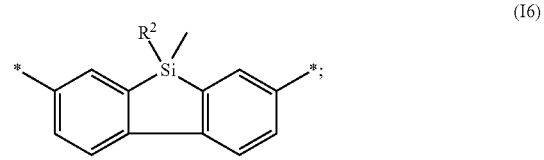
(I8)

-continued (I9)
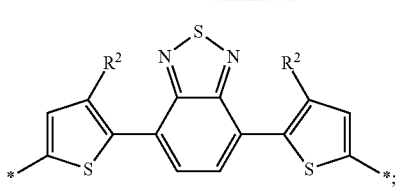

(I10)
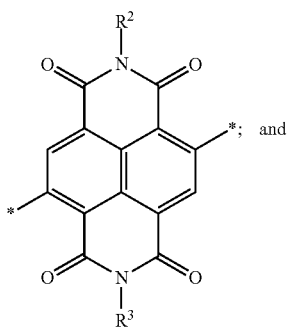

(I11)
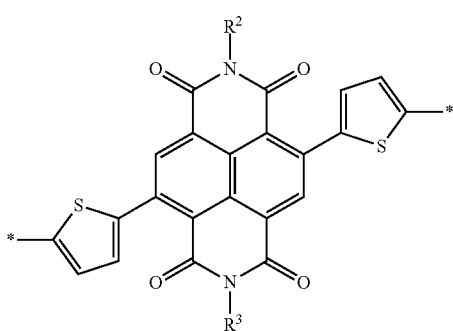

wherein
R² and R³
are the same or different in each instance and are each independently a -Sp¹-X¹—C(O)—O—R¹ radical; and
R⁴ is the same or different in each instance and is a straight-chain or branched alkyl radical having 1 to 25 carbon atoms;
Ar¹, Ar², Ar³
are each independently the same or different in each instance and are an optionally substituted aryl or heteroaryl group different than U;
R$^S$ is the same or different in each instance and is selected from the group consisting of F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, an optionally substituted silyl or hydrocarbyl group having 1 to 40 carbon atoms and which optionally comprises one or more heteroatoms;
X⁰ is halogen;
a, b, and c
are the same or different in each instance and are each independently 0, 1, or 2;
d is the same or different in each instance and is 0 or an integer from 1 to 10;
wherein the conjugated polymer comprises at least one repeat unit of formula (Ia) or (IIb) wherein b is at least 1.

11. The process of claim 10, wherein the conjugated polymer further comprises one or more optionally substituted mono- or polycyclic aryl or heteroaryl units.

12. The process of claim 11, wherein the optionally substituted mono- or polycyclic aryl or heteroaryl units are selected from the group consisting of formulae (IIIa) and (IIIb):

—[(Ar¹)$_a$—(Ar⁴)$_b$—(Ar²)$_c$—(Ar³)$_d$]—  (IIIa); and

—[(Ar⁴)$_b$—(Ar¹)$_a$—(Ar⁴)$_b$—(Ar²)$_c$—(Ar³)$_d$]—  (IIIb);

wherein
Ar⁴ is an optionally substituted aryl or heteroaryl group different than U and Ar¹⁻³; and
the conjugated polymer comprises at least one repeat unit of formula (IIIa) or (IIIb) wherein b is at least 1.

13. The process of claim 12, wherein the conjugated polymer is selected from formula (IV):

(IV)

wherein
A, B, and C
are each independently a different unit of formulae (I), (IIa), (IIb), (IIIa), or (IIIb);
x is >0 and ≤1;
y is ≥0 and <1;
z is ≥0 and <1;
x+y+z is equal to 1; and
n is an integer >1.

14. The process of claim 13, wherein the conjugated polymer is selected from the group consisting of subformulae (IVa), (IVb), (IVc), (IVd), (IVe), (IVf), (IVg), (IVh), (IVi), and (IVk):

*—[(Ar¹—U—Ar²)$_x$—(Ar³)$_y$]$_n$—*  (IVa);

*—[(Ar¹—U—Ar₂)$_x$—(Ar¹—Ar³)$_y$]$_n$—*  (IVb);

*—[(Ar¹—U—Ar²)$_x$—(Ar³—Ar³—Ar³)$_y$]$_n$—*  (IVc);

*—[(Ar¹)$_a$—(U)$_b$—(Ar²)$_c$—(Ar³)$_d$]$_n$—*  (IVd);

*—([(Ar¹)$_a$—(U)$_b$—(Ar²)$_c$—(Ar³)$_d$]$_x$—[(Ar¹)$_a$—(Ar⁴)$_b$—(Ar²)$_c$—(Ar³)$_d$]$_y$)$_n$—*  (IVe);

*—[(U—Ar¹—U)$_x$—(Ar²—Ar³)$_y$]$_n$—*  (IVf);

*—[(U—Ar¹—U)$_x$—(Ar²—Ar³—Ar²)$_y$]$_n$—*  (IVg);

*—[(U)$_b$—(Ar¹)$_a$—(U)$_b$—(Ar²)$^c$]$_n$—*  (IVh);

*—([(U)$_b$—(Ar¹)$^a$—(U)$_b$—(Ar²)$_c$]$_x$—[(A$^c$)$_b$-(Ar¹)$_a$—(Ar⁴)$_b$—(Ar²)$_d$]$_y$)$_n$—*  (IVi);

and

*—[(U—Ar¹)$_x$—(U—Ar²)$_y$—(U—Ar³)$_z$]$_n$—*  (IVk);

wherein
the conjugated polymer is optionally an alternating or random copolymer;
in formula IVd and IVe, in at least one repeat unit [(Ar¹)$_a$—(U)$_b$—(Ar²)$_c$—(Ar³)$_d$] and in at least one repeat unit [(Ar¹)$_a$—(Ar⁴)$_b$—(Ar²)$_c$—(Ar³)$_d$], b is at least 1; and
in formula IVh and IVi, in at least one repeat unit [(U)$_b$—(Ar¹)$_a$—(U)$_b$—(Ar²)$_d$] and in at least one repeat unit [(U)$_b$—(Ar¹)$_a$—(U)$_b$—(Ar²)$_d$], b is 1.

15. The process of claim 13, wherein the conjugated polymer is a polymer of formula (V):

R⁵-chain-R⁶   (V)

wherein

"chain"
denotes a polymer chain of formula (PV), a polymer chain selected from the group consisting of subformulae (IVa), (IVb), (IVc), (IVd), (IVe), (IVf), (IVg), (IVh), (IVi), and (IVk):

*—[(Ar¹—U—Ar²)ₓ—(Ar³)ᵧ]ₙ—*   (IVa);

*—[(Ar¹—U—Ar₂)ₓ—(Ar¹—Ar³)ᵧ]ₙ—*   (IVb);

*—[(Ar¹—U—Ar²)ₓ—(Ar³—Ar³—Ar³)ᵧ]ₙ—*   (IVc);

*—[(Ar¹)ₐ—(U)ᵦ—(Ar²)꜀—(Ar³)ₔ]ₙ—*   (IVd);

*—([(Ar¹)ₐ—(U)ᵦ—(Ar²)꜀—(Ar³)ₔ]ₓ—[(Ar¹)ₐ—(Ar⁴)ᵦ—(Ar²)꜀—(Ar³)ₔ]ᵧ)ₙ—*   (IVe);

*—[(U—Ar¹—U)ₓ—(Ar²—Ar³)ᵧ]ₙ—*   (IVf);

*—[(U—Ar¹—U)ₓ—(Ar²—Ar³—Ar²)ᵧ]ₙ—*   (IVg);

*—[(U)ᵦ—(Ar¹)ₐ—(U)ᵦ—(Ar²)ᶜ]ₙ—*   (IVh);

*—([(U)ᵦ—(Ar¹)ᵃ—(U)ᵦ—(Ar²)꜀]ₓ—[(Aᶜ)ᵦ-(Ar¹)ₐ—(Ar⁴)ᵦ—(Ar²)ₔ]ᵧ)ₙ—*   (IVi);

and

*—[(U—Ar¹)ₓ—(U—Ar²)ᵧ—(U—Ar³)_z]ₙ—*   (IVk);

wherein
the conjugated polymer is optionally an alternating or random copolymer;
in formula IVd and IVe, in at least one repeat unit [(Ar¹)ₐ—(U)ᵦ—(Ar²)꜀—(Ar³)ₔ] and in at least one repeat unit [(Ar¹)ₐ—(Ar⁴)ᵦ—(Ar²)꜀—(Ar³)ₔ], b is at least 1; and
in formula IVh and IVi, in at least one repeat unit [(U)ᵦ—(Ar¹)ₐ—(U)ᵦ—(Ar²)ₔ] and in at least one repeat unit [(U)ᵦ—(Ar)ₐ—(U)ᵦ—(Ar²)ₔ], b is 1;
or a polymer chain selected from the group consisting of formulae (IV1) through (IV9):

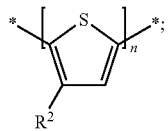   (IV1)

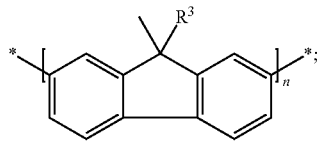   (IV2)

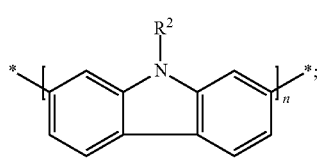   (IV3)

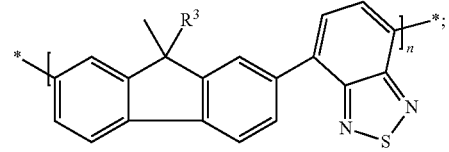   (IV4)

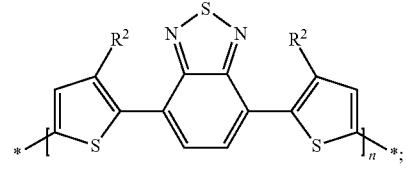   (IV5)

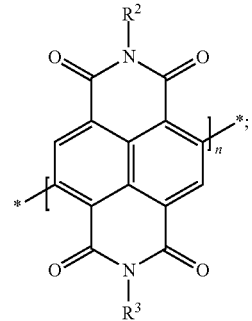   (IV6)

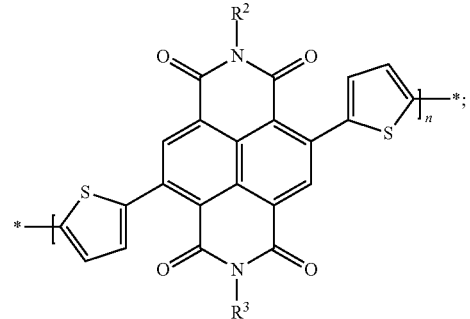   (IV7)

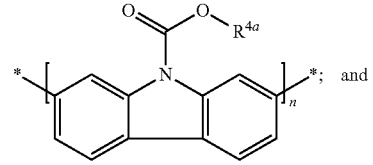   (IV8)

and

-continued

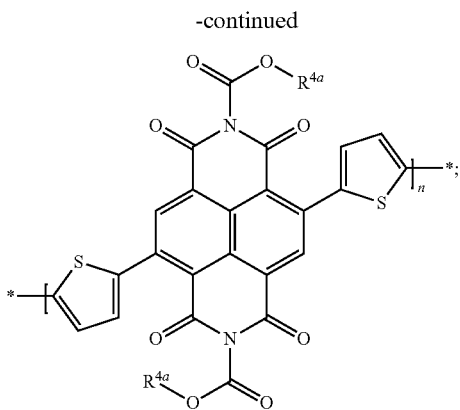

(IV9)

wherein

R² and R³
are the same or different in each instance and are each independently a -Sp¹-X¹—C(O)—O—R¹ radical; wherein Sp¹ is a single bond or alkylene radical having 1 to 20 carbon atoms and is unsubstituted or mono- or polysubstituted by F, Cl, Br, I or CN, and wherein one or more nonadjacent CH₂ groups are each optionally independently replaced by —O—, —S—, —NH—, —NR⁰—, —SiR⁰R⁰⁰—, —CO—, —COO—, —OCO—, —OCO—O—, —S—CO—, —CO—S—, —CR⁰=CR⁰⁰—, or —C≡C— such that no oxygen and/or sulfur atoms are directly bonded to one another;

X¹ is NR⁰ or O;

R¹ is a hydrocarbyl radical having 1 to 40 carbon atoms,

R⁴ is the same or different in each instance and is a straight-chain or branched alkyl radical having 1 to 25 carbon atoms; and n is an integer >1

R⁵ and R⁶
are each independently the same or different in each instance and are selected from the group consisting of H, F, Br, Cl, I, —CN, —NC, —NCO, —NCS, —OCN, —SCN, —C(O)NR⁰R⁰⁰, —C(O)X⁰, —C(O)R, —NH₂, —NR⁰R⁰⁰, —SH, —SR⁰, —SO₃H, —SO₂R, —OH, —NO₂, —CF₃, —SF₅, an optionally substituted silyl or hydrocarbyl group having 1 to 40 carbon atoms and which optionally comprises one or more heteroatoms, —CH₂Cl, —CHO, —CR'=CR"₂, —SiR'R"R'", —SiR'X'X", —SiR'R"X', —SnR'R"R'", —BR'R", —B(OR')(OR"), —B(OH)₂, —O—SO₂—R', —C≡CH, —C≡C—SiR'₃ or —ZnX', wherein X' and X" are halogen, R', R" and R'" and two of the R', R" and R'" radicals together with the respective heteroatom to which they are bonded optionally define a cyclosilyl, cyclostannyl, cycloborane or cycloboronate group having 2 to 20 carbon atoms.

16. The process of claim 12, wherein Ar¹, Ar², Ar³, and Ar⁴ are the same or different in each instance and are each a radical independently selected from the group consisting of 1,4-phenylene, thiophene-2,5-diyl, selenophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, 2,2-dithiophene, 2,2-diselenophene, dithieno[3,2-b:2',3'-d]silole-5,5-diyl, 4H-cyclopenta[2,1-b:3,4-b']dithiophene-2,6-diyl, carbazole-2,7-diyl, fluorene-2,7-diyl, indaceno[1,2-b:5,6-b']dithiophene-2,7-diyl, benzo[1",2":4,5;4",5":4',5']bis(silolo[3,2-b:3',2'-b']thiophene)-2,7-diyl, phenanthro[1,10,9,8-c,d,e,f,g]carbazole-2,7-diyl, benzo[2,1,3]thiadiazole-4,7-diyl, benzo[2,1,3]selenadiazole-4,7-diyl, benzo[2,1,3]oxadiazole-4,7-diyl, 2H-benzotriazole-4,7-diyl, 3,4-difluorothiophene-2,5-diyl, thieno[3,4-b]pyrazine-2,5-diyl, quinoxaline-5,8-diyl, thieno[3,4-b]thiophene-4,6-diyl, thieno[3,4-b]thiophene-6,4-diyl, 3,6-dithien-2-ylpyrrolo[3,4-c]pyrrole-1,4-dione or [1,3]thiazolo[5,4-d][1,3]thiazole-2,5-diyl, wherein the above radicals are optionally unsubstituted or mono- or polysubstituted.

17. The process of claim 1, wherein the conjugated polymer is selected from the group consisting of formulae (IV1) through (IV9):

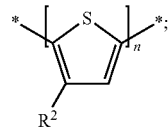

(IV1)

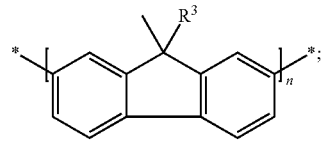

(IV2)

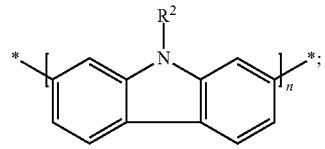

(IV3)

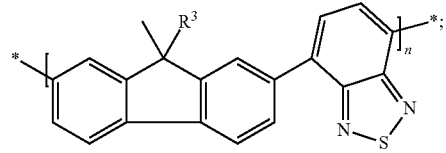

(IV4)

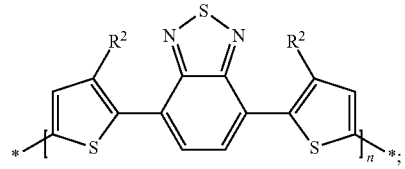

(IV5)

-continued (IV6)

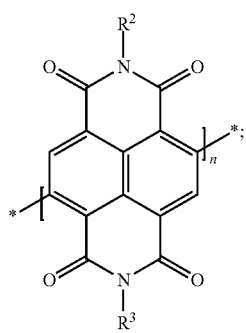

(IV7)

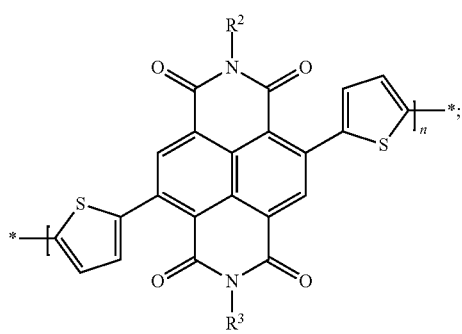

(IV8)

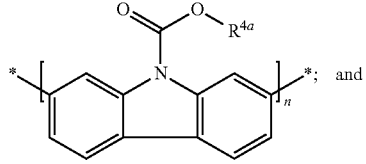
and

-continued (IV9)

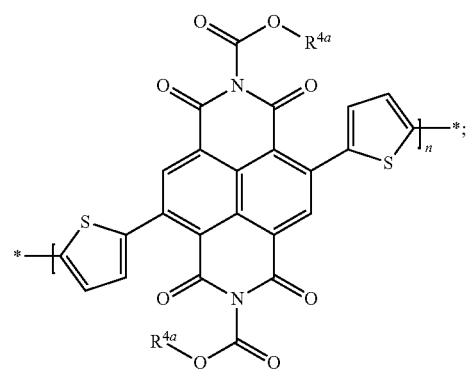

wherein
R² and R³
are the same or different in each instance and are each independently a -Sp¹-X¹—C(O)—O—R¹ radical; wherein
Sp¹ is a single bond or alkylene radical having 1 to 20 carbon atoms and is unsubstituted or mono- or polysubstituted by F, Cl, Br, I or CN, and wherein one or more nonadjacent CH₂ groups are each optionally independently replaced by —O—, —S—, —NH—, —NR⁰—, —SiR⁰R⁰⁰—, —CO—, —COO—, —OCO—, —OCO—O—, —S—CO—, —CO—S—, —CR⁰=CR⁰⁰—, or —C≡C— such that no oxygen and/or sulfur atoms are directly bonded to one another;
X¹ is NR⁰ or O;
R¹ is a hydrocarbyl radical having 1 to 40 carbon atoms,
R⁴ is the same or different in each instance and is a straight-chain or branched alkyl radical having 1 to 25 carbon atoms; and
n is an integer >1.

* * * * *